US012479860B2

(12) United States Patent
Jun et al.

(10) Patent No.: US 12,479,860 B2
(45) Date of Patent: Nov. 25, 2025

(54) ORGANIC ELECTROLUMINESCENT COMPOUND, A PLURALITY OF HOST MATERIALS, AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Ji-Song Jun, Gyeonggi-do (KR); Kyoung-Jin Park, Gyeonggi-do (KR); Chi-Sik Kim, Gyeonggi-do (KR); Sang-Hee Cho, Gyeonggi-do (KR); Su-Hyun Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 885 days.

(21) Appl. No.: 17/675,393

(22) Filed: Feb. 18, 2022

(65) Prior Publication Data

US 2022/0281894 A1 Sep. 8, 2022

(30) Foreign Application Priority Data

Feb. 22, 2021 (KR) ........................ 10-2021-0023299
Dec. 10, 2021 (KR) ........................ 10-2021-0176228

(51) Int. Cl.
*C07D 517/00* (2006.01)
*C07D 519/00* (2006.01)
*H10K 85/60* (2023.01)
*H10K 101/00* (2023.01)

(52) U.S. Cl.
CPC ......... *C07D 517/00* (2013.01); *C07D 519/00* (2013.01); *H10K 85/622* (2023.02); *H10K 85/626* (2023.02); *H10K 85/633* (2023.02); *H10K 85/654* (2023.02); *H10K 85/6572* (2023.02); *H10K 85/6574* (2023.02); *H10K 2101/90* (2023.02)

(58) Field of Classification Search
None
See application file for complete search history.

(56) References Cited

U.S. PATENT DOCUMENTS

2010/0072887 A1* 3/2010 Kwong ................ H10K 85/654 548/440
2012/0211736 A1* 8/2012 Kim ................... H10K 85/6576 548/440
2013/0056720 A1* 3/2013 Kim ....................... H05B 33/14 257/E51.026
2015/0021556 A1* 1/2015 Xia .................... H10K 85/6572 257/40
2015/0249221 A1 9/2015 Zeng et al.
2015/0349268 A1* 12/2015 Zeng .................... C07D 409/04 544/215
2016/0028021 A1 1/2016 Zeng et al.
2016/0093808 A1 3/2016 Adamovich et al.
2016/0197285 A1* 7/2016 Zeng .................. H10K 85/6576 544/216
2017/0054087 A1 2/2017 Zeng et al.
2018/0138425 A1 5/2018 Ma et al.
2018/0301639 A1* 10/2018 Zeng .................... C07D 487/04
2019/0207123 A1* 7/2019 Yoon .................... H10K 85/611
2019/0273210 A1* 9/2019 Yen ...................... H10K 85/624
2020/0106028 A1* 4/2020 Yen ...................... H10K 85/342
2020/0127212 A1 4/2020 Adamovich et al.
2022/0077404 A1* 3/2022 Zhang .................... C09K 11/06
2022/0123233 A1 4/2022 Lee et al.
2022/0194956 A1* 6/2022 Li ............................ C07F 7/30

OTHER PUBLICATIONS

Search Report from China National Intellectual Property Administration, Application No. 202210133288.4, Filing Date: Feb. 7, 2022.

* cited by examiner

*Primary Examiner* — Robert S Loewe
(74) *Attorney, Agent, or Firm* — G. Creston Campbell

(57) ABSTRACT

The present disclosure relates to an organic electroluminescent compound, a plurality of host materials, and an organic electroluminescent device comprising the same. An organic electroluminescent device having improved driving voltage, luminous efficiency, and/or lifespan properties can be provided by including the organic electroluminescent compound according to the present disclosure as a single host material or by including a specific combination of compounds according to the present disclosure as a plurality of host materials.

8 Claims, No Drawings

ORGANIC ELECTROLUMINESCENT COMPOUND, A PLURALITY OF HOST MATERIALS, AND ORGANIC ELECTROLUMINESCENT DEVICE COMPRISING THE SAME

TECHNICAL FIELD

The present disclosure relates to an organic electroluminescent compound, a plurality of host materials, and an organic electroluminescent device comprising the same.

BACKGROUND ART

In 1987, Tang et al. of Eastman Kodak first developed a small molecular green organic electroluminescent device (OLED) by using TPD/$Alq_3$ bilayer consisting of a light-emitting layer and a charge transport layer. Thereafter, the development of OLEDs was rapidly effected and OLEDs have been commercialized. Currently, organic electroluminescent devices mainly use phosphorescent materials having excellent luminous efficiency in panel implementation. However, in many applications such as TV and lighting, the lifespan of OLEDs is insufficient, and higher efficiency of OLEDs is still required. In general, the lifespan of an OLED becomes shorter as the luminance of the OLED becomes higher. Thus, OLEDs having high luminous efficiency and/or long lifespan are required for long-term use and high resolution of a display.

In order to improve luminous efficiency, driving voltage, and/or lifespan, various materials or concepts for an organic layer of an organic electroluminescent device have been proposed. However, they were not satisfied in practical use.

Meanwhile, Korean Patent Application Laid-Open No. 2016-0006633 and U.S. Patent Application Publication No. 2017-0054087 disclose a fluorene derivative compound. However, the aforementioned references fail to specifically disclose a specific compound or a specific combination of host materials claimed herein. In addition, there has been a need to develop an electroluminescent material having improved performances, for example, low driving voltage, high luminous efficiency, and/or improved lifespan properties, compared to the compound disclosed in the aforementioned references.

DISCLOSURE OF INVENTION

Technical Problems

The objective of the present disclosure is to provide an organic electroluminescent compound having a novel structure suitable for application to an organic electroluminescent device. Another objective of the present disclosure is to provide an improved organic electroluminescent material capable of providing an organic electroluminescent device with improved driving voltage, luminous efficiency and/or lifespan properties. Still another objective of the present disclosure is to provide an organic electroluminescent device with improved driving voltage, luminous efficiency, and/or lifespan properties by including a specific combination of compounds as host materials.

Solution to Problem

As a result of intensive research to solve the above technical problems, the present inventors found that the above objective can be achieved by an organic electroluminescent compound represented by the following formula 1'. In addition, the present inventors found that the above objective can be achieved by a plurality of host materials comprising a first host material comprising a compound represented by the following formula 1 and a second host material comprising a compound represented by the following formula 2.

(1)

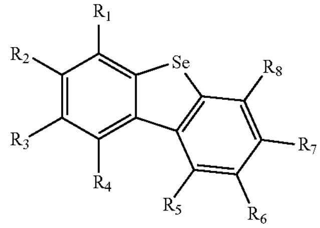

In formula 1, $R_1$ to $R_8$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30)aliphatic ring(s) and a (C6-C30)aromatic ring(s), or $-(L)_a$-HAr;

at least one of $R_1$ to $R_8$ is $-(L)_a$-HAr;

HAr represents a substituted or unsubstituted nitrogen-containing (3- to 20-membered)heteroaryl;

L each independently represents a single bond, a substituted or unsubstituted (C6-C30)arylene, or a substituted or unsubstituted (3- to 30-membered)heteroarylene; and a represents 1 or 2;

(2)

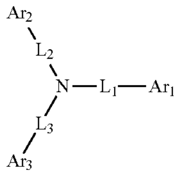

in formula 2, $L_1$ to $L_3$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ to $Ar_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-

C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or an unsubstituted fused ring group of a (C3-C30)aliphatic ring(s) and a (C6-C30)aromatic ring(s), or $-L_b-N(Ar_e)(Ar_d)$;

$L_b$ represents a single bond, a substituted or unsubstituted (C6-C30)arylene, or a substituted or unsubstituted (3- to 30-membered)heteroarylene; and $Ar_c$ and $Ar_d$ each independently represent hydrogen, a substituted or unsubstituted (C1-C30)alkyl, a substituted or unsubstituted (C2-C30)alkenyl, a substituted or unsubstituted fused ring group of a (C3-C30)aliphatic ring(s) and a (C6-C30)aromatic ring(s), a substituted or unsubstituted (C6-C30)aryl, or a substituted or unsubstituted (3- to 30-membered)heteroaryl;

with the proviso that the case where all of $L_1$ to $L_3$ are single bonds and all of $Ar_1$ to $Ar_3$ are hydrogen is excluded.

(1')

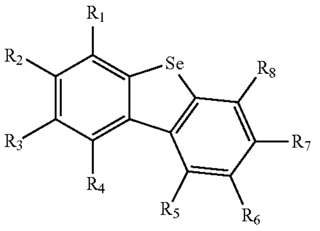

In formula 1', $R_1$ to $R_8$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30)aliphatic ring(s) and a (C6-C30)aromatic ring(s), or $-(L)_a$-HAr, with the proviso that $R_1$ to $R_8$ are not 9,9-dimethylfluorenyl or 9,9-diphenylfluorenyl;

at least one of $R_1$ to $R_8$ is $-(L)_a$-HAr;

HAr represents a substituted or unsubstituted nitrogen-containing (3- to 20-membered)heteroaryl;

L each independently represents a single bond, a substituted or unsubstituted (C6-C30)arylene, or a substituted or unsubstituted (3- to 30-membered)heteroarylene; and a represents 1 or 2;

with the proviso that the case where any one of $R_1$ to $R_8$ is $-(L)_a$-HAr; a is 1; L is a substituted or unsubstituted phenylene or a substituted or unsubstituted biphenylene; and HAr is a triazinyl substituted with any two each independently selected from the group consisting of a phenyl(s), a biphenyl(s), a terphenyl(s), a 9,9-dimethylfluorenyl(s), and a pyridyl(s) substituted with a phenyl(s) is excluded;

with the proviso that the case where any one of $R_1$ to $R_8$ is $-(L)_a$-HAr; a is 1; L is a single bond or a pyridylene; HAr is a triazinyl substituted with any two each independently selected from the group consisting of a phenyl(s) unsubstituted or substituted with deuterium or a 9,9-dimethylfluorenyl(s), a biphenyl(s) unsubstituted or substituted with deuterium, a pyridyl(s) substituted with a phenyl(s), a 9,9-dimethylfluorenyl(s) unsubstituted or substituted with deuterium, a 9,9-dimethylazafluorenyl(s), a spiro[cyclohexane-1,9'-fluoren]yl(s), and a 9,9'-spirobifluorenyl(s); and any one or two of the remaining $R_1$ to $R_8$ is an unsubstituted phenyl or an unsubstituted biphenyl is excluded; and with the proviso that the organic electroluminescent compounds having the following structures are excluded.

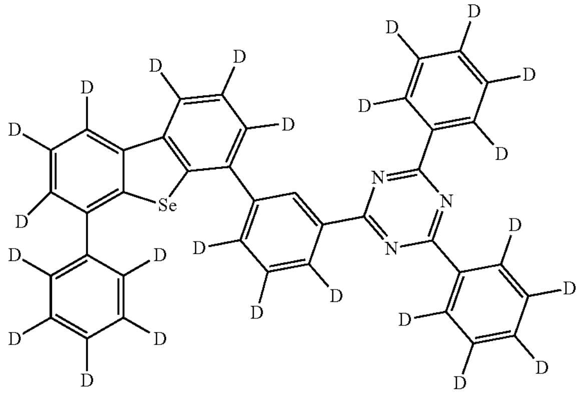

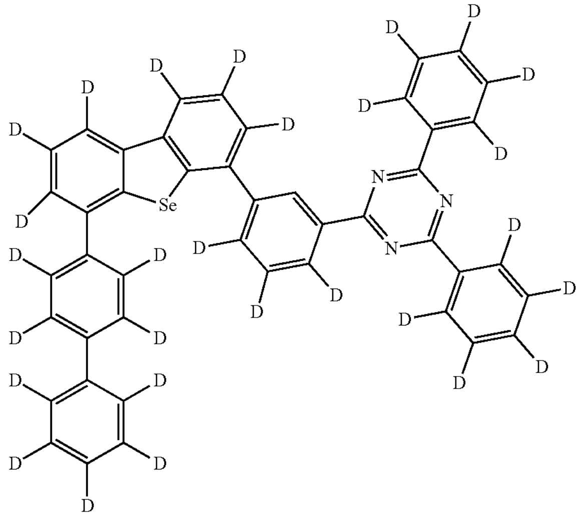

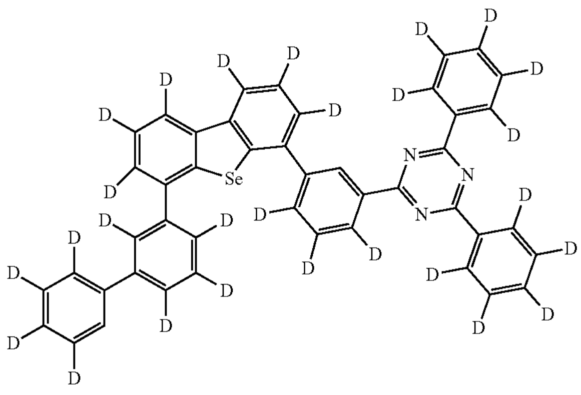

-continued

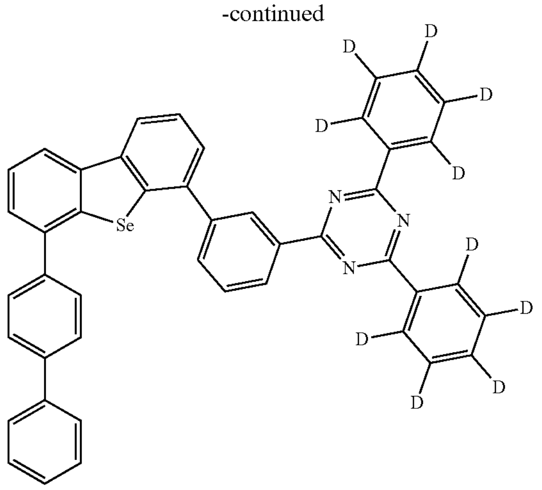

Advantageous Effects of Invention

The organic electroluminescent compound according to the present disclosure exhibits suitable performance for use in organic electroluminescent devices. In addition, an organic electroluminescent device having lower driving voltage, higher luminous efficiency, and/or excellent lifespan properties compared to a conventional organic electroluminescent device is provided by including the organic electroluminescent compound according to the present disclosure as a single host material or by including a specific combination of compounds according to the present disclosure as a plurality of host materials, and it is possible to manufacture a display device or a lighting device using the same.

MODE FOR THE INVENTION

Hereinafter, the present disclosure will be described in detail. However, the following description is intended to explain the present disclosure, and is not meant to restrict the scope of the present disclosure.

The term “organic electroluminescent compound” in the present disclosure means a compound that may be used in an organic electroluminescent device, and may be comprised in any layer constituting an organic electroluminescent device, as necessary.

The term “organic electroluminescent material” in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term “a plurality of host materials” in the present disclosure means a host material(s) comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of host materials of the present disclosure may be a combination of two or more host materials that may optionally further comprise a conventional material included in an organic electroluminescent material. Two or more compounds included in the plurality of host materials of the present disclosure may be together included in one light-emitting layer or may be respectively included in different light-emitting layers. For example, the two or more host materials may be mixture-evaporated or co-evaporated, or may be individually evaporated.

Herein, the term “(C1-C30)alkyl” is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, isopropyl, n-butyl, isobutyl, tert-butyl, sec-butyl, etc. The term “(C3-C30)cycloalkyl” is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term “(3- to 7-membered)heterocycloalkyl” is meant to be a cycloalkyl having 3 to 7 ring backbone atoms, and including at least one heteroatom selected from the group consisting of B, N, O, S, Si, and P, preferably the group consisting of O, S, and N. The above heterocycloalkyl may include tetrahydrofuran, pyrrolidine, thiolane, tetrahydropyran, etc. The term “(C6-C30)aryl(ene)” is meant to be a monocyclic or fused ring radical derived from an aromatic hydrocarbon having 6 to 30 ring backbone carbon atoms. The above aryl may be partially saturated; and may comprise a spiro structure. The above aryl may include phenyl, biphenyl, terphenyl, naphthyl, binaphthyl, phenylnaphthyl, naphthylphenyl, fluorenyl, phenylfluorenyl, diphenylfluorenyl, benzofluorenyl, dibenzofluorenyl, phenanthrenyl, phenylphenanthrenyl, benzophenanthrenyl, anthracenyl, indenyl, triphenylenyl, pyrenyl, tetracenyl, perylenyl, chrysenyl, naphthacenyl, fluoranthenyl, spirobifluorenyl, spiro[fluorene-benzofluoren]yl, spiro[cyclopenten-fluoren]yl, spiro[dihydroinden-fluoren]yl, azulenyl, tetramethyldihydrophenanthrenyl, etc. Specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl(ene)" means an aryl group or an arylene group having 3 to 30 ring backbone atoms and including at least one, preferably 1 to 4 heteroatom(s) selected from the group consisting of B, N, O, S, Si, P, and Se. The above heteroaryl(ene) may be a monocyclic ring or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenanthridinyl, benzodioxolyl, dihydroacridinyl, benzotriazolephenazinyl, imidazopyridyl, chromenoquinazolinyl, thiochromenoquinazolinyl, dimethylbenzoperimidinyl, indolocarbazolyl, indenocarbazolyl, etc. More specifically, the heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. In the present disclosure, "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

"Substituted" in the expression "substituted or unsubstituted" means that a hydrogen atom in a certain functional group is replaced with another atom or another functional group (i.e., a substituent), and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as one heteroaryl substituent or as substituents in which two heteroaryl substituents are linked. In the present disclosure, the substituent(s) of the substituted alkyl(ene), the substituted alkenyl, the substituted aryl(ene), the substituted heteroaryl(ene), the substituted cycloalkyl(ene), the substituted alkoxy, the substituted trialkylsilyl, the substituted dialkylarylsilyl, the substituted alkyldiarylsilyl, the substituted triarylsilyl, and the substituted fused ring group of an aliphatic ring(s) and an aromatic ring(s) each independently are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium and a (3- to 30-membered)heteroaryl(s); tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30)aromatic ring(s); an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituent(s), each independently, are at least one selected from the group consisting of deuterium; a (C1-C20)alkyl; a (5- to 25-membered)heteroaryl unsubstituted or substituted with at least one of deuterium and a (C6-C25)aryl(s); a (C6-C30)aryl unsubstituted or substituted with at least one of deuterium and a (5- to 25-membered)heteroaryl(s); and a di-(C6-C30)arylamino. According to another embodiment of the present disclosure, the substituent(s), each independently, are at least one selected from the group consisting of deuterium; a (C1-C10)alkyl; a (5- to 25-membered)heteroaryl unsubstituted or substituted with at least one of deuterium and a (C6-C18)aryl(s); a (C6-C30)aryl unsubstituted or substituted with at least one of deuterium and a (5- to 25-membered)heteroaryl(s); and a di-(C6-C12)arylamino. For example, the substituent(s), each independently, may be at least one selected from the group consisting of deuterium; methyl; a tert-butyl; a phenyl unsubstituted or substituted with deuterium, a chrysenyl(s), a phenyl-substituted phenanthrooxazole(s), or a 23-membered nitrogen-containing heteroaryl(s); a naphthyl unsubstituted or substituted with a chrysenyl(s); a biphenyl unsubstituted or substituted with deuterium; a terphenyl; a phenanthrenyl; a phenylphenanthrenyl; a chrysenyl unsubstituted or substituted with a phenyl(s); a triphenylenyl; a pyridyl; a carbazolyl unsubstituted or substituted with a phenyl(s); a dibenzofuranyl; a dibenzoselenophenyl unsubstituted or substituted with deuterium; a phenanthrooxazolyl substituted with at least one of deuterium, a phenyl(s) unsubstituted or substituted with deuterium, and a biphenyl(s); a phenanthrothiazolyl substituted with a phenyl(s); a phenanthroimidazolyl substituted with a phenyl(s); an indolocarbazolyl substituted with a phenyl(s); a 23-membered nitrogen-containing heteroaryl; and an amino group substituted with a phenyl(s).

Herein, a ring formed by a linkage of adjacent substituents means that at least two adjacent substituents are linked to or fused with each other to form a substituted or unsubstituted mono- or polycyclic (3- to 30-membered) alicyclic or aromatic ring, or the combination thereof. The ring may be preferably a substituted or unsubstituted mono- or polycyclic (3- to 26-membered) alicyclic or aromatic ring, or the combination thereof, more preferably a monocyclic (3- to 6-membered) alicyclic ring unsubstituted or substituted with a (C1-C10)alkyl(s), or a mono- or polycyclic (5- to 25-membered) aromatic ring unsubstituted or substituted with at least one of a (C6-C18)aryl(s) and a (3- to 20-membered) heteroaryl(s). In addition, the formed ring may contain at least one heteroatom selected from B, N, O, S, Si, P, and Se, preferably at least one heteroatom selected from N, O, S, and Se. For example, the ring may be a benzene ring, a cyclopentane ring unsubstituted or substituted with a methyl(s), a fluorene ring, etc.

In the present disclosure, the heteroaryl, the heteroarylene, and the heterocycloalkyl, each independently, may contain at least one heteroatom selected from B, N, O, S, Si, P, and Se. Also, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered) heteroarylamino, and a substituted or unsubstituted (C6-C30)aryl(3- to 30-membered)heteroarylamino.

A plurality of host materials according to the present disclosure comprise a first host material and a second host material, wherein the first host material comprises at least one compound represented by formula 1, and the second host material comprises at least one compound represented by formula 2. It may be included in a light-emitting layer of an organic electroluminescent device according to one embodiment of the present disclosure.

Hereinafter, the compound represented by formula 1 will be described in more detail.

In formula 1, $R_1$ to $R_8$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30)aromatic ring(s), or $-(L)_a$-HAr. According to one embodiment of the present disclosure, $R_1$ to $R_8$ each independently represent hydrogen, deuterium, a substituted or unsubstituted (C6-C25)aryl, a substituted or unsubstituted (5- to 25-membered)heteroaryl, or $-(L)_a$-HAr. According to another embodiment of the present disclosure, $R_1$ to $R_8$ each independently represent hydrogen; deuterium; a (C6-C18)aryl unsubstituted or substituted with at least one of deuterium, a (C6-C18)aryl(s), and a (5- to 25-membered)heteroaryl(s); a (5- to 25-membered)heteroaryl unsubstituted or substituted with a (C6-C12)aryl(s); or $-(L)_a$-HAr. For example, $R_1$ to $R_8$ may each independently be hydrogen, deuterium, an unsubstituted phenyl, a phenyl substituted with deuterium, a phenyl substituted with a chrysenyl, a phenyl substituted with a phenyl-substituted phenanthrooxazolyl(s), a naphthyl, a naphthyl substituted with a phenyl(s), a naphthyl substituted with a dibenzofuranyl(s), a chrysenyl, a chrysenyl substituted with deuterium, a triphenylenyl, a phenanthrenyl, a phenanthrooxazolyl substituted with a phenyl(s), a phenanthrooxazolyl substituted with a naphthyl(s), a phenanthrothiazolyl substituted with a phenyl(s), a carbazolyl substituted with a phenyl(s), a 23-membered nitrogen-containing heteroaryl, $-(L)_a$-HAr, etc.

In formula 1, at least one of $R_1$ to $R_8$ is $-(L)_a$-HAr, wherein a is 1 or 2.

Herein, L each independently represents a single bond, a substituted or unsubstituted (C6-C30)arylene, or a substituted or unsubstituted (3- to 30-membered)heteroarylene. According to one embodiment of the present disclosure, L represents a single bond, a substituted or unsubstituted (C6-C18)arylene, or a substituted or unsubstituted (5- to 20-membered)heteroarylene. According to another embodiment of the present disclosure, L represents a single bond, a substituted or unsubstituted (C6-C14)arylene, or a substituted or unsubstituted (5- to 17-membered)heteroarylene. For example, L may be a single bond, a phenylene unsubstituted or substituted with a phenyl(s), a naphthylene unsubstituted or substituted with a phenyl(s), a biphenylene, a phenanthrenylene, a phenanthrooxazolylene unsubstituted or substituted with a phenyl(s), a carbazolylene, etc.

HAr represents a substituted or unsubstituted nitrogen-containing (3- to 20-membered)heteroaryl. According to one embodiment of the present disclosure, HAr represents a substituted or unsubstituted nitrogen-containing (6- to 14-membered)heteroaryl. According to another embodiment of the present disclosure, HAr represents a substituted nitrogen-containing (6- to 14-membered)heteroaryl. For example, HAr may be a substituted triazinyl, a substituted quinoxalinyl, a substituted quinazolinyl, a substituted 1,6-naphthyridinyl, a substituted benzoquinoxalinyl, a substituted benzoquinazolinyl, etc; wherein the substituent(s) of the substituted triazinyl, the substituted quinoxalinyl, the substituted quinazolinyl, the substituted 1,6-naphthyridinyl, the substituted benzoquinoxalinyl, and the substituted benzoquinazolinyl may each independently be at least one, preferably any two selected from the group consisting of deuterium; a phenyl unsubstituted or substituted with deuterium, a chrysenyl(s), a phenyl-substituted phenanthrooxazolyl(s), or a 23-membered nitrogen-containing heteroaryl(s); a biphenyl unsubstituted or substituted with deuterium; a naphthyl unsubstituted or substituted with a chrysenyl(s); a phenanthrenyl; a phenylphenanthrenyl; a terphenyl; a triphenylenyl; a dibenzofuranyl; a dibenzoselenophenyl unsubstituted or substituted with deuterium; a chrysenyl unsubstituted or substituted with a phenyl(s); a phenanthrooxazolyl substituted with at least one of deuterium, a phenyl(s) unsubstituted or substituted with deuterium, and a biphenyl(s); a phenanthroimidazolyl substituted with a phenyl(s); a phenanthrothiazolyl substituted with a phenyl(s); a carbazolyl unsubstituted or substituted with a phenyl(s); an indolocarbazolyl substituted with a phenyl(s); and a 23-membered nitrogen-containing heteroaryl.

According to one embodiment of the present disclosure, the formula 1 may be represented by any one of the following formulas 1-1 to 1-4.

(1-1)

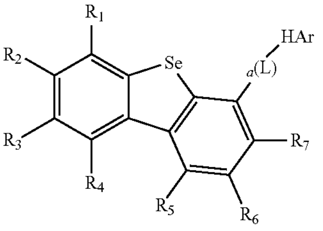

(1-2)

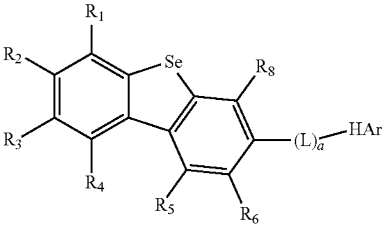

(1-3)

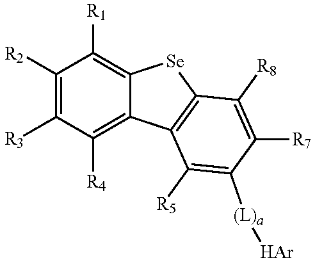

(1-4)

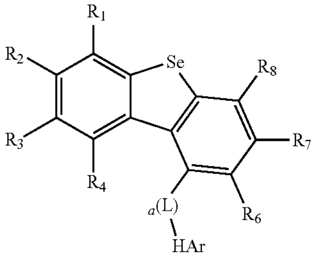

In formulas 1-1 to 1-4, $R_1$ to $R_8$, L, HAr, and a are as defined in formula 1.

According to one embodiment of the present disclosure, HAr of formula 1 may be represented by any one of the following formulas 1-5 to 1-7.

(1-5)

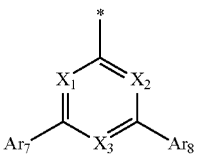

(1-6)

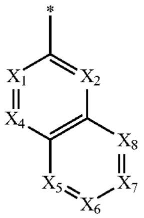

-continued (1-7)

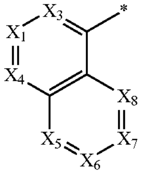

In formulas 1-5 to 1-7, $X_1$ to $X_8$ each independently represent $CR_{25}$ or N;

$R_{25}$, $Ar_7$, and $Ar_8$ each independently represent hydrogen, deuterium, a substituted or unsubstituted (C1-C30) alkyl, a substituted or unsubstituted (C6-C30)aryl, or a substituted or unsubstituted (3- to 30-membered)heteroaryl, wherein $R_{25}$ may be linked to an adjacent substituent to form a ring(s); and

* represents a site linked to dibenzoselenophene.

According to one embodiment of the present disclosure, in formula 1-5, all of $X_1$ to $X_3$ represent N. According to one embodiment of the present disclosure, in formula 1-5, $Ar_7$ and $Ar_8$ each independently represent a substituted or unsubstituted (C6-C30)aryl or a substituted or unsubstituted (5- to 25-membered)heteroaryl. For example, $Ar_7$ and $Ar_8$ may each independently be a phenyl unsubstituted or substituted with deuterium, a chrysenyl(s), a phenyl-substituted phenanthrooxazolyl(s), and a 23-membered nitrogen-containing heteroaryl(s); a biphenyl unsubstituted or substituted with deuterium; a naphthyl unsubstituted or substituted with a chrysenyl(s); a phenanthrenyl; a phenylphenanthrenyl; a terphenyl; a chrysenyl; a triphenylenyl; a dibenzofuranyl; a carbazolyl unsubstituted or substituted with a phenyl(s); a dibenzoselenophenyl unsubstituted or substituted with deuterium; a phenanthrooxazolyl substituted with at least one of deuterium, a phenyl(s) unsubstituted or substituted with deuterium, and a biphenyl(s); an indolocarbazolyl substituted with a phenyl(s); a 23-membered nitrogen-containing heteroaryl; etc.

According to one embodiment of the present disclosure, in formulas 1-6 and 1-7, any two of $X_1$, $X_2$, and $X_4$ to $X_8$ represent N, and the remainders represent $CR_{25}$. According to one embodiment of the present disclosure, in formulas 1-6 and 1-7, $R_{25}$ represents a substituted or unsubstituted (C6-C30)aryl, or a substituted or unsubstituted (5- to 25-membered)heteroaryl; or may be linked to an adjacent substituent to form a ring(s). For example, $R_{25}$ may be a phenyl, a biphenyl, a chrysenyl unsubstituted or substituted with a phenyl(s), a phenanthrooxazolyl substituted with a phenyl (s), a phenanthrothiazolyl substituted with a phenyl(s), or a 23-membered nitrogen-containing heteroaryl; or may be linked to an adjacent substituent to form a fused benzene, etc.

Hereinafter, the compound represented by formula 2 will be described in more detail.

In formula 2, $L_1$ to $L_3$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene. According to one embodiment of the present disclosure, $L_1$ to $L_3$ each independently represent a single bond, a substituted or unsubstituted (C6-C12)arylene, or a substituted or unsubstituted (5- to 15-membered)heteroarylene. According to another embodiment of the present disclosure, $L_1$ to $L_3$ each independently represent a single bond, a substituted or unsubstituted (C6-C12)arylene, or an unsubstituted (5- to 15-membered)heteroarylene. For example, $L_1$ to $L_3$ may each independently be a single bond, a phenylene, a phenylene substituted with deuterium, a biphenylene, a naphthylene, a dibenzofuranylene, a dibenzothiophenylene, etc.

In formula 2, $Ar_1$ to $Ar_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or an unsubstituted fused ring group of a (C3-C30)aliphatic ring(s) and a (C6-C30)aromatic ring(s), or $-L_b-N(Ar_c)(Ar_d)$.

According to one embodiment of the present disclosure, $Ar_n$ to $Ar_3$ each independently represent a substituted or unsubstituted (C6-C30)aryl, a substituted or unsubstituted (3- to 30-membered)heteroaryl, a substituted or unsubstituted (C3-C10)cycloalkyl, or $-L_b-N(Ar_c)(Ar_d)$. According to another embodiment of the present disclosure, $Ar_1$ to $Ar_3$ each independently represent a (C6-C30)aryl unsubstituted or substituted with at least one of deuterium, a (C1-C6)alkyl (s), and a (C6-C20)aryl(s); a (3- to 30-membered)heteroaryl unsubstituted or substituted with at least one of deuterium, a (3- to 25-membered)heteroaryl(s), and a (C6-C15)aryl(s) unsubstituted or substituted with deuterium; an unsubstituted (C3-C10)cycloalkyl; or $-L_b-N(Ar_c)(Ar_d)$. For example, $Ar_n$ to $Ar_3$ may each independently be a phenyl unsubstituted or substituted with deuterium, a tert-butylphenyl, a naphthyl, a biphenyl unsubstituted or substituted with deuterium, a terphenyl, a chrysenyl, an anthracenyl, a phenanthrenyl, a fluoranthenyl, a dimethylfluorenyl, a diphenylfluorenyl, a methylphenylfluorenyl, a dimethylbenzofluorenyl, a spirobifluorenyl, a spirocyclopentanefluorenyl, a (C22)aryl; a phenanthrooxazolyl substituted with at least one of deuterium, a phenyl(s) unsubstituted or substituted with deuterium, a biphenyl(s), a naphthyl(s) and a pyridyl(s); a phenanthrothiazolyl substituted with a phenyl(s) or a biphenyl(s); a dibenzofuranyl unsubstituted or substituted with deuterium or a phenyl(s); a benzonaphthofuranyl, a dibenzothiophenyl, a carbazolyl unsubstituted or substituted with a phenyl(s), a carbazolyl fused with a dimethyl-substituted cyclopentyl from a linkage with an adjacent substituent(s), a naphthooxazolyl substituted with a phenyl(s), a phenoxazinyl, a pyridyl substituted with a phenyl(s), a benzothiophenyl, a benzimidazolyl substituted with a phenyl(s), a dibenzocarbazolyl, a 23-membered nitrogen-containing heteroaryl unsubstituted or substituted with a phenyl(s), a 26-membered nitrogen-containing heteroaryl unsubstituted or substituted with a phenyl(s), a 27-membered nitrogen-containing heteroaryl, a 30-membered nitrogen-containing heteroaryl, a cyclohexyl, a diphenylamino, etc.

Herein, $L_b$ represents a single bond, a substituted or unsubstituted (C6-C30)arylene, or a substituted or unsubstituted (3- to 30-membered)heteroarylene. For example, $L_b$ may be a single bond.

$Ar_c$ and $Ar_d$ each independently represent hydrogen, a substituted or unsubstituted (C1-C30)alkyl, a substituted or unsubstituted (C2-C30)alkenyl, a substituted or unsubstituted fused ring group of a (C3-C30)aliphatic ring(s) and a (C6-C30)aromatic ring(s), a substituted or unsubstituted (C6-C30)aryl, or a substituted or unsubstituted (3- to 30-membered)heteroaryl. According to one embodiment of the present disclosure, $Ar_c$ and $Ar_d$ each independently represent a substituted or unsubstituted (C6-C12)aryl. According to another embodiment of the present disclosure, $Ar_c$ and $Ar_d$ each independently represent an unsubstituted (C6-C12)aryl. For example, $Ar_c$ and $Ar_d$ may each independently be a phenyl, etc.

In formula 2, the case where all of $L_1$ to $L_3$ are single bonds and all of $Ar_1$ to $Ar_3$ are hydrogen is excluded.

According to one embodiment of the present disclosure, the formula 2 may be represented by any one of the following formulas 2-1 to 2-14.

(2-1)

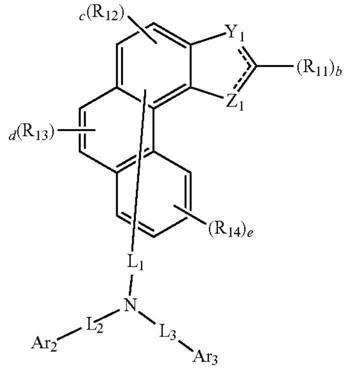

(2-2)

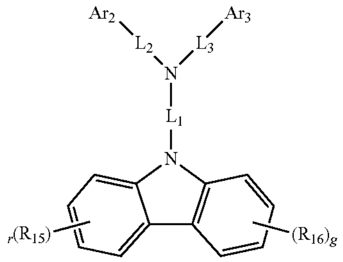

(2-3)

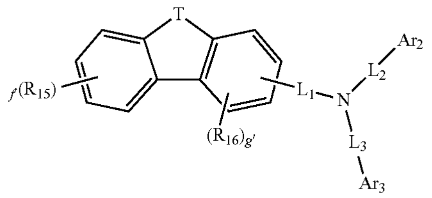

(2-4)

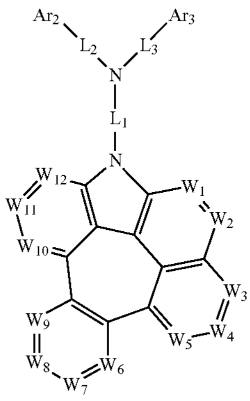

-continued
(2-5)
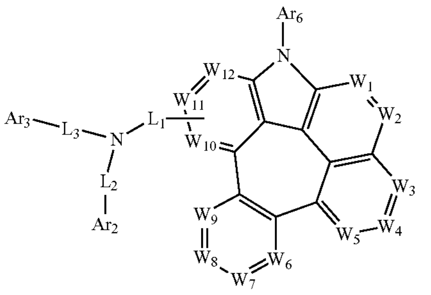
(2-6)
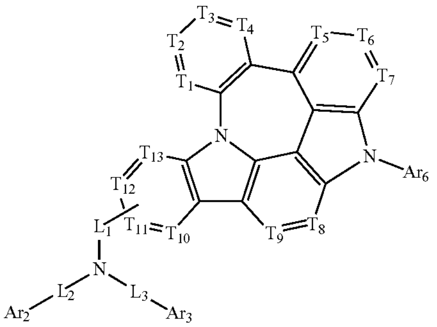
(2-7)
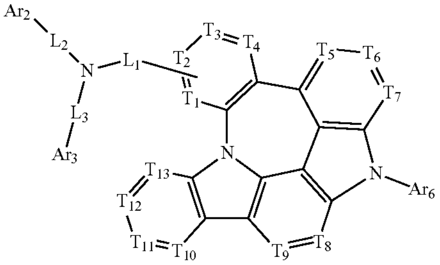
(2-8)
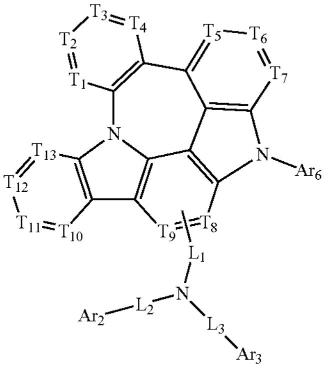
(2-9)
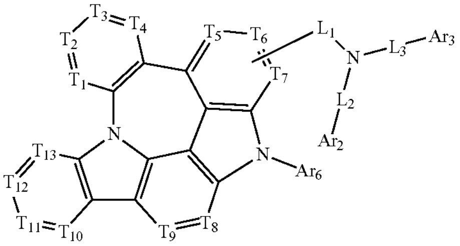
-continued
(2-10)
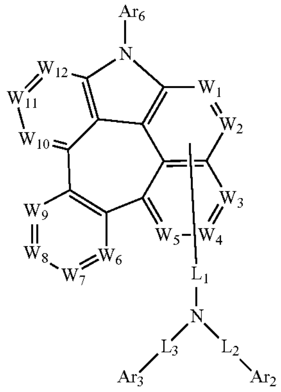
(2-11)
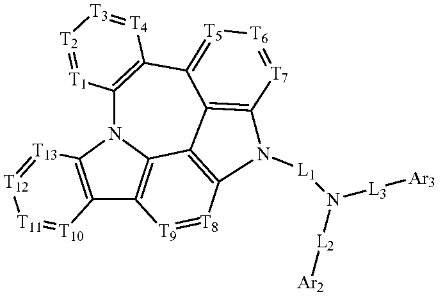
(2-12)
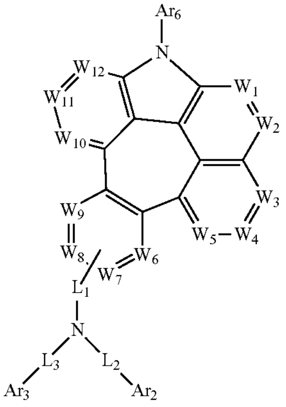
(2-13)
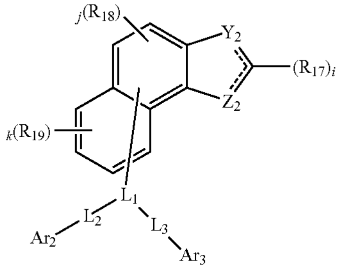

-continued (2-14)

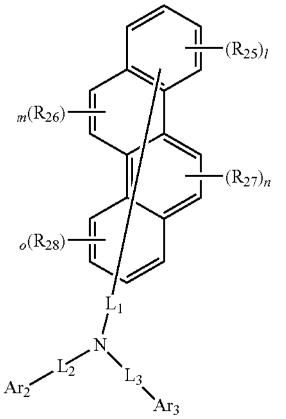

In formulas 2-1 to 2-14, $Y_1$, $Y_2$, $Z_1$, and $Z_2$ each independently represent —N═, —$NR_{21}$—, —O—, or —S—, with the proviso that any one of $Y_1$ and $Z_1$ represents —N═, and the other one of $Y_1$ and $Z_1$ represents —$NR_{21}$—, —O—, or —S—, and with the proviso that any one of $Y_2$ and $Z_2$ represents —N═, and the other one of $Y_2$ and $Z_2$ represents —$NR_{21}$—, —O—, or —S—;

T represents $CR_{22}R_{23}$, $NR_{24}$, O, or S;

$T_1$ to $T_{13}$ and $W_1$ to $W_{12}$ each independently represent N or $CV_1$;

$R_{11}$ and $Ar_6$ each independently represent a substituted or unsubstituted (C6-C30)aryl, or a substituted or unsubstituted (3- to 30-membered)heteroaryl;

$R_{12}$ to $R_{19}$, $R_{21}$ to $R_{28}$, and $V_1$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30)aliphatic ring(s) and a (C6-C30)aromatic ring(s), or -$L_c$-N($Ar_e$)($Ar_f$); or may be linked to an adjacent substituent to form a substituted or unsubstituted ring(s);

$L_c$ represents a single bond, a substituted or unsubstituted (C6-C30)arylene, or a substituted or unsubstituted (3- to 30-membered)heteroarylene;

$Ar_e$ and $Ar_f$ each independently represent hydrogen, a substituted or unsubstituted (C1-C30)alkyl, a substituted or unsubstituted (C2-C30)alkenyl, a substituted or unsubstituted fused ring group of a (C3-C30)aliphatic ring(s) and a (C6-C30)aromatic ring(s), a substituted or unsubstituted (C6-C30)aryl, or a substituted or unsubstituted (3- to 30-membered)heteroaryl;

b and i represent 1; c, d, j, m, and n each independently represent 1 or 2; e, f, g, f', k, l, and o each independently represent an integer of 1 to 4; g' represents an integer of 1 to 3; in which if c to g, f', g', l, m, n, and o are an integer of 2 or more, each of $R_{12}$ to each of $R_{19}$ and each of $R_{25}$ to each of $R_{28}$ may be the same as or different from each other; and $Ar_2$, $Ar_3$, and $L_1$ to $L_3$ are as defined in formula 2.

According to one embodiment of the present disclosure, $Y_1$, $Y_2$, $Z_1$, and $Z_2$ each independently represent —N═, —O—, or —S—, with the proviso that any one of $Y_1$ and $Z_1$ represents —N═, and the other one of $Y_1$ and $Z_1$ represents —O— or —S—, and with the proviso that any one of $Y_2$ and $Z_2$ represents —N═, and the other one of $Y_2$ and $Z_2$ represents —O—.

According to one embodiment of the present disclosure, T represents $CR_{22}R_{23}$, $NR_{24}$, O, or S.

According to one embodiment of the present disclosure, $T_1$ to $T_{13}$ and $W_1$ to $W_{12}$ each independently represent $CV_1$.

According to one embodiment of the present disclosure, $R_{11}$ represents a substituted or unsubstituted (C6-C30)aryl, or an unsubstituted (5- to 25-membered)heteroaryl. For example, $R_{11}$ may be a phenyl unsubstituted or substituted with deuterium, a naphthyl, a biphenyl, a pyridyl, etc.

According to one embodiment of the present disclosure, $Ar_6$ represents an unsubstituted (C6-C30)aryl, for example, may be a phenyl, etc.

According to one embodiment of the present disclosure, $R_{12}$ to $R_{14}$ each independently represent hydrogen, deuterium, or an unsubstituted (C6-C30)aryl; or may be linked to an adjacent substituent to form a ring(s). For example, $R_{12}$ to $R_{14}$ may each independently be hydrogen, deuterium, or a phenyl; or may be linked to an adjacent substituent to form a benzene, etc.

According to one embodiment of the present disclosure, $R_{15}$ and $R_{16}$ each independently represent hydrogen or deuterium; or may be linked to an adjacent substituent to form a substituted or unsubstituted ring(s). For example, $R_{15}$ and $R_{16}$ may each independently be hydrogen or deuterium; or may be linked to an adjacent substituent to form a fused, dimethyl-substituted cyclopentane, a benzene, etc.

According to one embodiment of the present disclosure, $R_{17}$ to $R_{19}$ each independently represent hydrogen or an unsubstituted (C6-C30)aryl. For example, $R_{17}$ to $R_{1g}$ may each independently be hydrogen, a phenyl, etc.

According to one embodiment of the present disclosure, $R_{22}$ and $R_{23}$ each independently represent an unsubstituted (C1-C30)alkyl or an unsubstituted (C6-C30)aryl; or may be linked to an adjacent substituent to form a substituted or unsubstituted ring(s). For example, $R_{22}$ and $R_{23}$ may each independently be a methyl or a phenyl; or may be linked to an adjacent substituent to form a cyclopentane, fluorene, etc.

According to one embodiment of the present disclosure, $R_{24}$ represents an unsubstituted (C6-C30)aryl. For example, $R_{24}$ may be a phenyl.

According to one embodiment of the present disclosure, $R_{25}$ to $R_{28}$ represent hydrogen.

According to one embodiment of the present disclosure, $V_1$ represents hydrogen or an unsubstituted (C6-C30)aryl; or may be linked to an adjacent substituent to form a substituted or unsubstituted ring(s). For example, $V_1$ may be hydrogen or a phenyl; or may be linked to an adjacent substituent to form a substituted or unsubstituted ring(s) which may be cyclopentane, fluorene, etc.

The compound represented by formula 1 may be at least one selected from the following compounds, but is not limited thereto.

-continued
H1-1
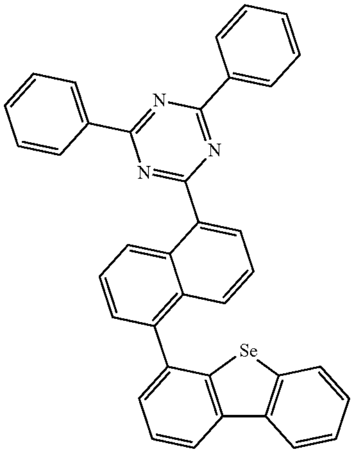
H1-2
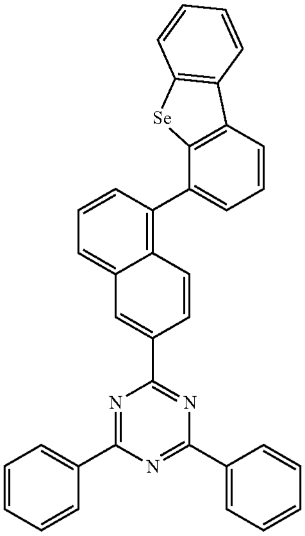
H1-3
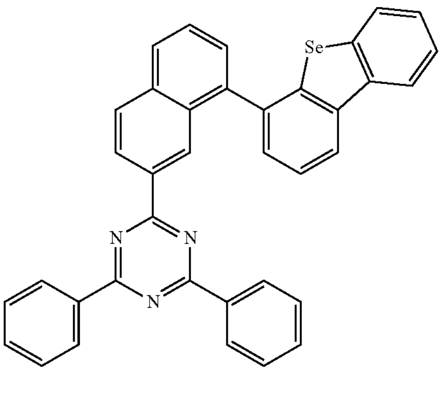
H1-4
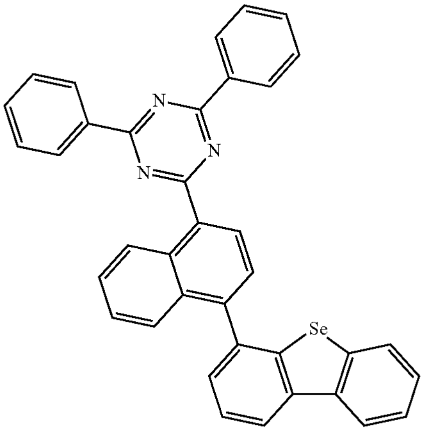
H1-5
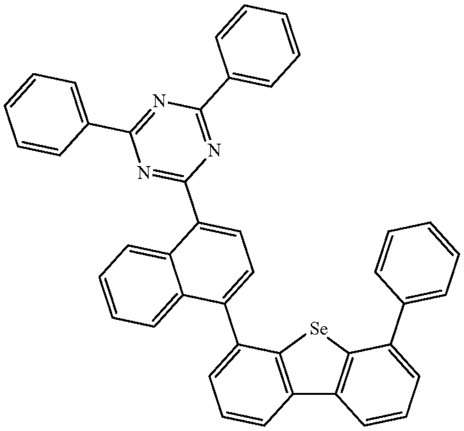
H1-6
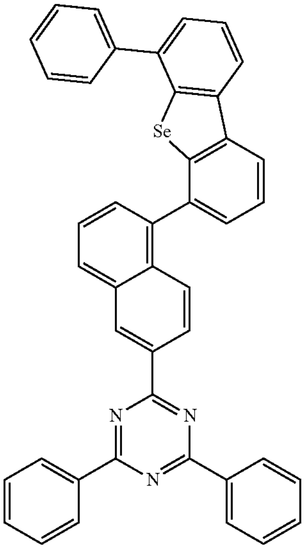

-continued
H1-7
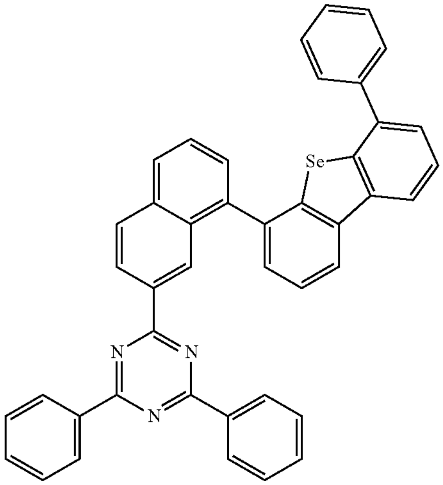
H1-8
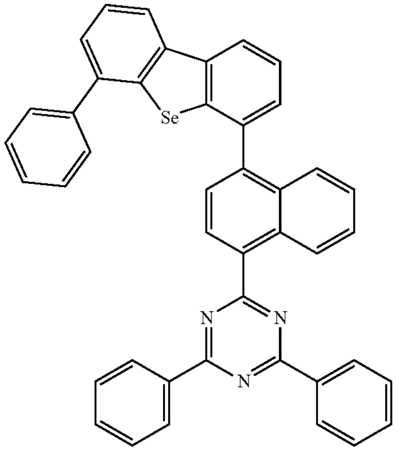
H1-9
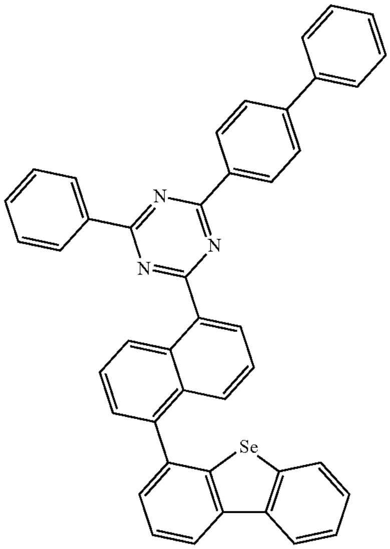
-continued
H1-10
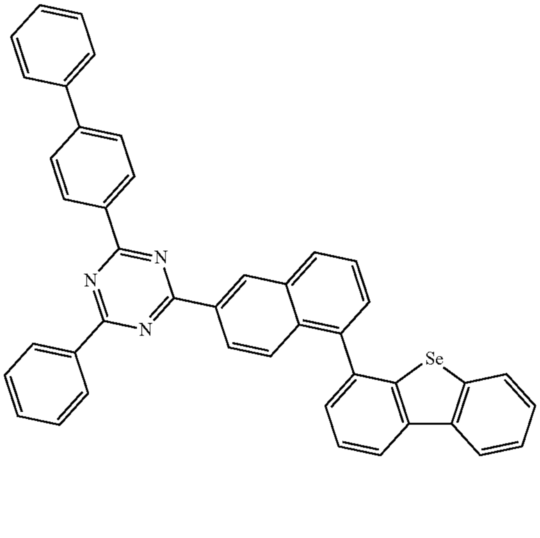
H1-11
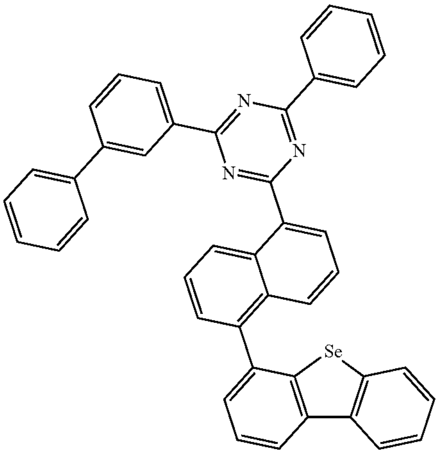
H1-12
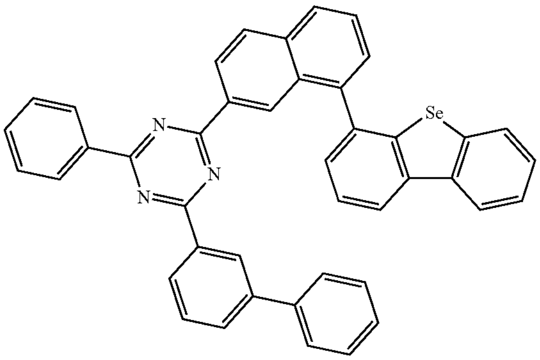

-continued
H1-13
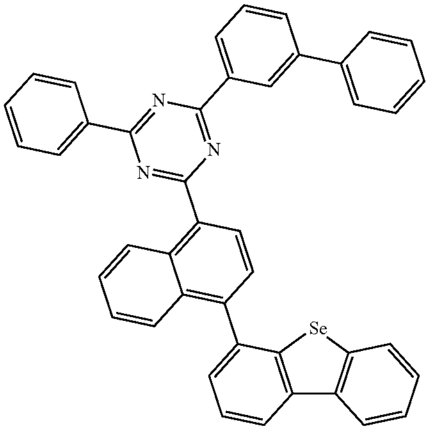
H1-14
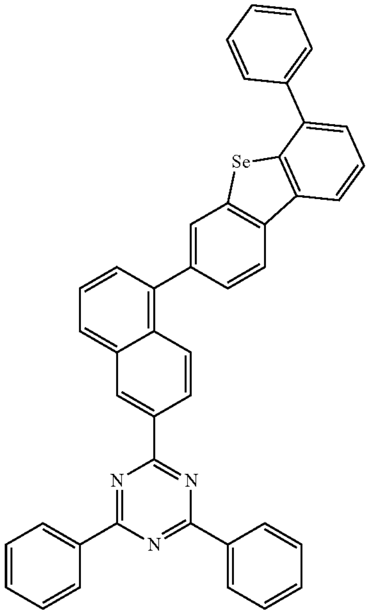
H1-15
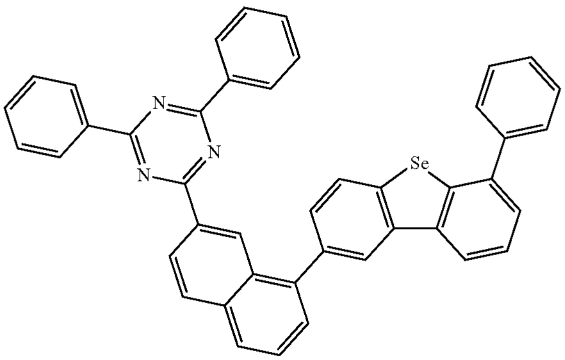
-continued
H1-16
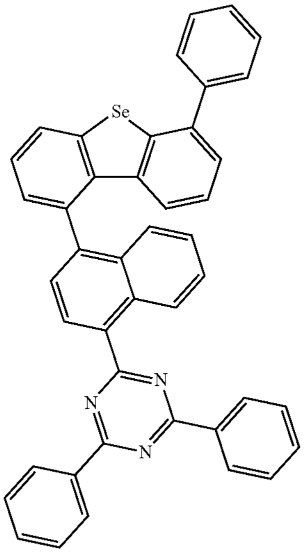
H1-17
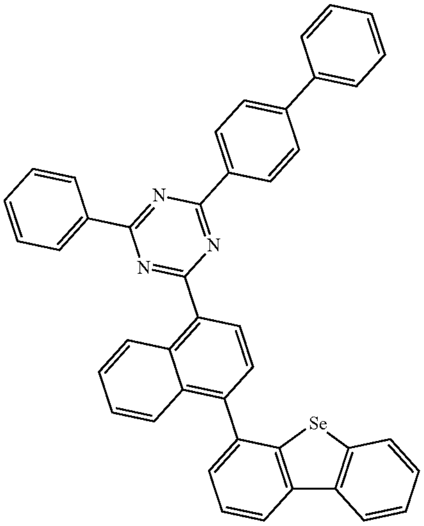
H1-18
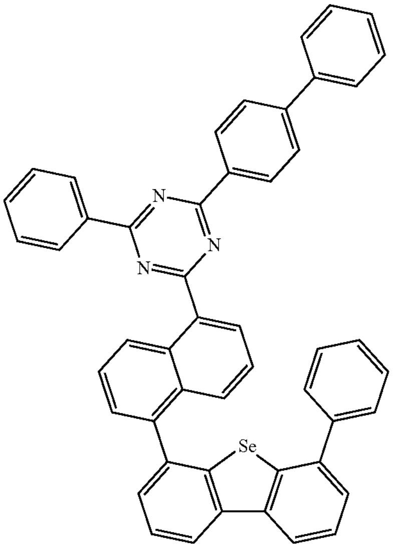

-continued
H1-19
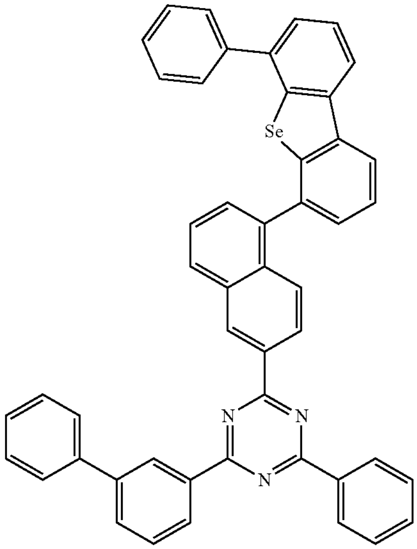
H1-20
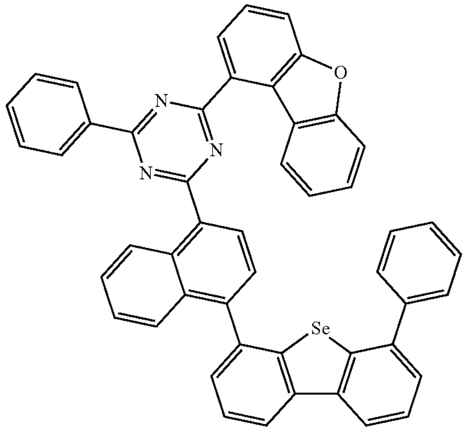
H1-21
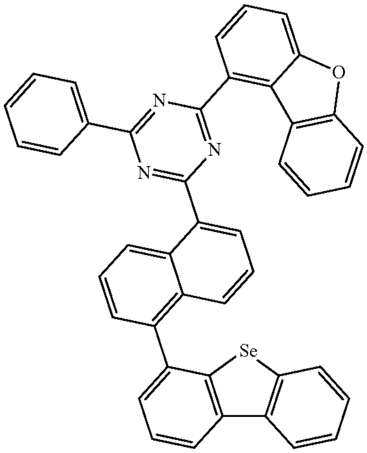
-continued
H1-22
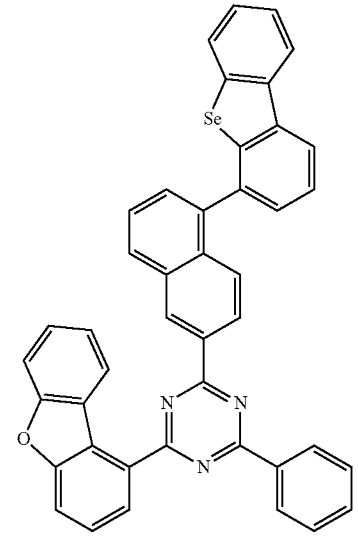
H1-23
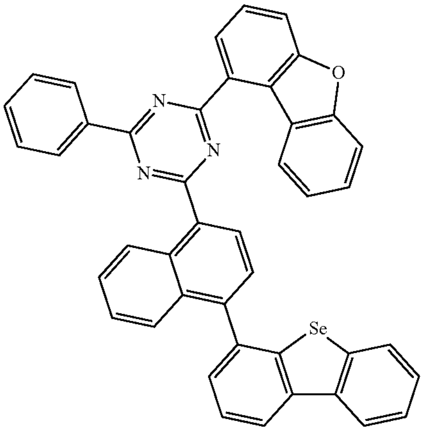
H1-24
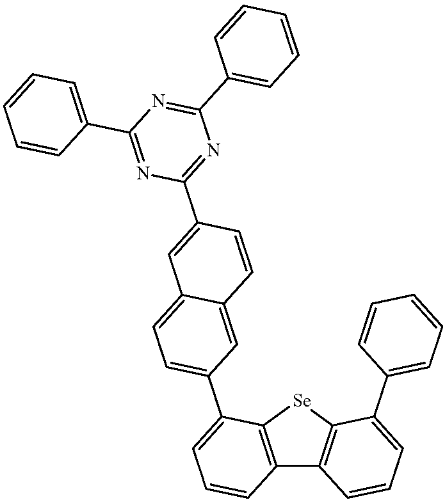

-continued
H1-25
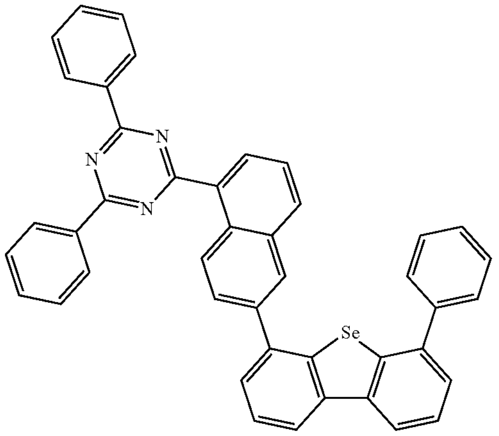
H1-26
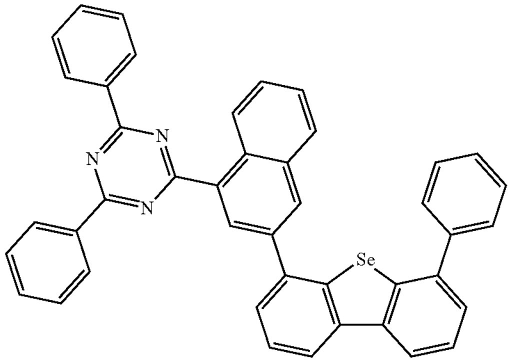
H1-27
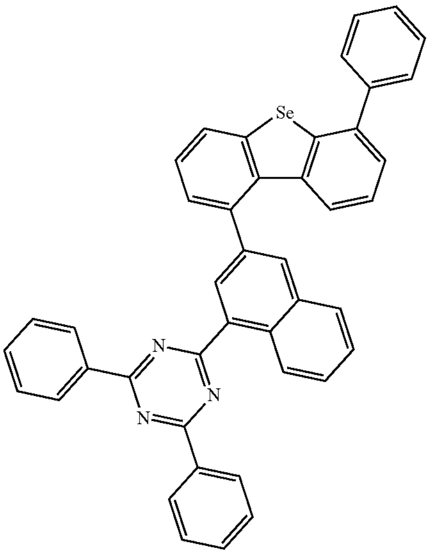
-continued
H1-28
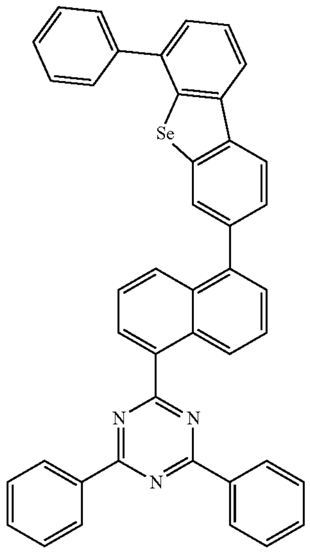
H1-29
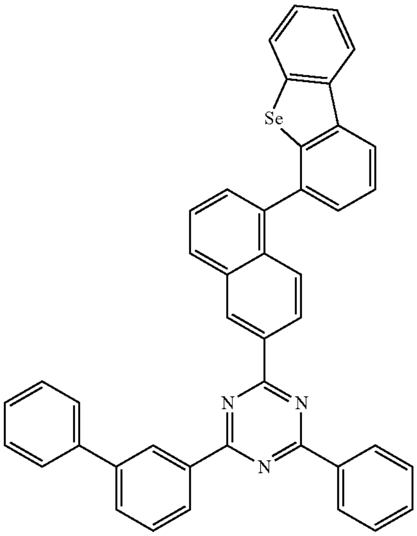
H1-30
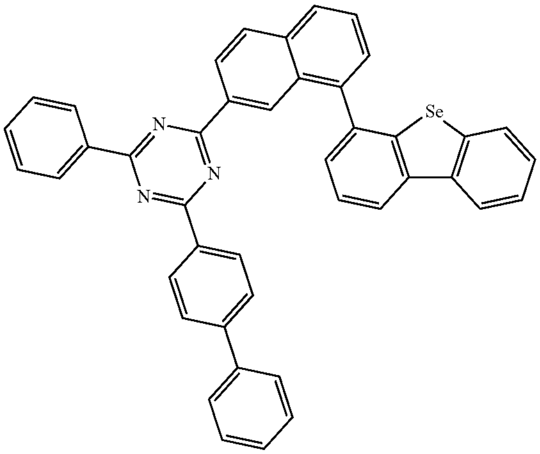

-continued
H1-31
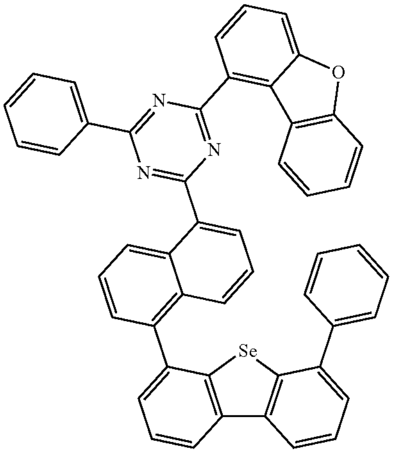
H1-32
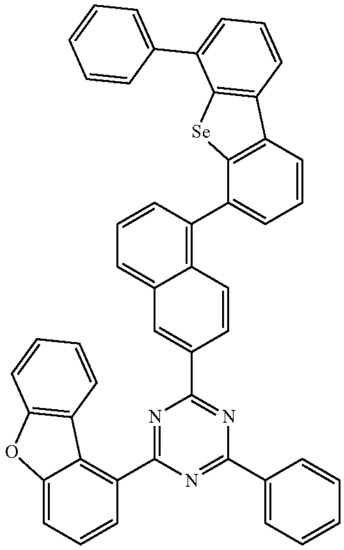
H1-33
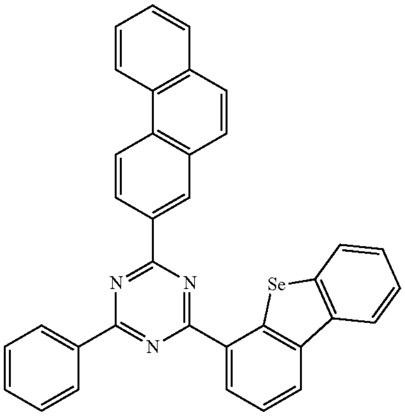
-continued
H1-34
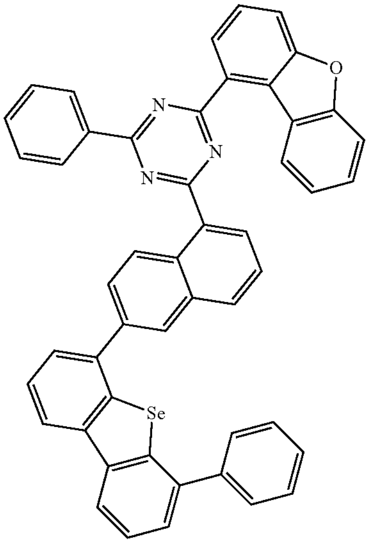
H1-35
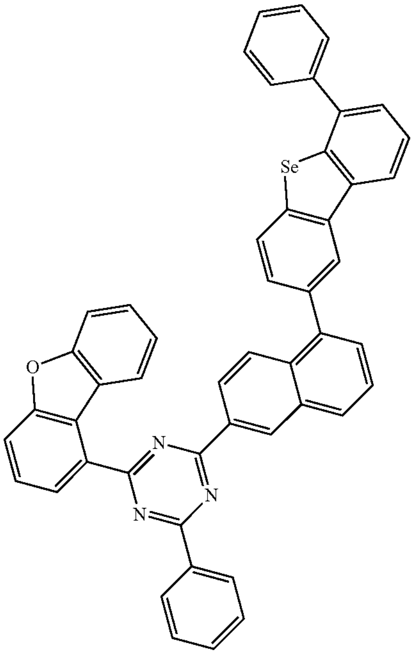
H1-36
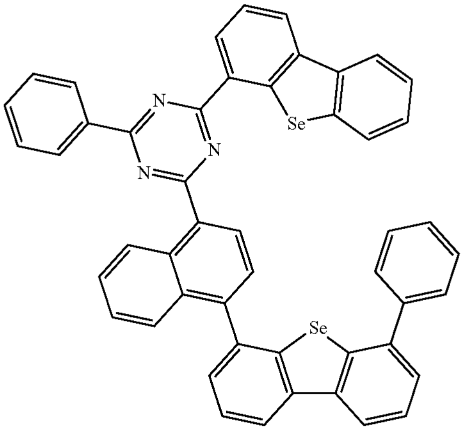

-continued
H1-37
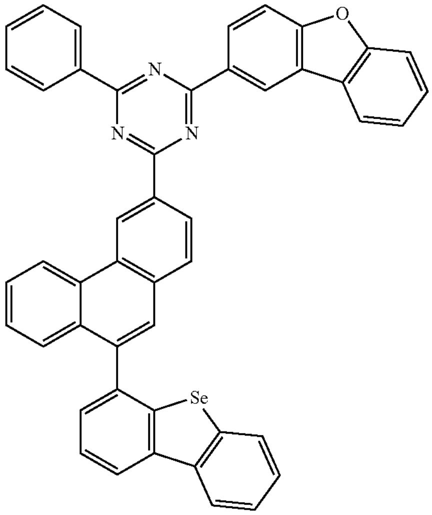
H1-38
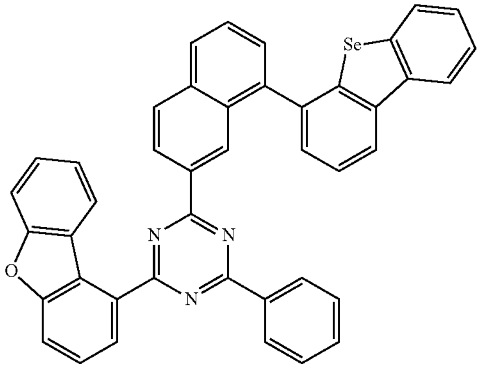
H1-39
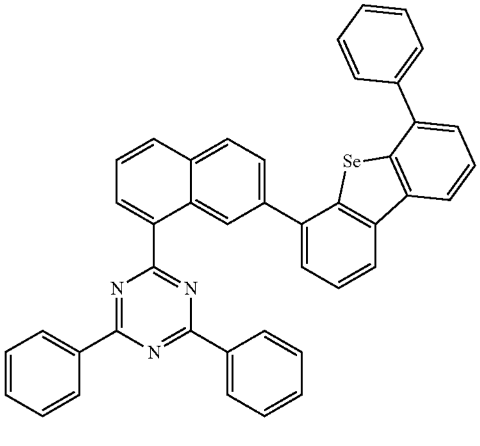
-continued
H1-40
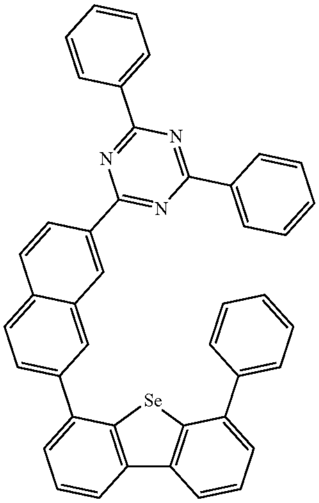
H1-41
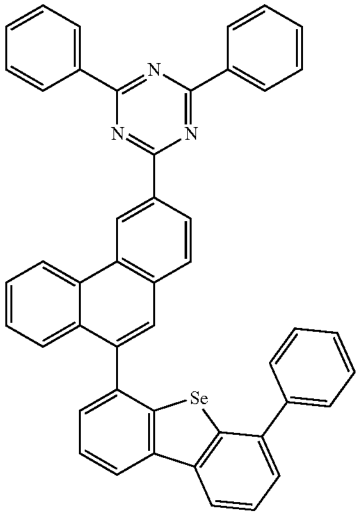
H1-42
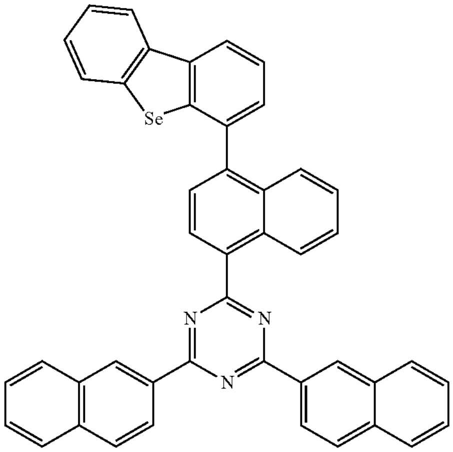

-continued
H1-43
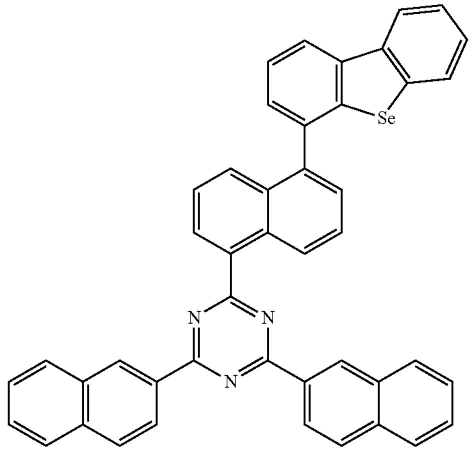
H1-44
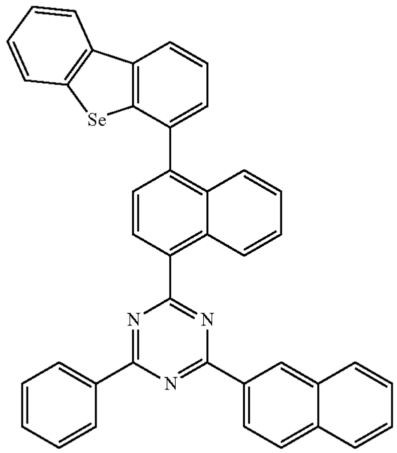
H1-45
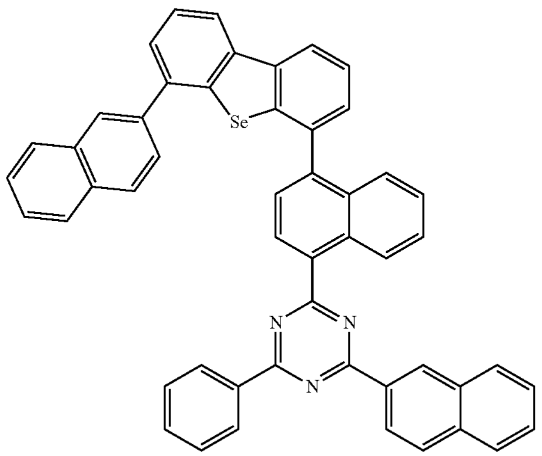
-continued
H1-46
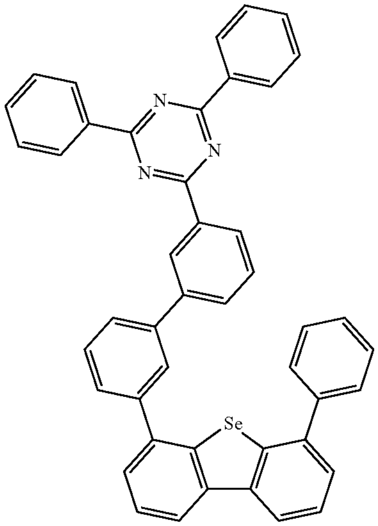
H1-47
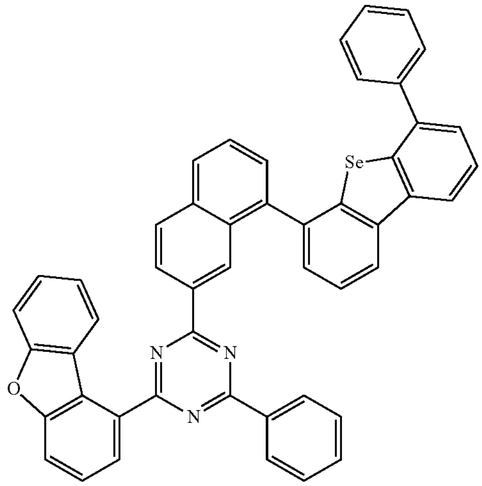
H1-48
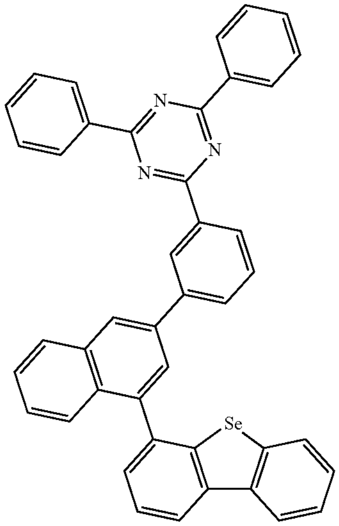

-continued
H1-49
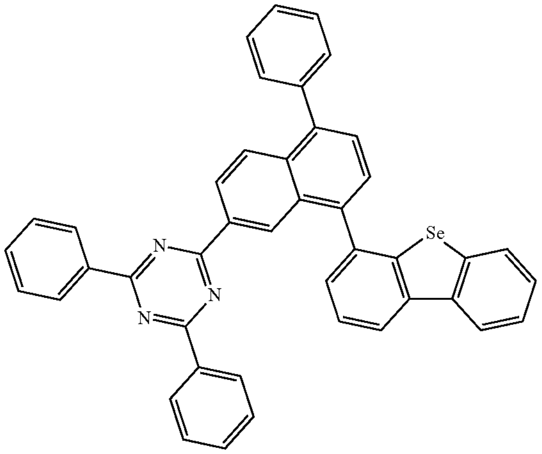
H1-50
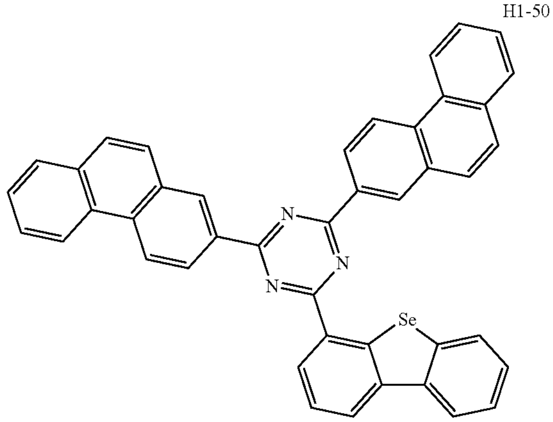
H1-51
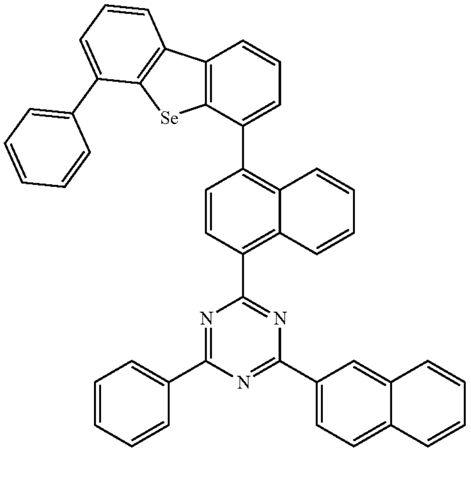
-continued
H1-52
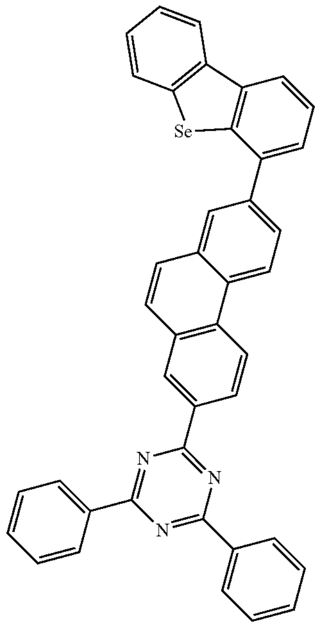
H1-53
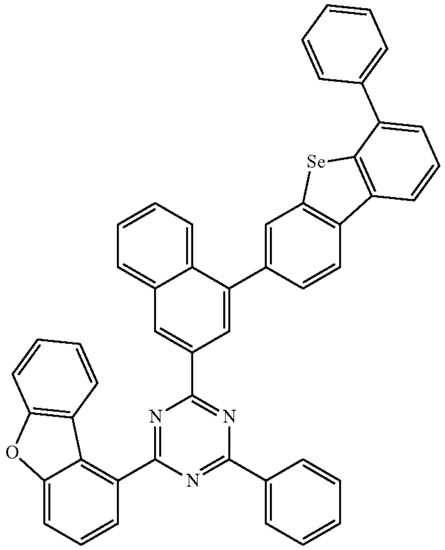
H1-54
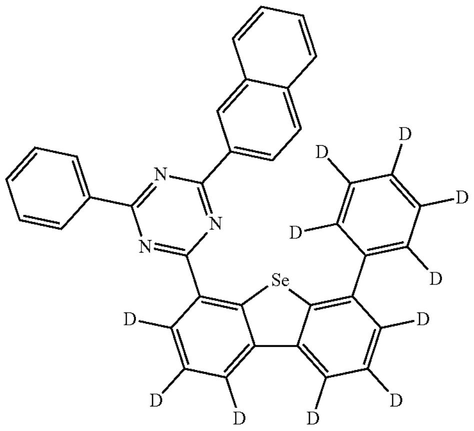

-continued
H1-55
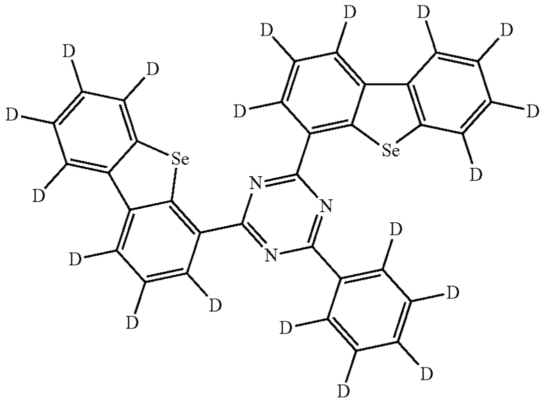
H1-56
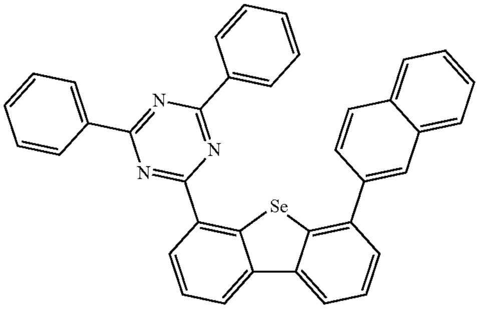
H1-57
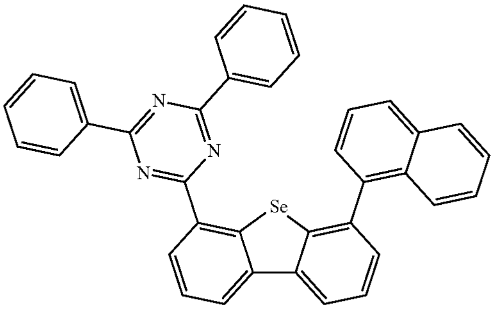
H1-58
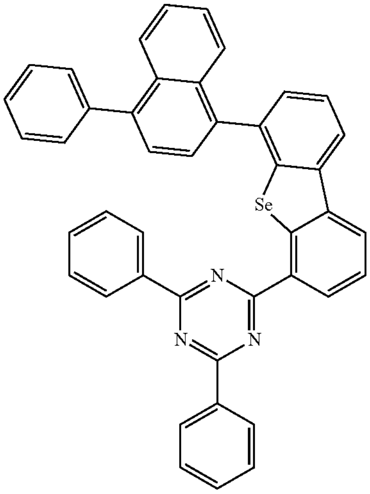
-continued
H1-59
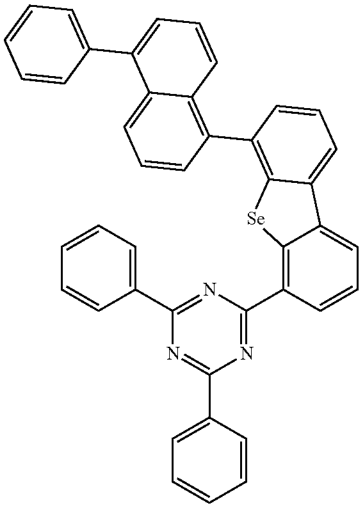
H1-60
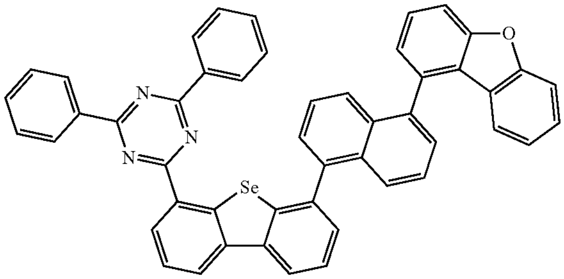
H1-61
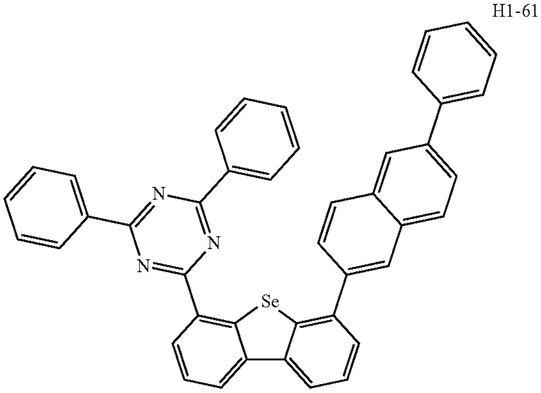
H1-62
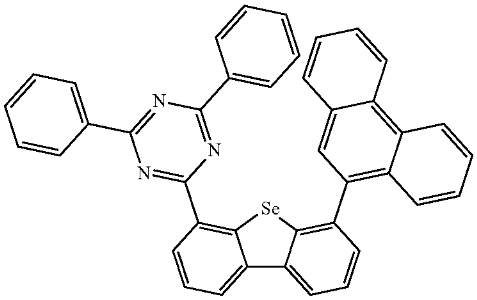

-continued
H1-63
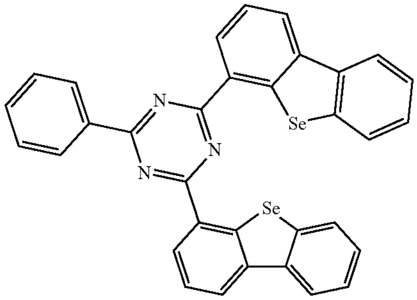
H1-64
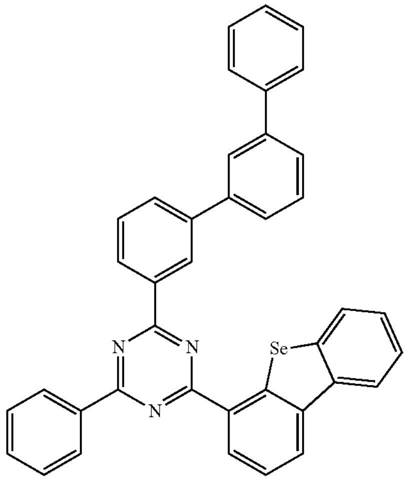
H1-65
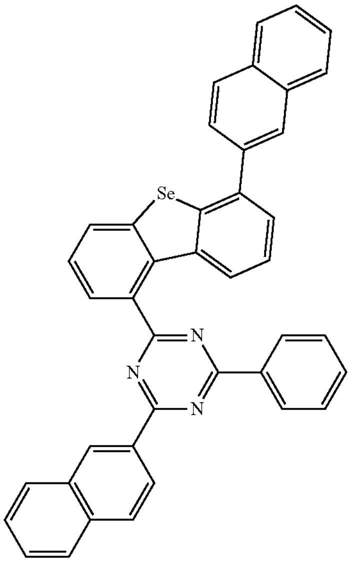
-continued
H1-66
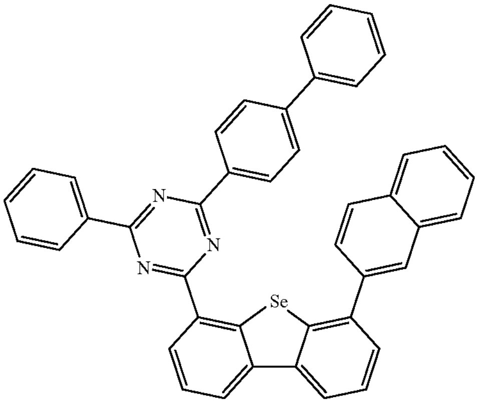
H1-67
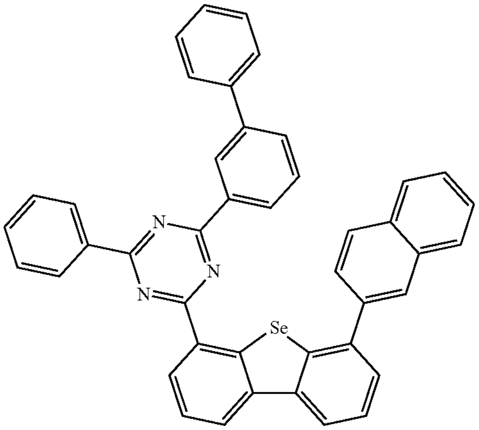
H1-68
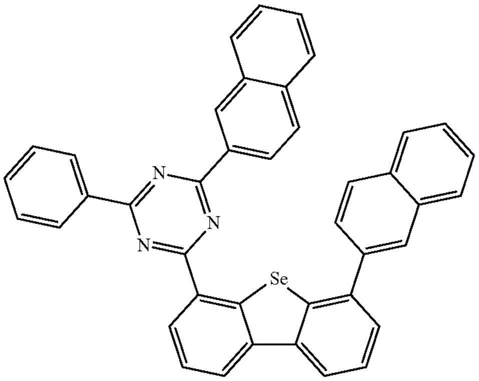

-continued
H1-69
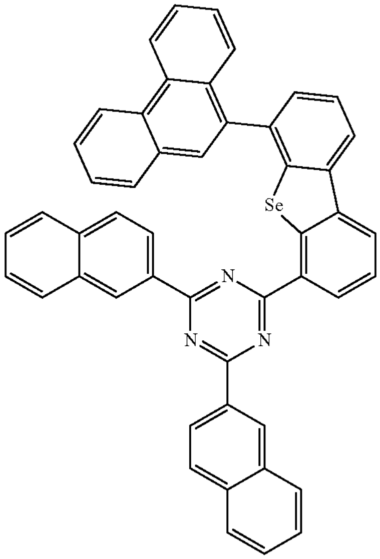
H1-70
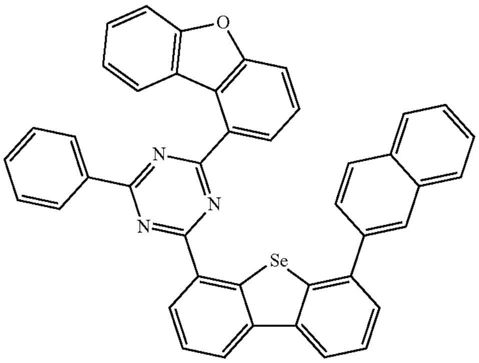
H1-71
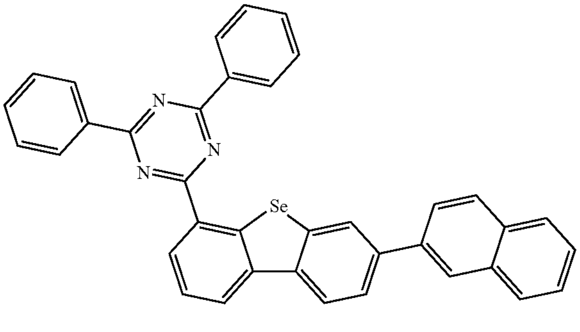
-continued
H1-72
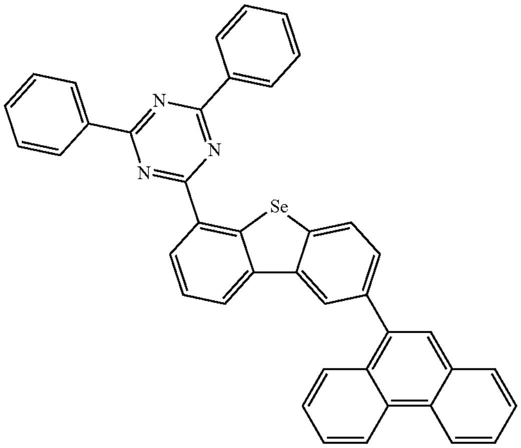
H1-73
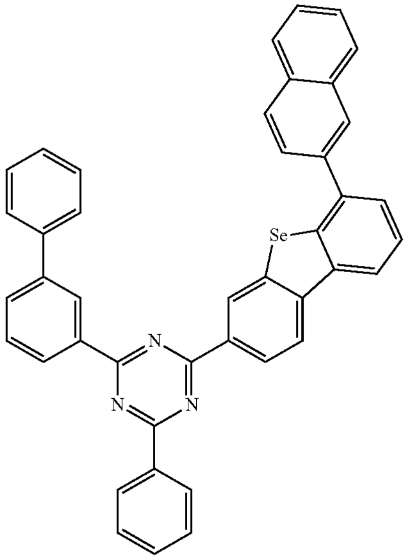
H1-74
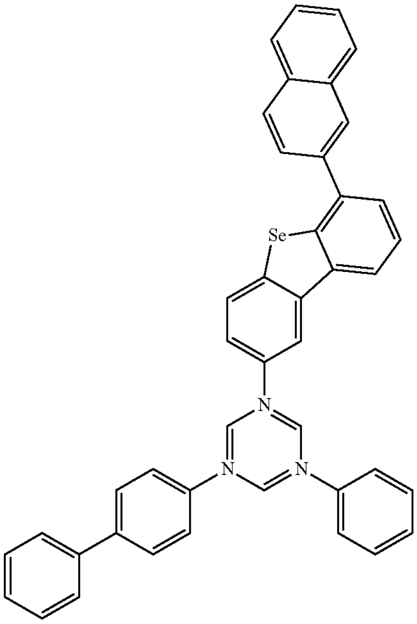

H1-75
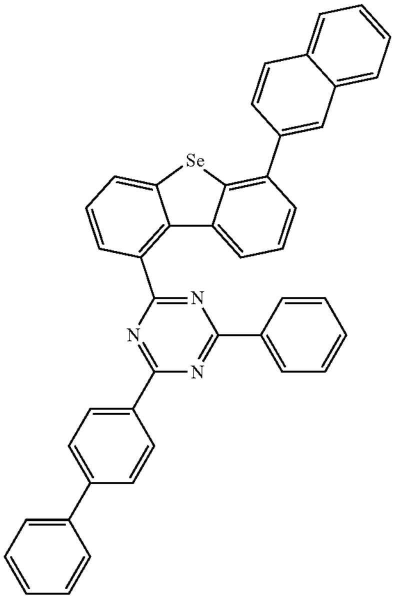
HI-76
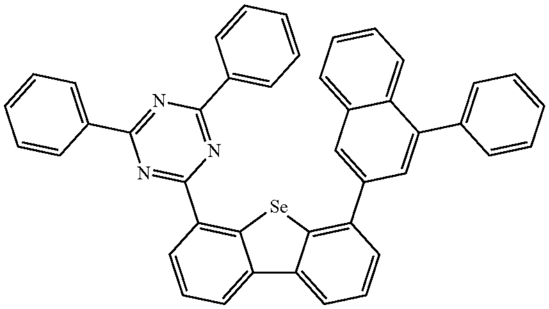
H1-77
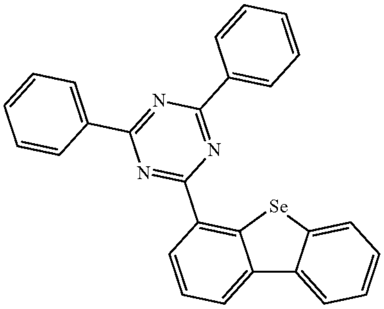
H1-78
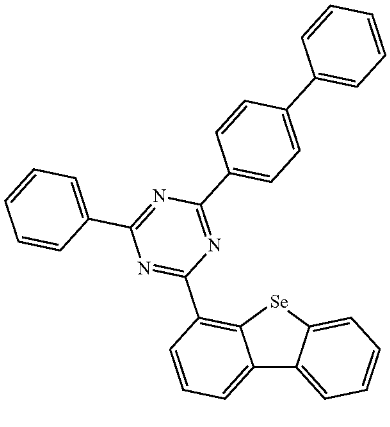
H1-79
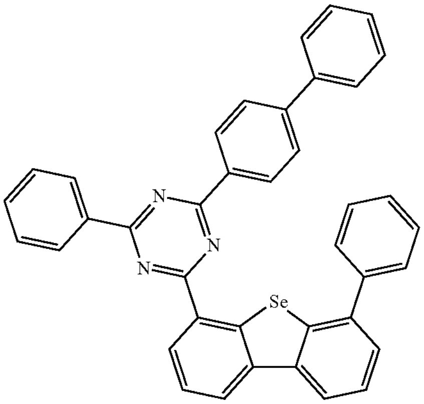
H1-80
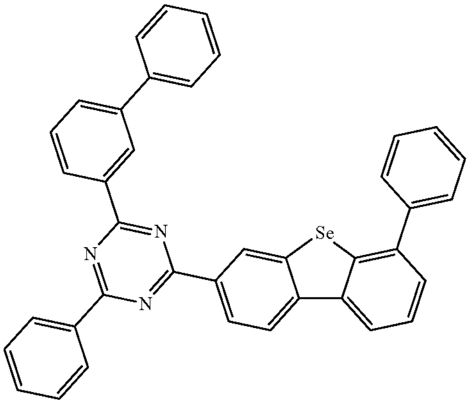
H1-81
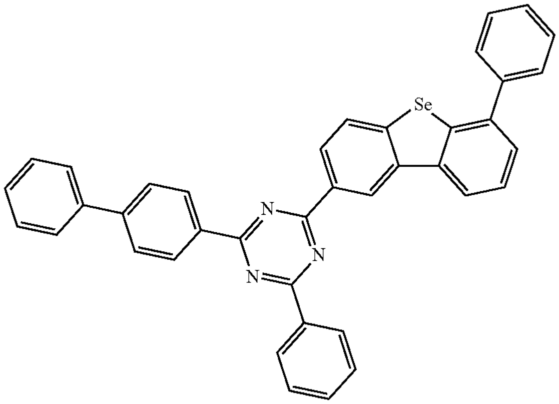

-continued
H1-82
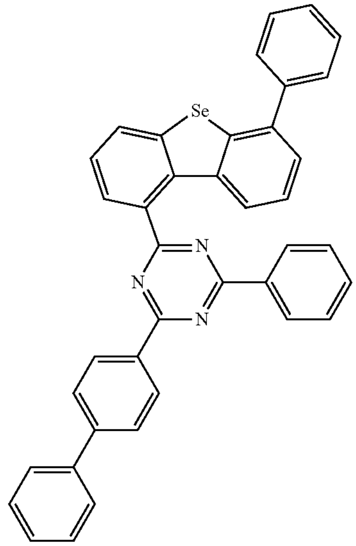
H1-83
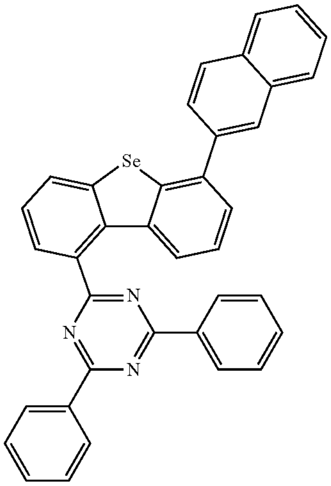
-continued
H1-84
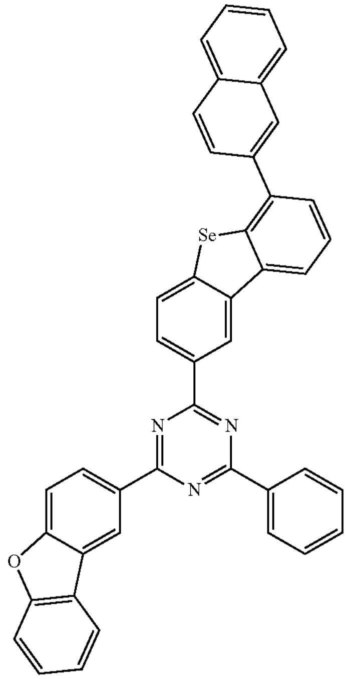
H1-85
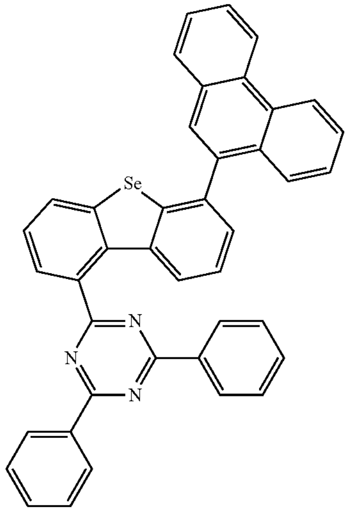
H1-86
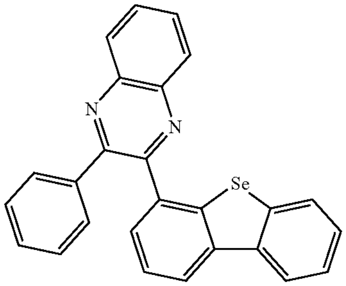

-continued
H1-87
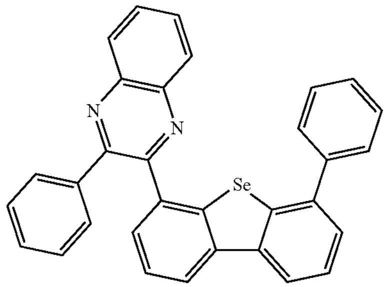
H1-88
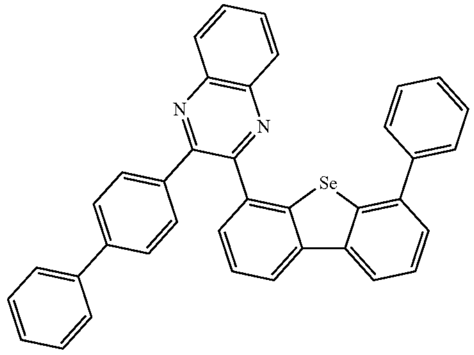
H1-89
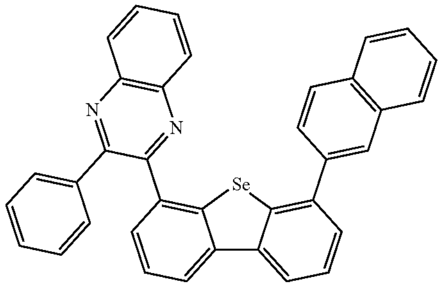
H1-90
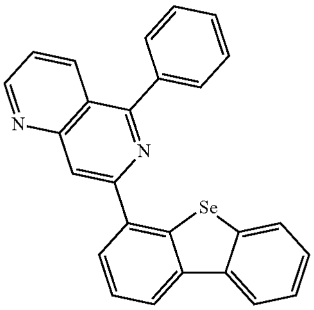
-continued
H1-91
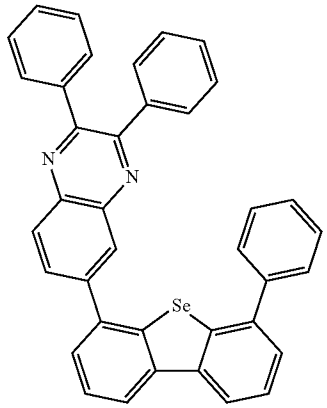
H1-92
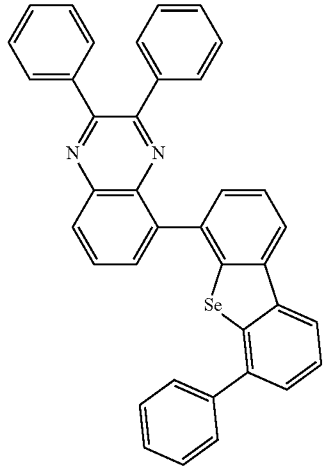
H1-93
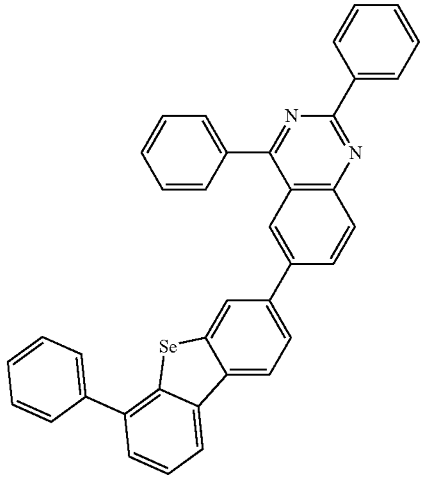

-continued
H1-94
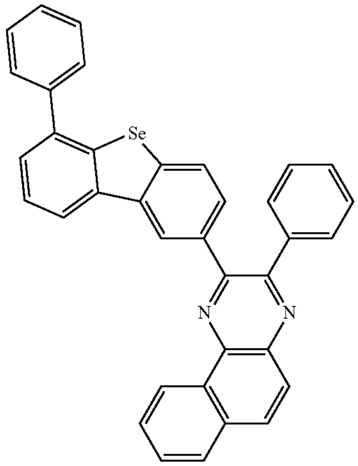
H1-95
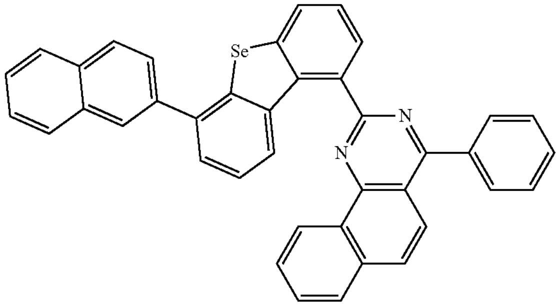
H1-96
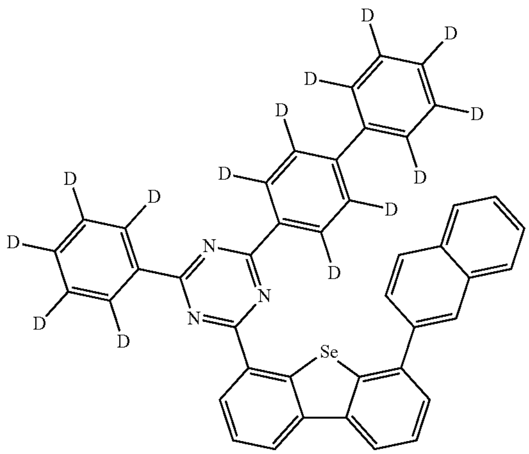
-continued
H1-97
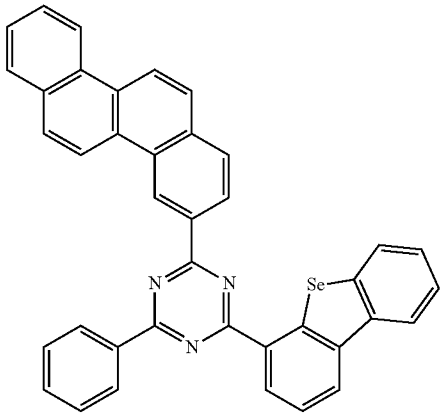
H1-98
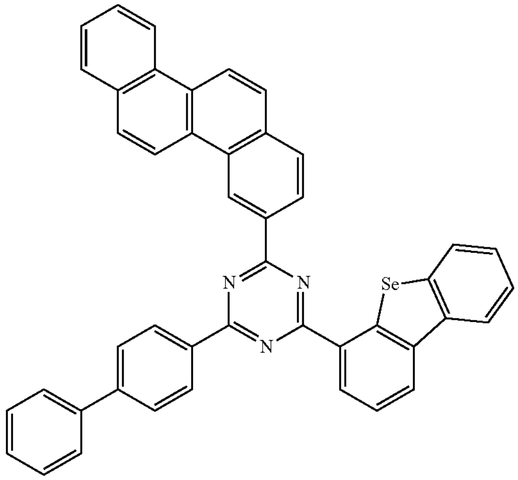
H1-99
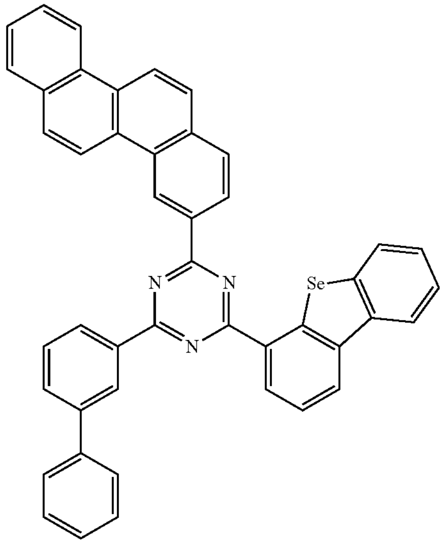

-continued
H1-100
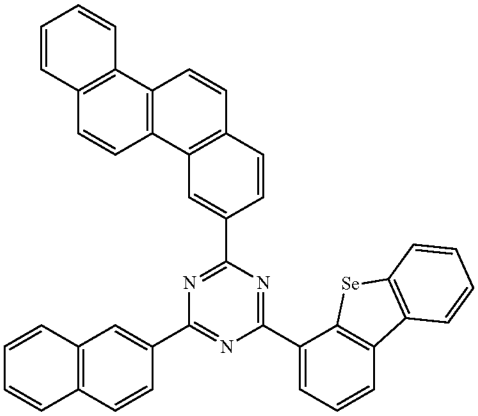
H1-101
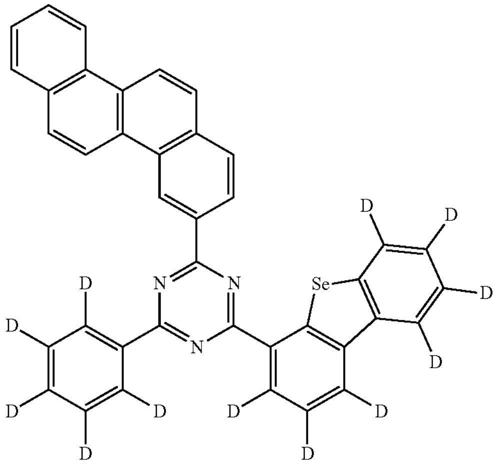
H1-102
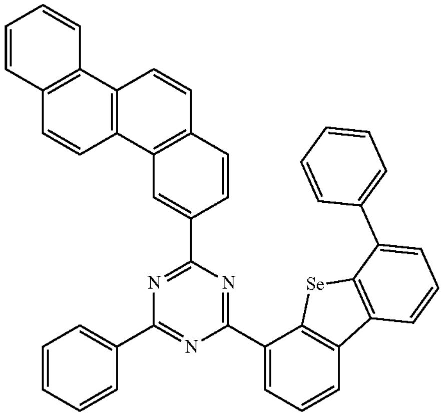
-continued
H1-103
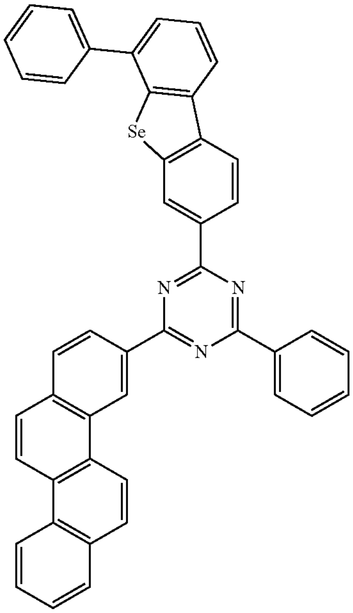
H1-104
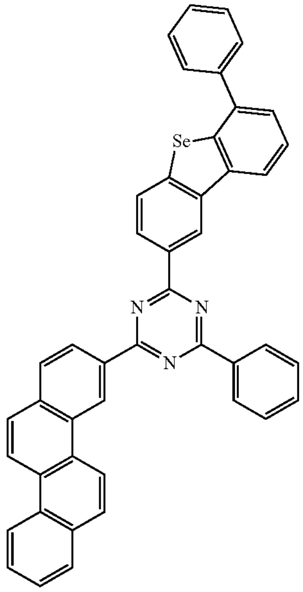

H1-105
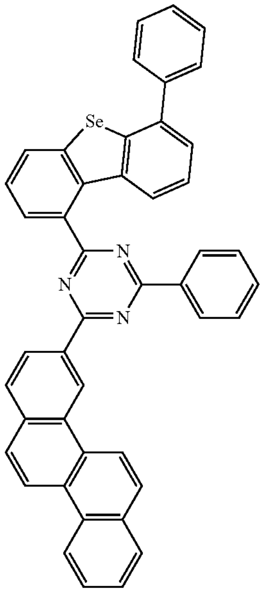
H1-106
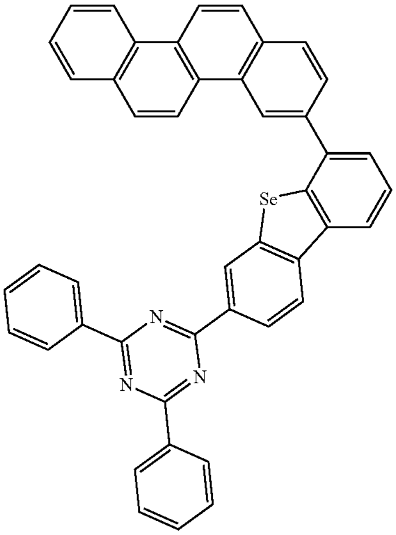
H1-107
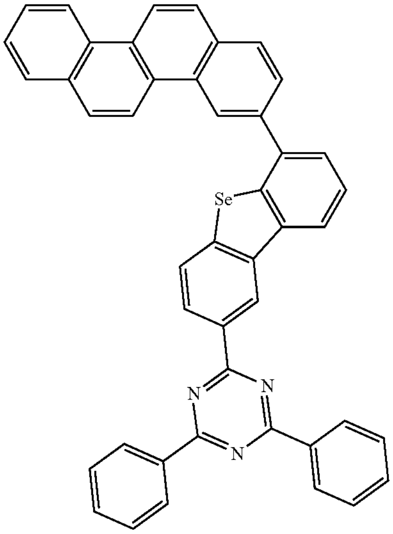
H1-108
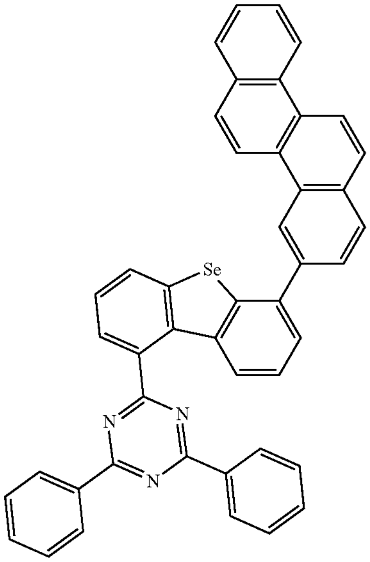
H1-109
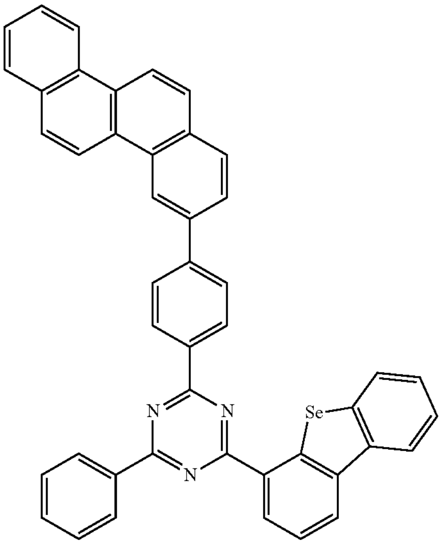
H1-110
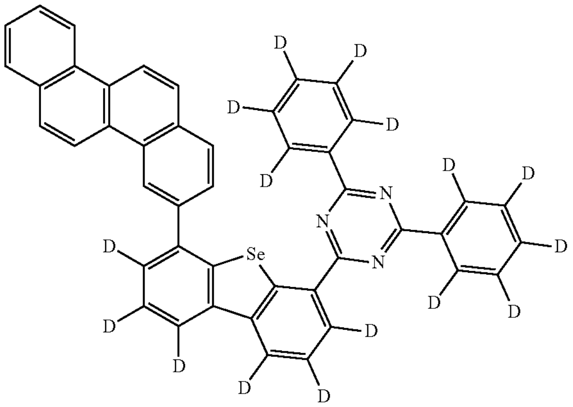

-continued
H1-111
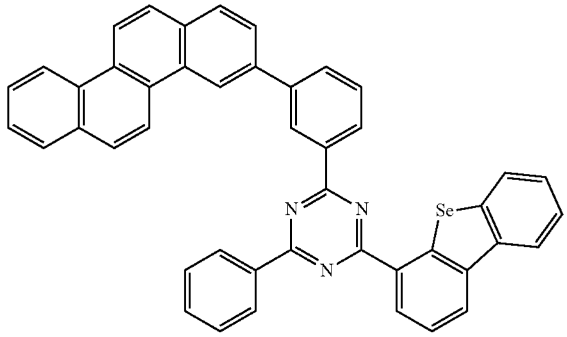
H1-112
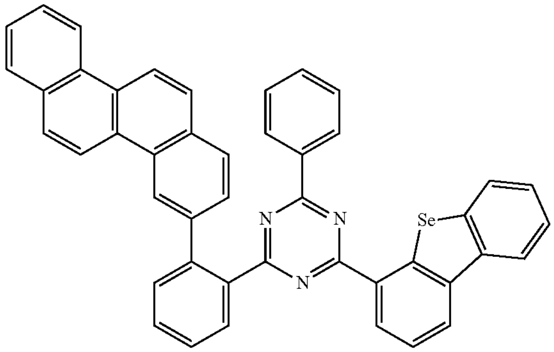
H1-113
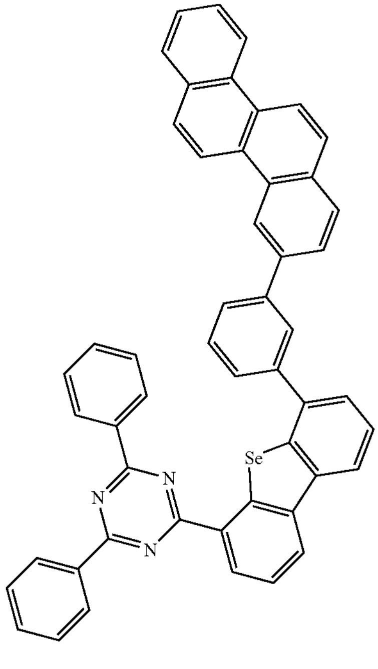
-continued
H1-114
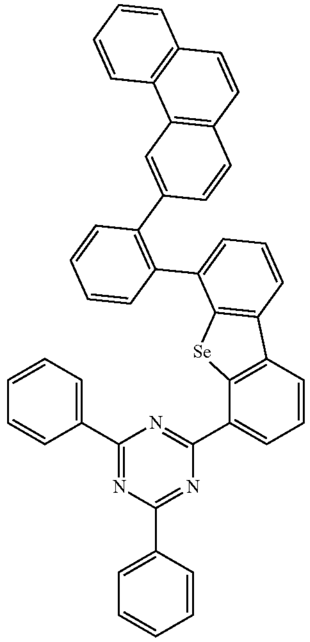
H1-115
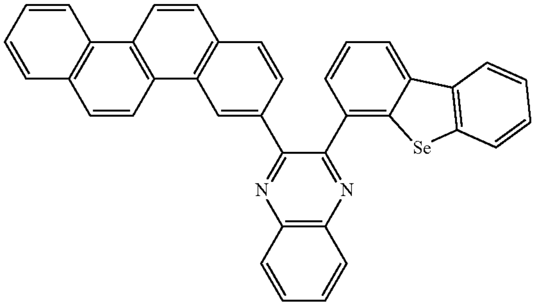
H1-116
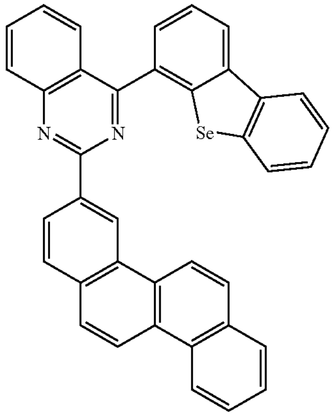

-continued
H1-117
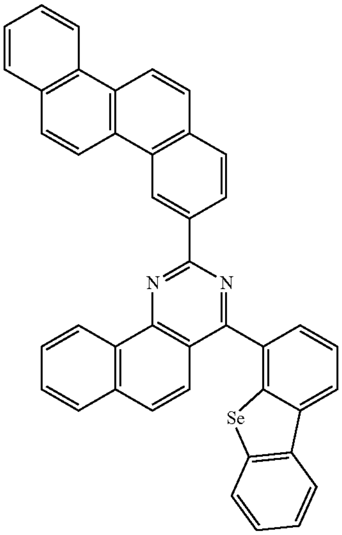
H1-118
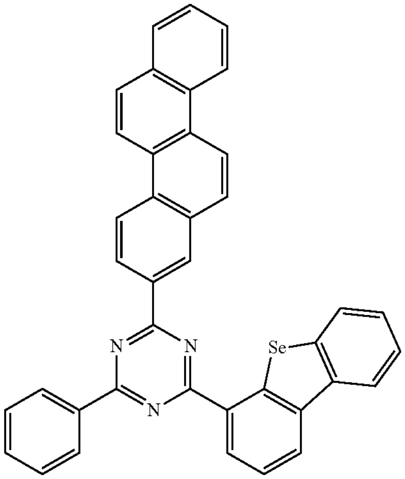
H1-119
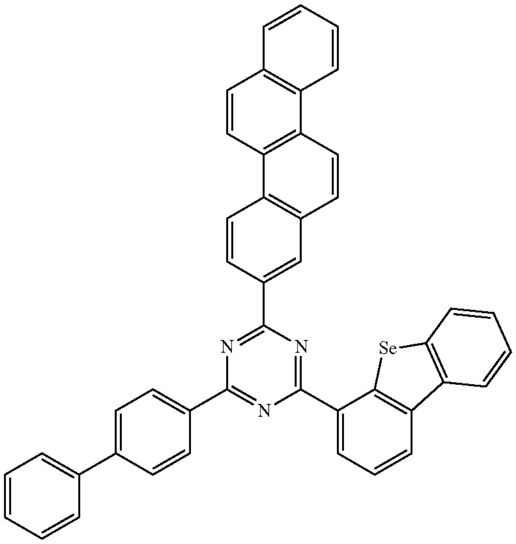
-continued
H1-120
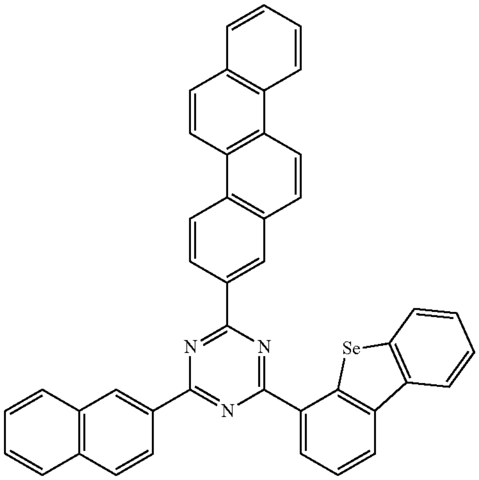
H1-121
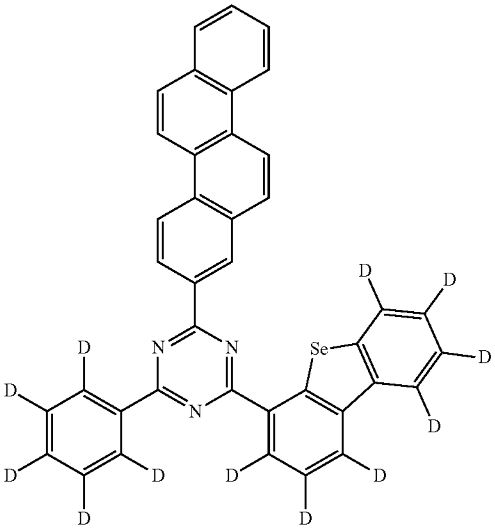
H1-122
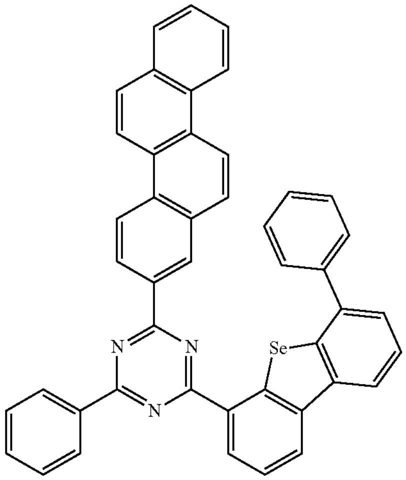

-continued
H1-123
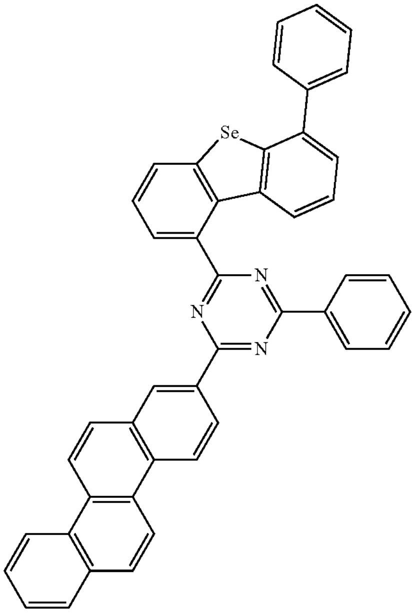
H1-124
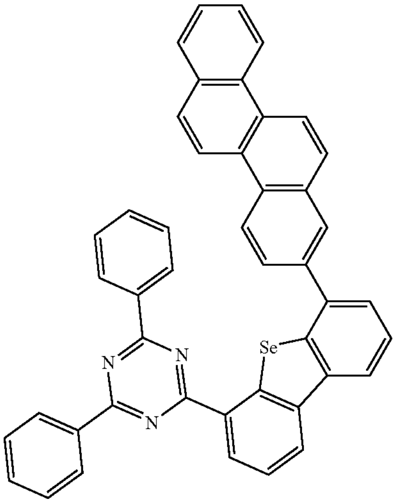
-continued
H1-125
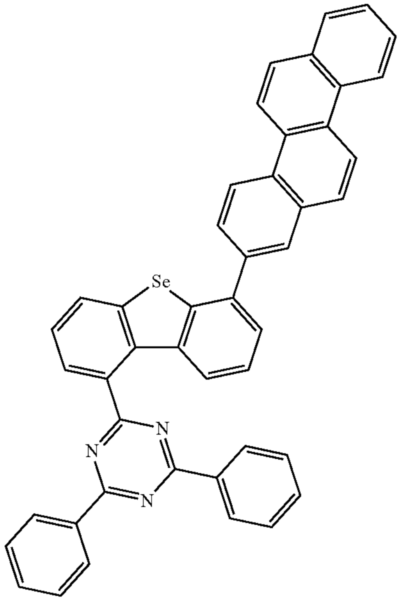
H1-126
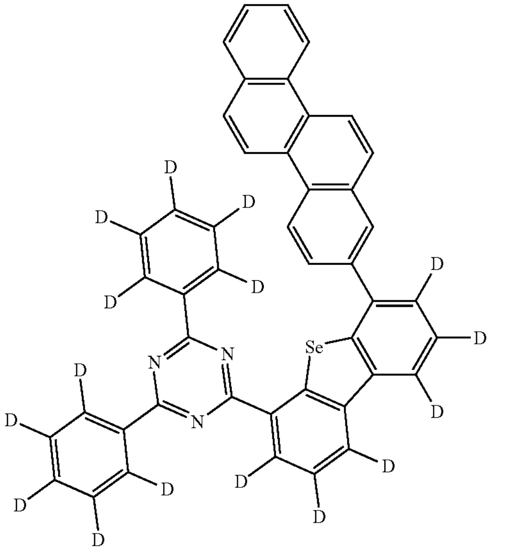

-continued
H1-127
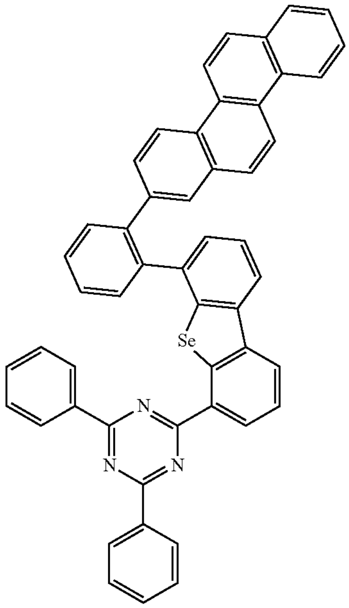
H1-128
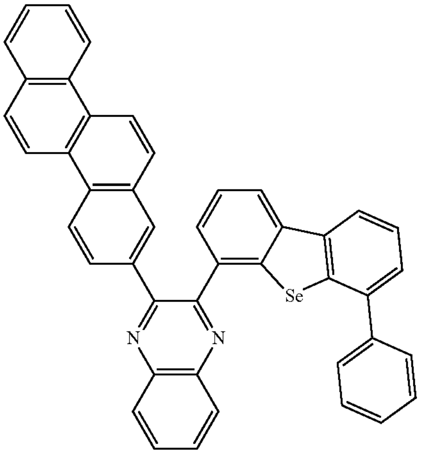
H1-129
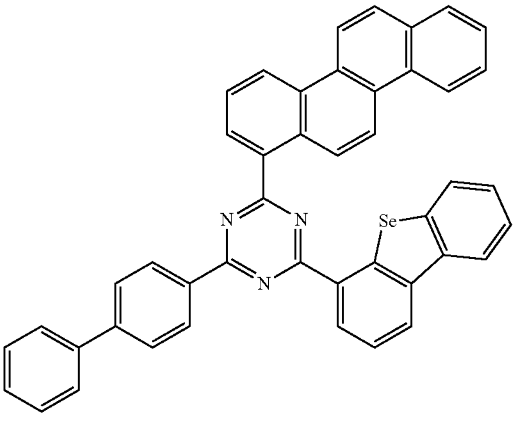
-continued
H1-130
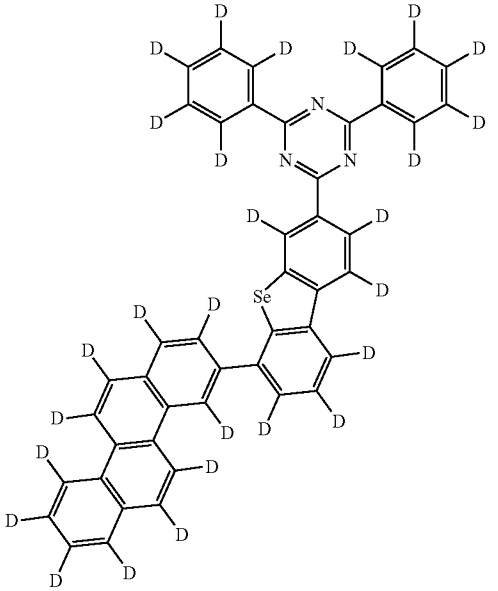
H1-131
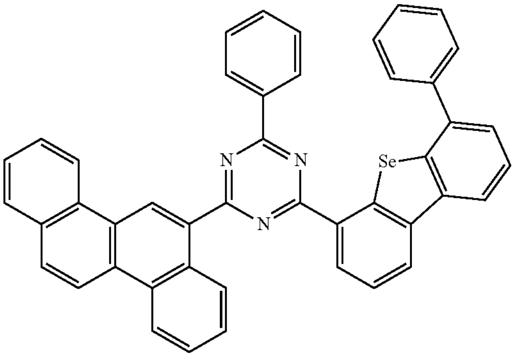
H1-132
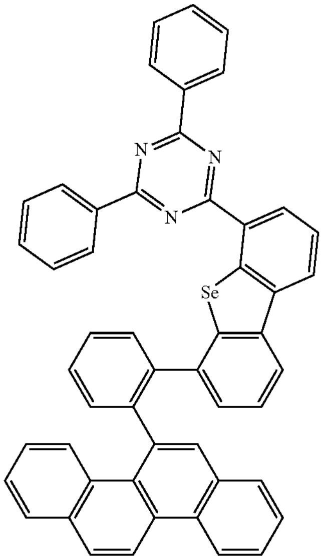

-continued
H1-133
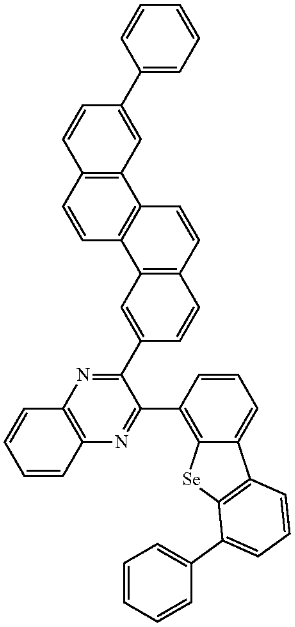
H1-134
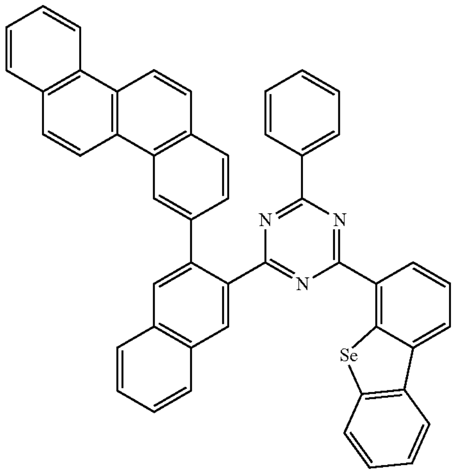
H1-135
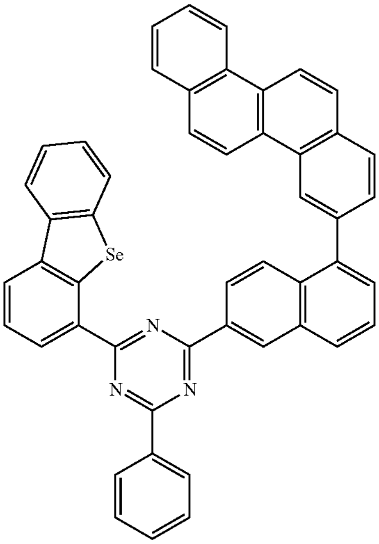
-continued
H1-136
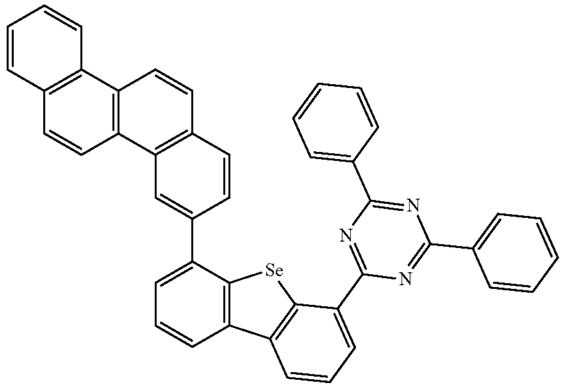
H1-137
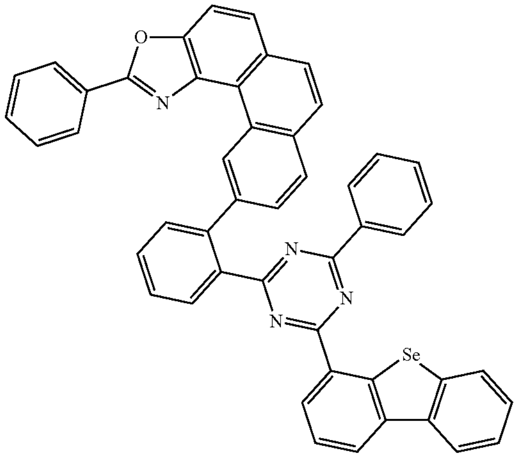
H1-138
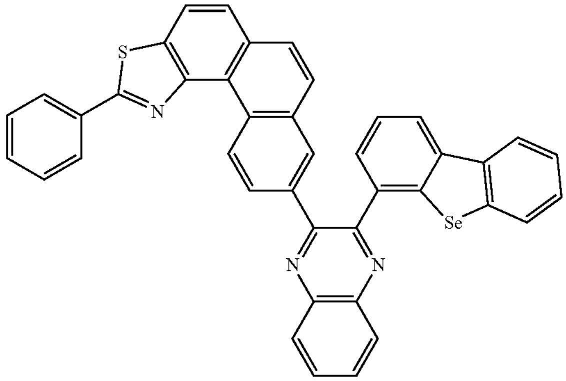

-continued
H1-139
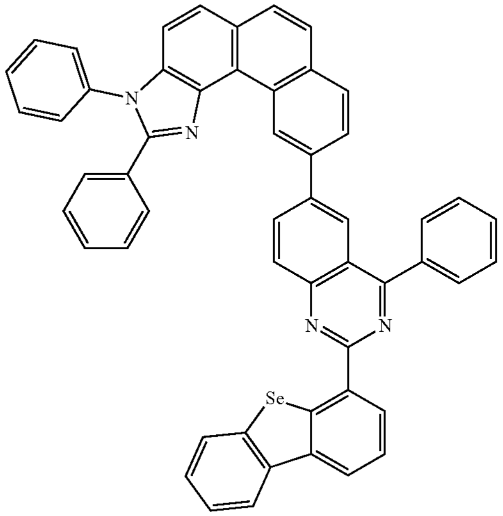
H1-140
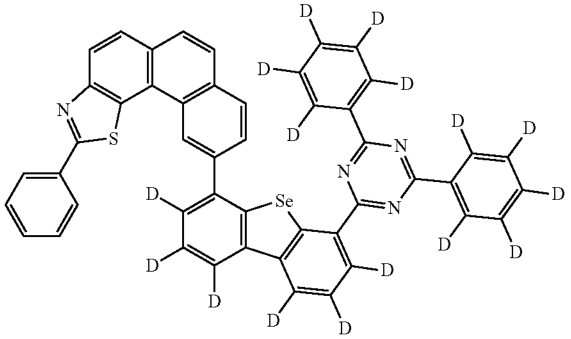
H1-141
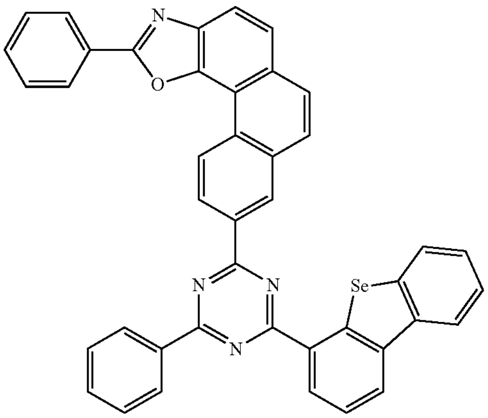
-continued
H1-142
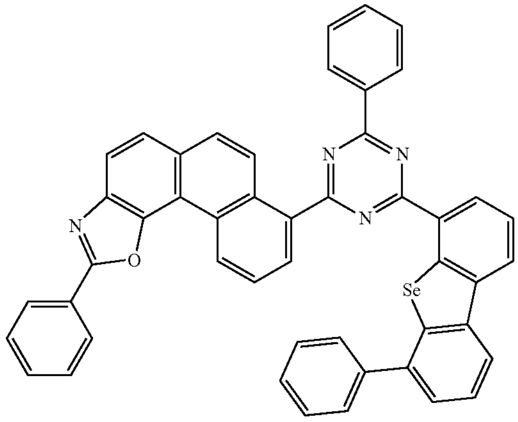
H1-143
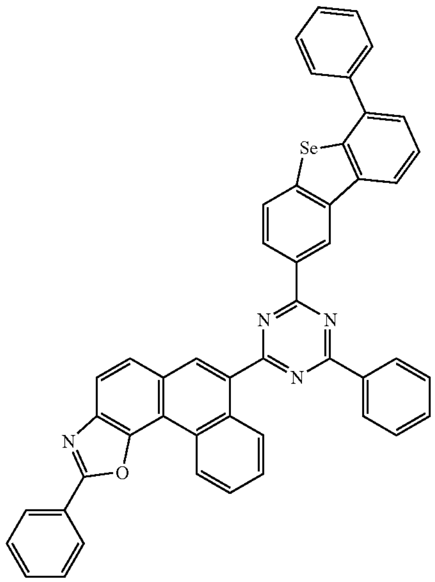
H1-144
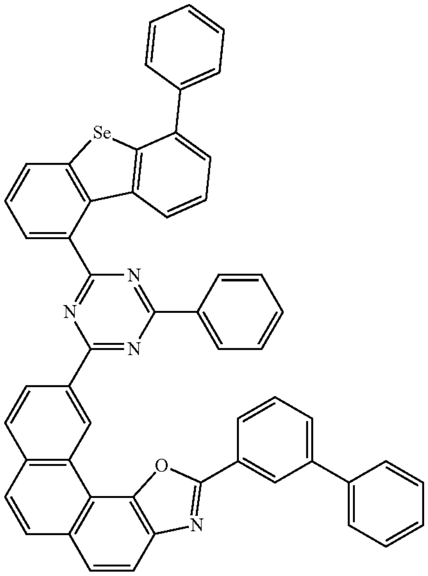

-continued
H1-145
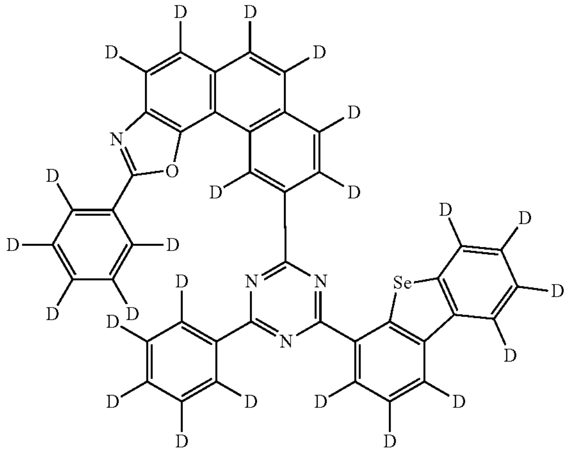
H1-146
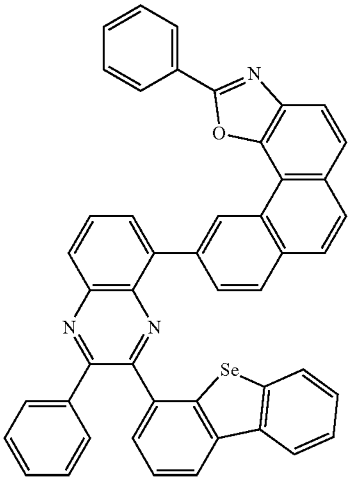
H1-147
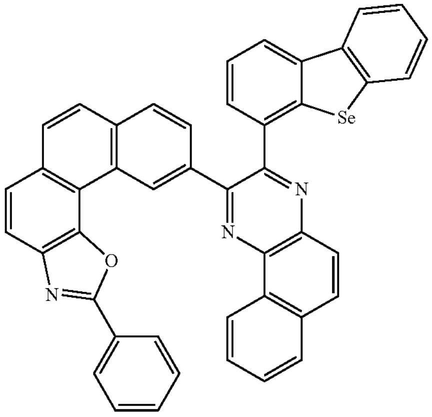
-continued
H1-148
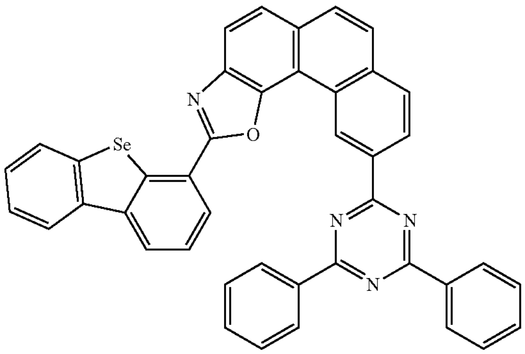
H1-149
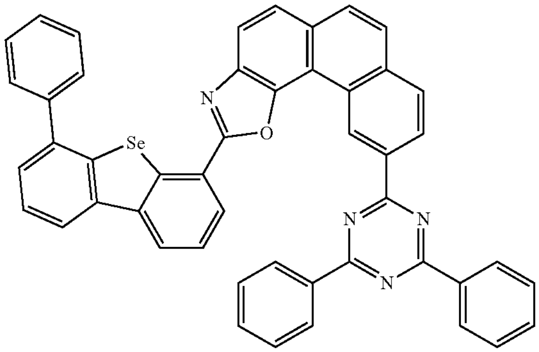
H1-150
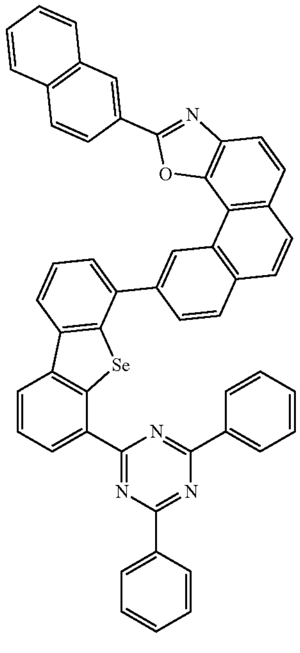

-continued
H1-151
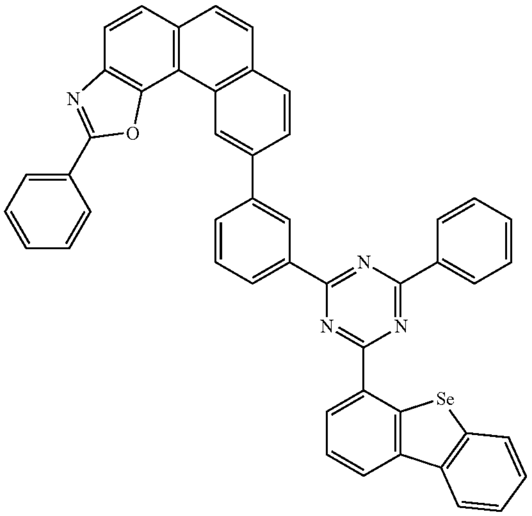
H1-152
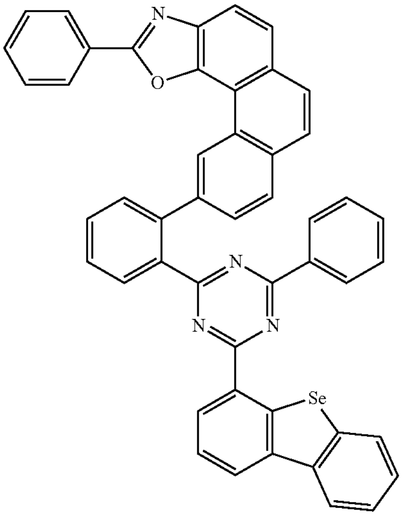
H1-153
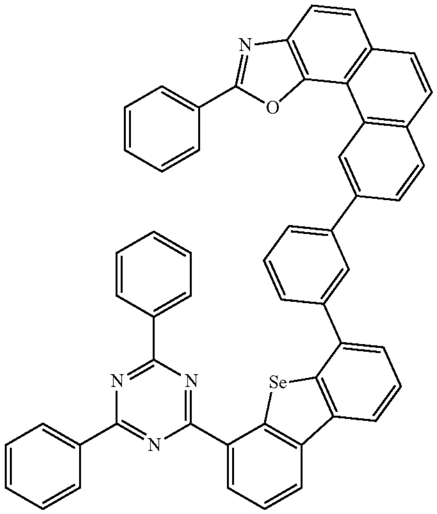
-continued
H1-154
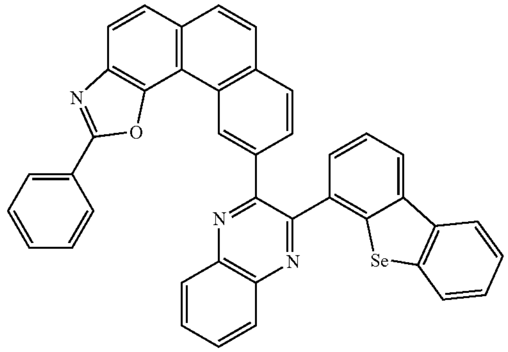
H1-155
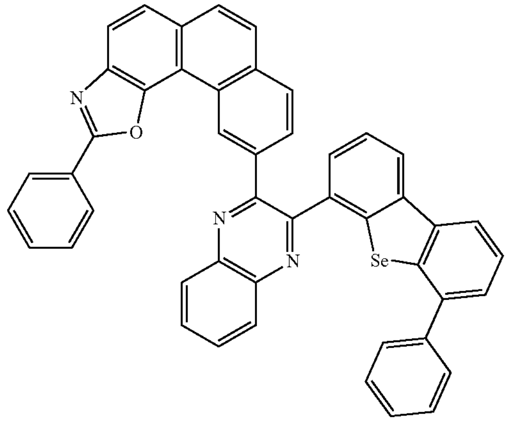
H1-156
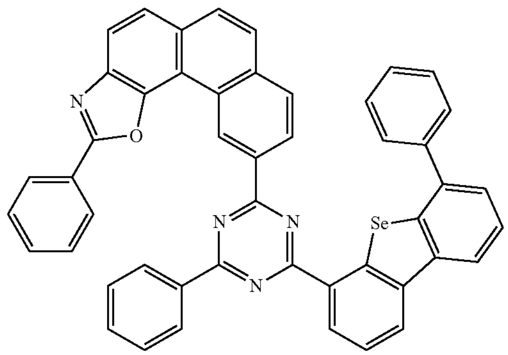

-continued
H1-157
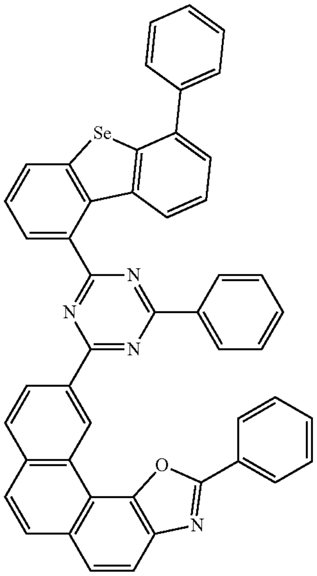
H1-158
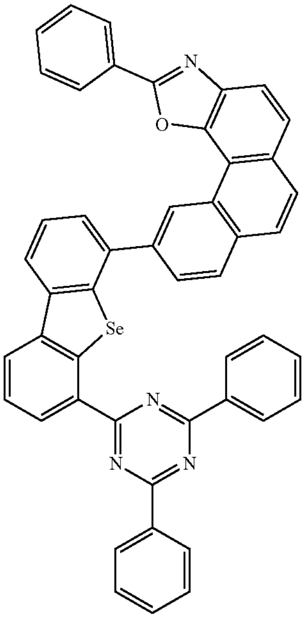
H1-159
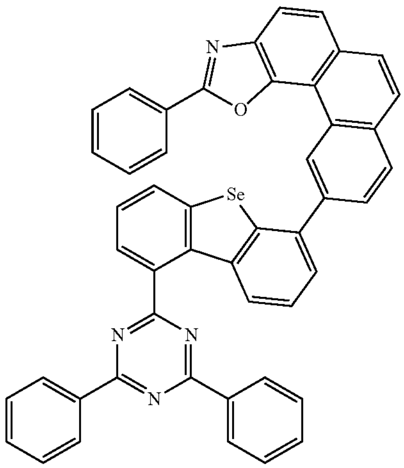
-continued
H1-160
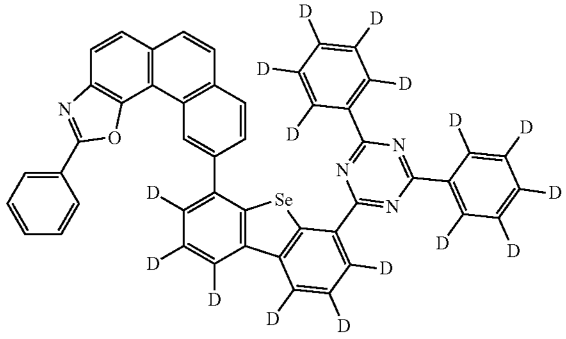
H1-161
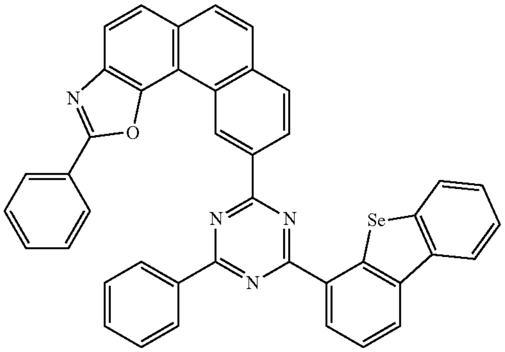
H1-162
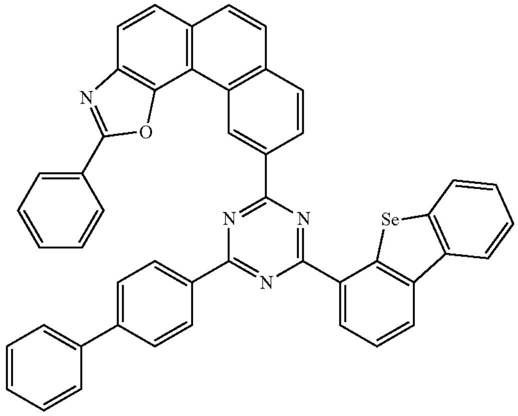

-continued
H1-163
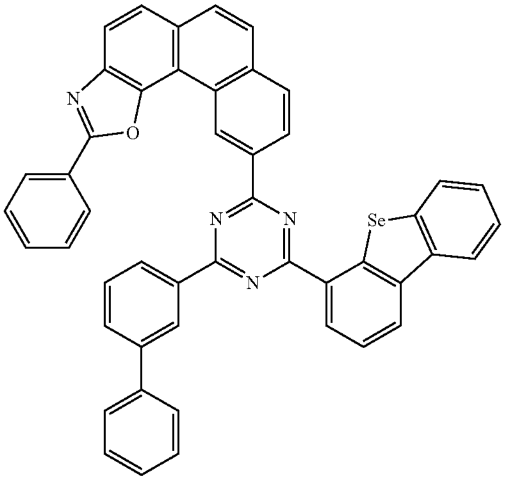
H1-164
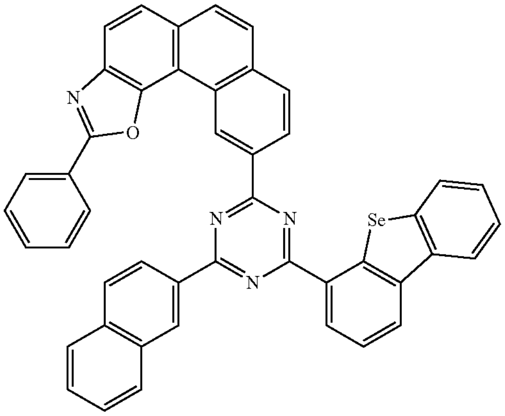
H1-165
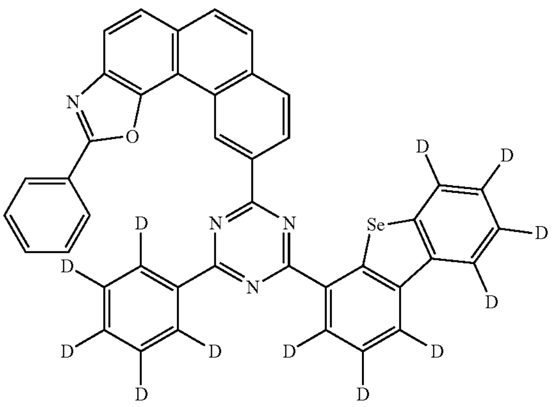
-continued
H1-166
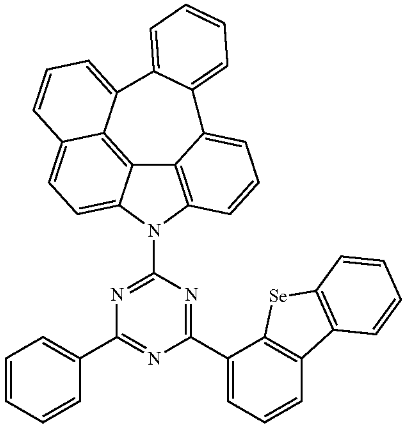
H1-167
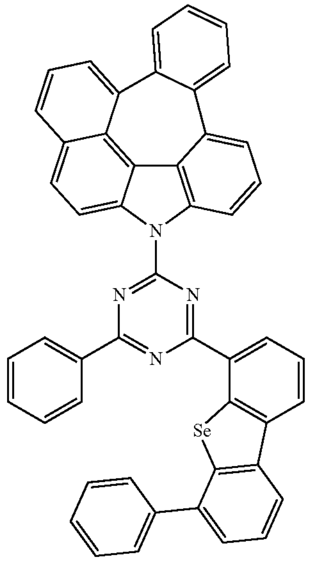
H1-168
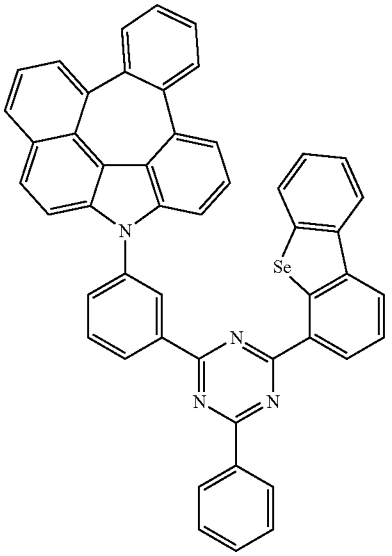

-continued
H1-169
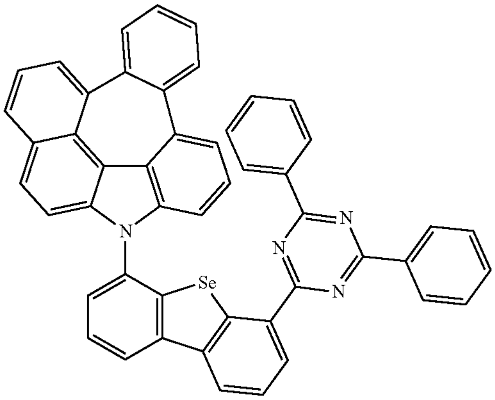
H1-170
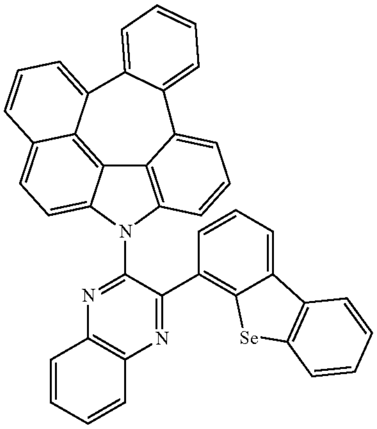
H1-171
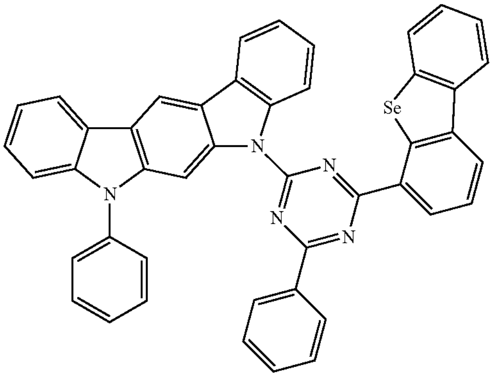
-continued
H1-172
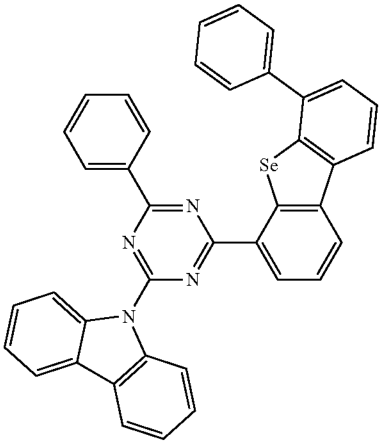
H1-173
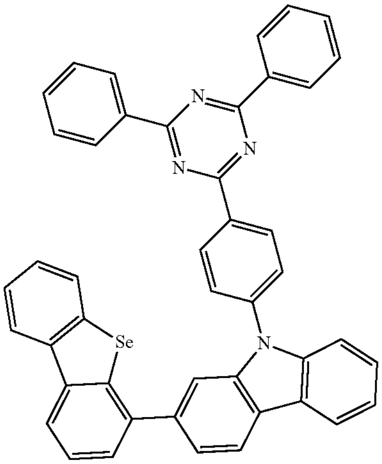
H1-174
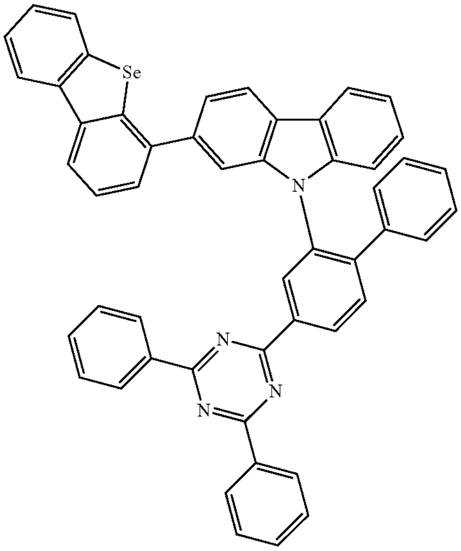

-continued
H1-175
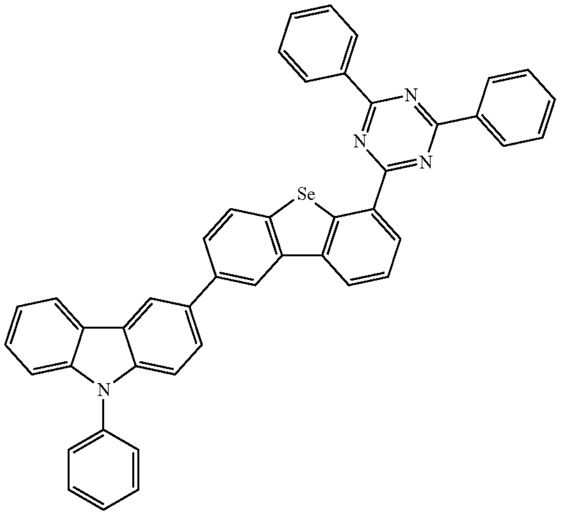
H1-176
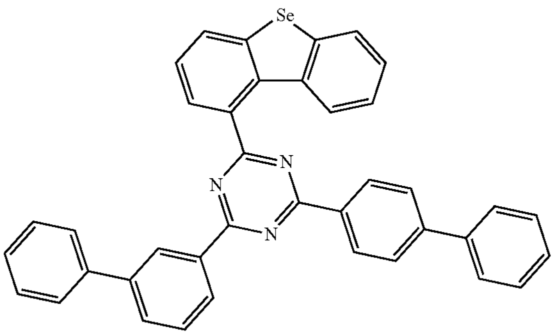
H1-177
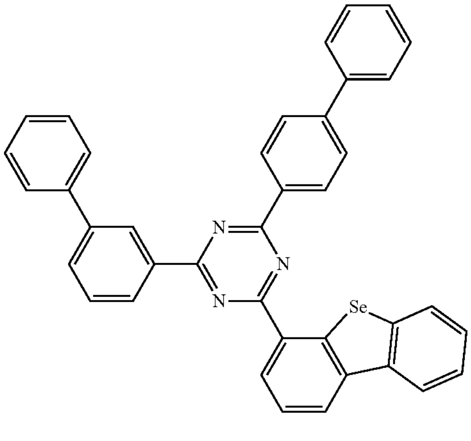
-continued
H1-178
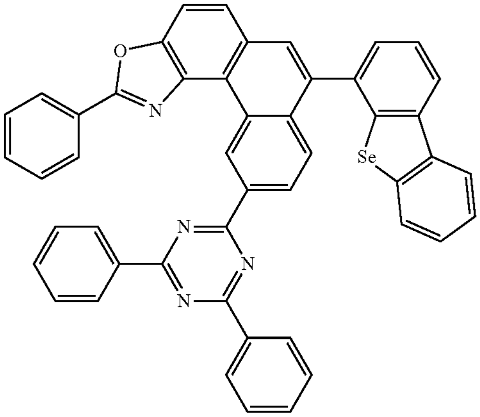
H1-179
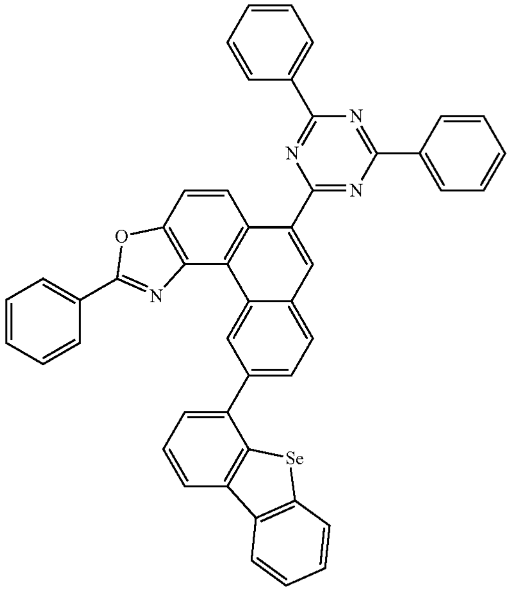
H1-180
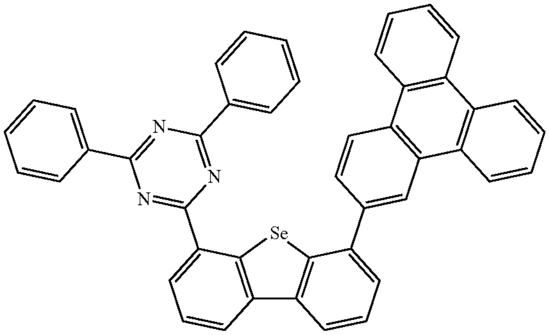

-continued
H1-181
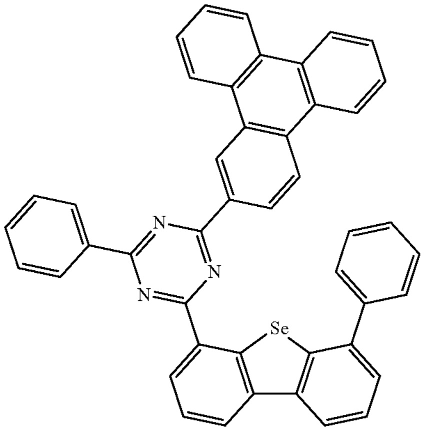
H1-182
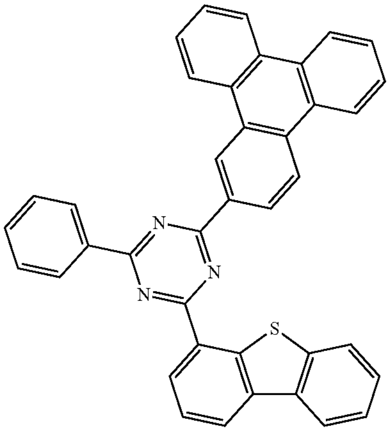
H1-183
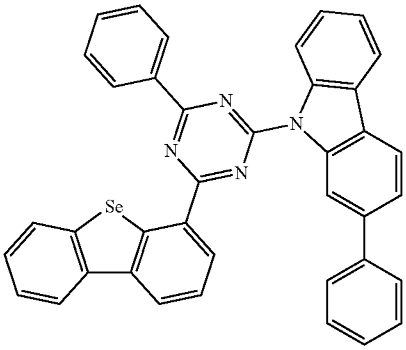
H1-184
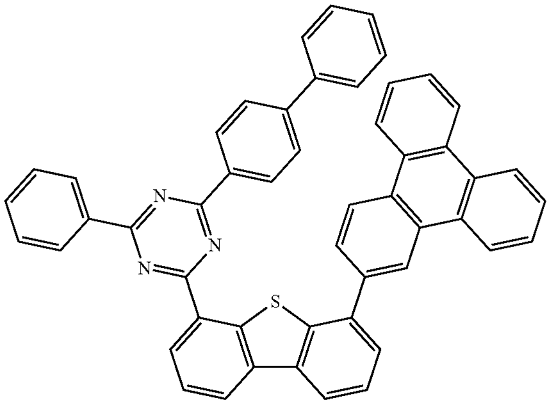
-continued
H1-185
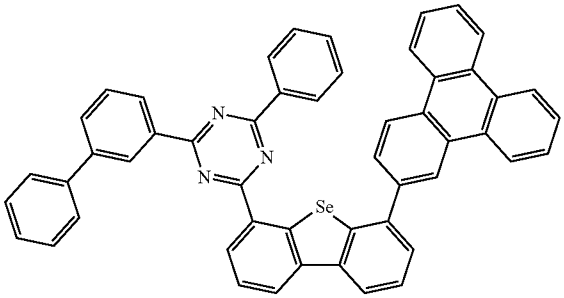
H1-186
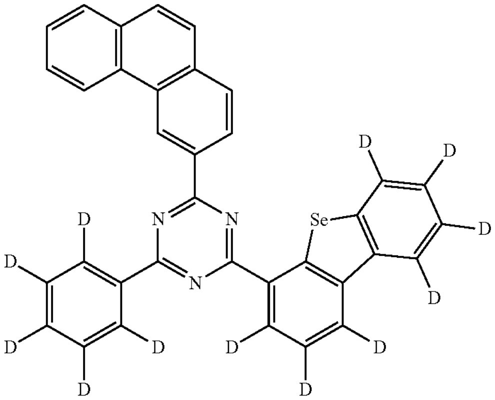
H1-187
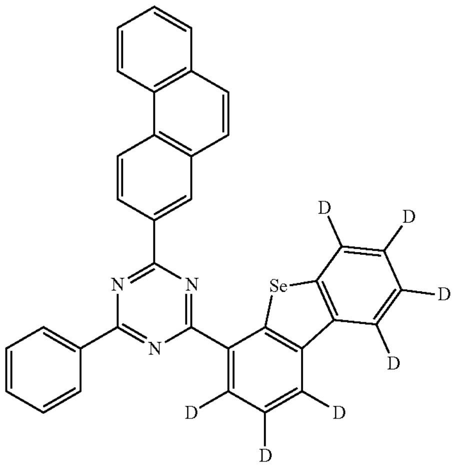
H1-188
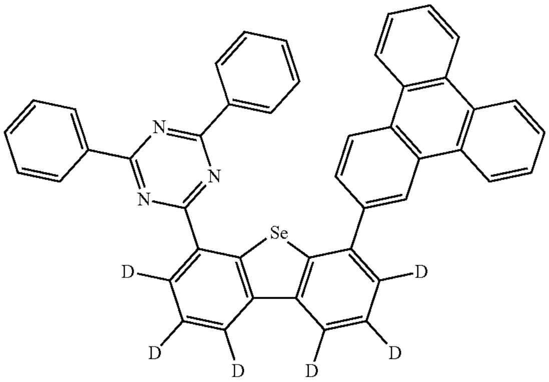

-continued
H1-189
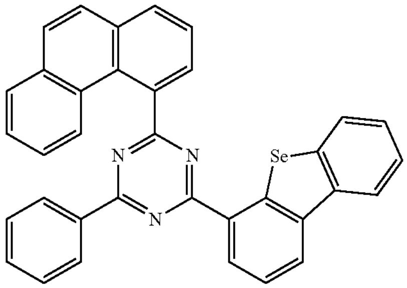
H1-190
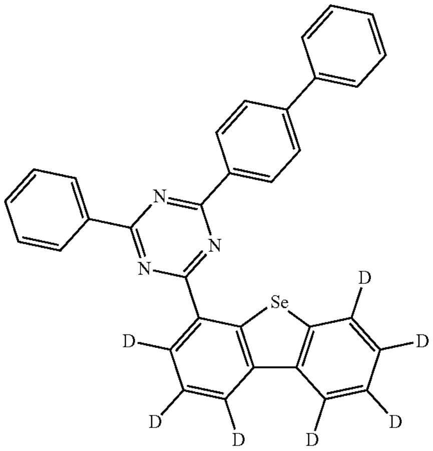
H1-191
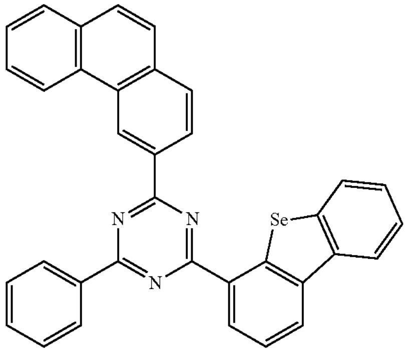
H1-192
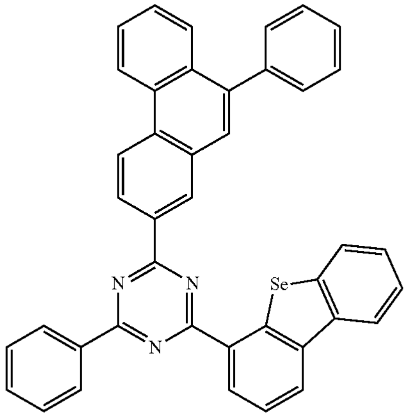
-continued
H1-193
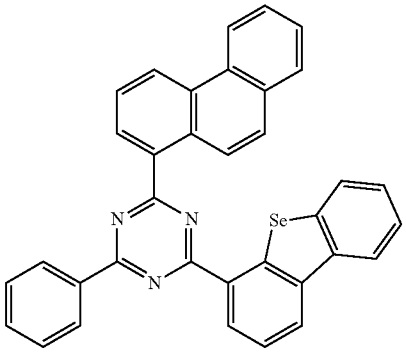
H1-194
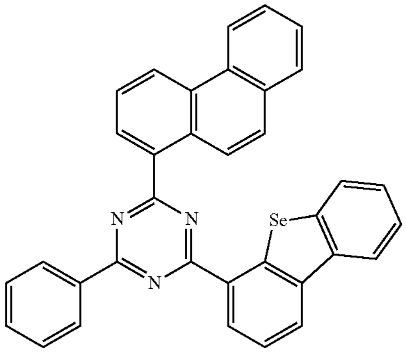
The compound represented by formula 2 may be at least one selected from the following compounds, but is not limited thereto.
H2-1
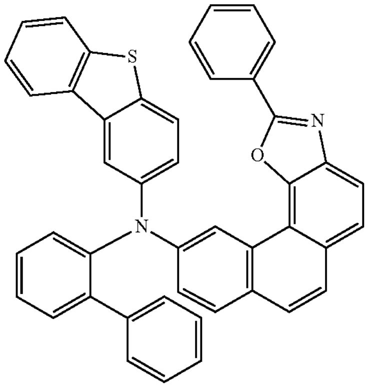
H2-2
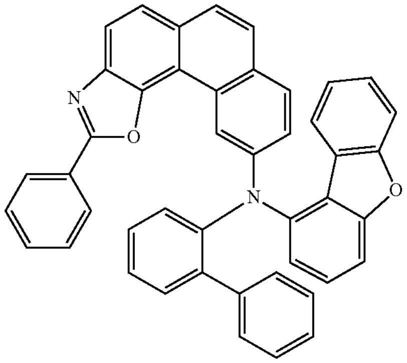

-continued
H2-3
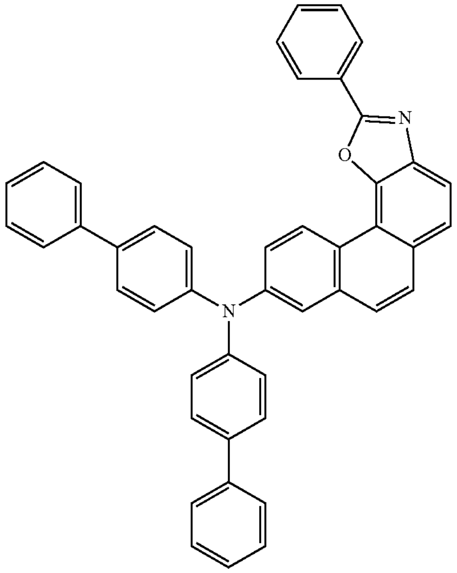
H2-4
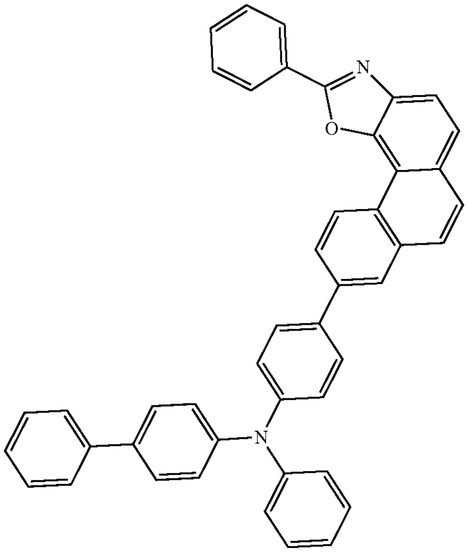
H2-5
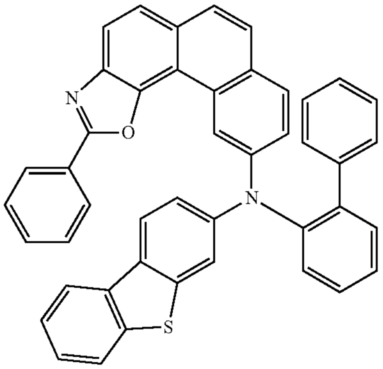
-continued
H2-6
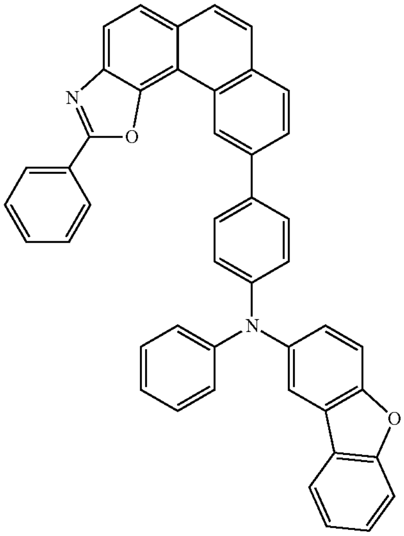
H2-7
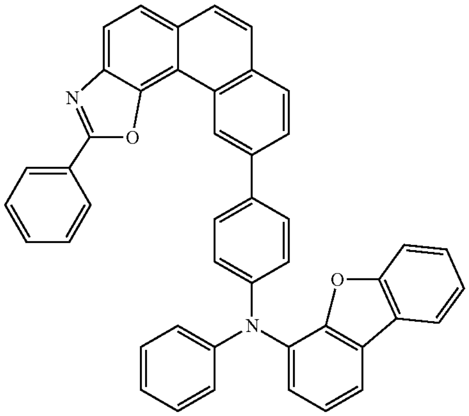
H2-8
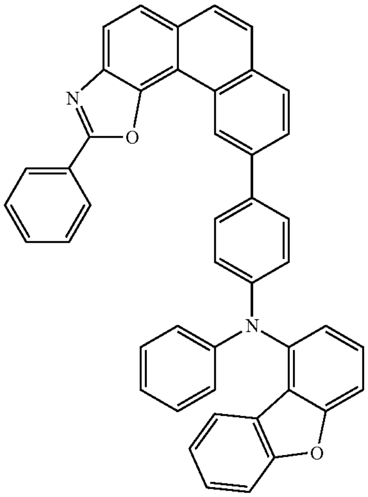

-continued
H2-9
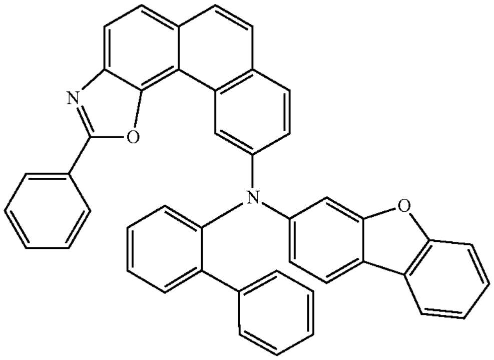
H2-10
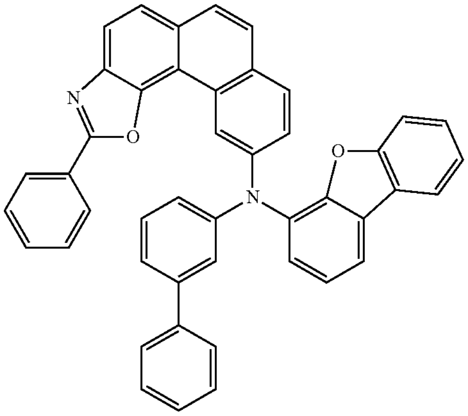
H2-11
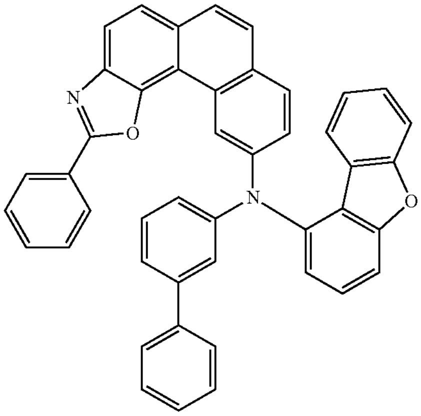
H2-12
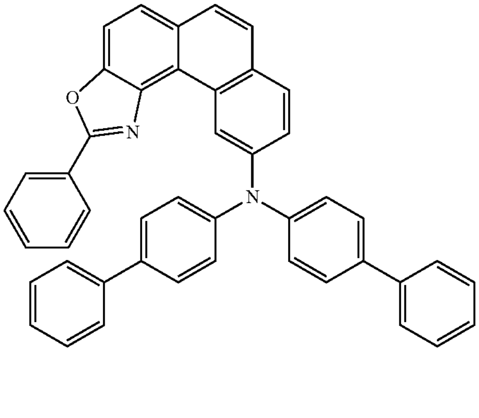
-continued
H2-13
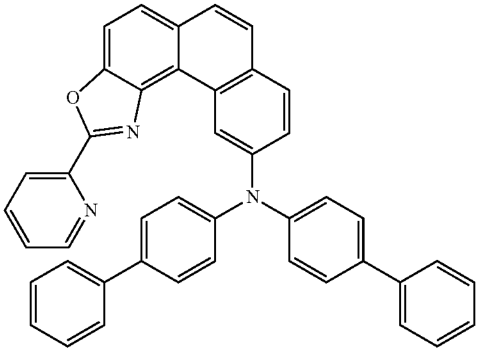
H2-14
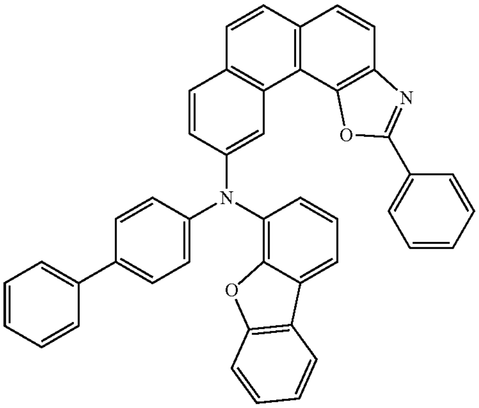
H2-15
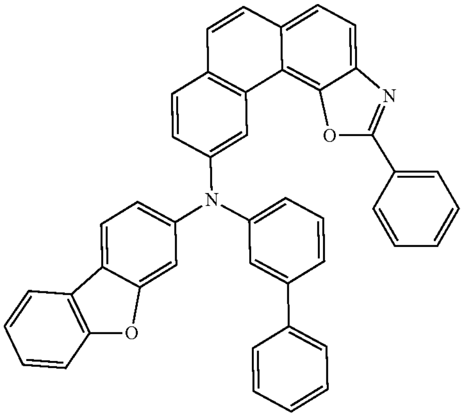
H2-16
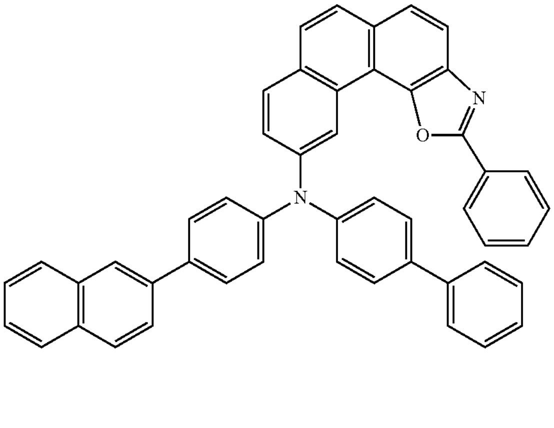

-continued
H2-17
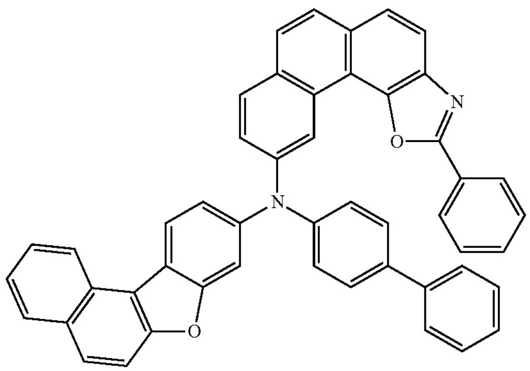
H2-18
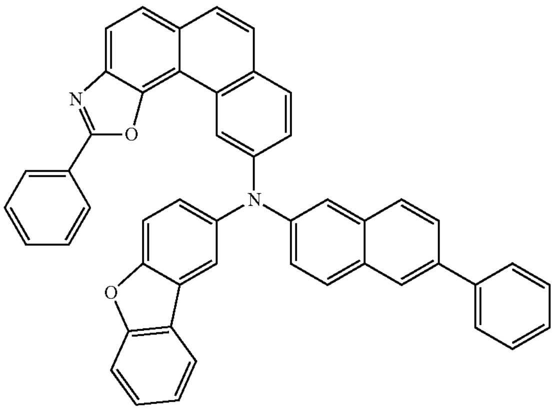
H2-19
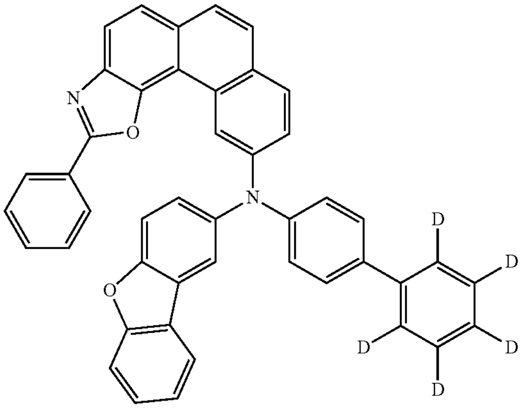
H2-20
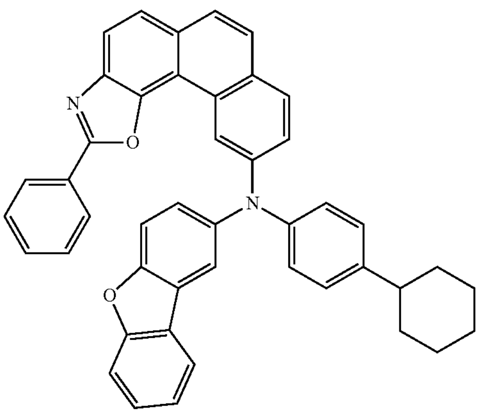
-continued
H2-21
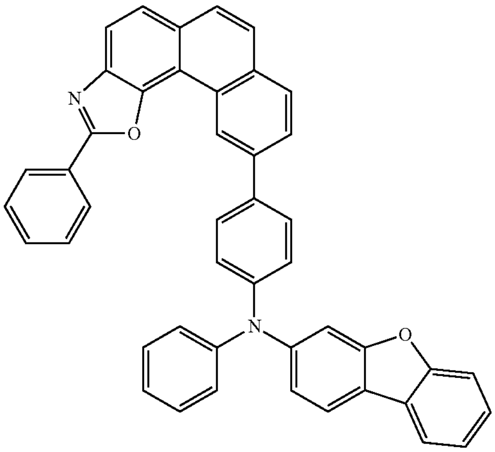
H2-22
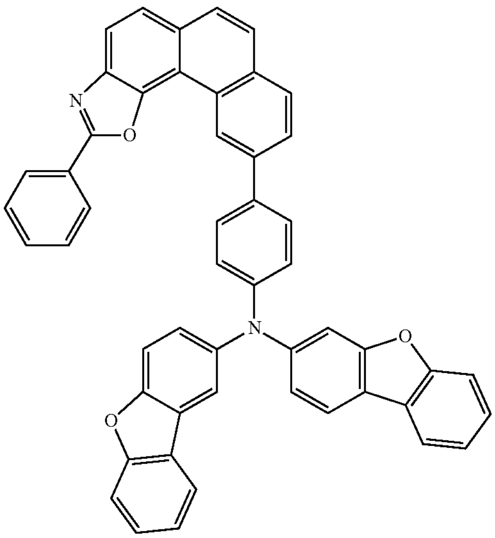
H2-23
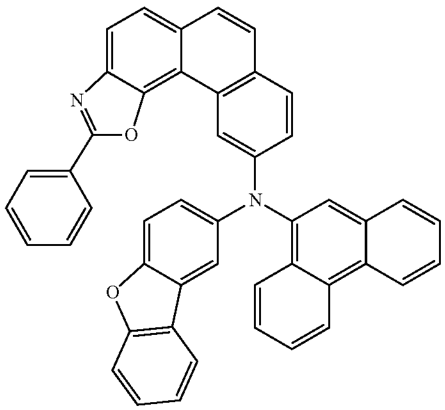

-continued
H2-24
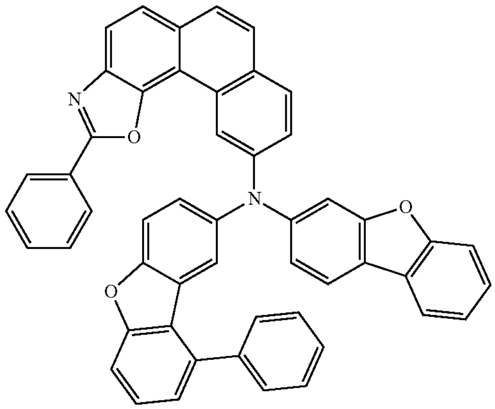
H2-25
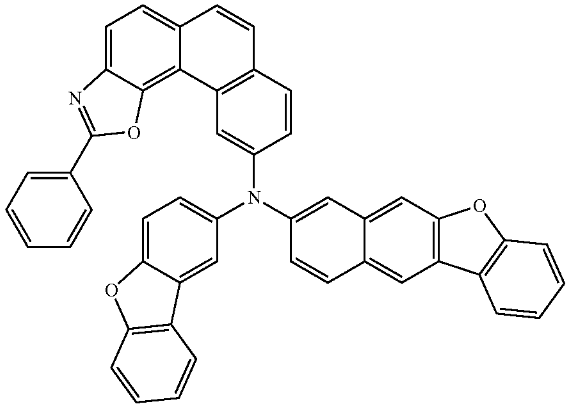
H2-26
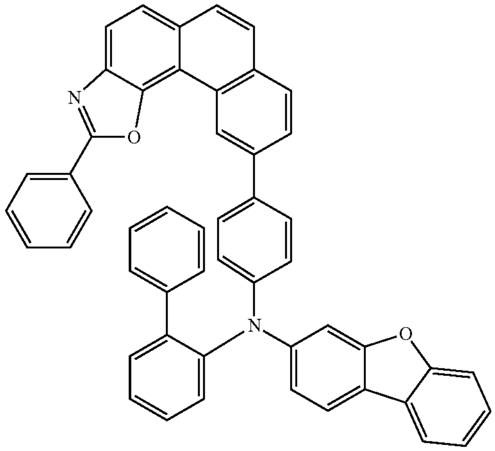
-continued
H2-27
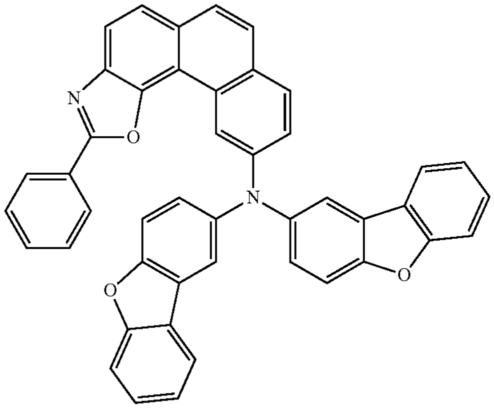
H2-28
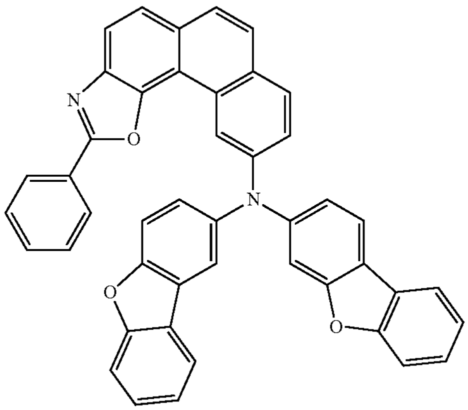
H2-29
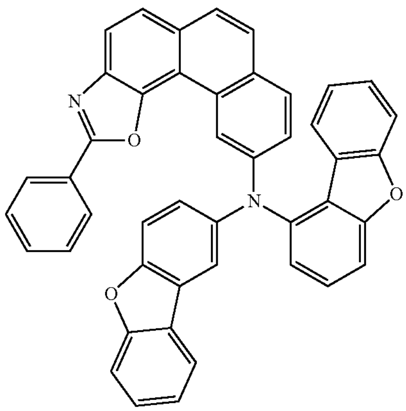
H2-30
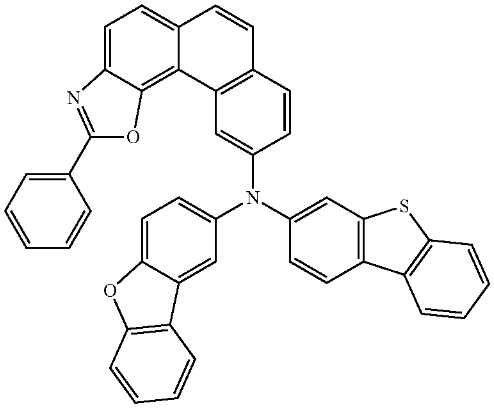

-continued
H2-31
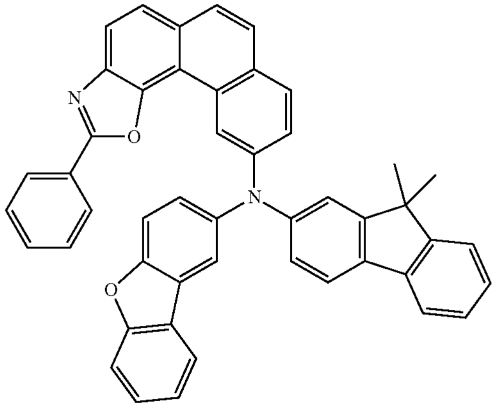
H2-32
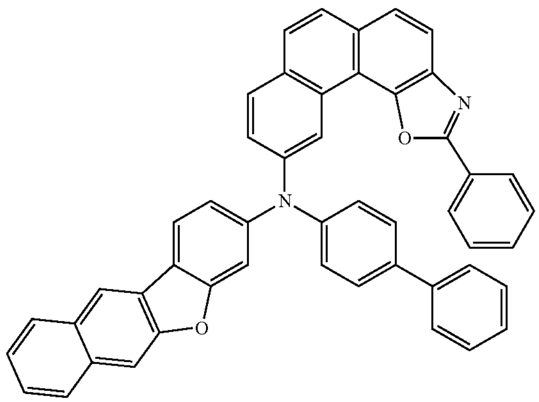
H2-33
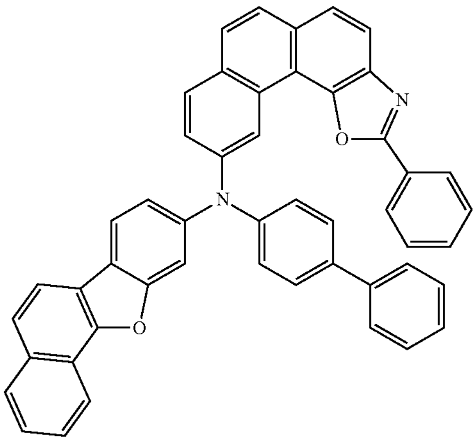
-continued
H2-34
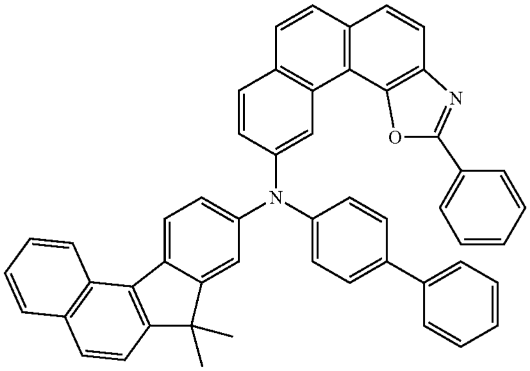
H2-35
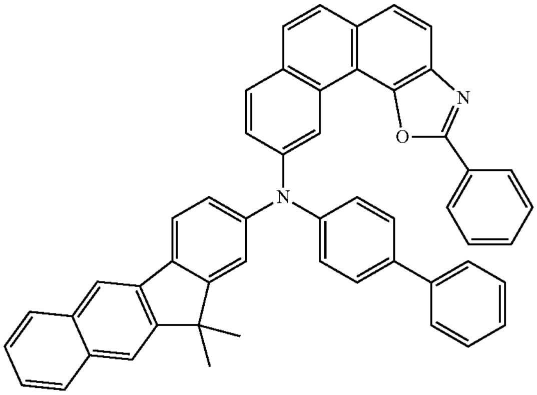
H2-36
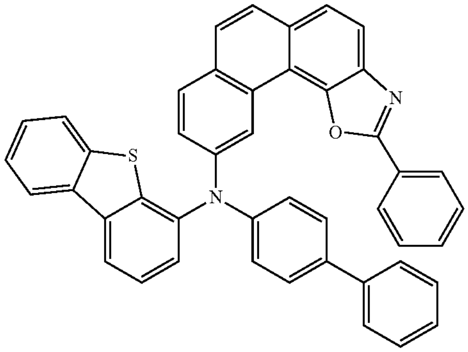
H2-37
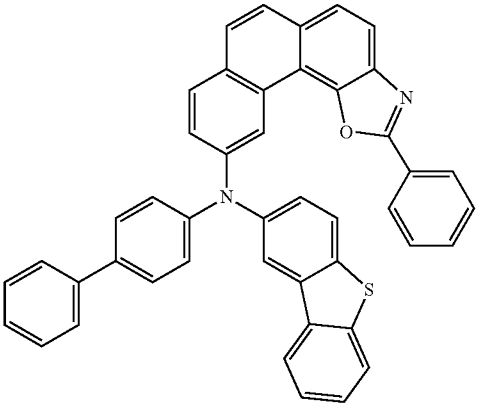

-continued
H2-38
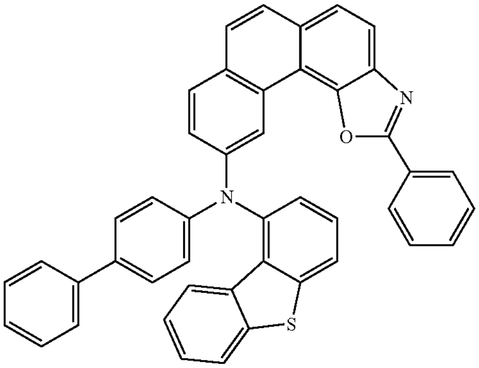
H2-39
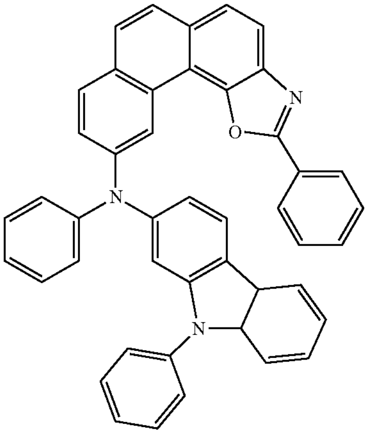
H2-40
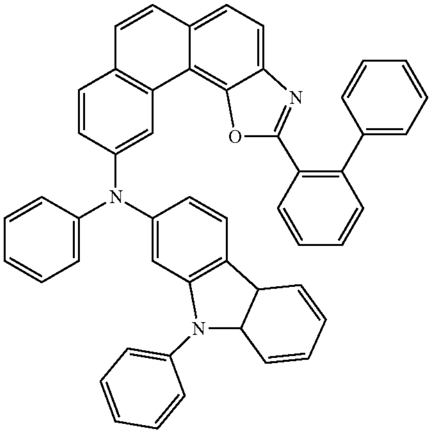
H2-41
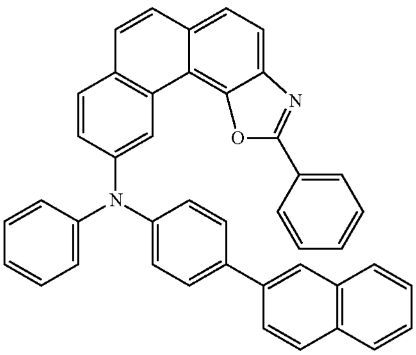
-continued
H2-42
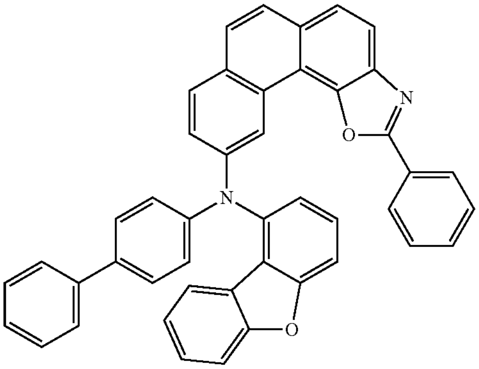
H2-43
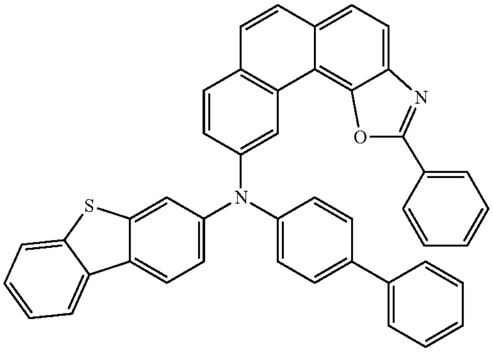
H2-44
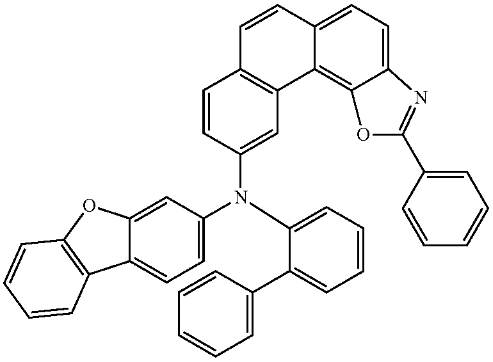
H2-45
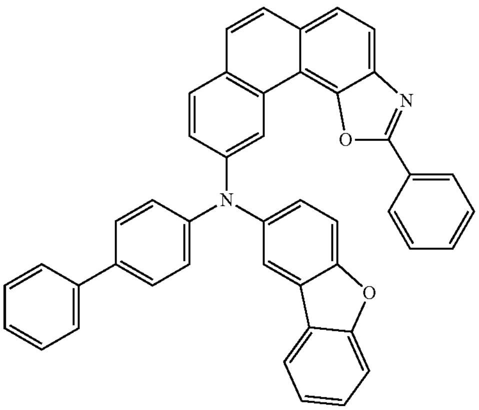

-continued
H2-46
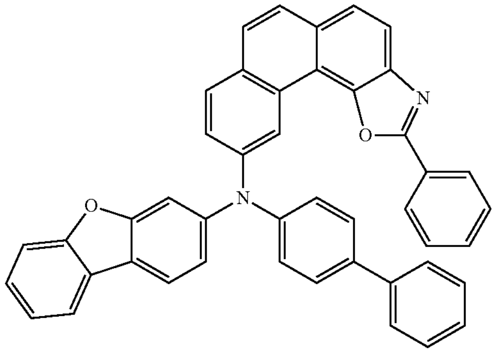
H2-47
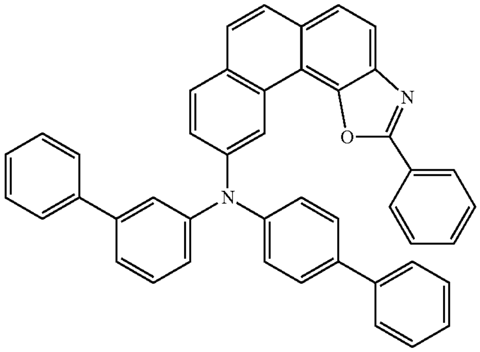
H2-48
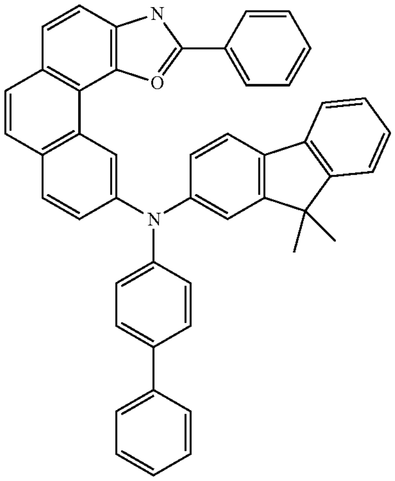
H2-49
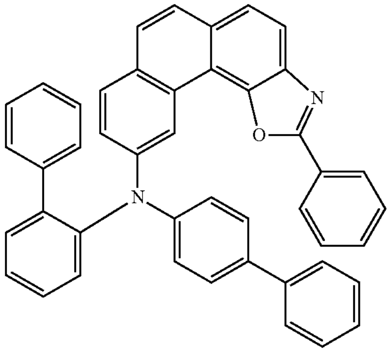
-continued
H2-50
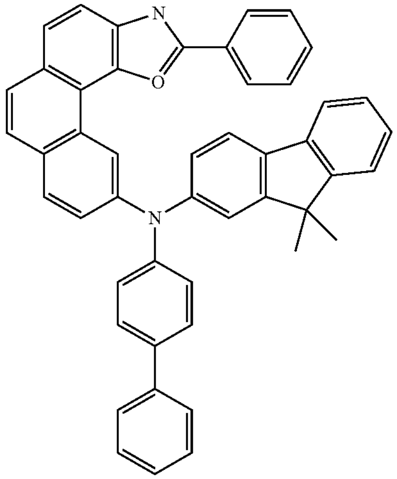
H2-51
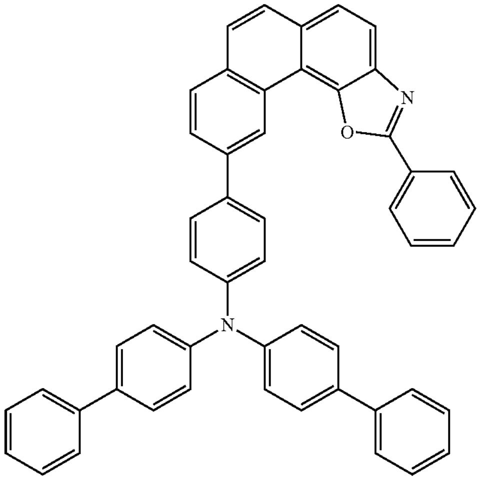
H2-52
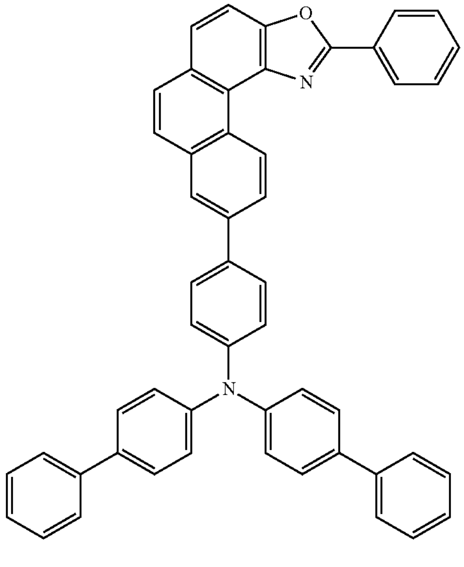

-continued
H2-53
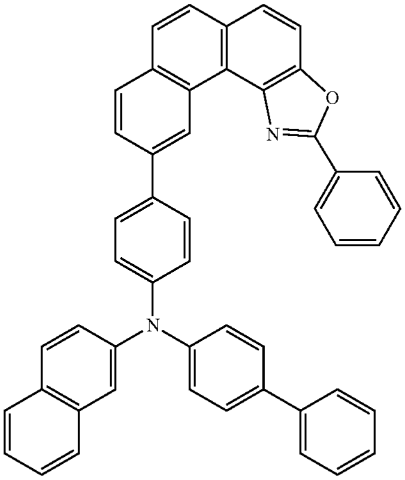
H2-54
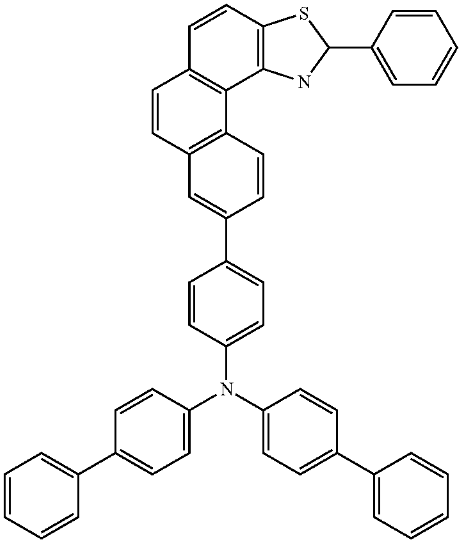
H2-55
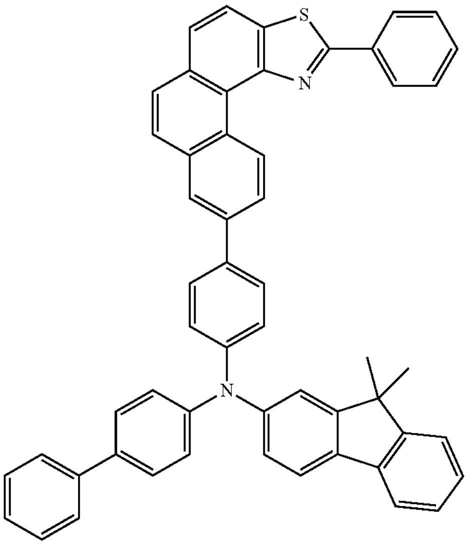
-continued
H2-56
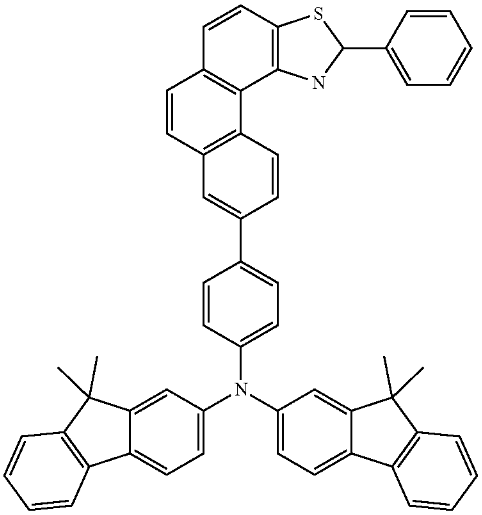
H2-57
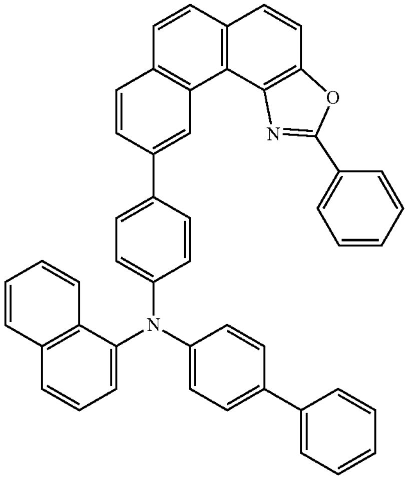
H2-58
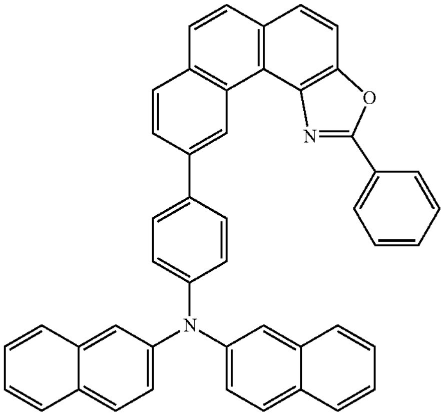

H2-59
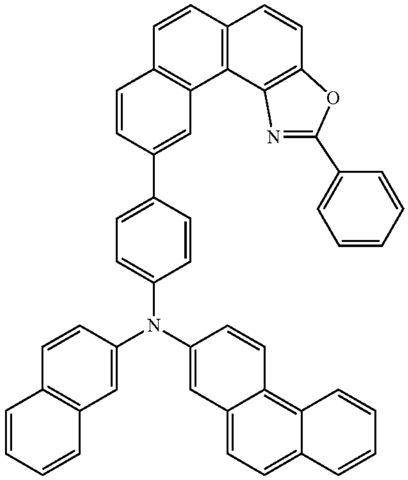
H2-60
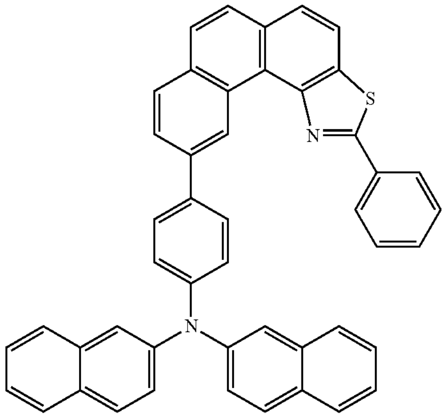
H2-61
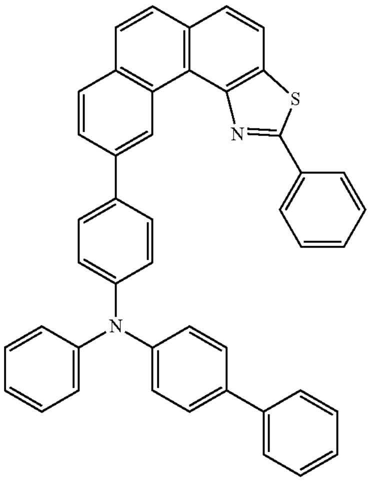
H2-62
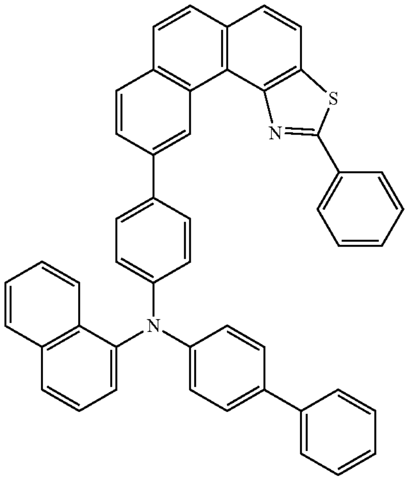
H2-63
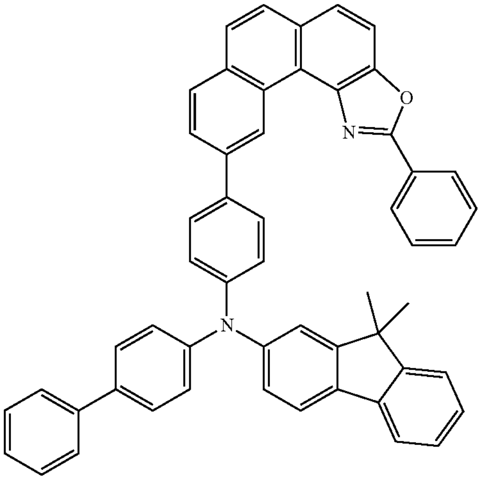
H2-64
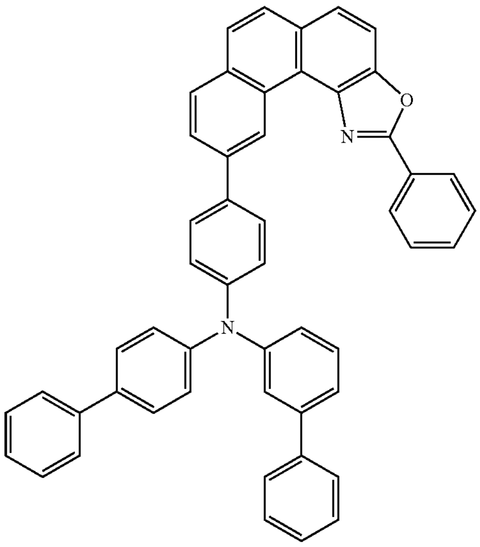

-continued
H2-65
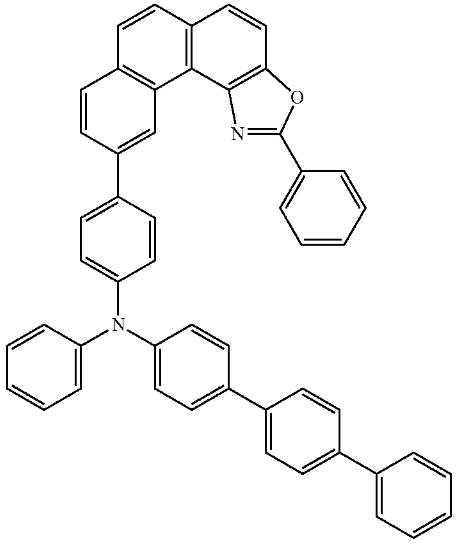
H2-66
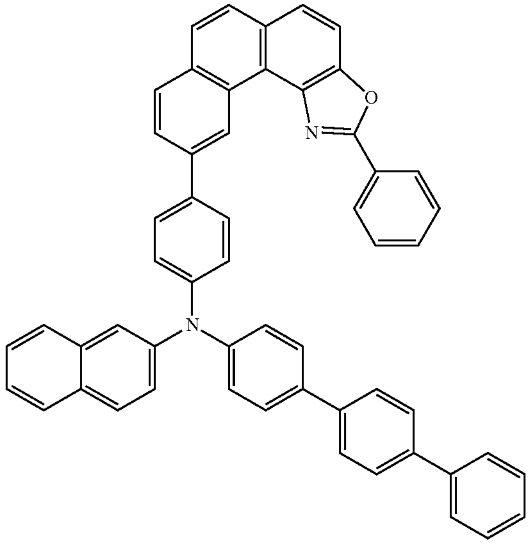
H2-67
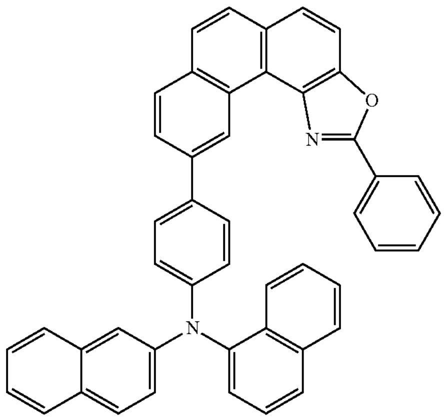
-continued
H2-68
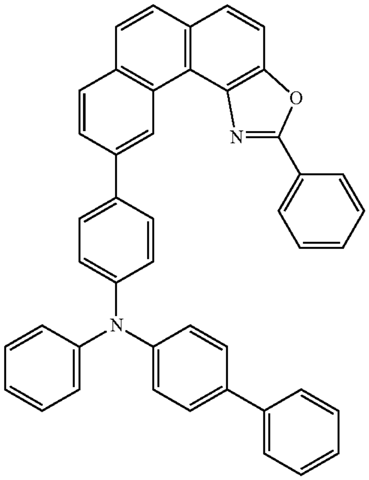
H2-69
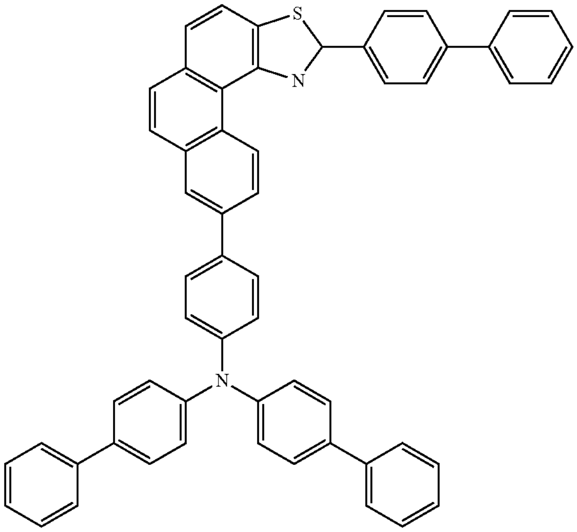
H2-70
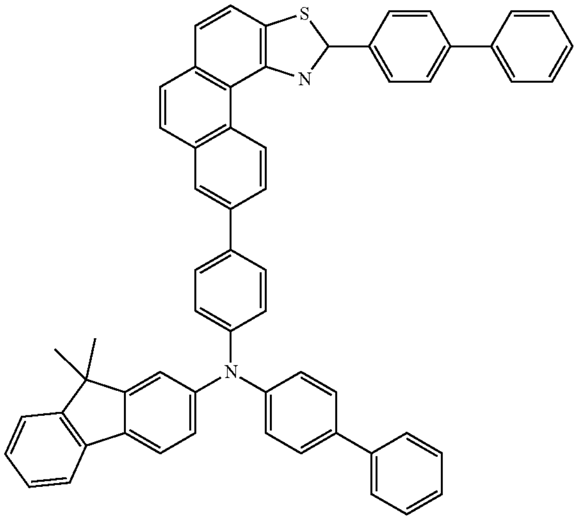

H2-71
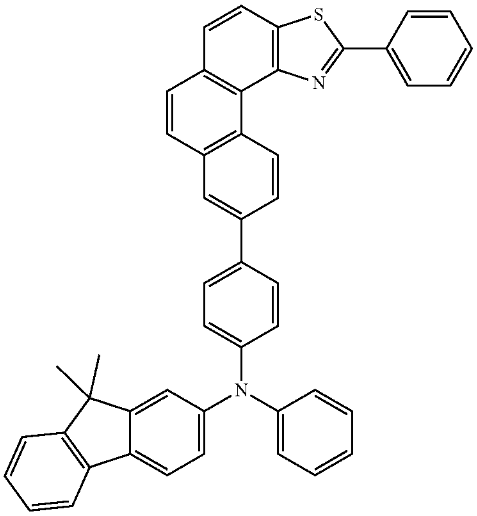
H2-72
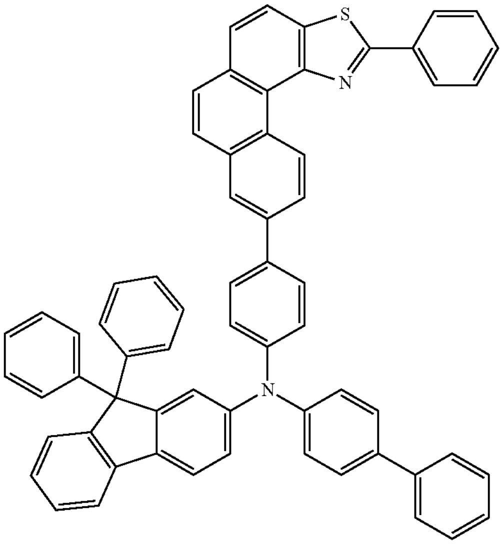
H2-73
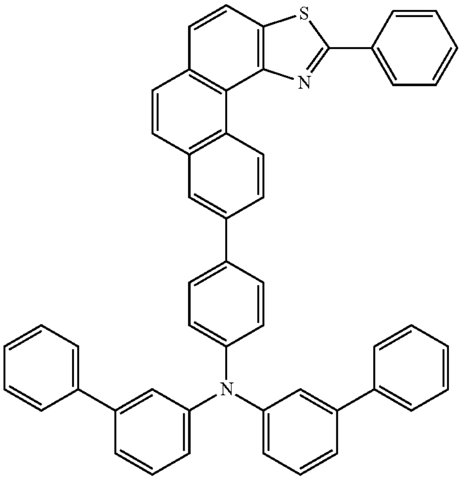
H2-74
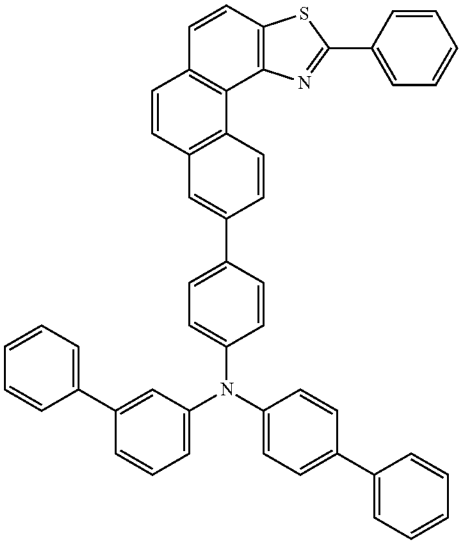
H2-75
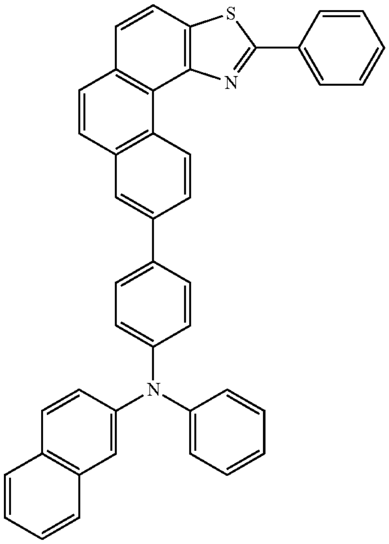
H2-76
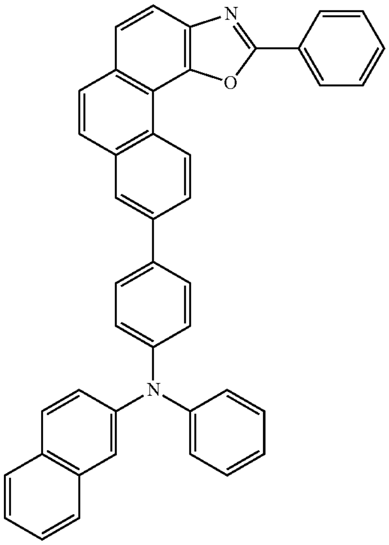

H2-77
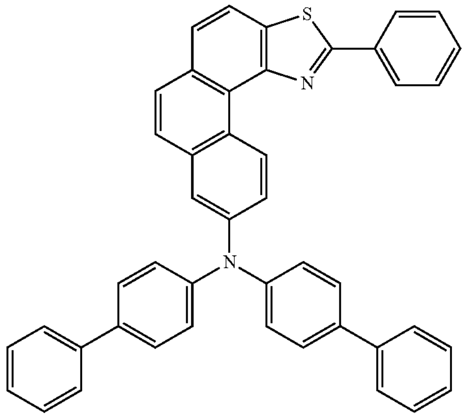
H2-78
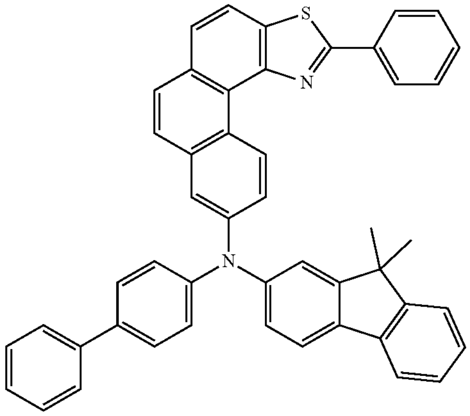
H2-79
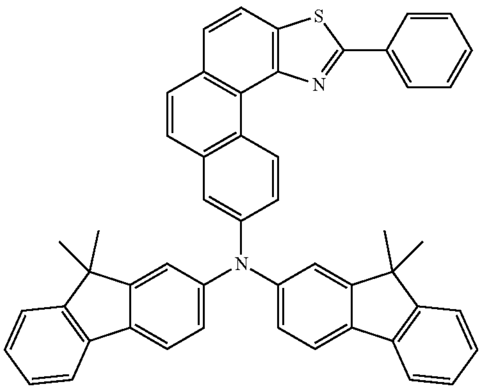
H2-80
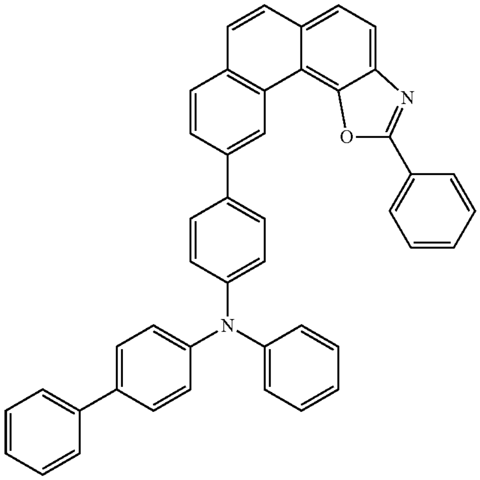
H2-81
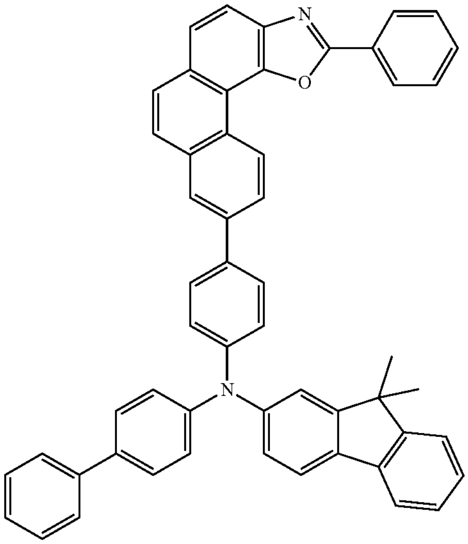
H2-82
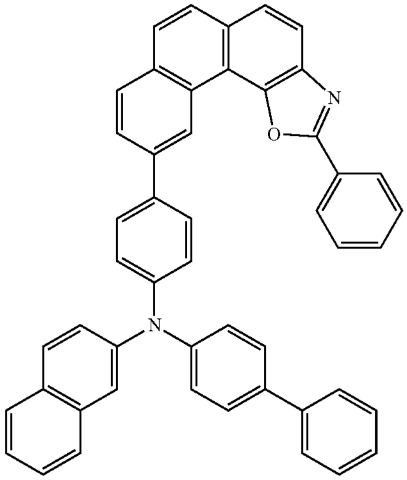

-continued
H2-83
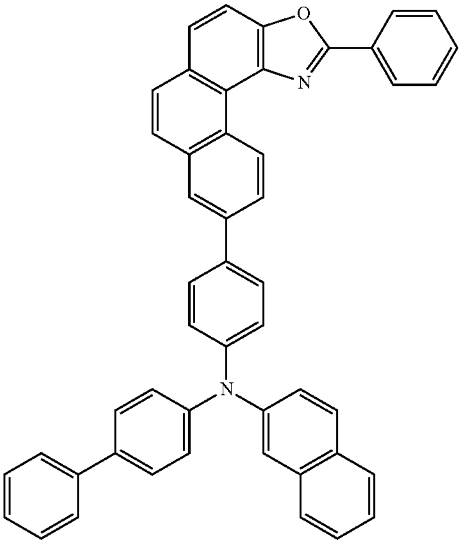
H2-84
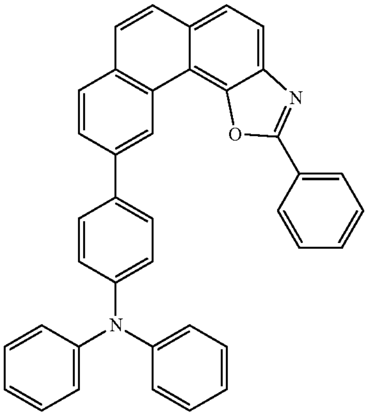
H2-85
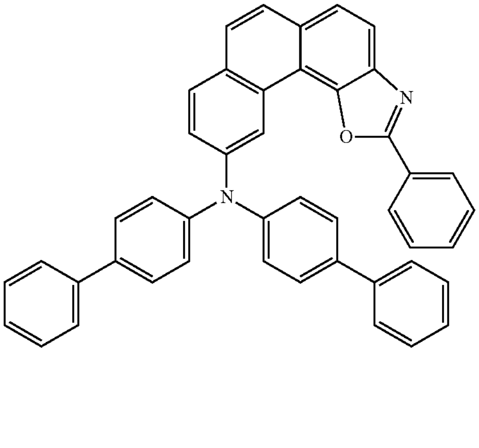
-continued
H2-86
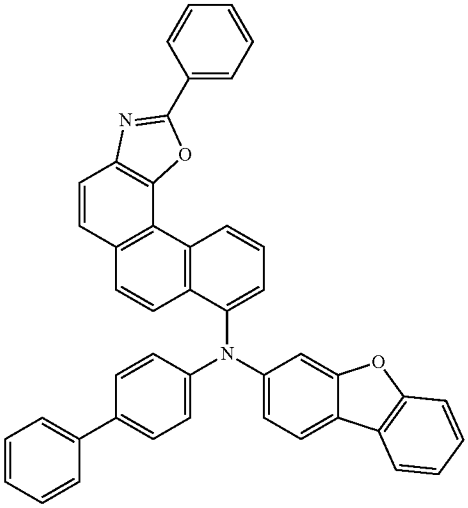
H2-87
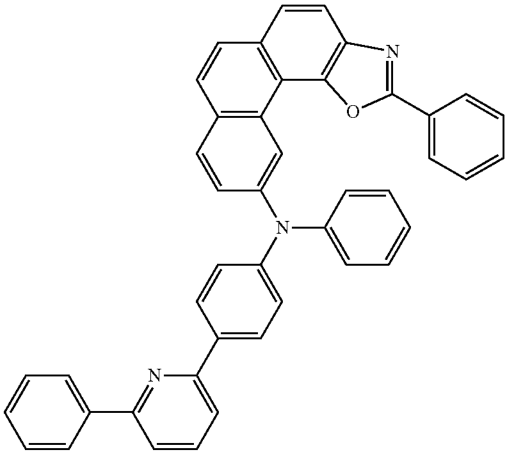
H2-88
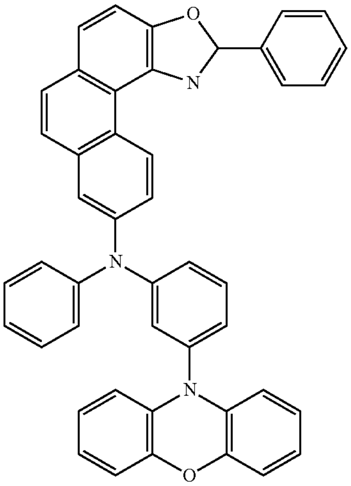

-continued
H2-89
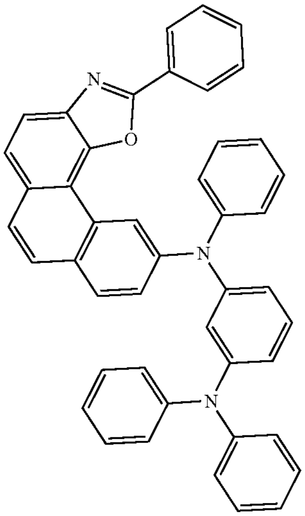
H2-90
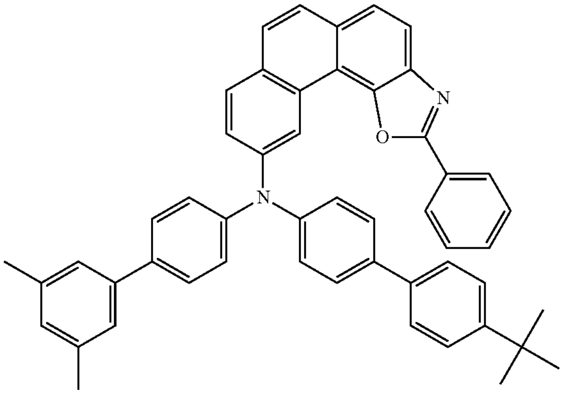
H2-91
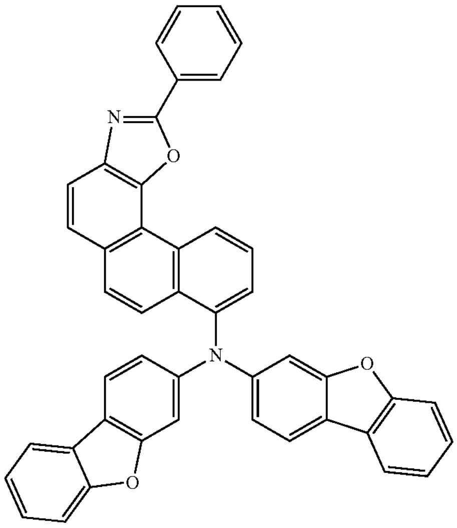
-continued
H2-92
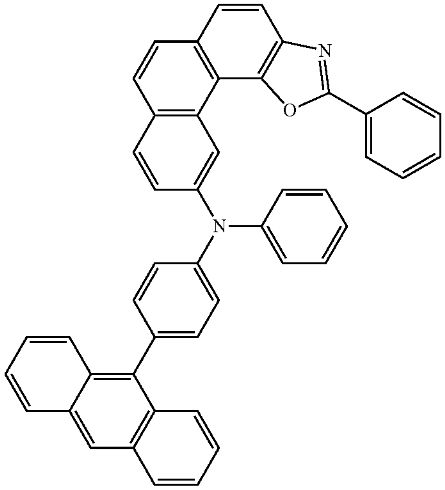
H2-93
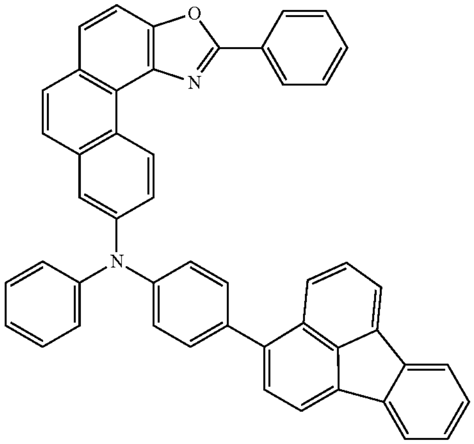
H2-94
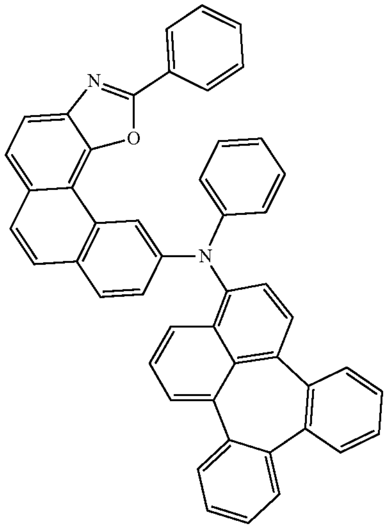

-continued
H2-95
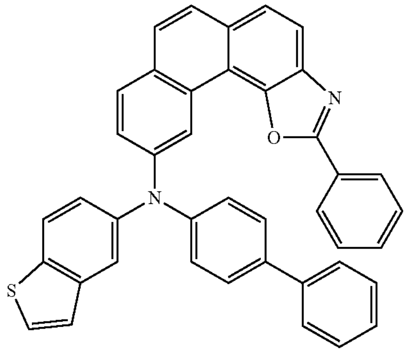
H2-96
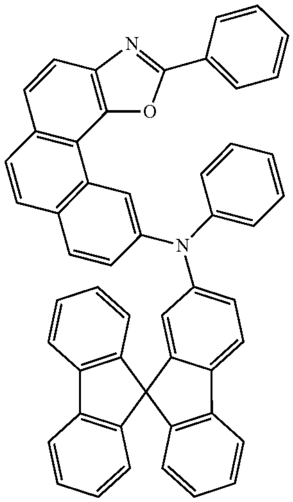
H2-97
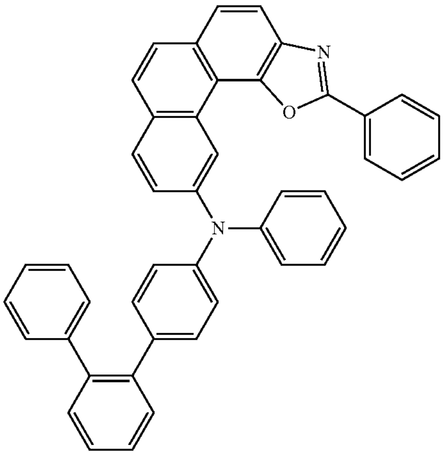
-continued
H2-98
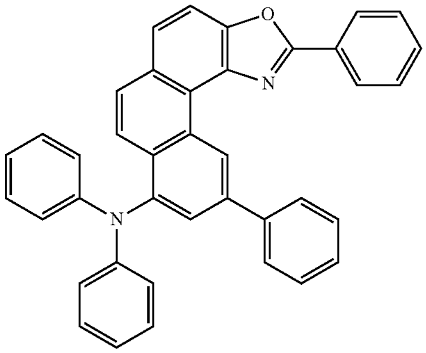
H2-99
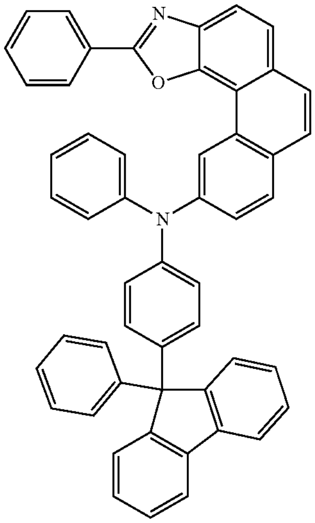
H2-100
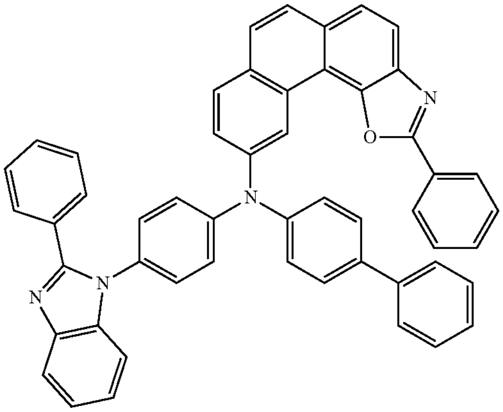

-continued
H2-101
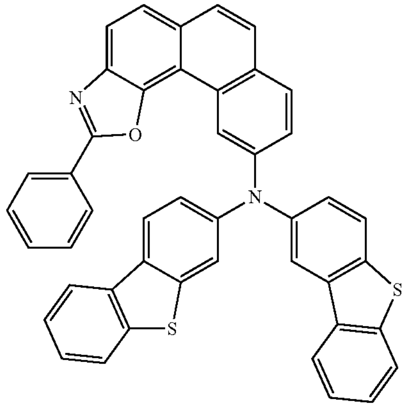
H2-102
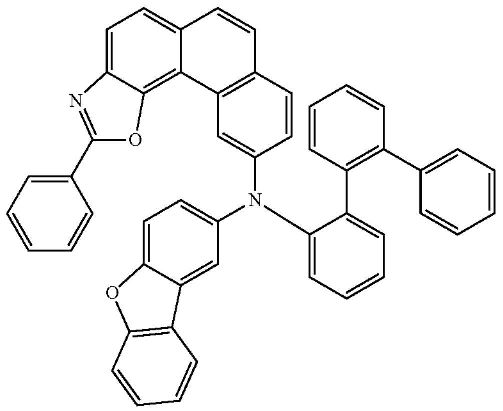
H2-103
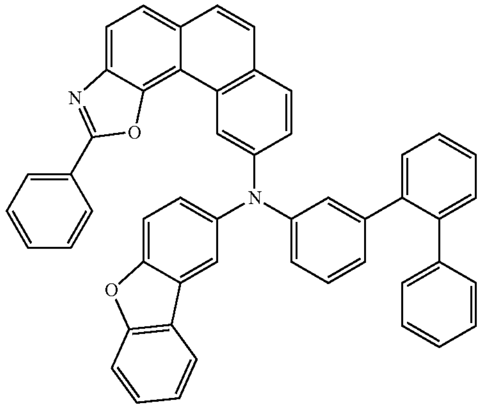
-continued
H2-104
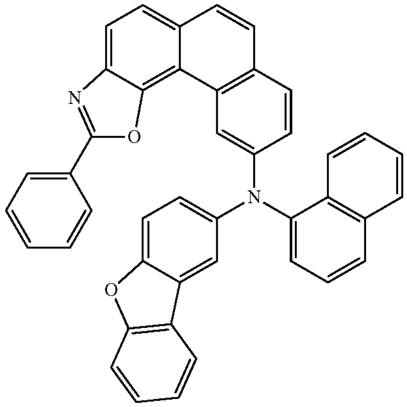
H2-105
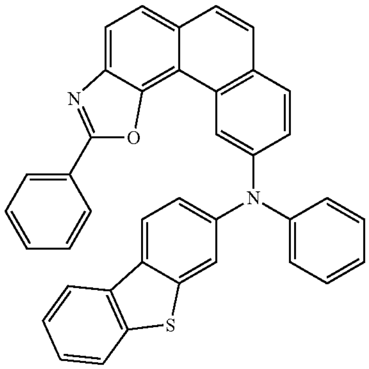
H2-106
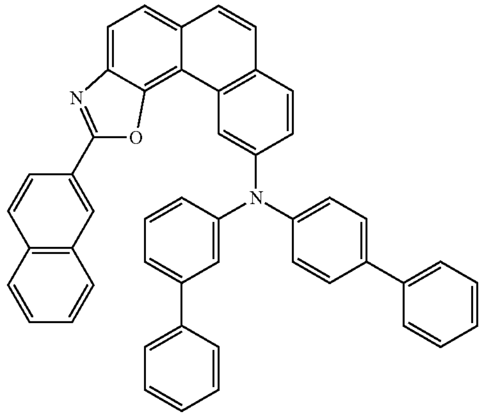
H2-107
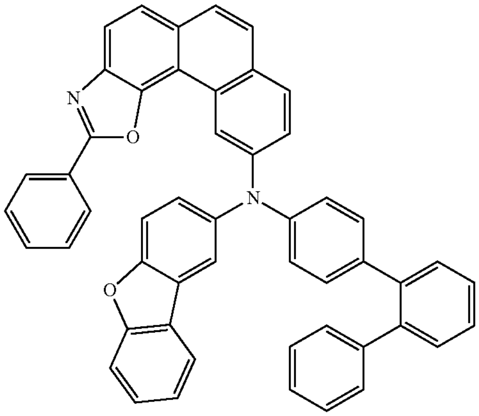

-continued
H2-108
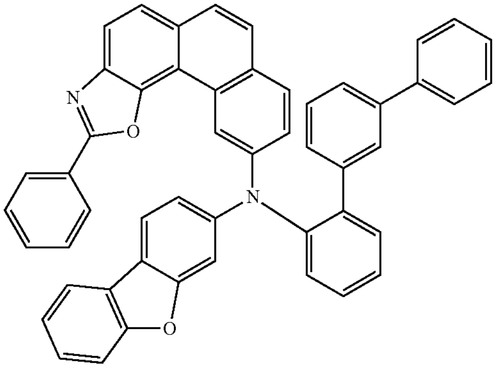
H2-109
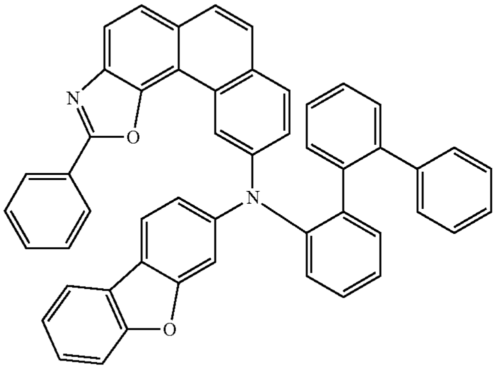
H2-110
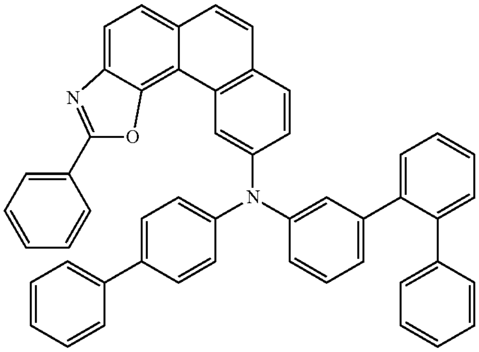
H2-111
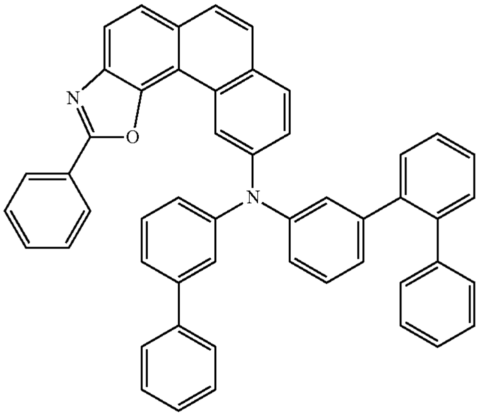
-continued
H2-112
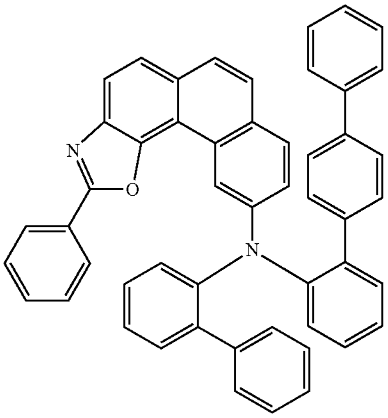
H2-113
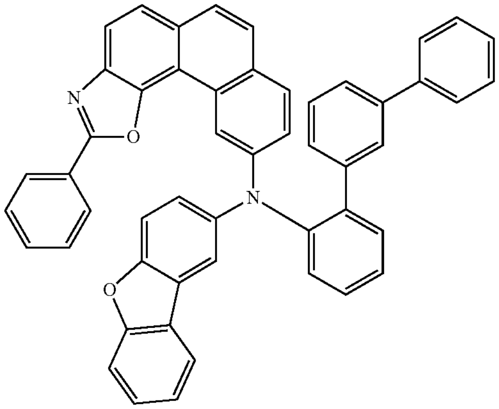
H2-114
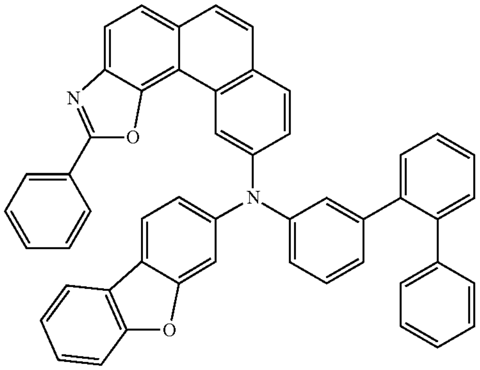
H2-115
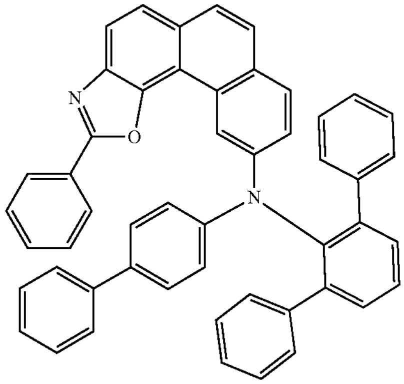

-continued
H2-116
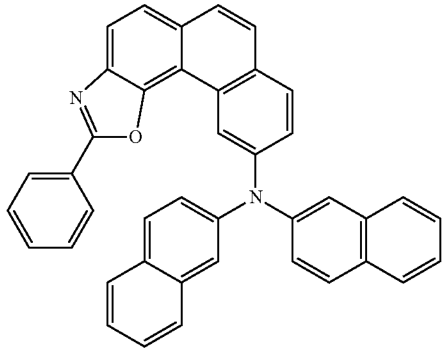
H2-117
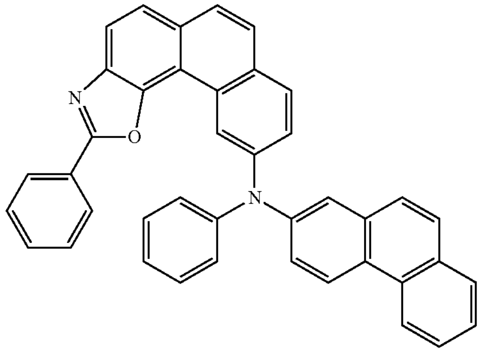
H2-118
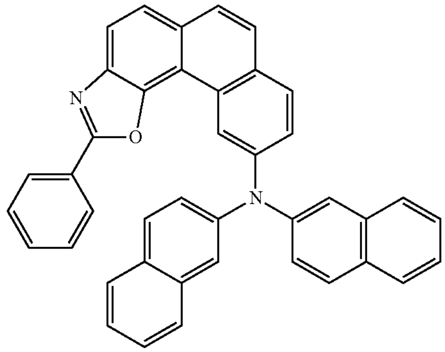
H2-119
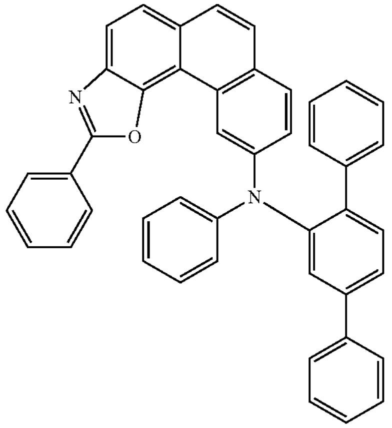
-continued
H2-120
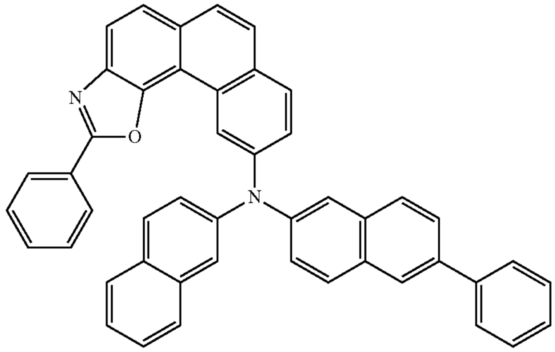
H2-121
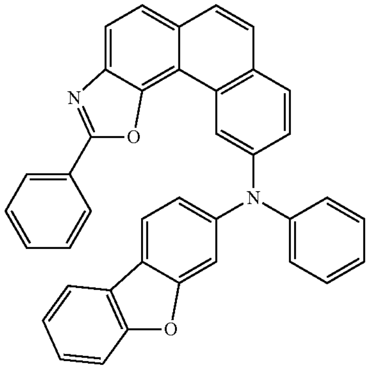
H2-122
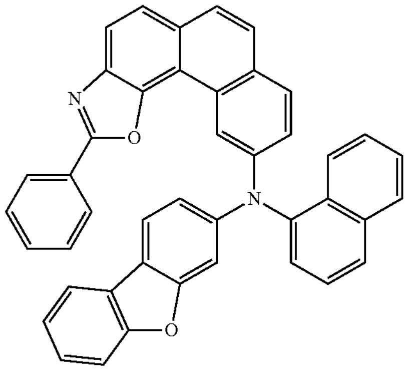
H2-123
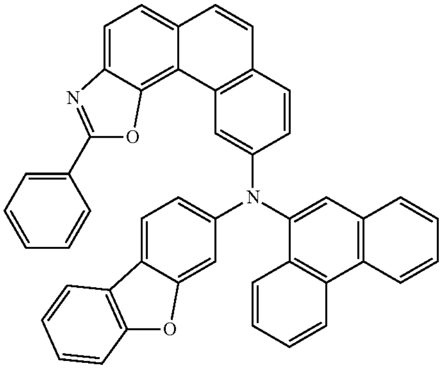

-continued
H2-124
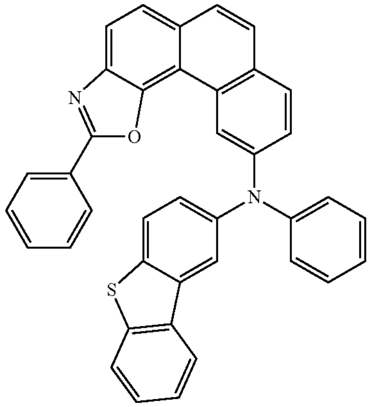
H2-125
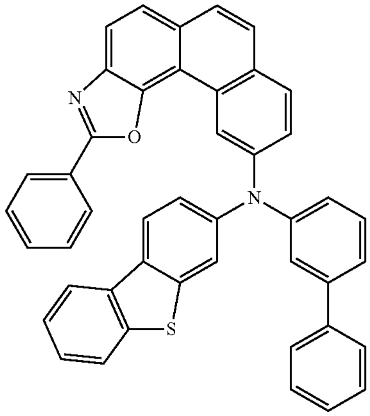
H2-126
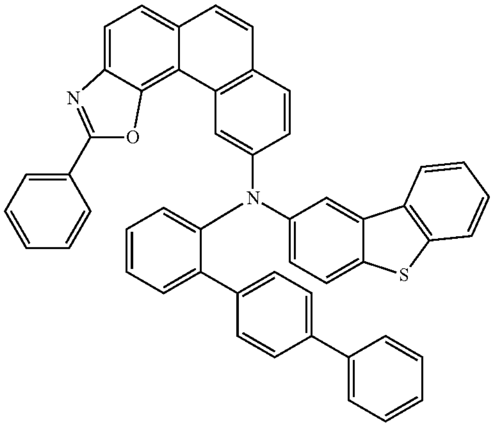
-continued
H2-127
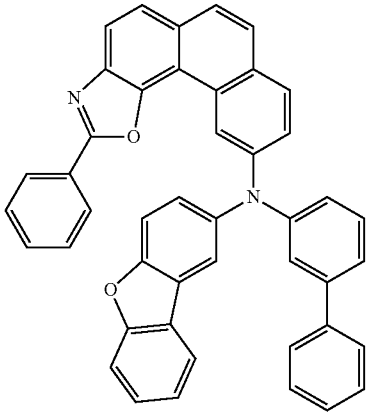
H2-128
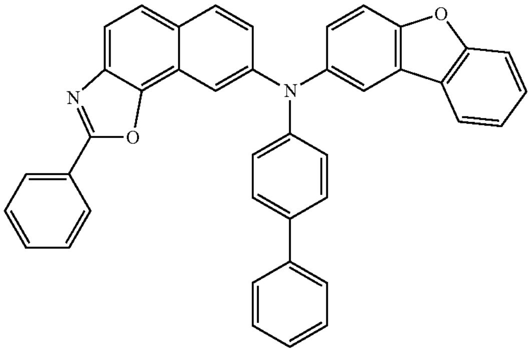
H2-129
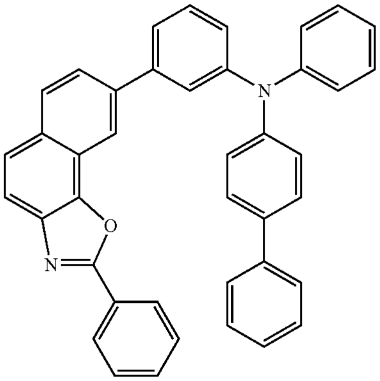
H2-130
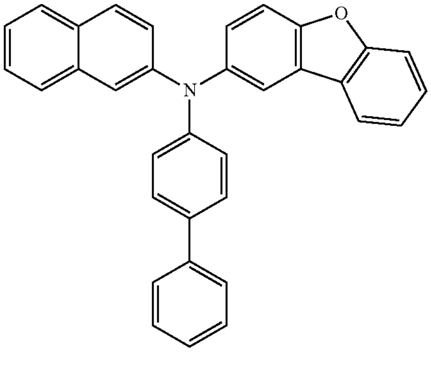

-continued
H2-131
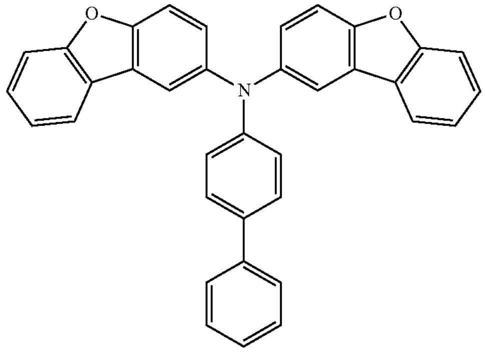
H2-132
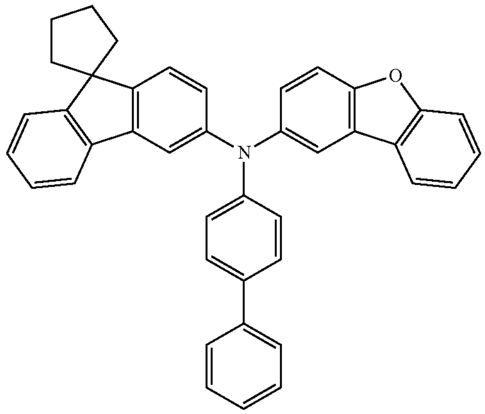
H2-133
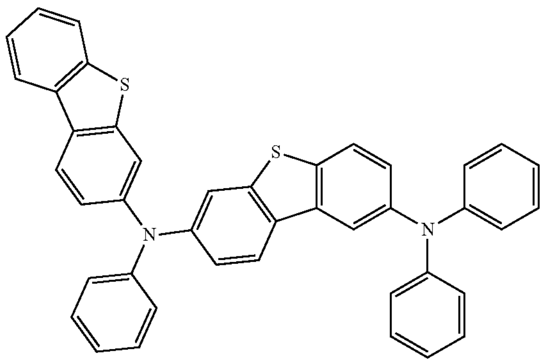
H2-134
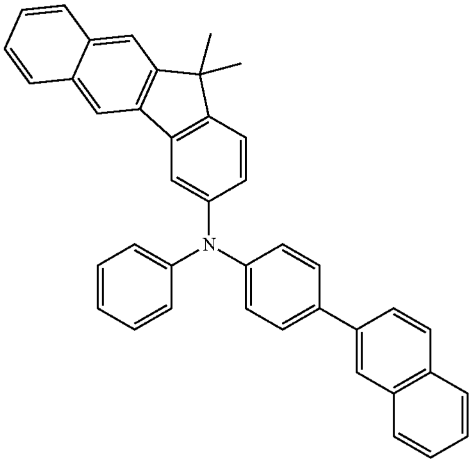
-continued
H2-135
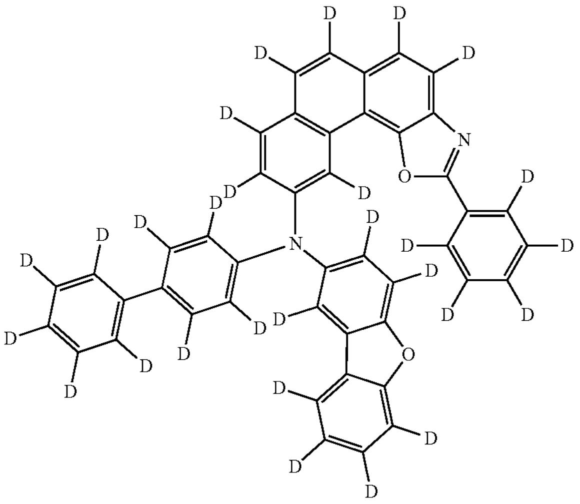
H2-136
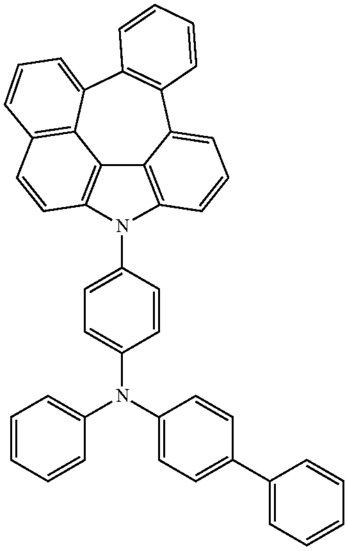
H2-137
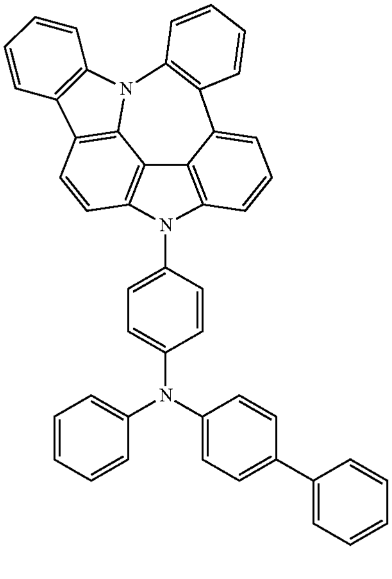

-continued
H2-138
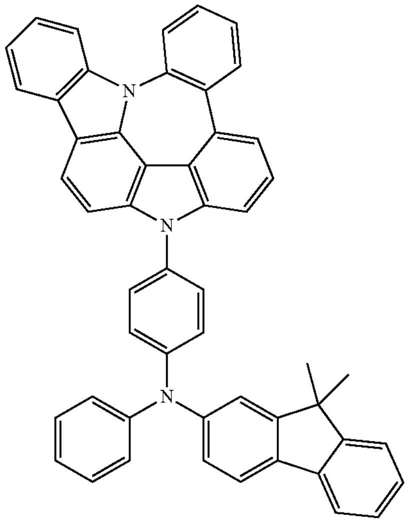
H2-139
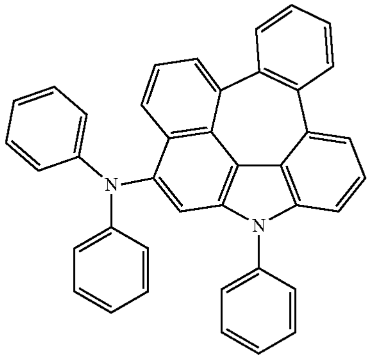
H2-140
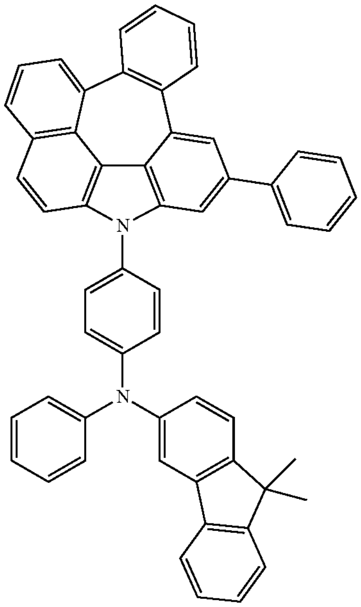
-continued
H2-141
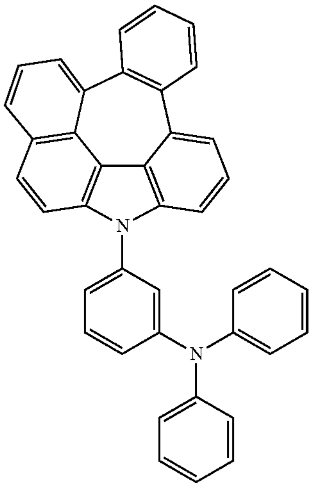
H2-142
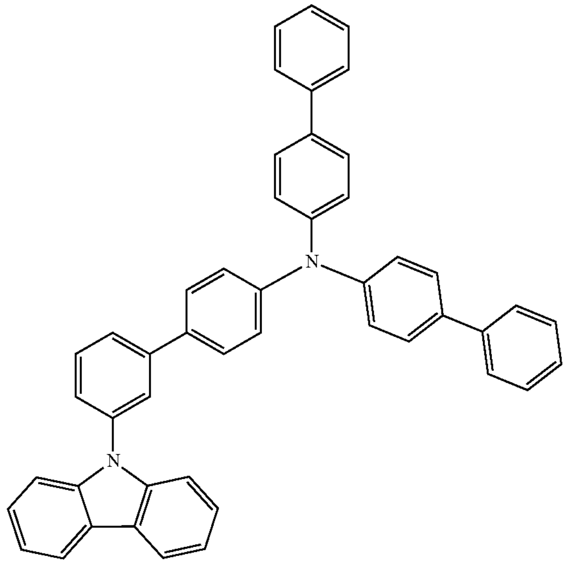
H2-143
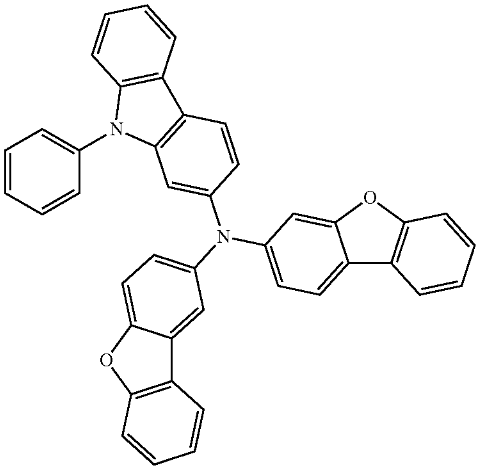

-continued
H2-144
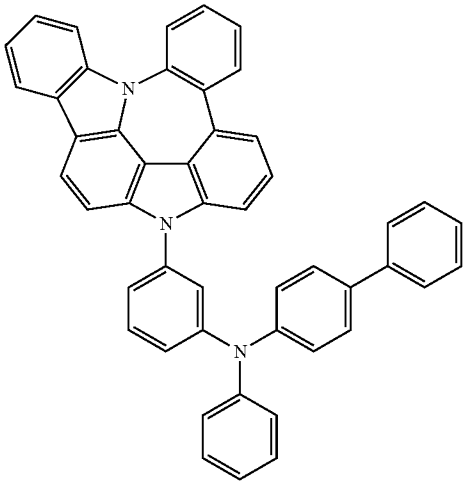
H2-145
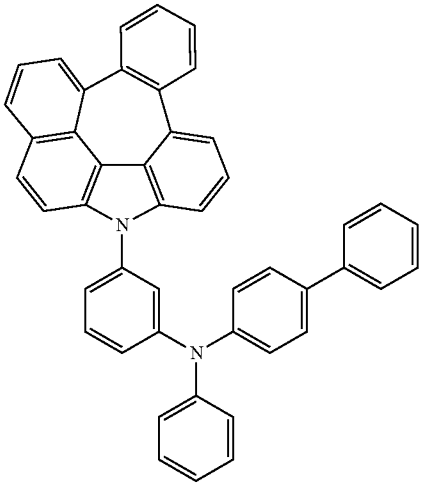
H2-146
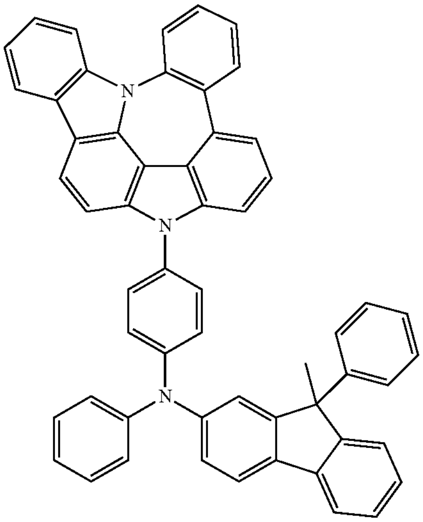
-continued
H2-147
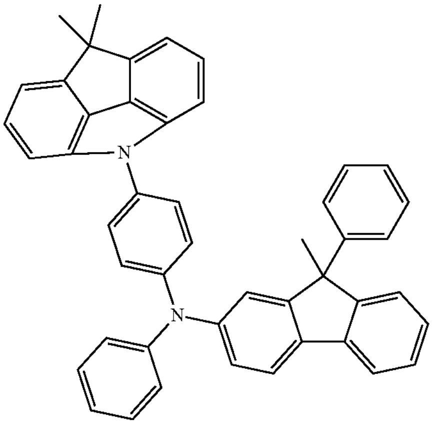
H2-148
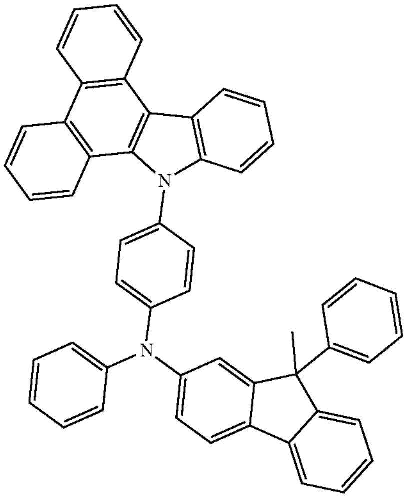
H2-149
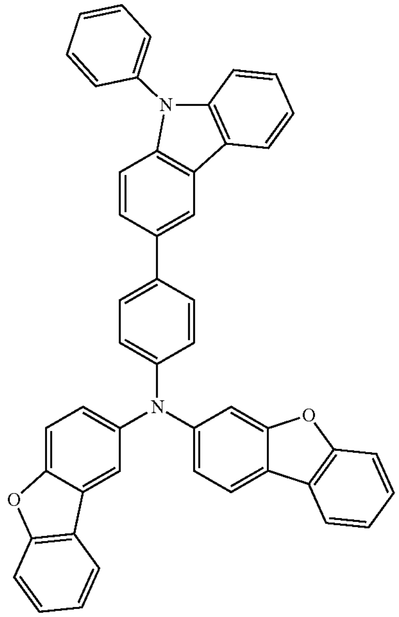

-continued
H2-150
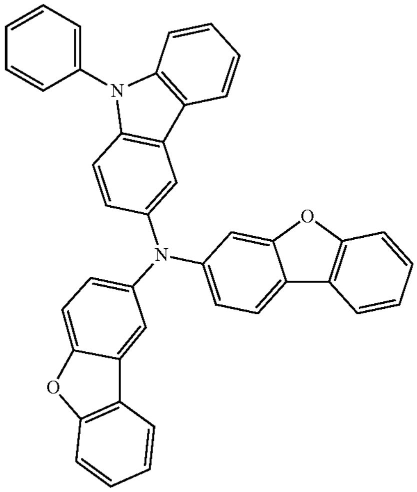
H2-151
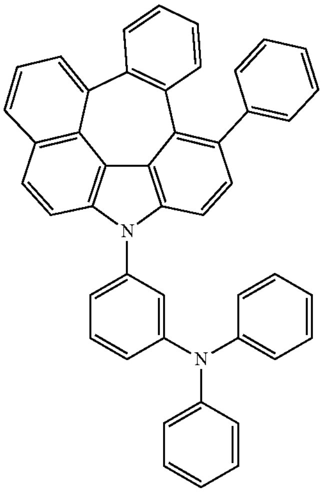
H2-152
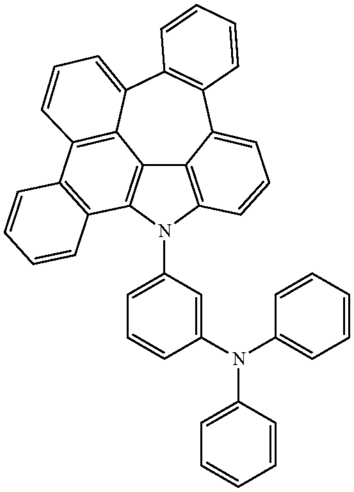
-continued
H2-153
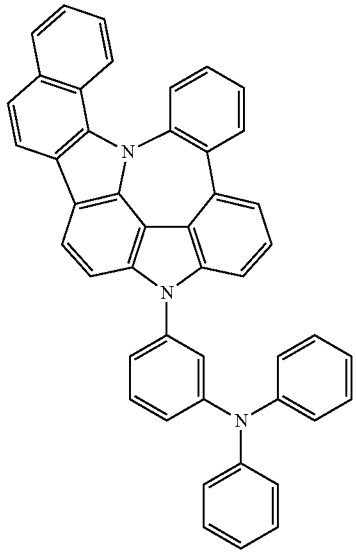
H2-154
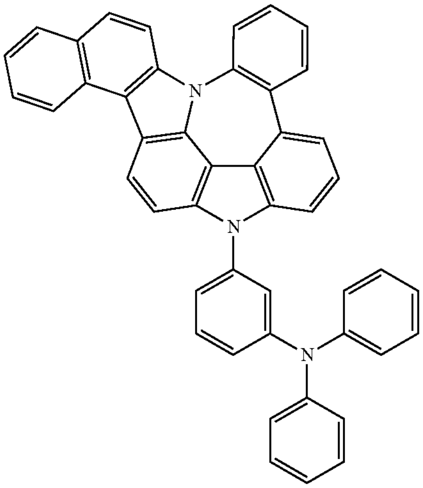
H2-155
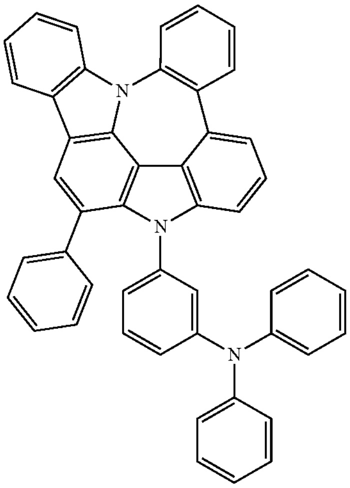

-continued

H2-156

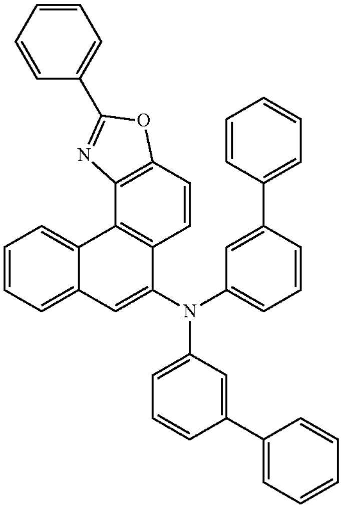

H2-157

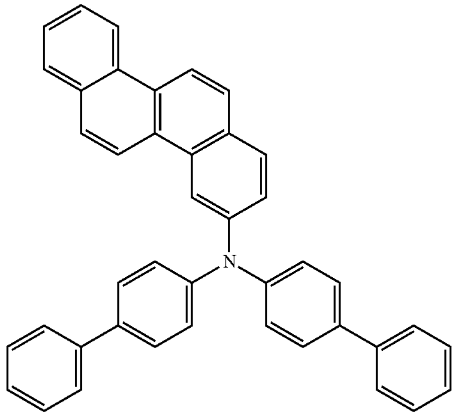

H2-158

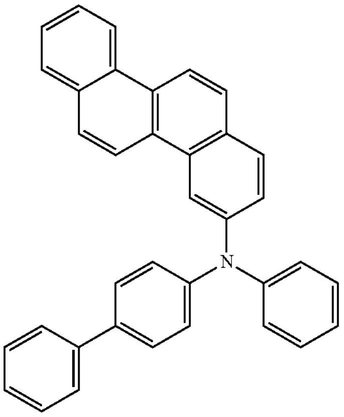

-continued

H2-159

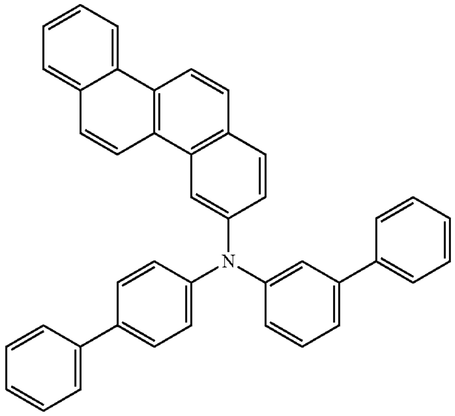

The combination of at least one of compounds H1-1 to H1-194 and at least one of compounds H2-1 to H2-159 may be used in an organic electroluminescent device.

In addition, the present disclosure provides an organic electroluminescent compound represented by the following formula 1'.

(1')

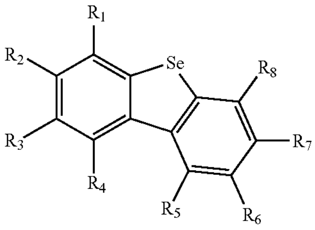

In formula 1', $R_1$ to $R_8$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30)aromatic ring(s), or $-(L)_a-$HAr, with the proviso that $R_1$ to $R_8$ are not 9,9-dimethylfluorenyl or 9,9-diphenylfluorenyl;

at least one of $R_1$ to $R_8$ is $-(L)_a-$HAr;

HAr represents a substituted or unsubstituted nitrogen-containing (3- to 20-membered)heteroaryl;

L each independently represents a single bond, a substituted or unsubstituted (C6-C30)arylene, or a substituted or unsubstituted (3- to 30-membered)heteroarylene; and a represents 1 or 2;

with the proviso that the case where any one of $R_1$ to $R_8$ is $-(L)_a-$HAr; a is 1; L is a substituted or unsubstituted phenylene, or a substituted or unsubstituted biphenylene; and HAr is a triazinyl substituted with any two each independently selected from the group consisting of a phenyl(s), a biphenyl(s), a terphenyl(s), a 9,9-dimethylfluorenyl(s), and a pyridyl(s) substituted with a phenyl(s) is excluded;

with the proviso that the case where any one of $R_1$ to $R_8$ is $-(L)_a$-HAr; a is 1; L is a single bond or a pyridylene; HAr is a triazinyl substituted with any two each independently selected from the group consisting of a phenyl(s) unsubstituted or substituted with deuterium or a 9,9-dimethylfluorenyl(s), a biphenyl(s) unsubstituted or substituted with deuterium, a pyridyl(s) substituted with a phenyl(s), a 9,9-dimethylfluorenyl(s) unsubstituted or substituted with deuterium, a 9,9-dimethylazafluorenyl(s), a spiro[cyclohexane-1,9'-fluoren]yl(s), and a 9,9'-spirobifluorenyl(s); and any one or two of the remaining $R_1$ to $R_8$ is an unsubstituted phenyl or an unsubstituted biphenyl is excluded; and with the proviso that the organic electroluminescent compounds having the following structures are excluded.

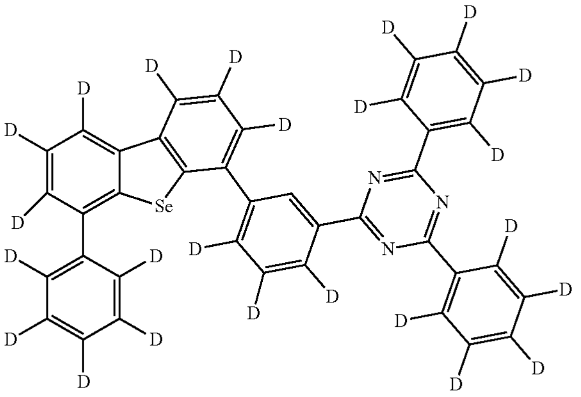

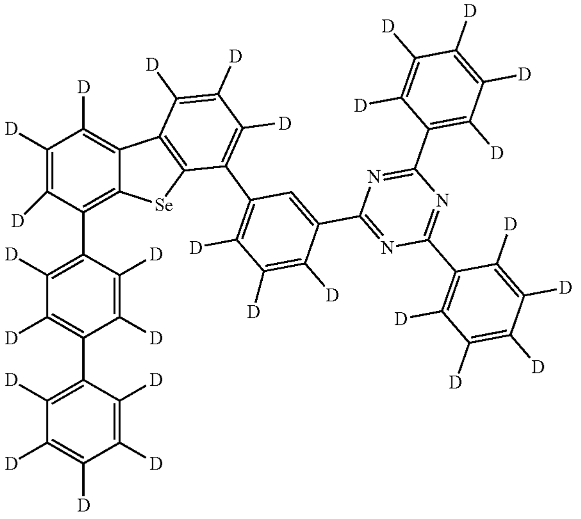

-continued

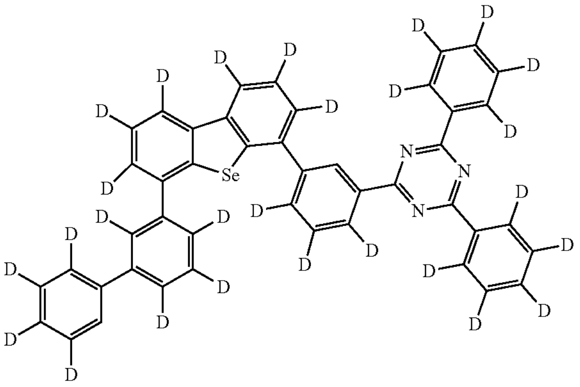

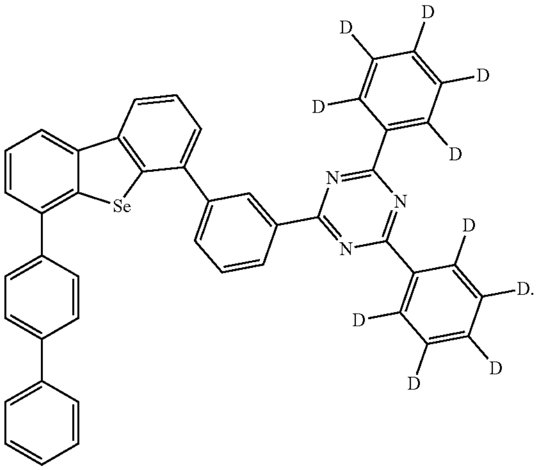

According to one embodiment of the present disclosure, the formula 1' may be represented by any one of the following formulas 1'-1 to 1'-4.

(1'-1)

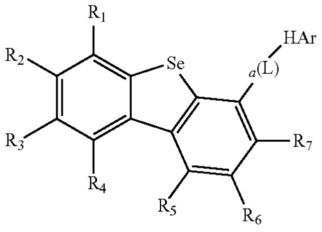

(1'-2)

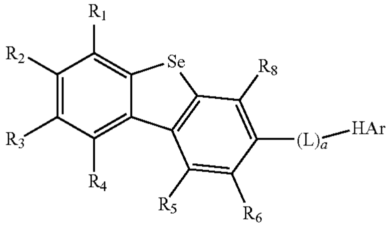

-continued (1'-3)

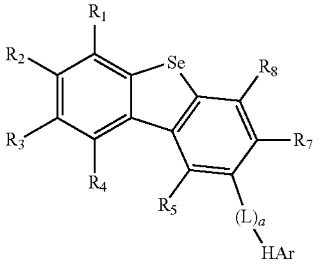

(1'-4)

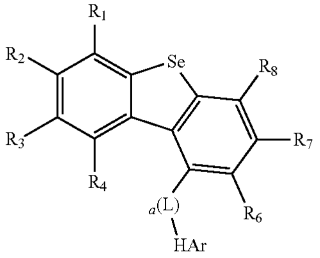

In formulas 1'-1 to 1'-4, $R_1$ to $R_8$, L, HAr, and a are as defined in formula 1'.

According to one embodiment of the present disclosure, HAr of formula 1' may be selected from the following formulas 1'-5 to 1'-7.

(1'-5)

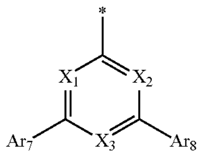

(1'-6)

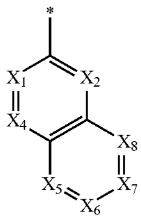

(1'-7)

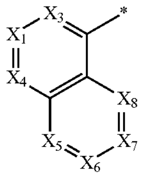

In formulas 1'-5 to 1'-7, $X_1$ to Xa each independently represent $CR_{25}$ or N;

$R_{25}$, $Ar_7$, and $Ar_8$ each independently represent hydrogen, deuterium, a substituted or unsubstituted (C1-C30) alkyl, a substituted or unsubstituted (C6-C30)aryl, or a substituted or unsubstituted (3- to 30-membered)heteroaryl, wherein $R_{25}$ may be linked to an adjacent substituent to form a ring(s); and

* represents a site linked to dibenzoselenophene.

The compound represented by formula 1' may be at least one selected from the following compounds, but is not limited thereto.

H1-1

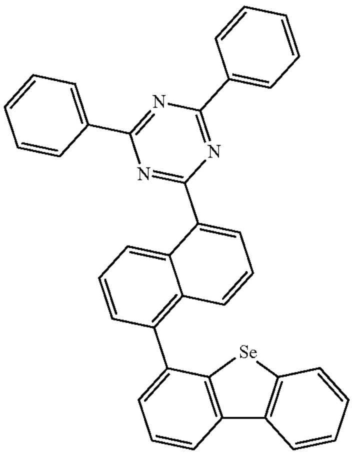

H1-2

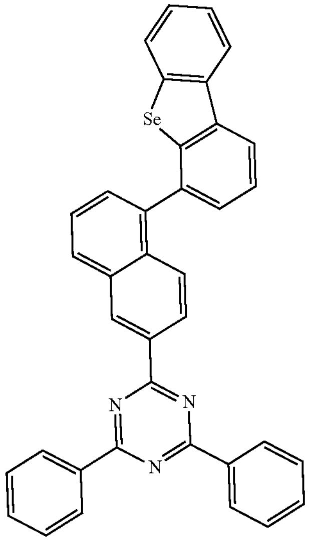

H1-3

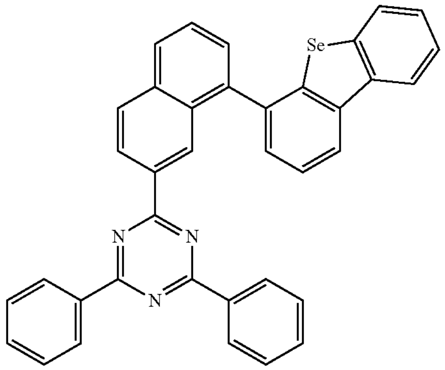

-continued
H1-4
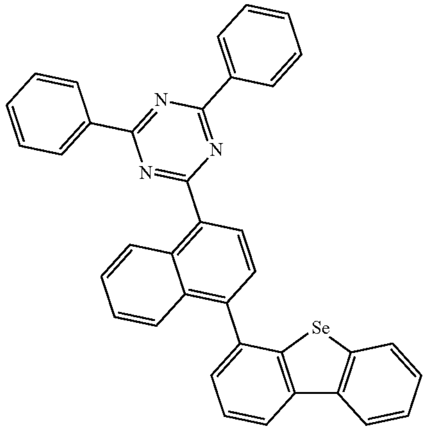
H1-5
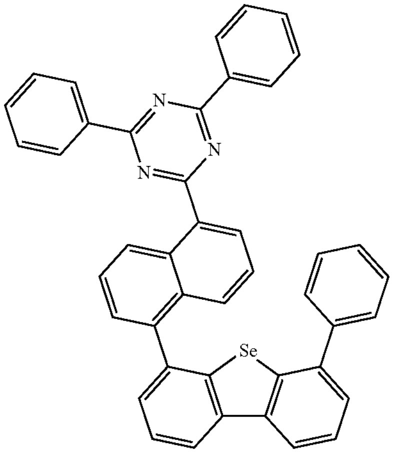
H1-6
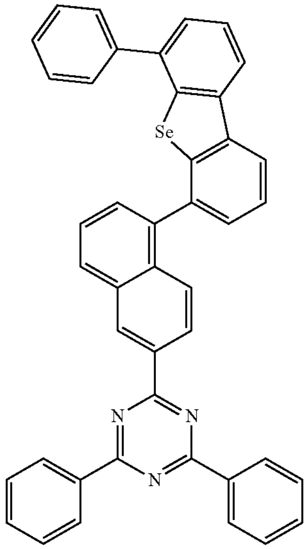
-continued
H1-7
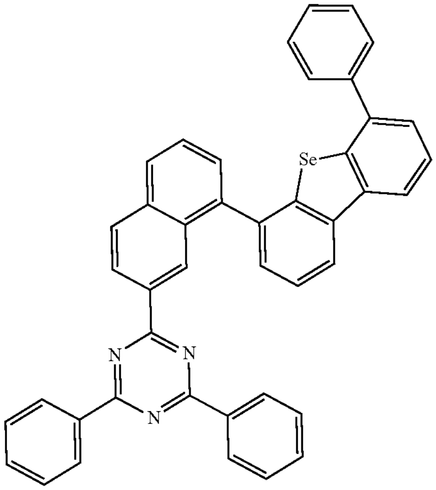
H1-8
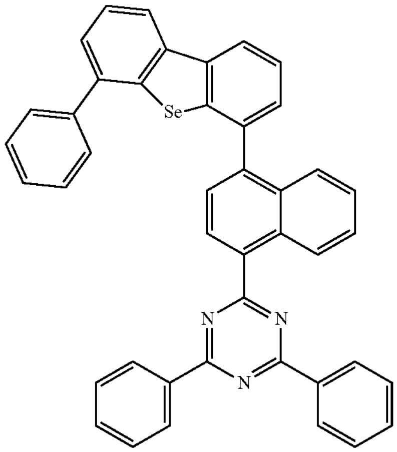
H1-9
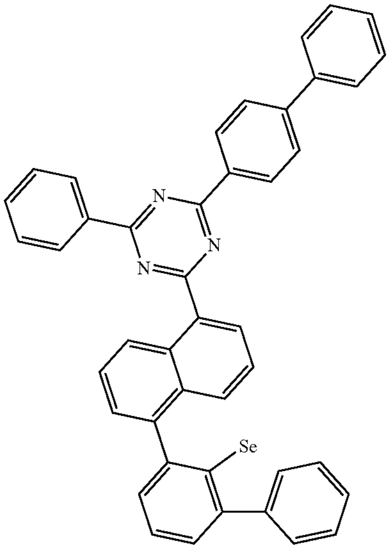

-continued
H1-10
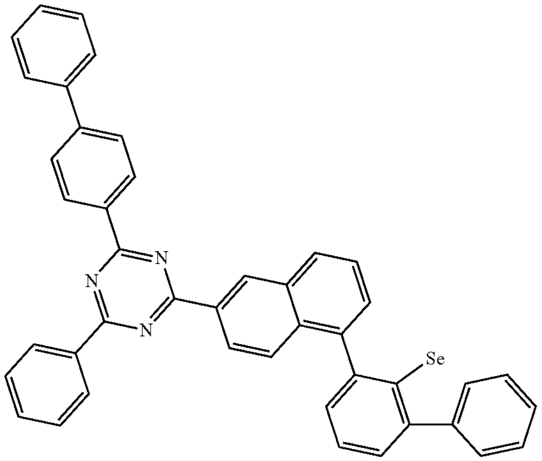
H1-11
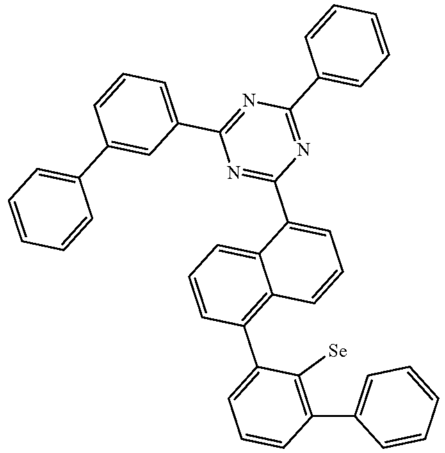
H1-12
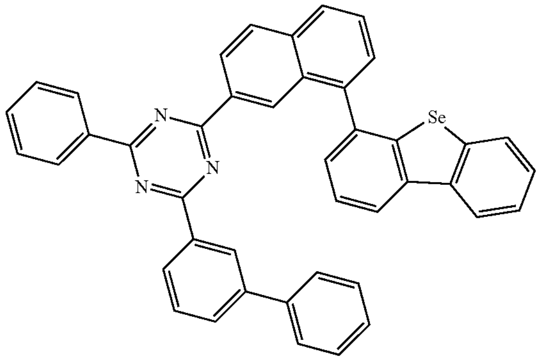
-continued
H1-13
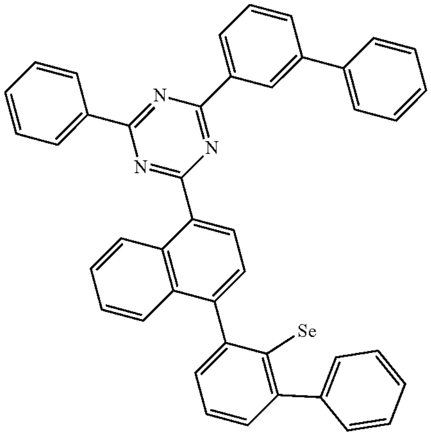
H1-14
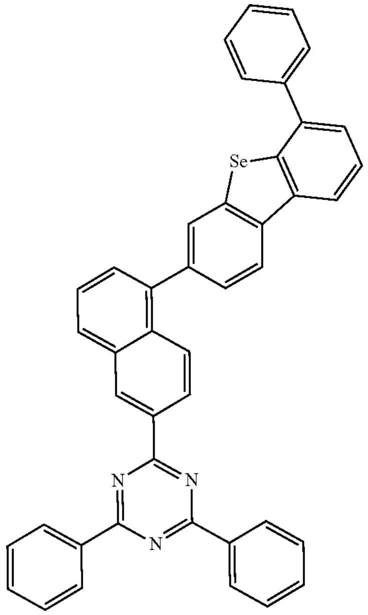
H1-15
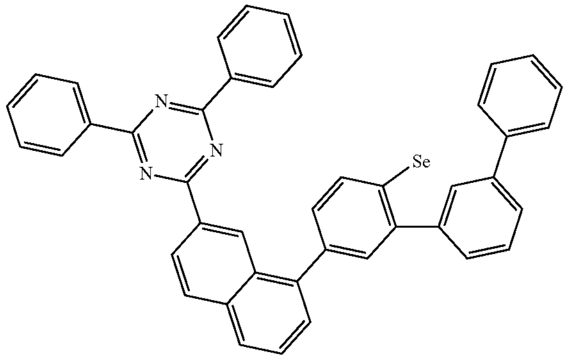

-continued
H1-16
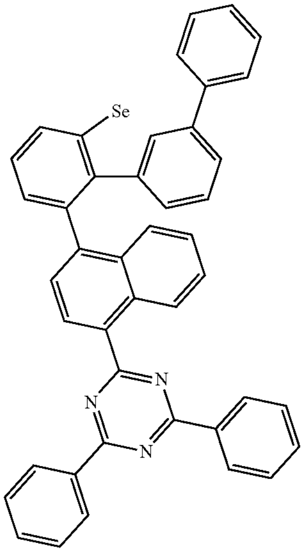
H1-17
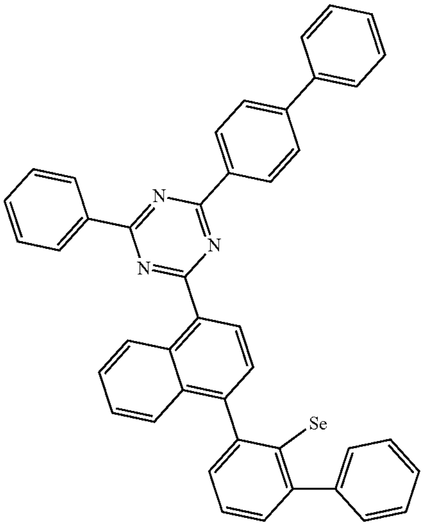
H1-18
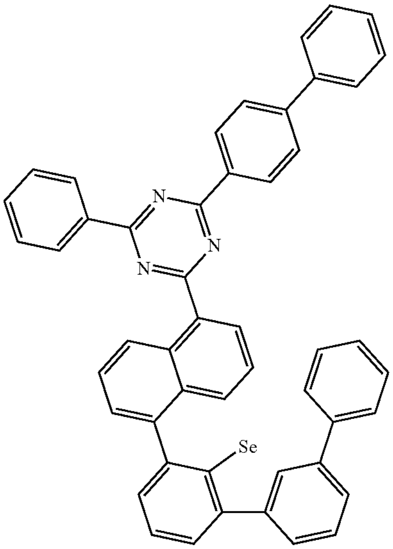
-continued
H1-19
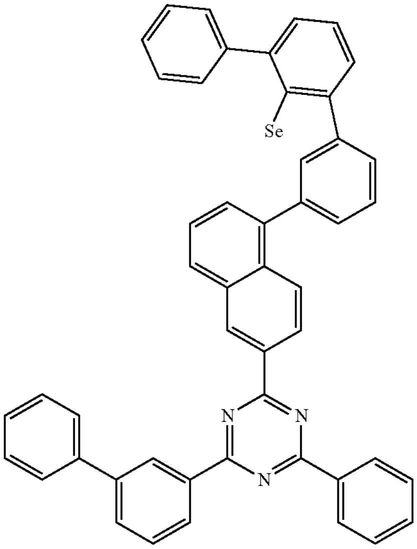
H1-20
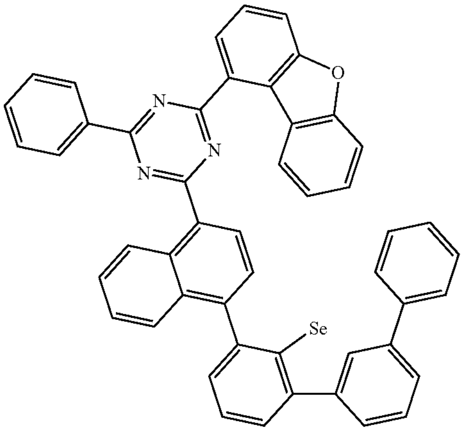
H1-21
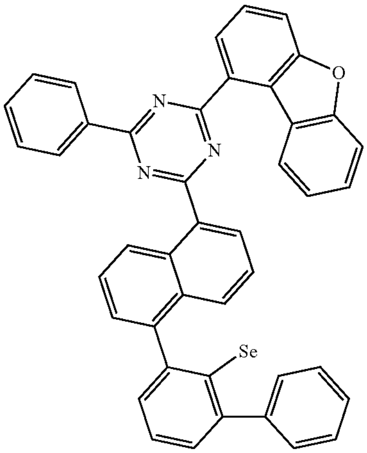

-continued
H1-22
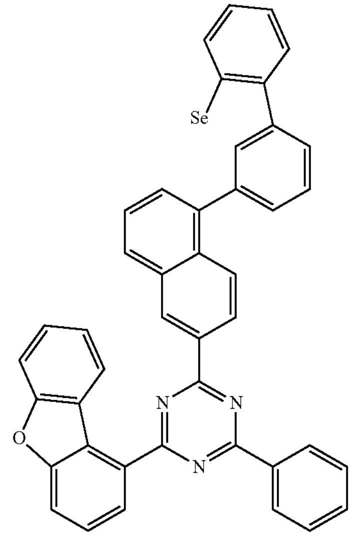
H1-23
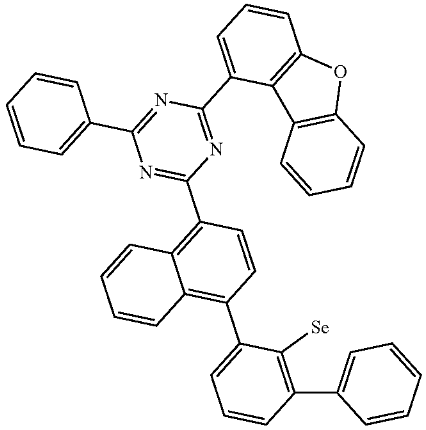
H1-24
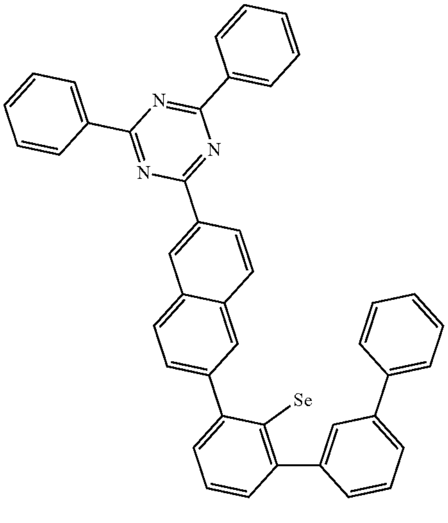
-continued
H1-25
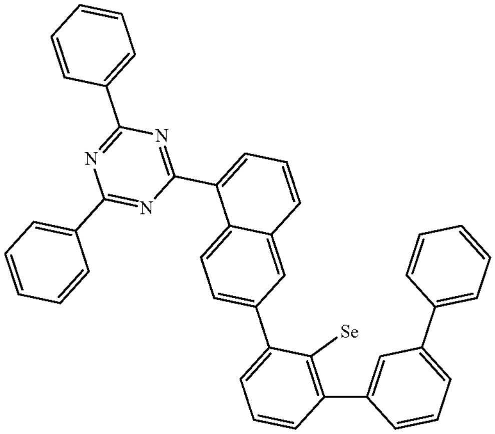
H1-26
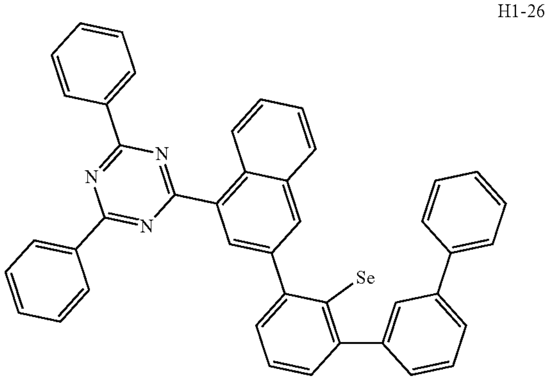
H1-27
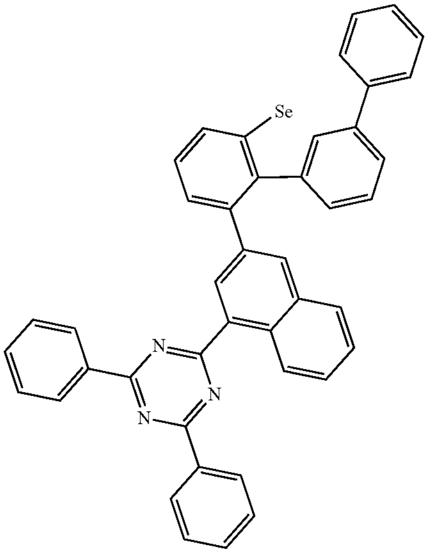

-continued
H1-28
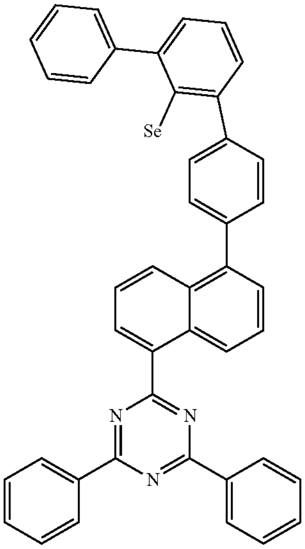
H1-29
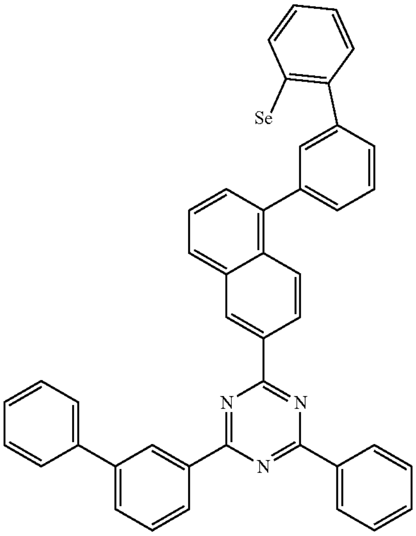
H1-30
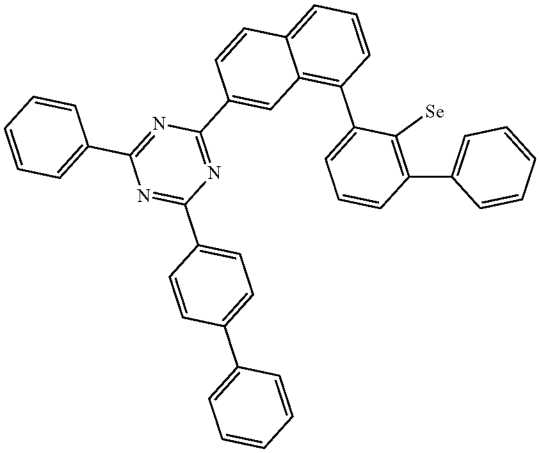
-continued
H1-31
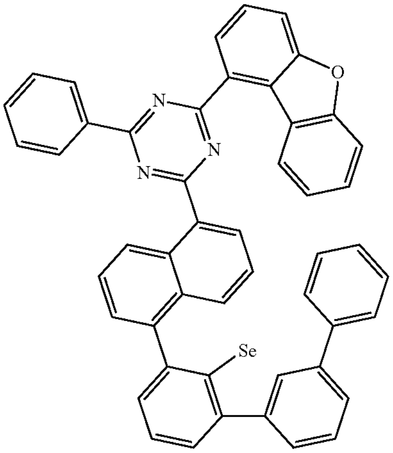
H1-32
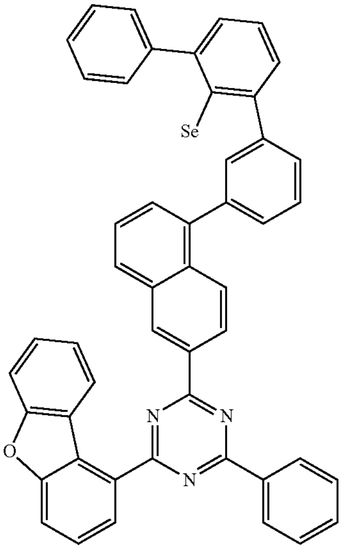
H1-33
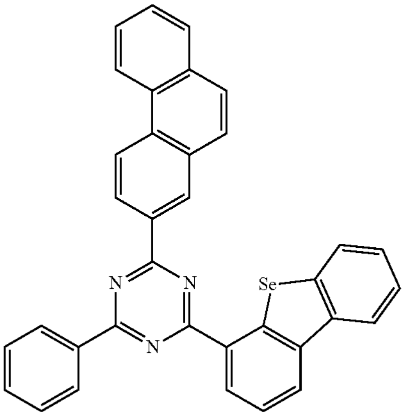

-continued
H1-34
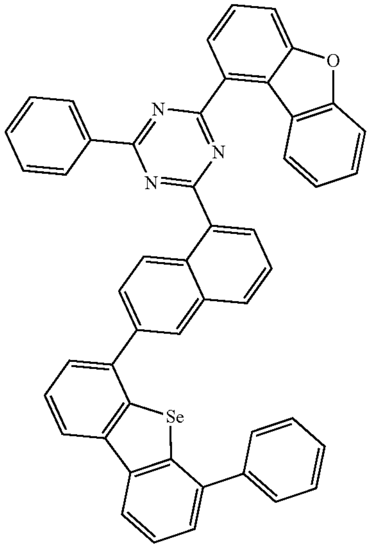
H1-35
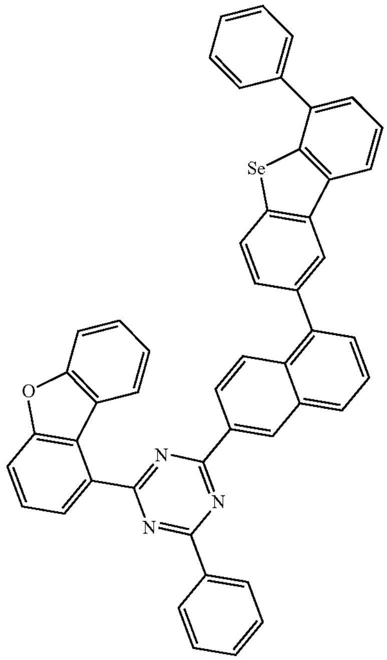
H1-36
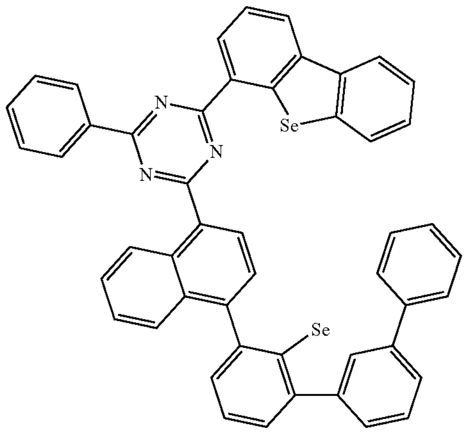
-continued
H1-37
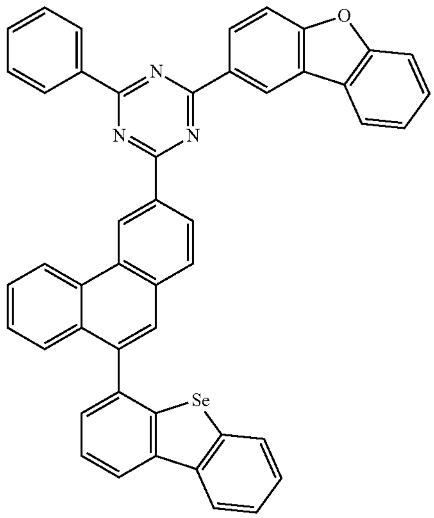
H1-38
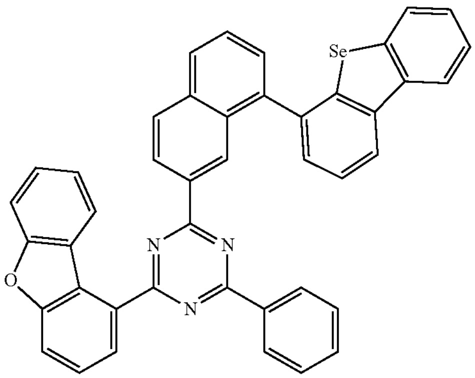
H1-39
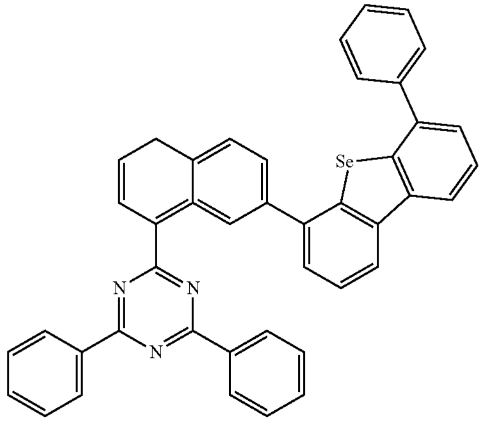

-continued
H1-40
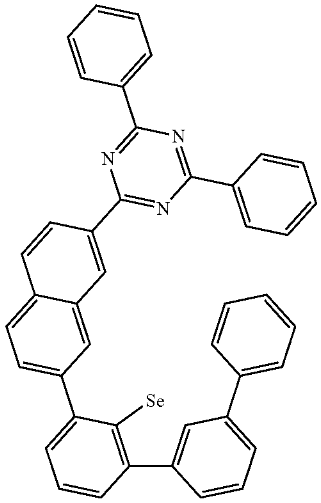
H1-41
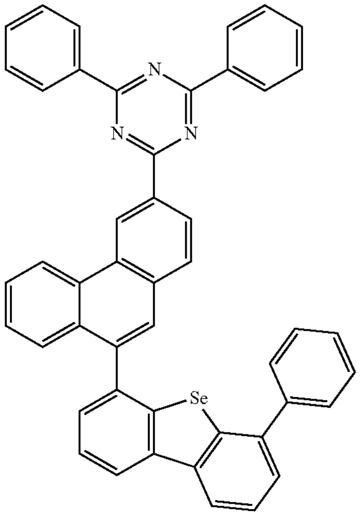
H1-42
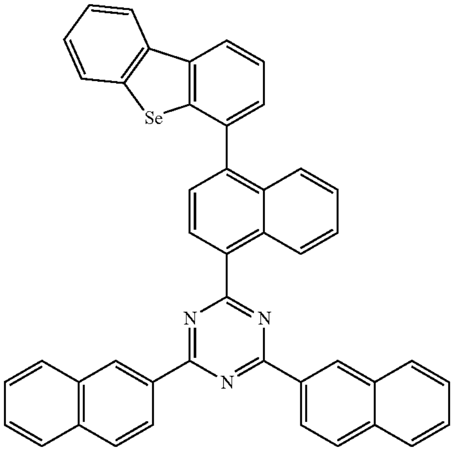
-continued
H1-43
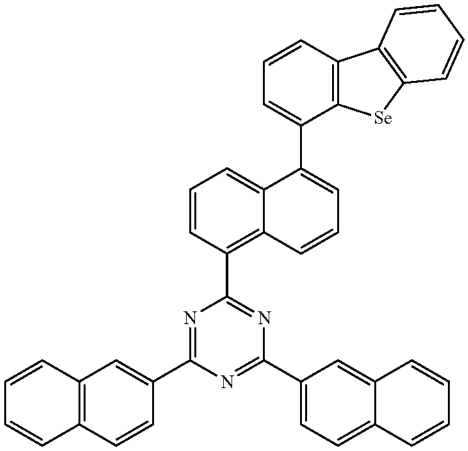
H1-44
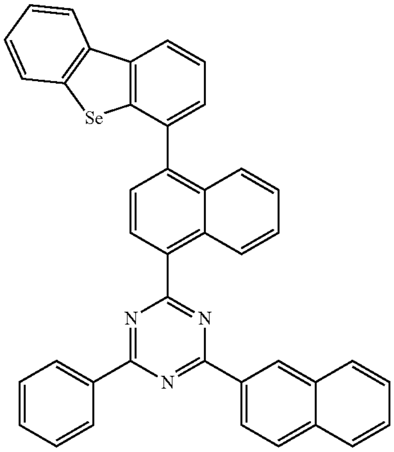
H1-45
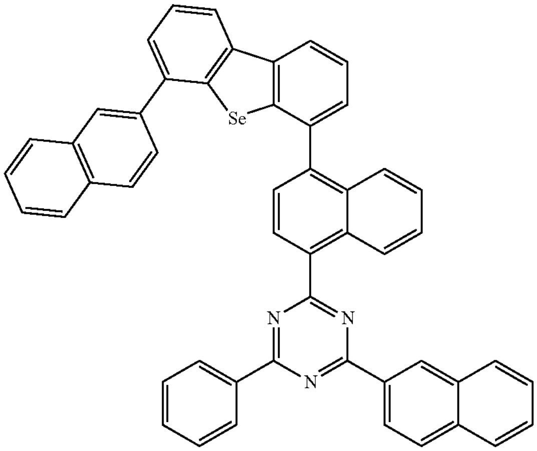

-continued
H1-47
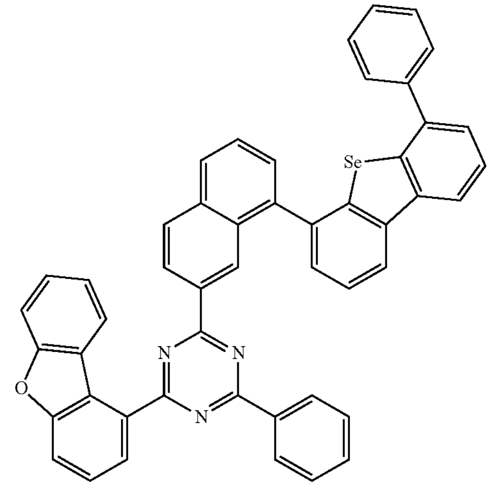
H1-48
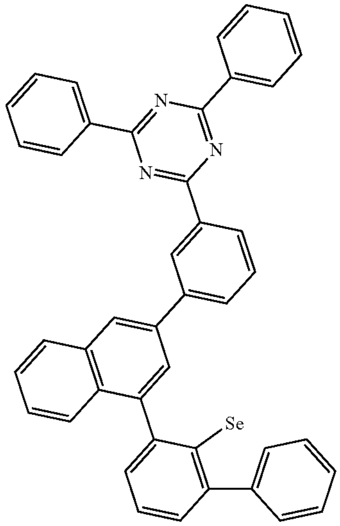
H1-49
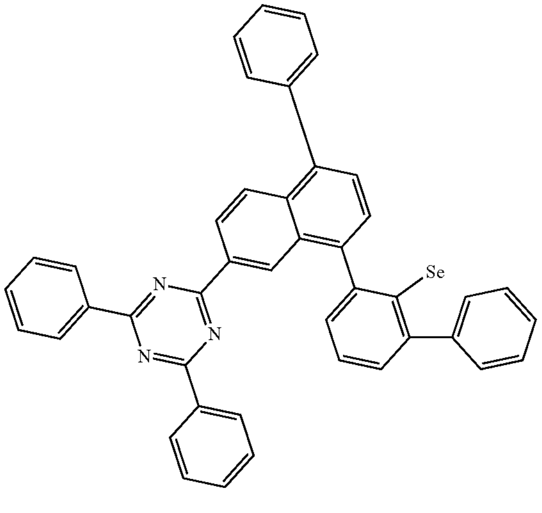
-continued
H1-50
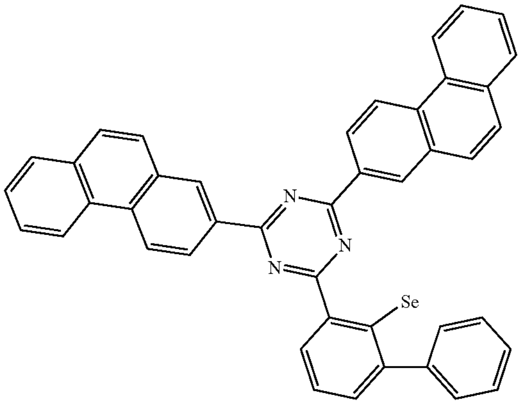
H1-51
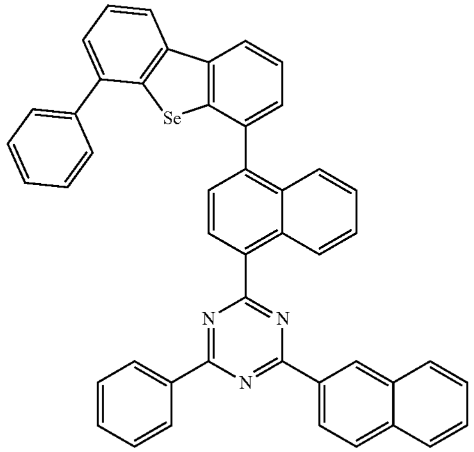
H1-52
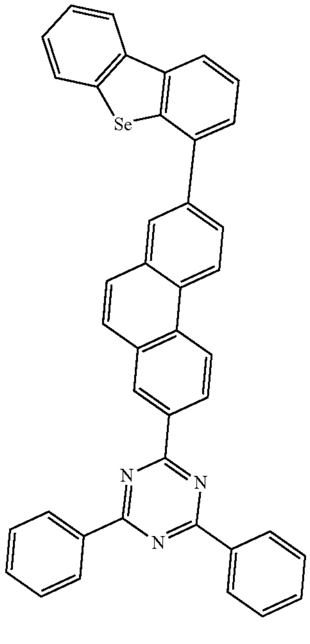

-continued
H1-53
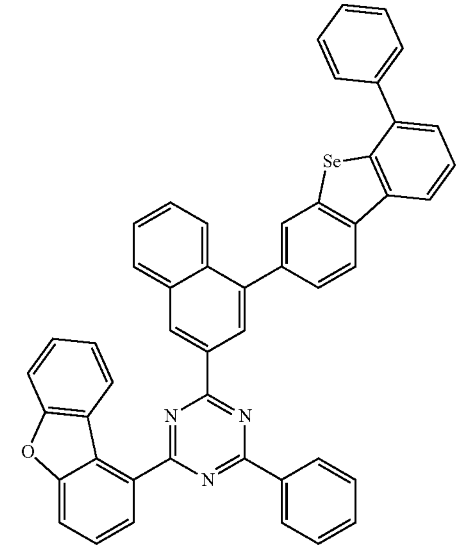
H1-54
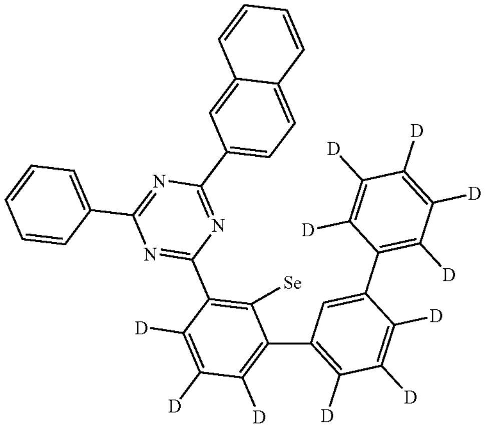
H1-55
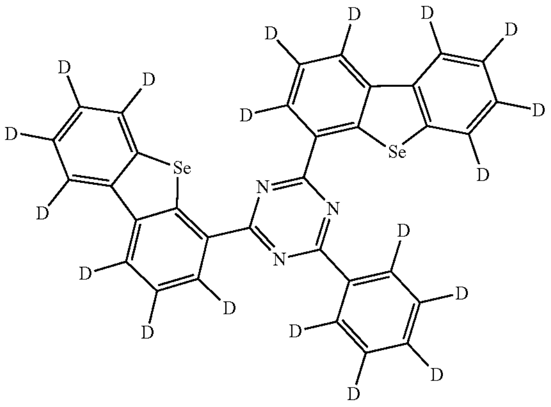
-continued
H1-56
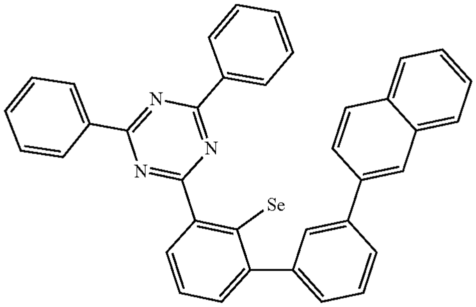
H1-57
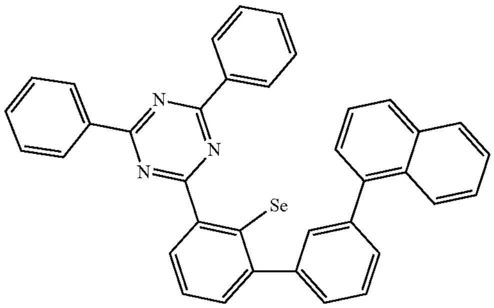
H1-58
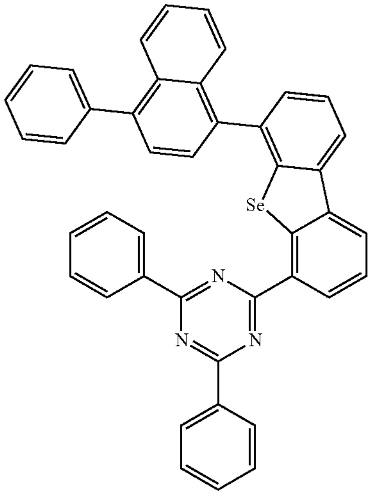
H1-59
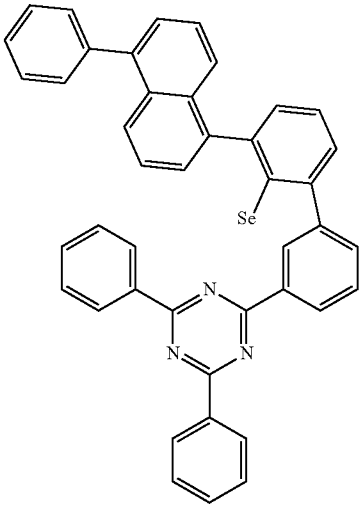

-continued
H1-60
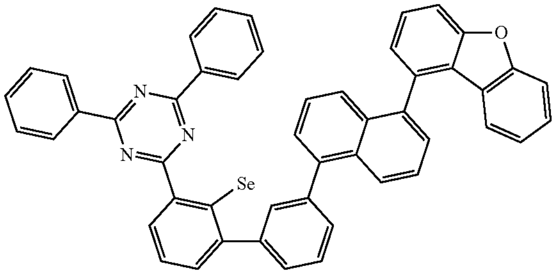
H1-61
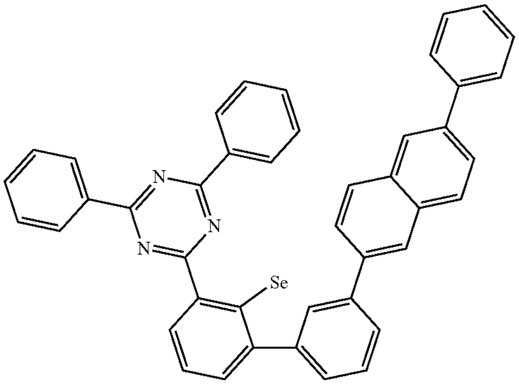
H1-62
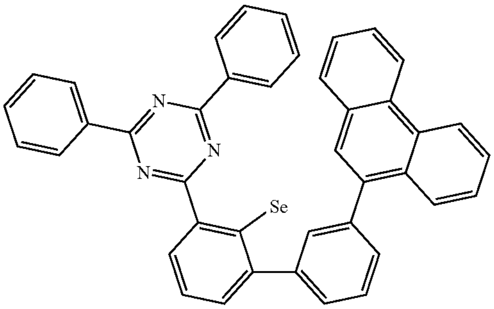
H1-63
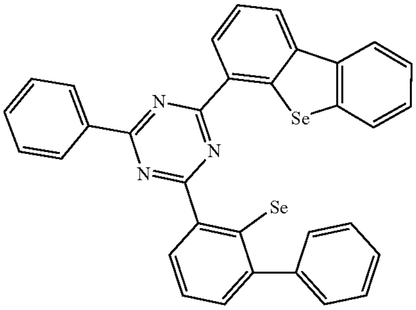
-continued
H1-64
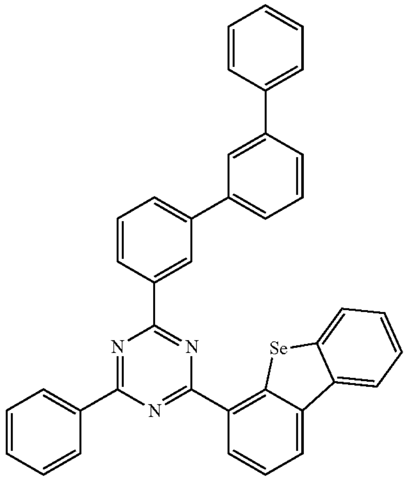
H1-65
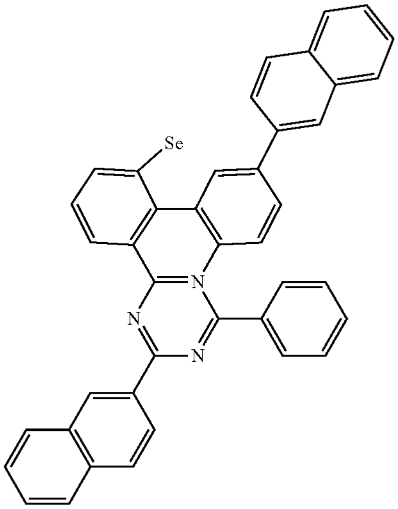
H1-66
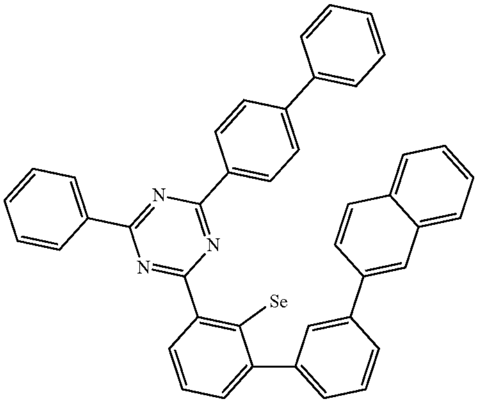

-continued
H1-67
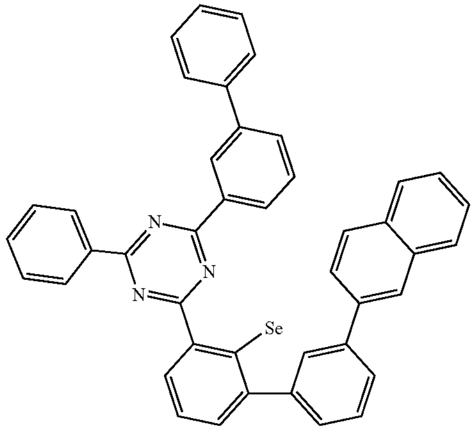
H1-68
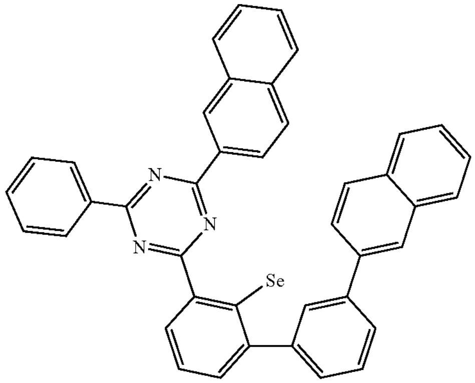
H1-69
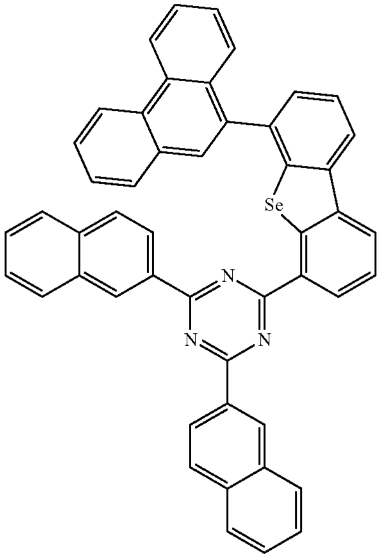
-continued
H1-70
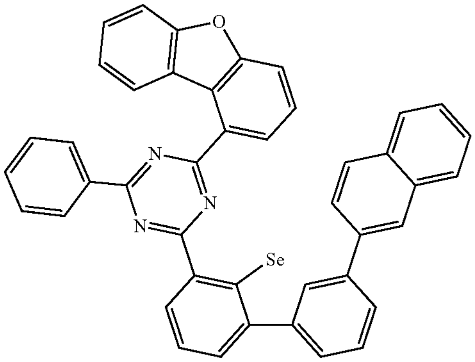
H1-71
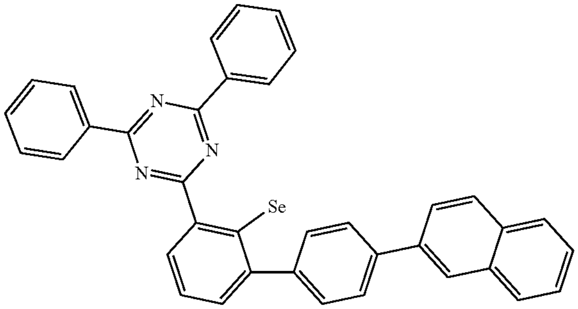
H1-72
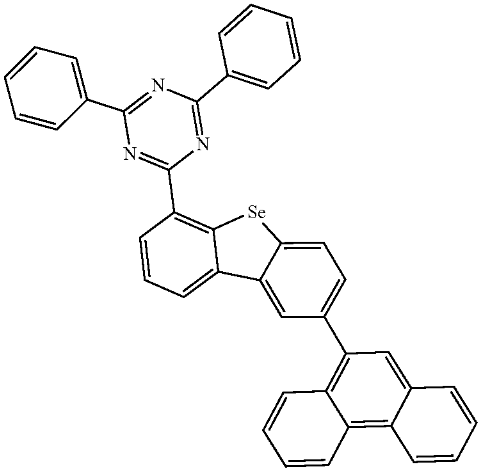

-continued
H1-73
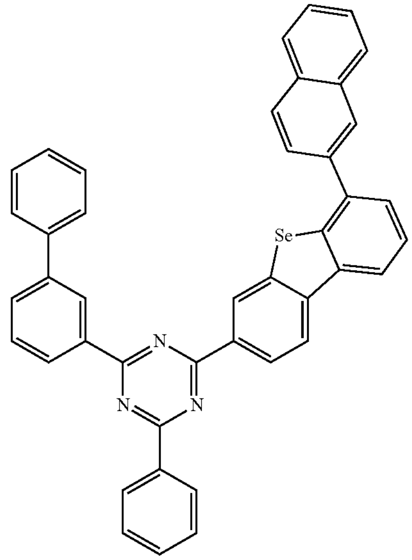
H1-74
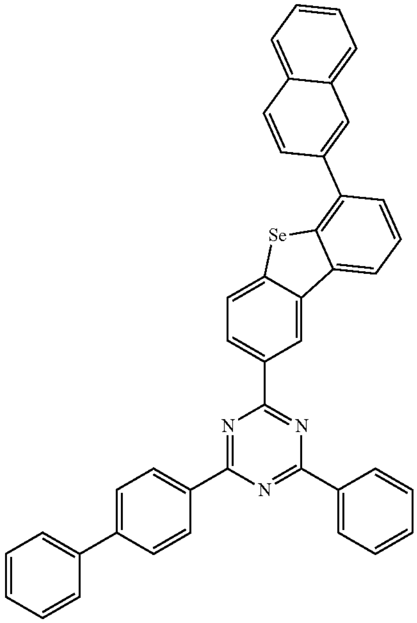
-continued
H1-75
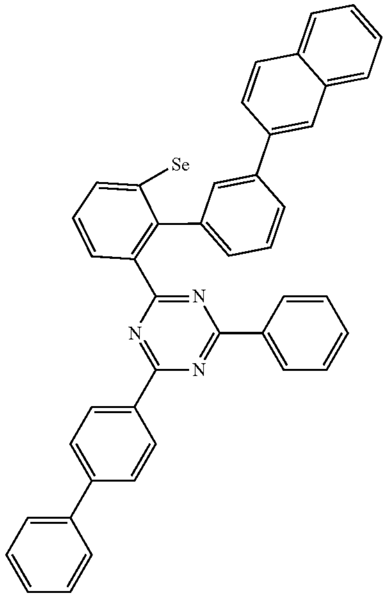
H1-76
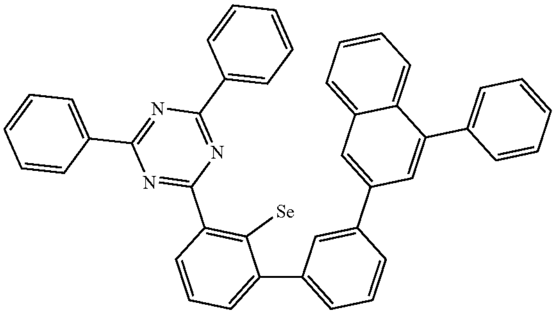
H1-77
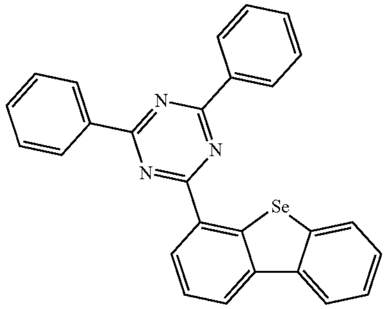
H1-78
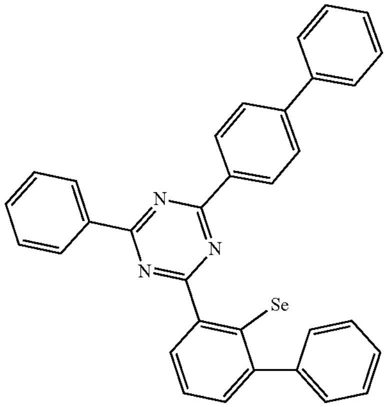

-continued
H1-83
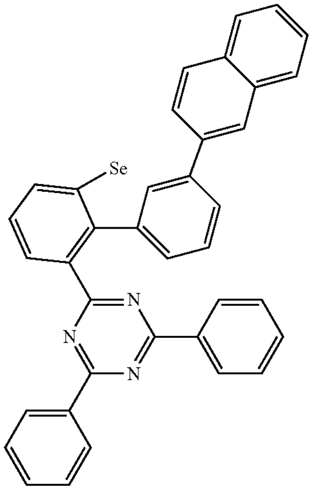
H1-84
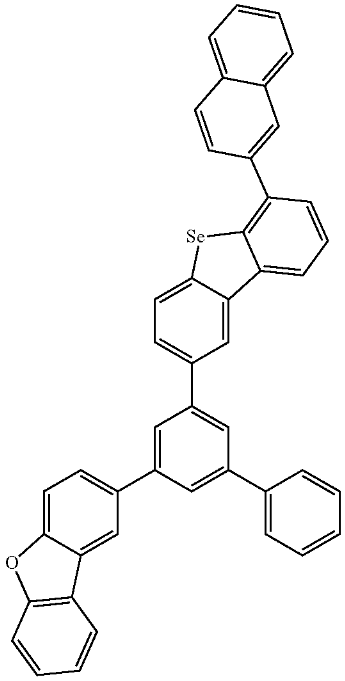
-continued
H1-85
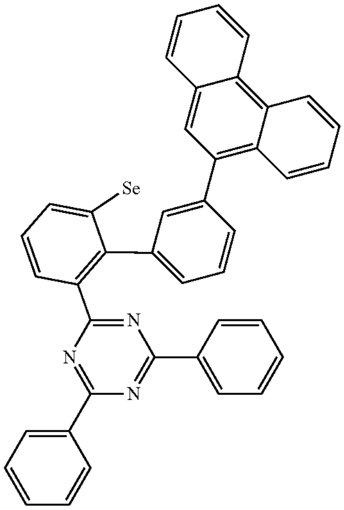
H1-86
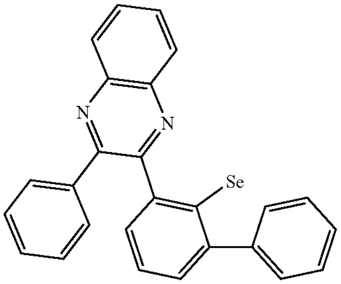
H1-87
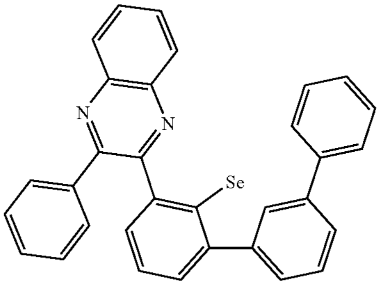
H1-88
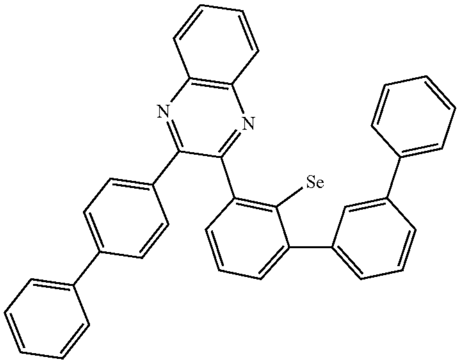

-continued
H1-89
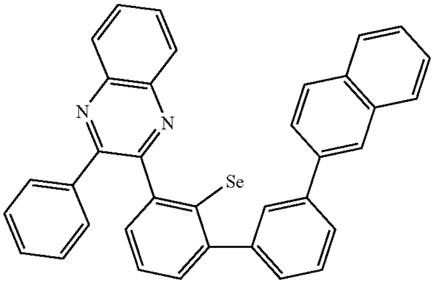
H1-90
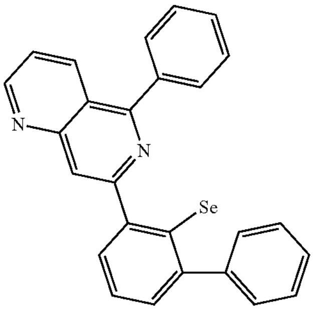
H1-91
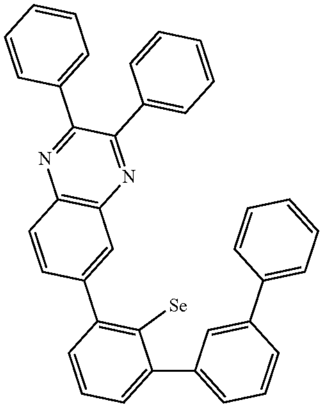
H1-92
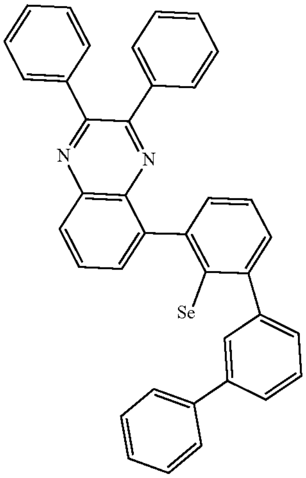
-continued
H1-93
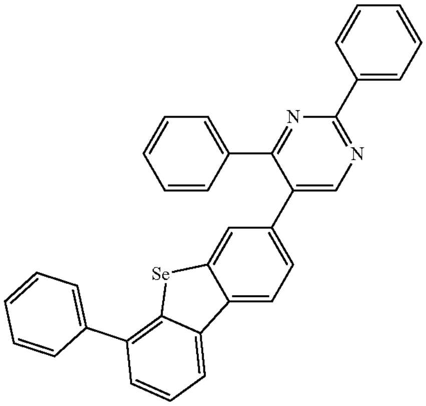
H1-94
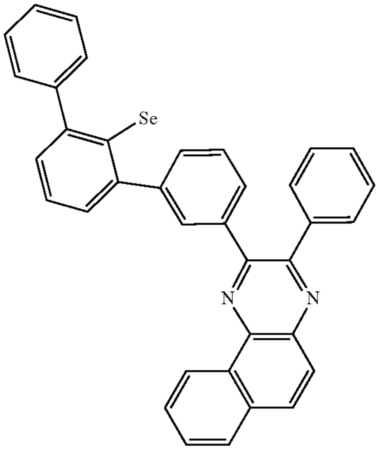
H1-95
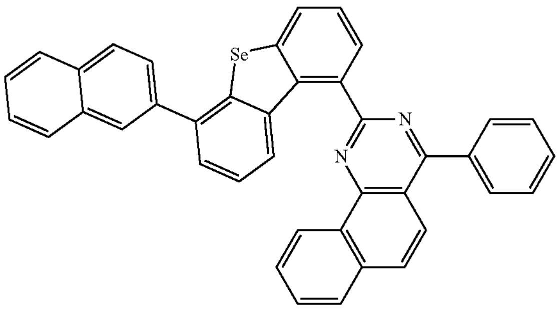

-continued
H1-96
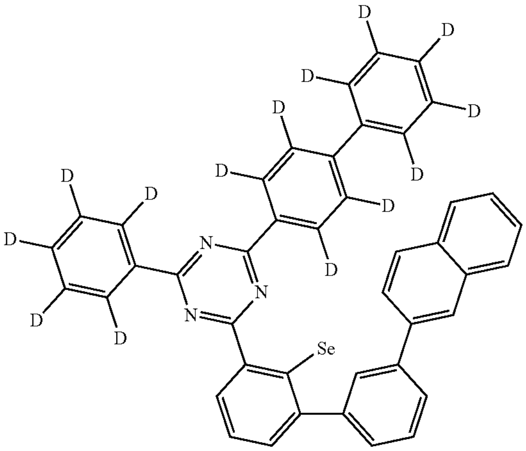
H1-97
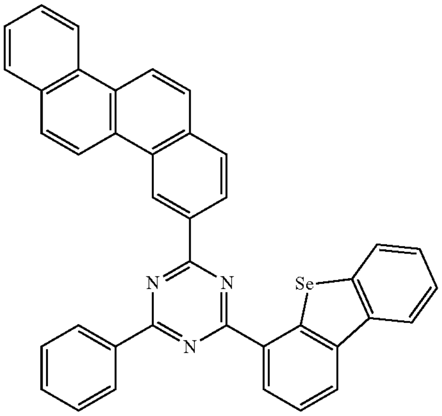
H1-98
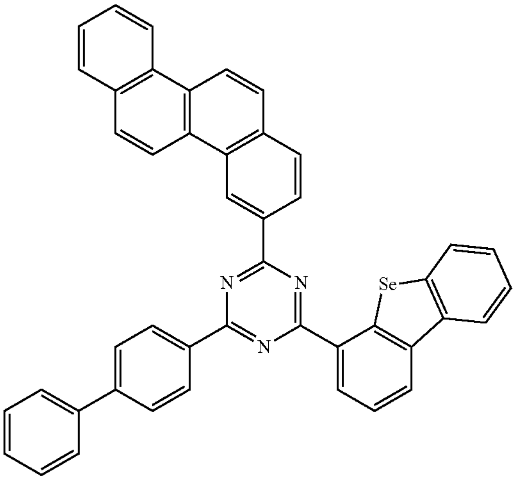
-continued
H1-99
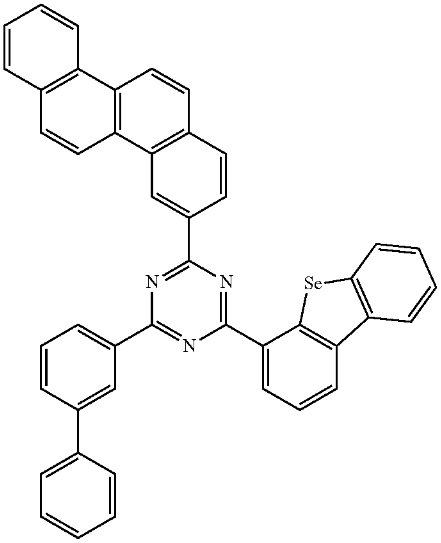
H1-100
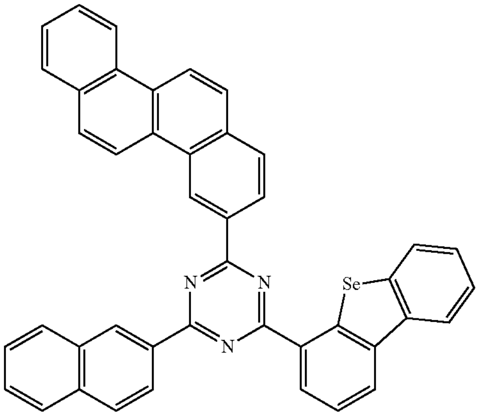
H1-101
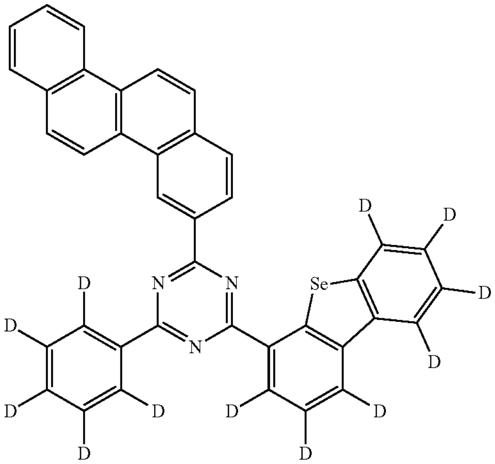

-continued
H1-106
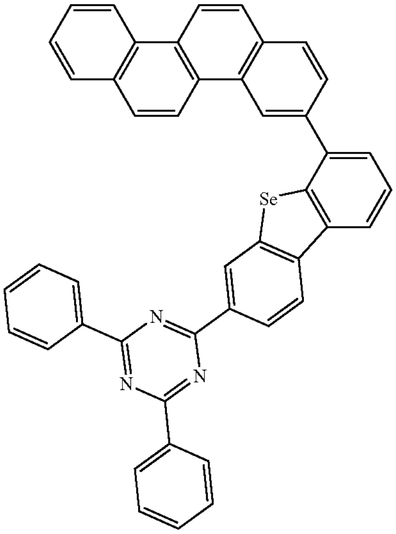
H1-107
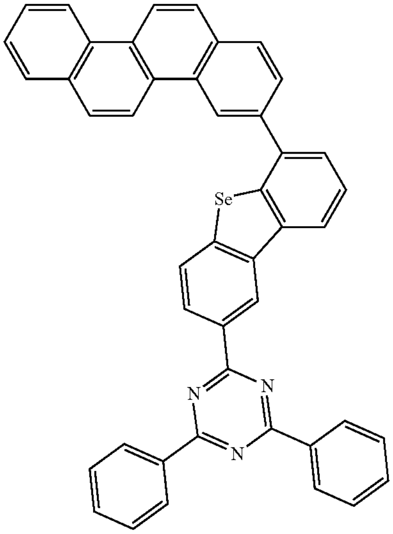
H1-108
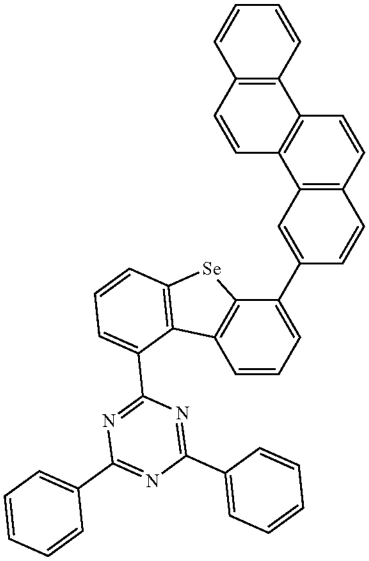
-continued
H1-109
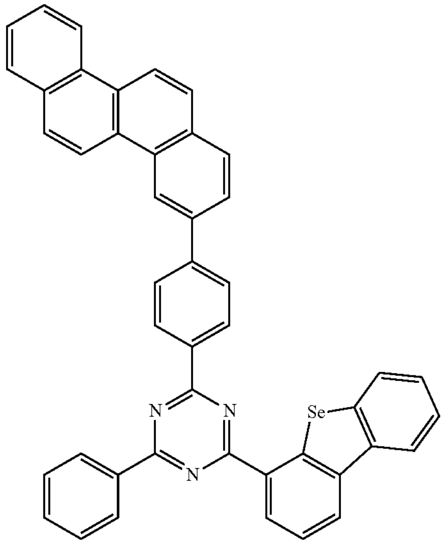
H1-110
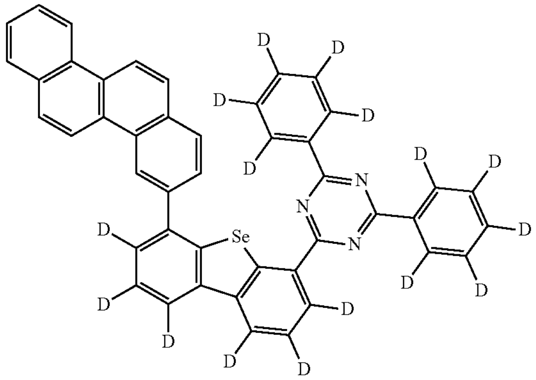
H1-111
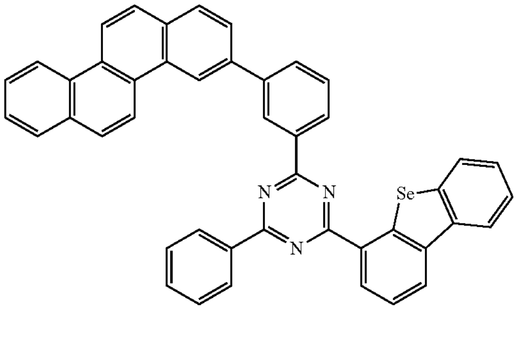

-continued
H1-112
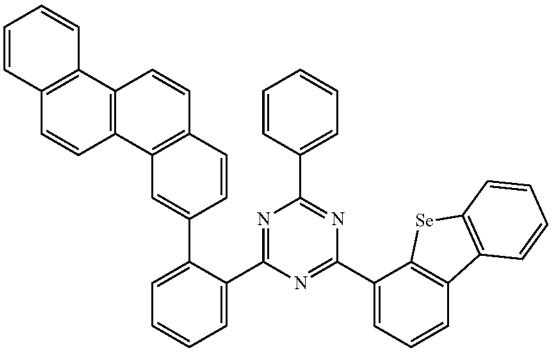
H1-113
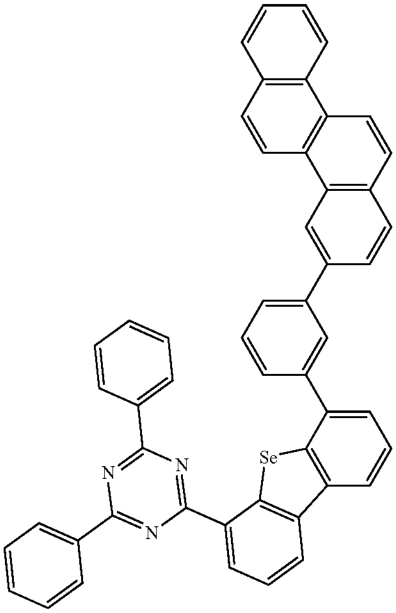
H1-114
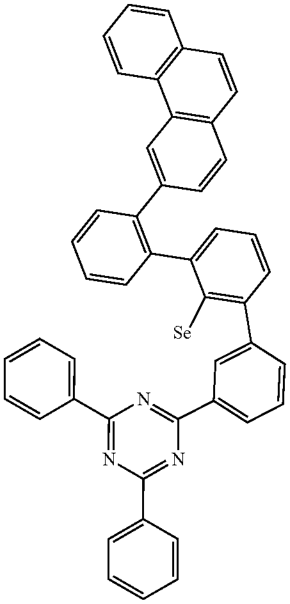
-continued
H1-115
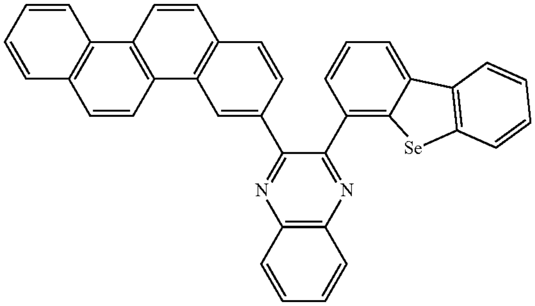
H1-116
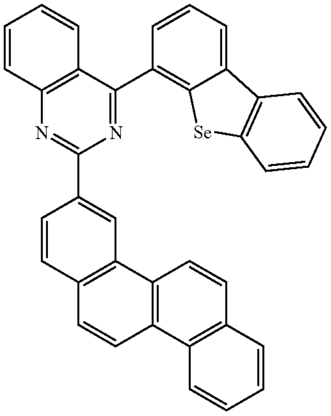
H1-117
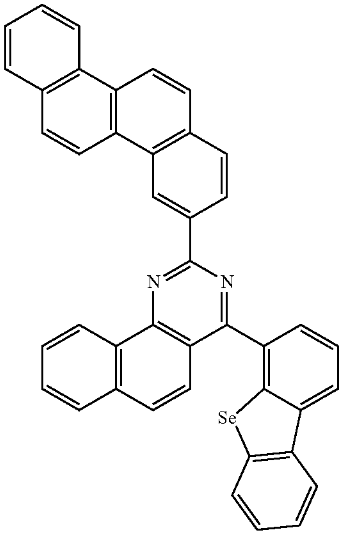

-continued
H1-118
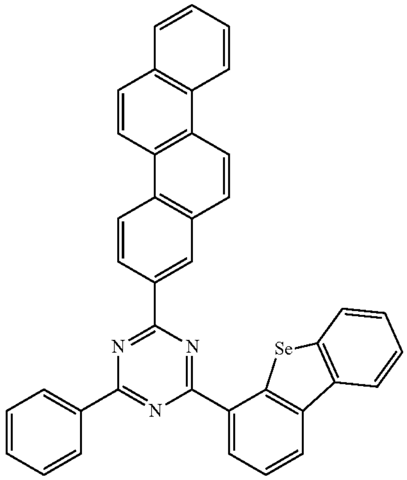
H1-119
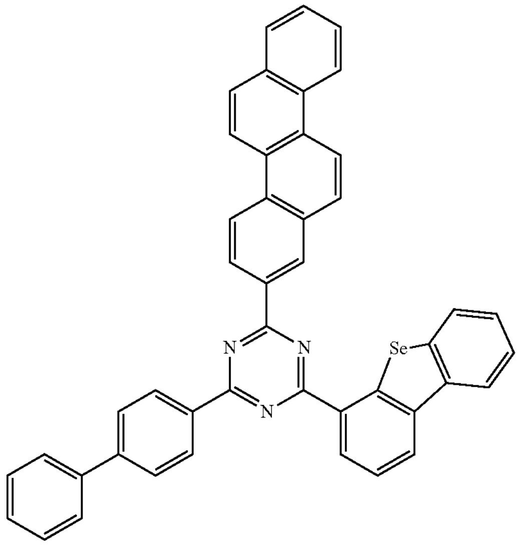
H1-120
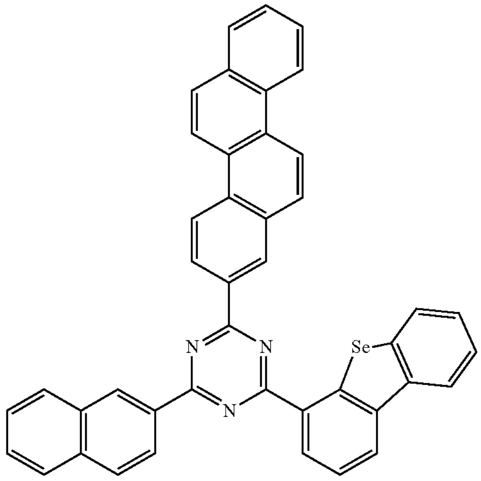
-continued
H1-121
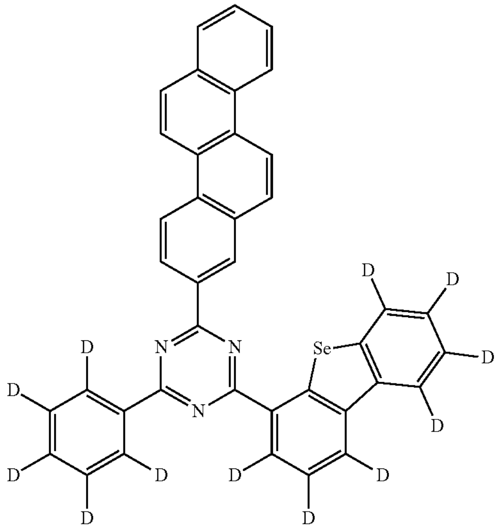
H1-122
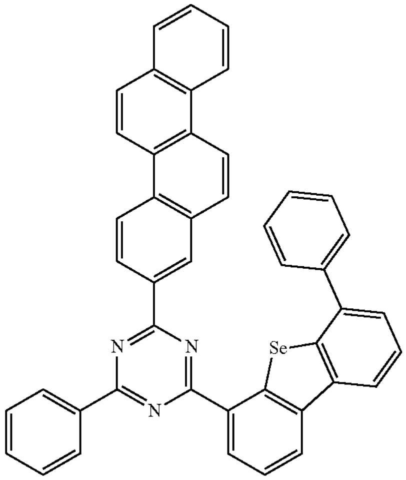
H1-123
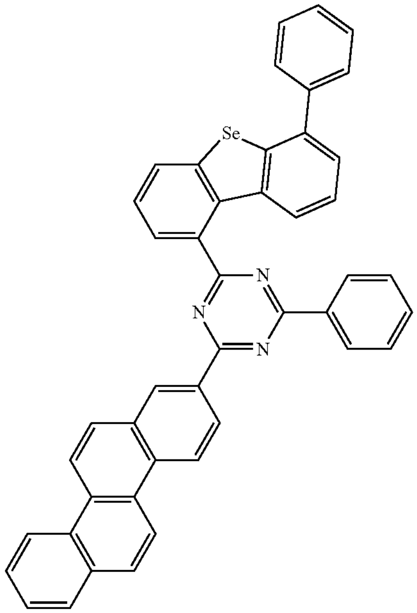

-continued
H1-124
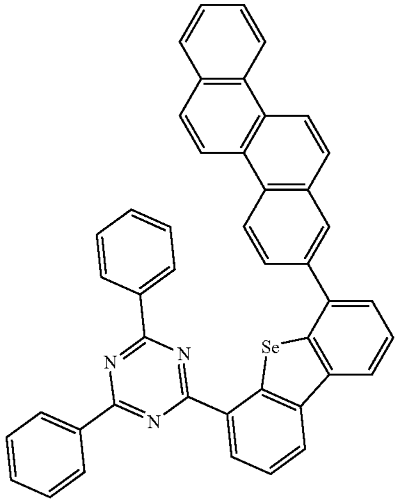
H1-125
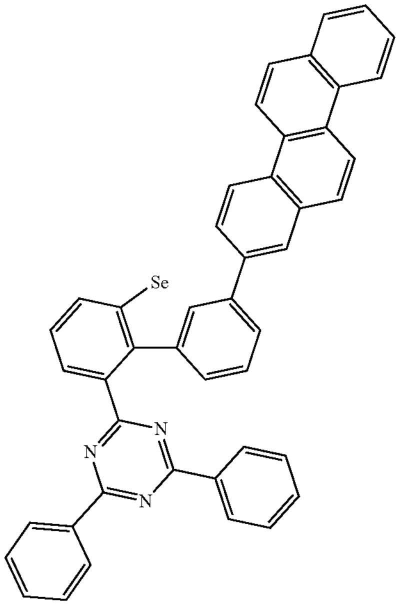
-continued
H1-126
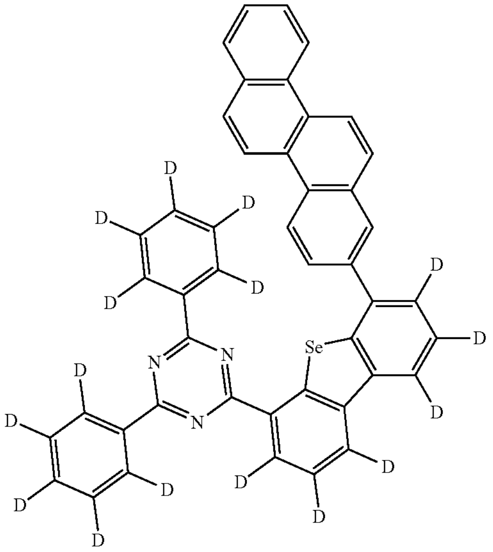
H1-127
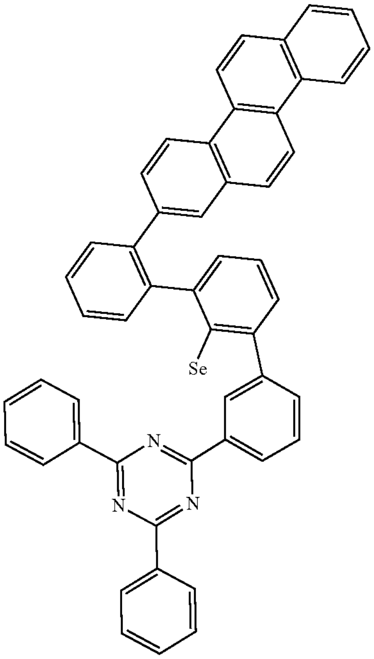

-continued
H1-128
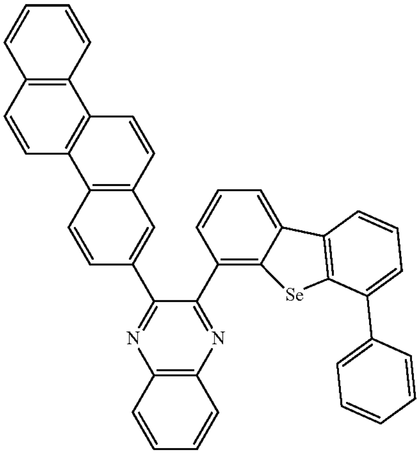
H1-129
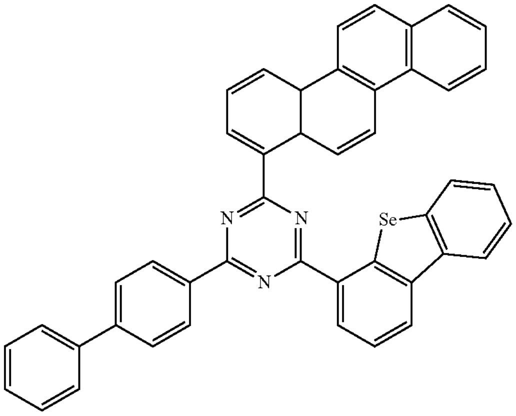
H1-130
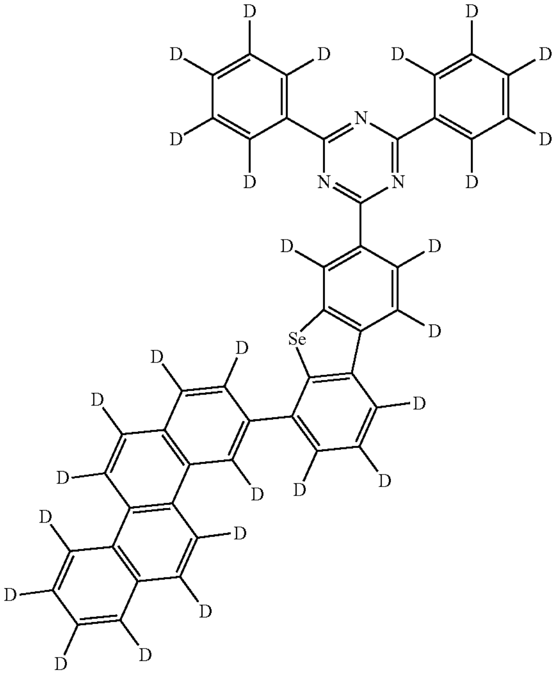
-continued
H1-131
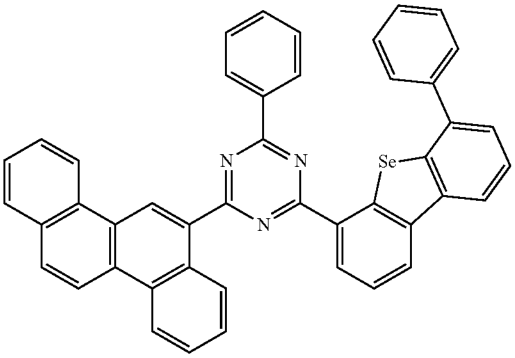
H1-132
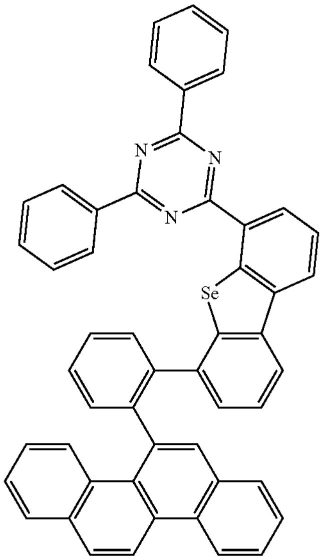
H1-133
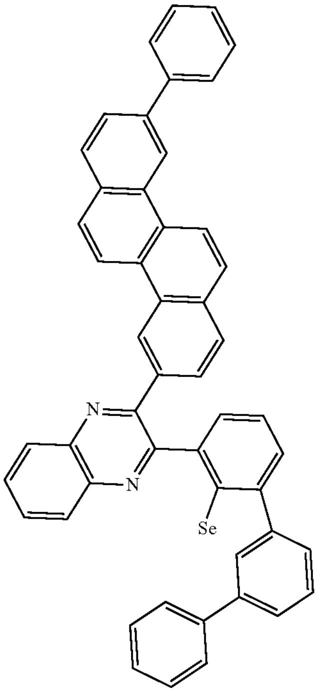

-continued
H1-134
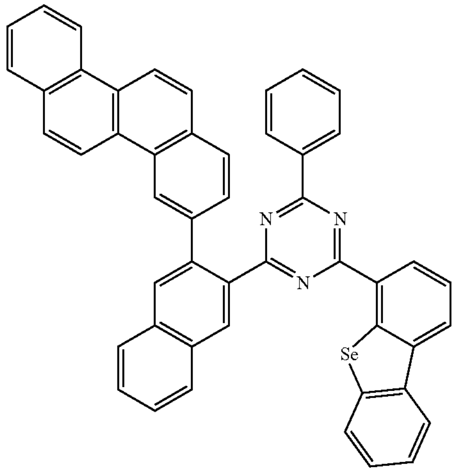
H1-135
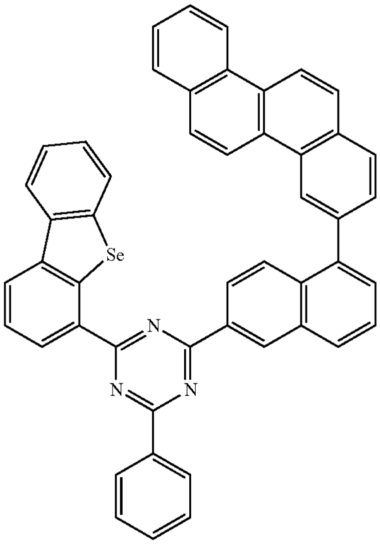
H1-136
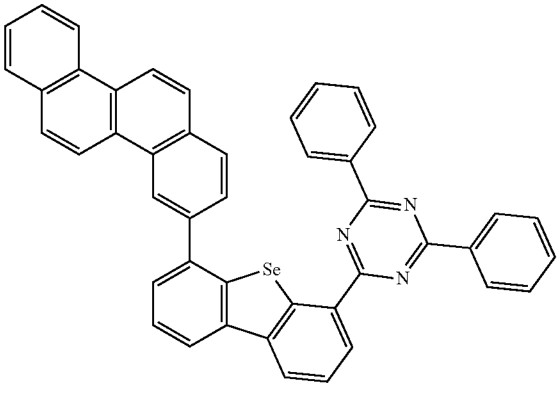
-continued
H1-137
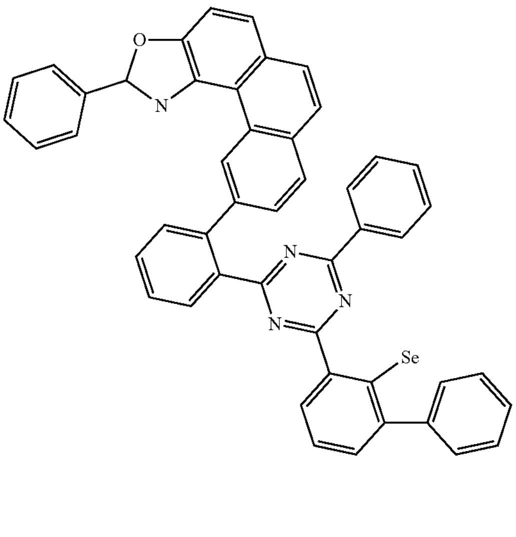
H1-138
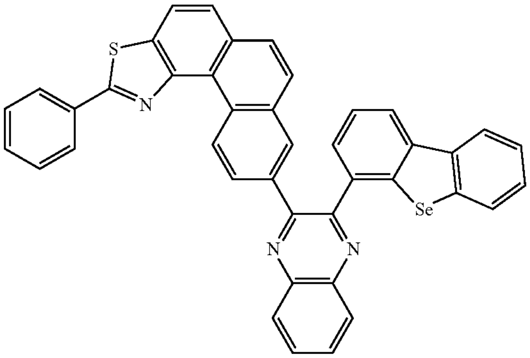
H1-139
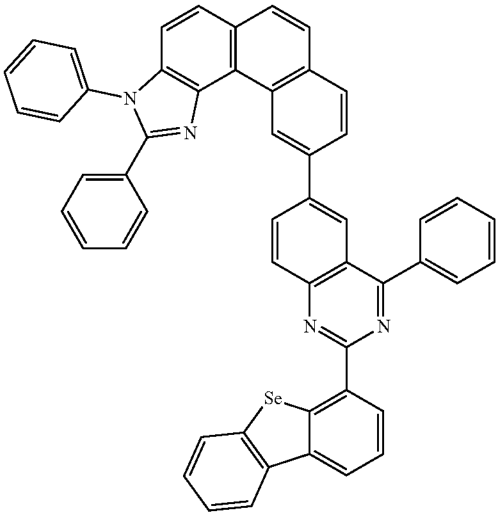

-continued
H1-140
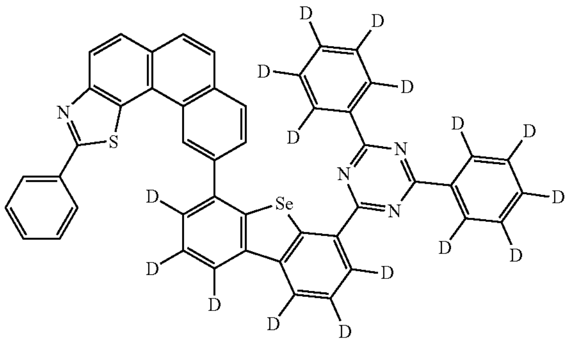
H1-141
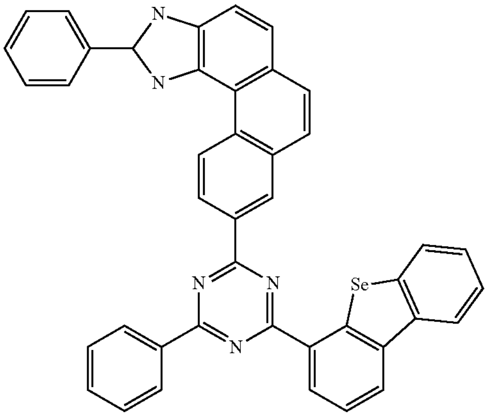
H1-145
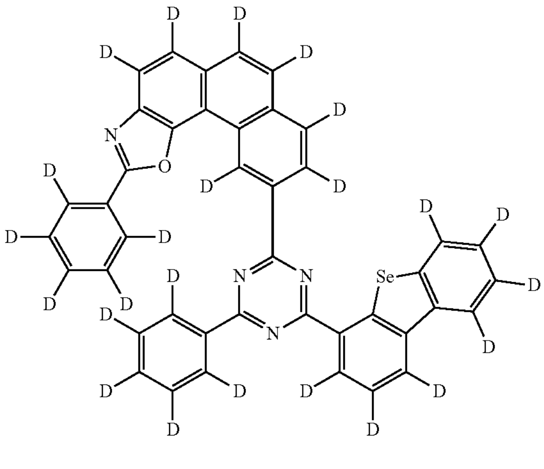
-continued
H1-146
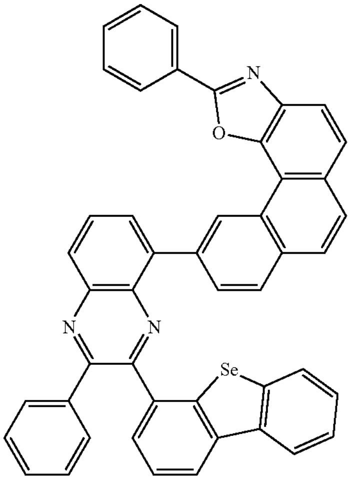
H1-147
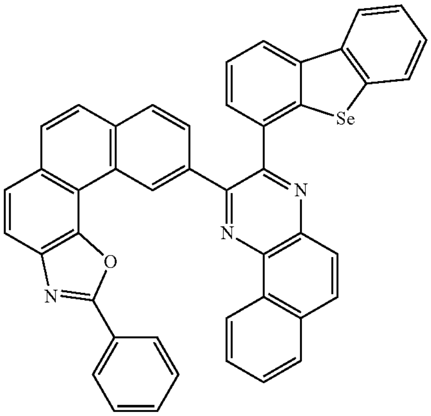
H1-148
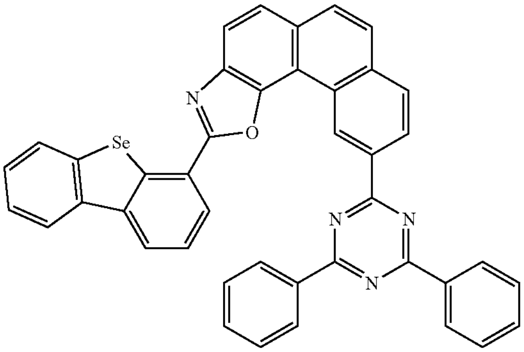
H1-149
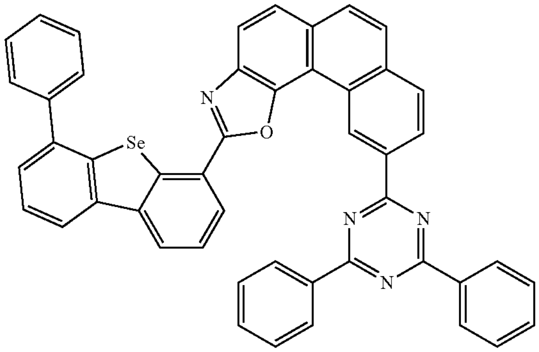

-continued
H1-150
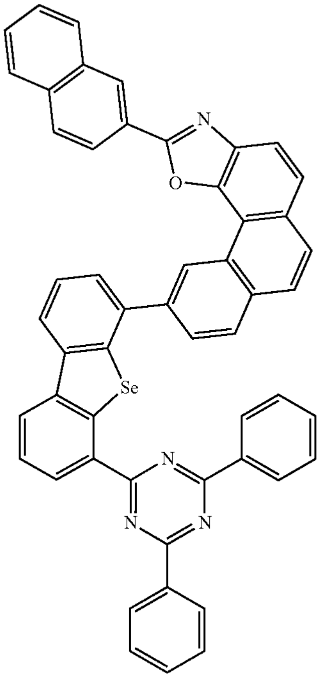
H1-151
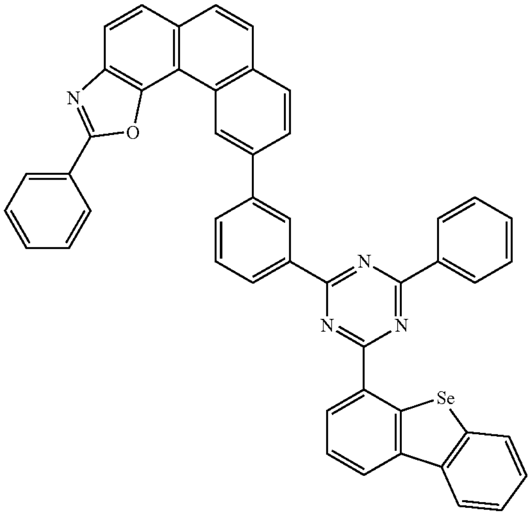
-continued
H1-152
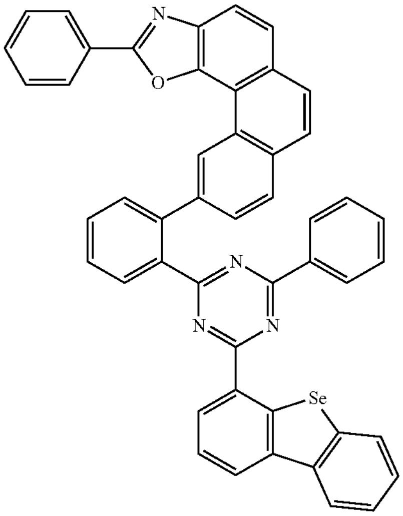
H1-153
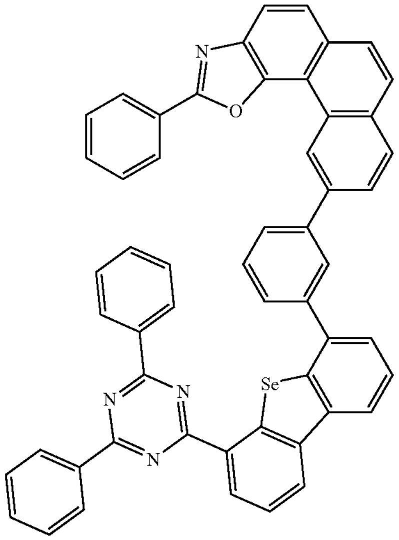
H1-154
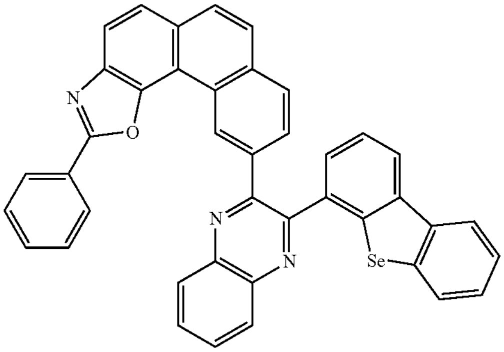

-continued
H1-155
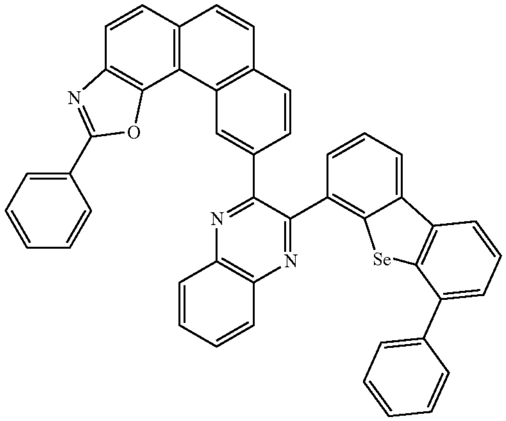
H1-156
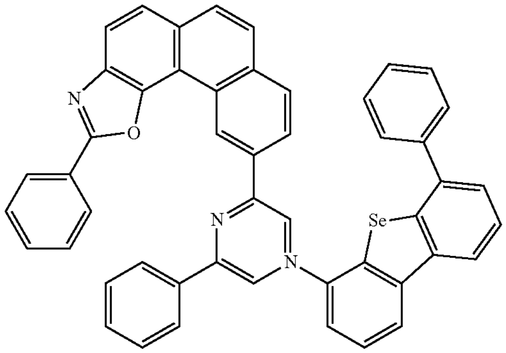
H1-157
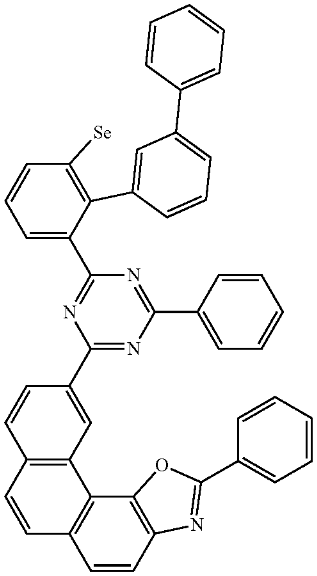
-continued
H1-158
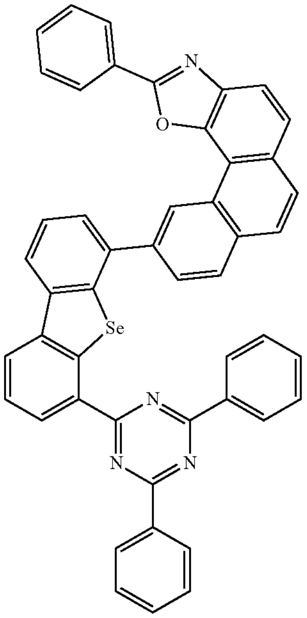
H1-159
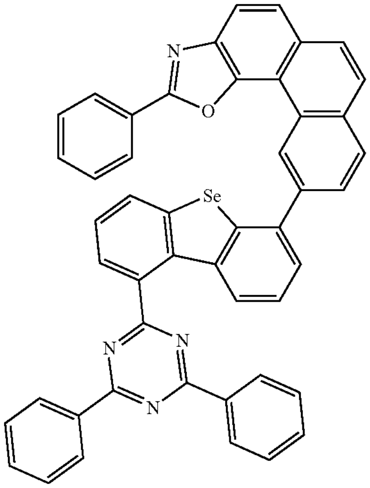
H1-160
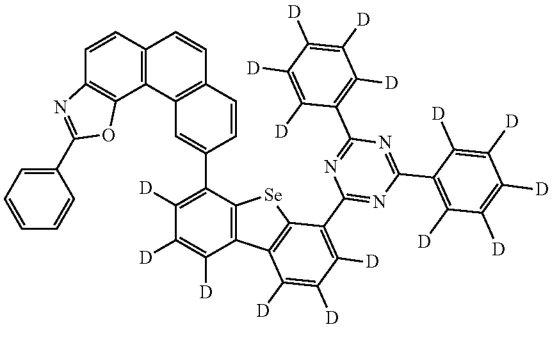

-continued
H1-161
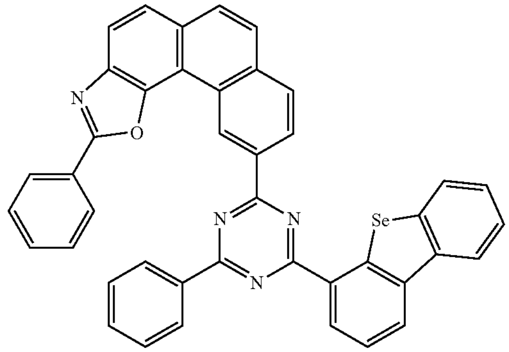
H1-162
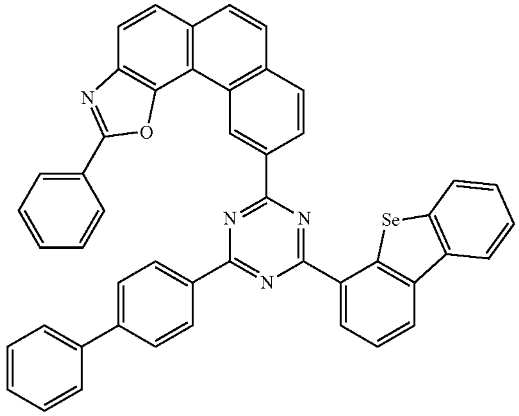
H1-163
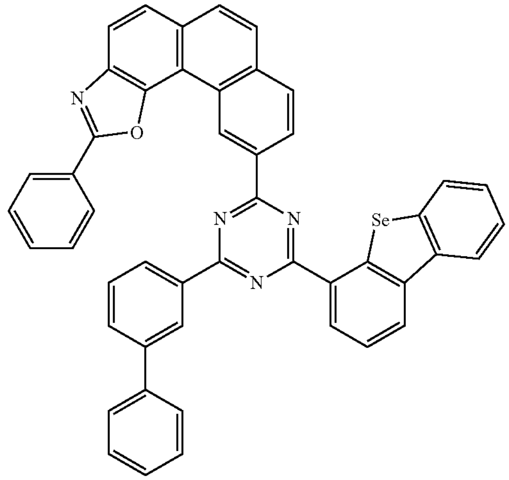
-continued
H1-164
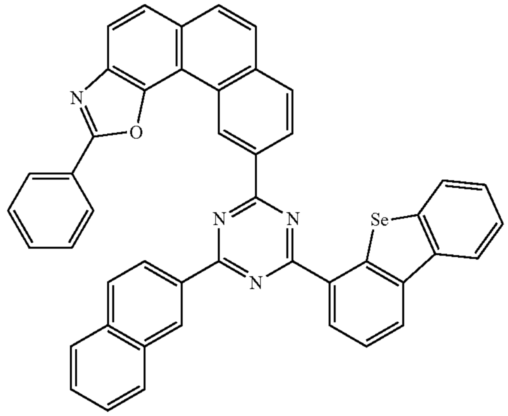
H1-165
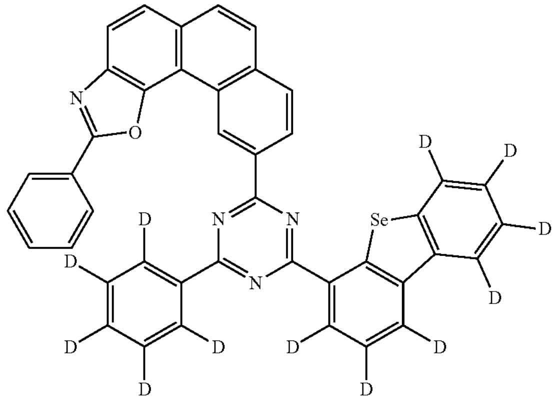
H1-166
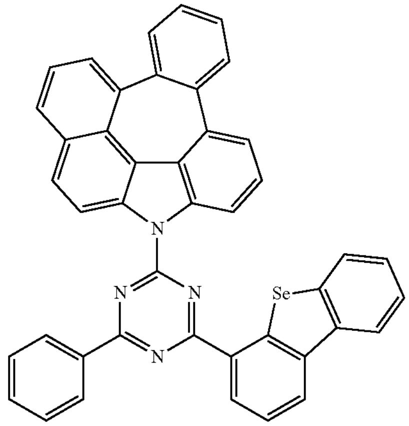

-continued
H1-167
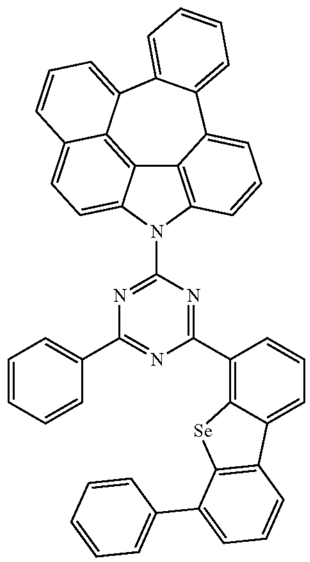
H1-168
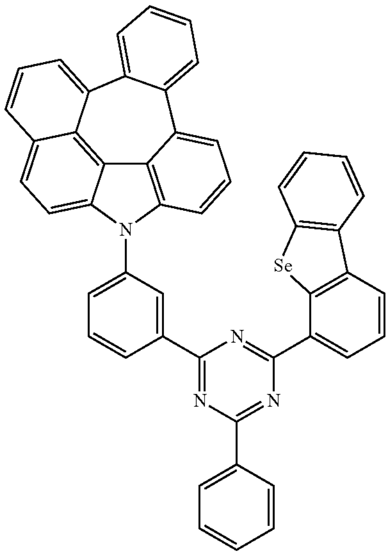
H1-169
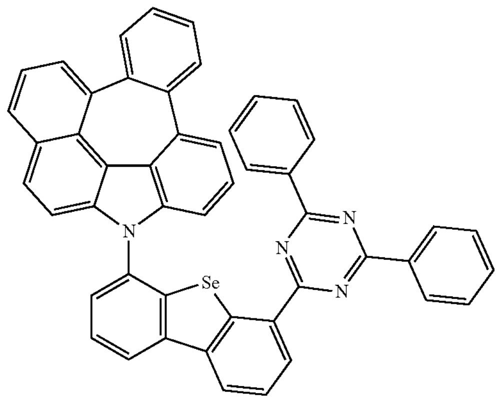
-continued
H1-170
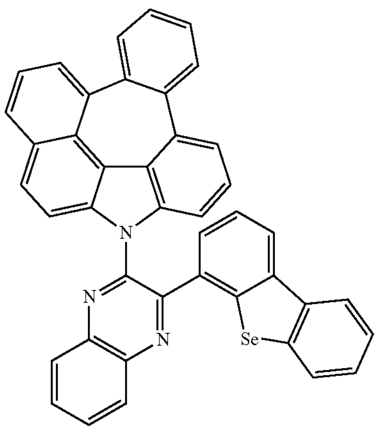
H1-171
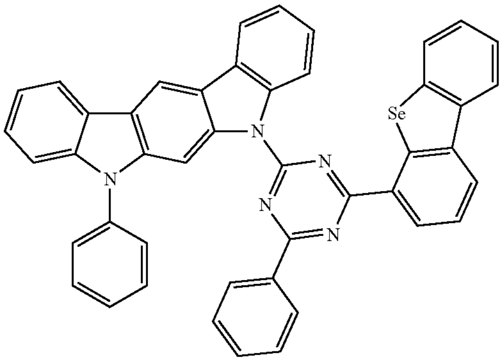
H1-173
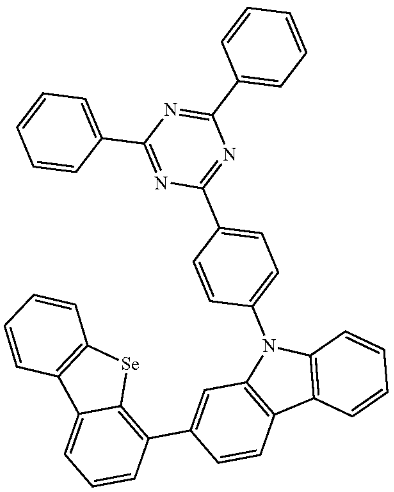

-continued
H1-174
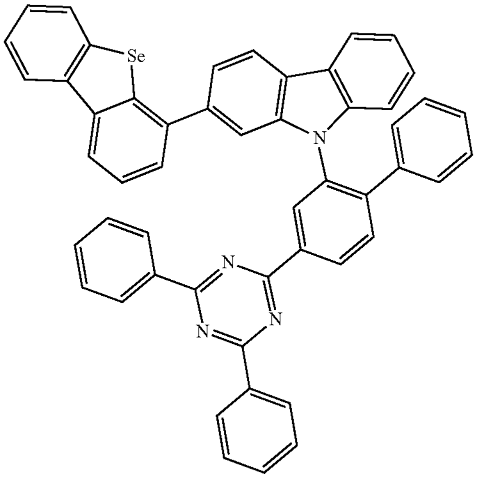
H1-175
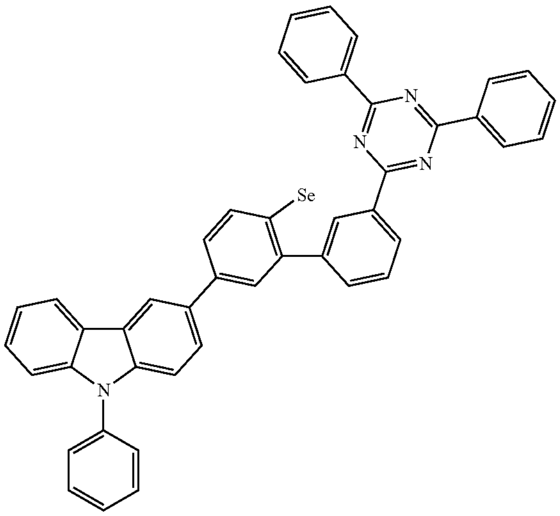
H1-176
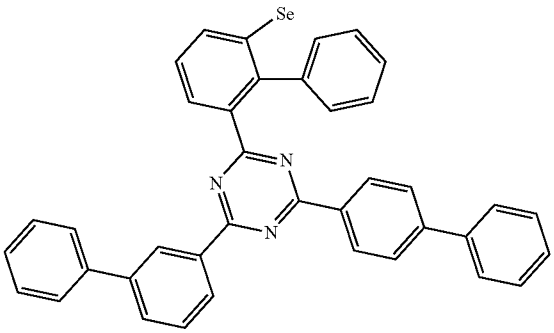
-continued
H1-177
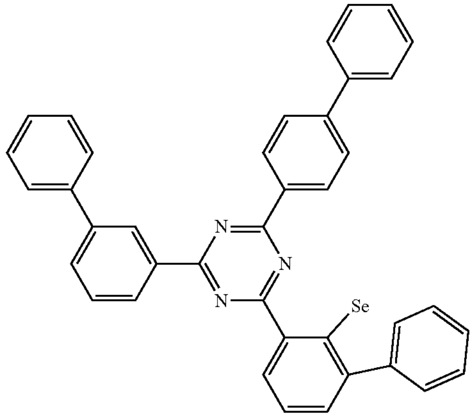
H1-178
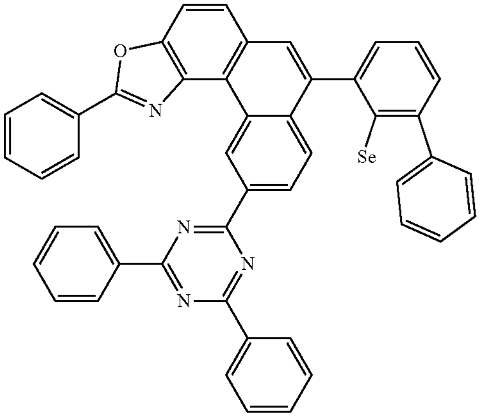
H1-179
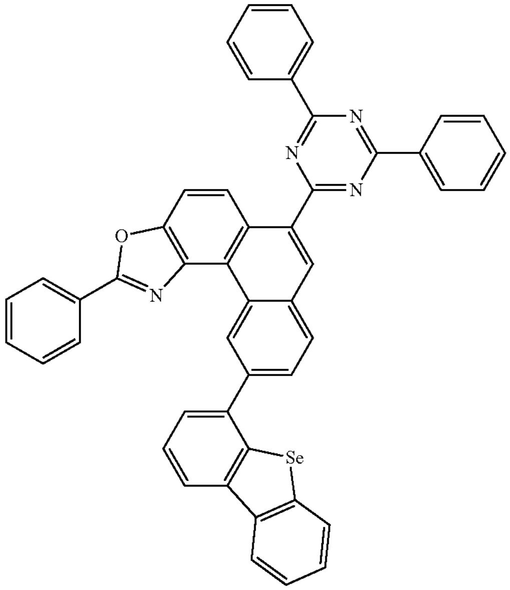

-continued
H1-180
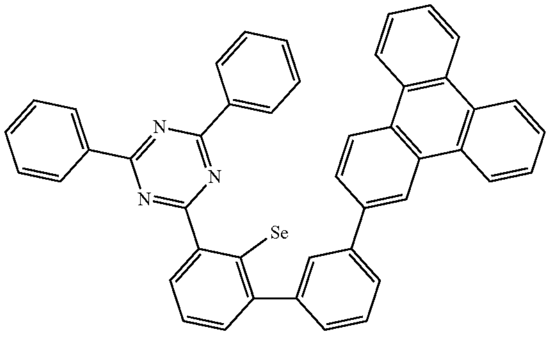
H1-181
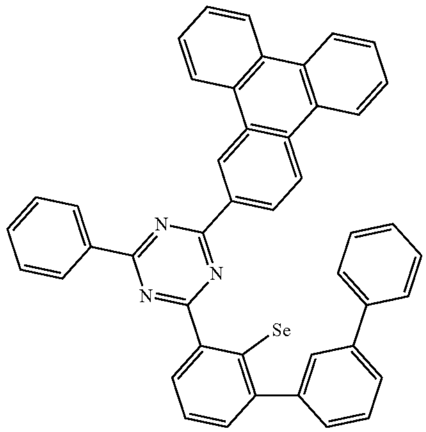
H1-182
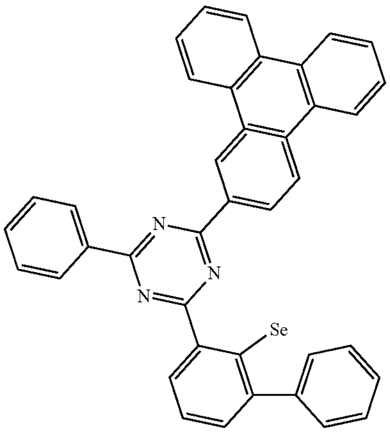
H1-183
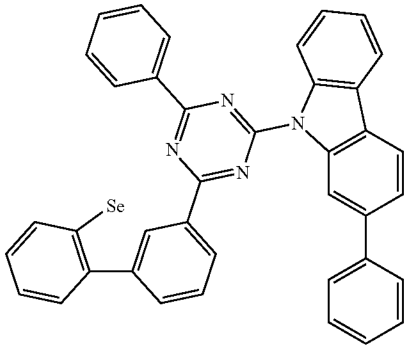
-continued
H1-184
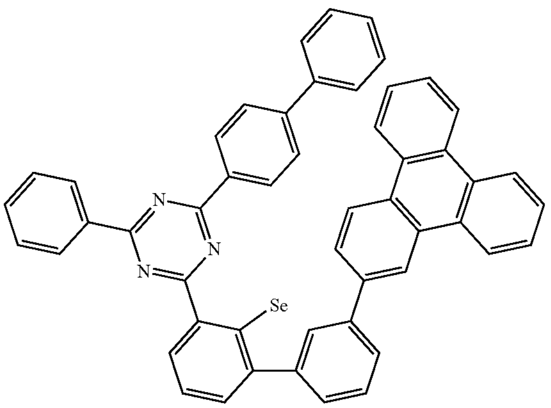
H1-185
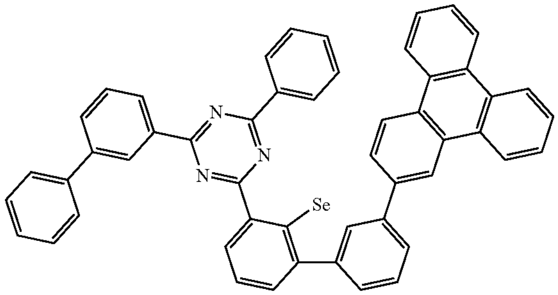
H1-186
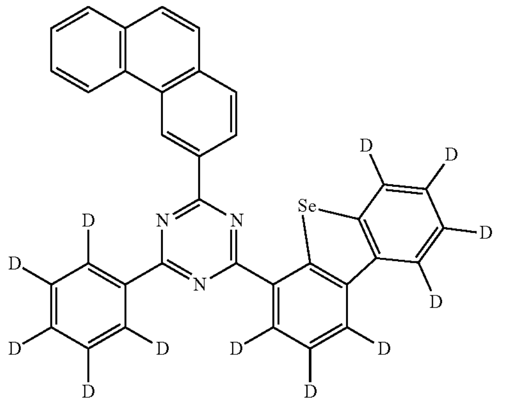
H1-187
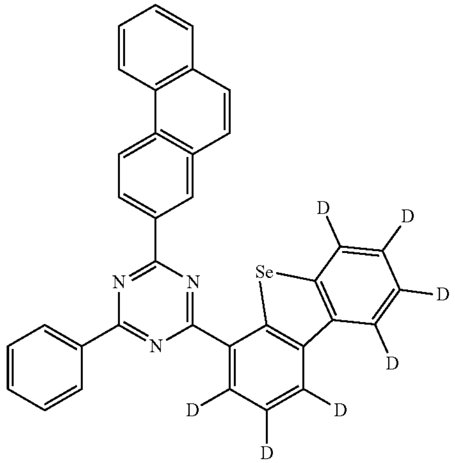

-continued

H1-188

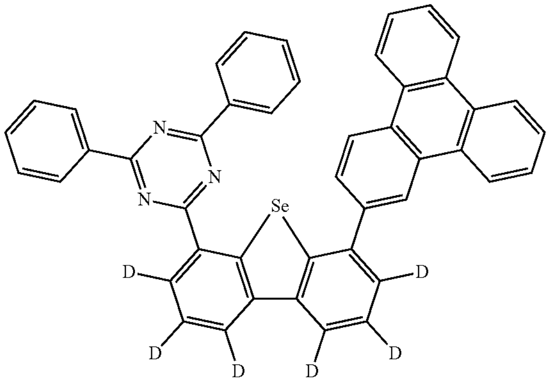

H1-189

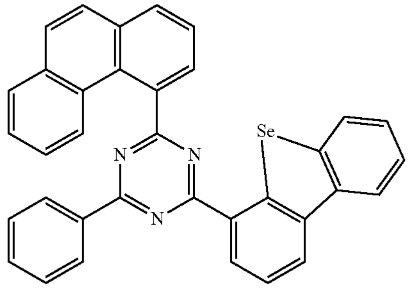

H1-190

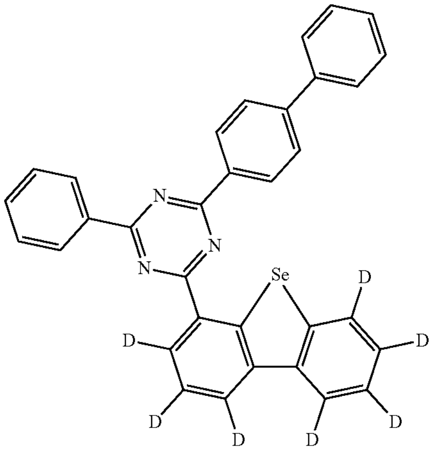

H1-191

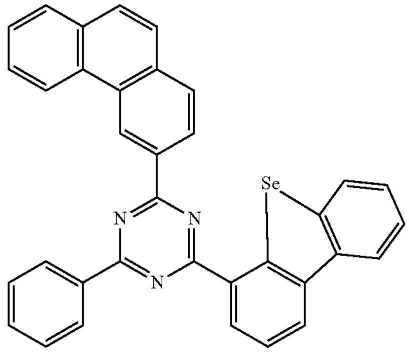

-continued

H1-192

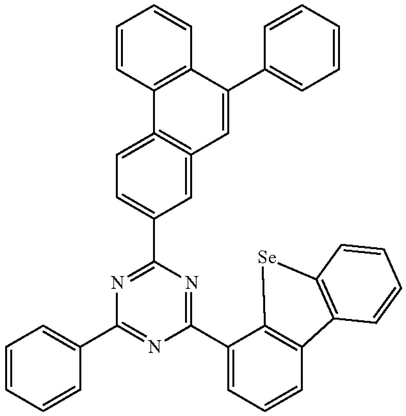

H1-193

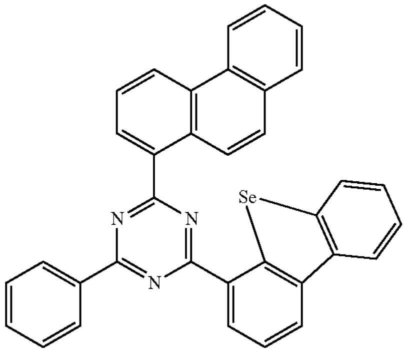

H1-194

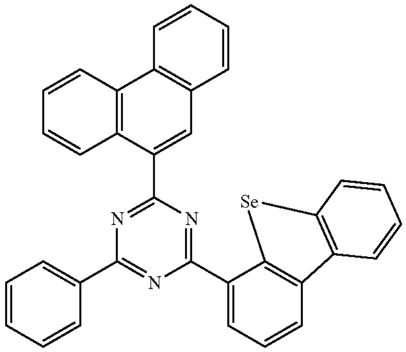

In addition, the present disclosure provides an organic electroluminescent device comprising an organic electroluminescent compound of formula 1'. Herein, the organic electroluminescent compound of formula 1' may be comprised in a light-emitting layer, an electron transport layer, or an electron buffer layer, but is not limited thereto.

The compounds represented by formulas 1, 1', and 2 according to the present disclosure may be prepared by a synthetic method known to one skilled in the art. For example, the compound represented by formula 1 or 1' may be prepared by referring to the following reaction schemes, but is not limited thereto. The compound represented by formula 2 may be prepared by referring to Korean Patent Application Laid-Open No. 2020-0007644 (published on Jan. 22, 2020), Korean Patent Application Laid-Open No. 2018-0099487 (published on Sep. 5, 2018), etc., but is not limited thereto.

[Reaction Scheme 1]

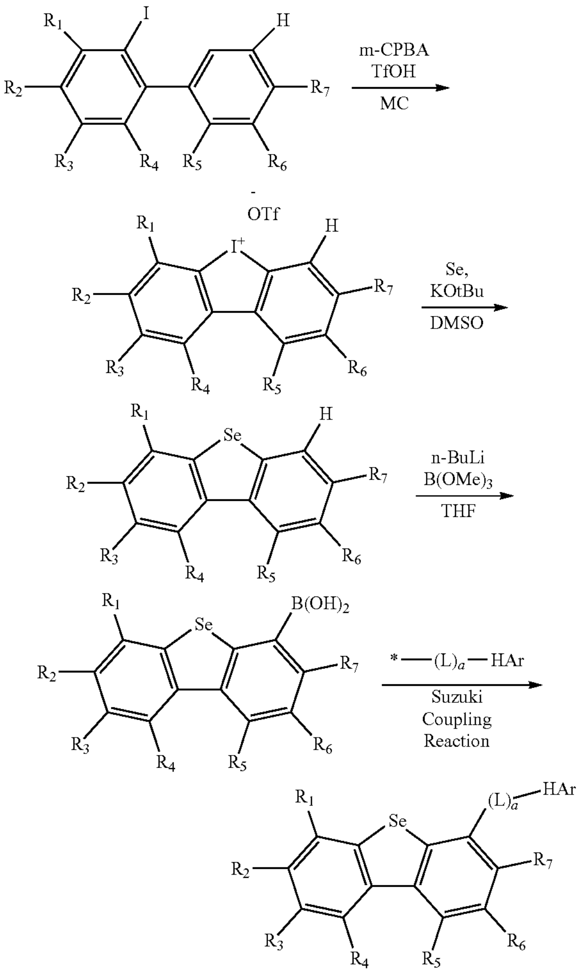

[Reaction Scheme 2]

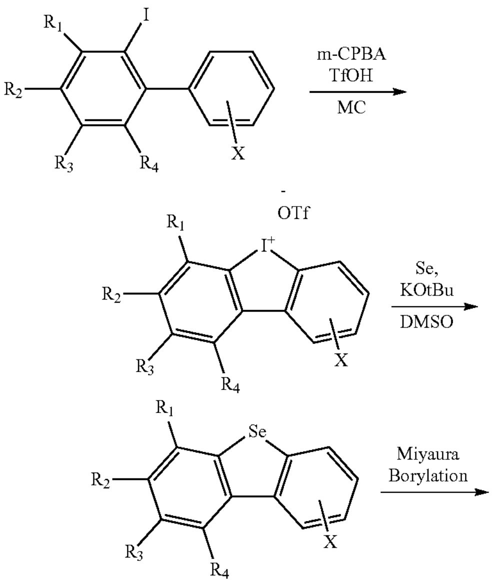

-continued

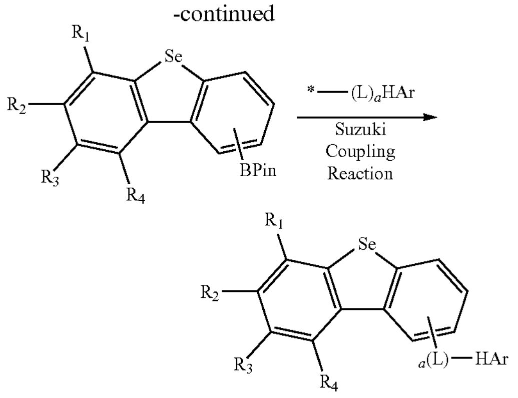

In reaction schemes 1 and 2, $R_1$ to $R_7$, L, HAr, and a are as defined in formula 1 or 1', and * represents a site linked to dibenzoselenophene.

Although illustrative synthesis examples of the compound represented by formula 1 or 1' are described above, one skilled in the art will be able to readily understand that all of them are based on a Buchwald-Hartwig cross-coupling reaction, an N-arylation reaction, H-mont-mediated etherification reaction, a Miyaura borylation reaction, a Suzuki cross-coupling reaction, an intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents, which are defined in formula 1 or 1' but are not specified in the specific synthesis examples, are bonded.

The organic electroluminescent device of the present disclosure comprises an anode, a cathode, and at least one organic layer between the anode and the cathode, wherein the organic layer may comprise a plurality of organic electroluminescent materials including the compound represented by formula 1 as a first organic electroluminescent material and the compound represented by formula 2 as a second organic electroluminescent material. According to one embodiment of the present disclosure, the organic electroluminescent device of the present disclosure comprises an anode, a cathode, and at least one light-emitting layer between the anode and the cathode, wherein the light-emitting layer may comprise the compound represented by formula 1 and the compound represented by formula 2.

The light-emitting layer comprises a host(s) and a dopant, wherein the host(s) includes a plurality of host materials, the compound represented by formula 1 may be included as a first host compound of the plurality of host materials, and the compound represented by formula 2 may be included as a second host compound of the plurality of host materials. Herein, the weight ratio of the first host compound to the second host compound is from about 1:99 to about 99:1, preferably from about 10:90 to about 90:10, more preferably from about 30:70 to about 70:30, even more preferably about 40:60 to about 60:40, and still more preferably about 50:50.

In the present disclosure, the light-emitting layer is a layer that emits light, which may be a single layer or a plurality of layers in which two or more layers are stacked. In the plurality of host materials of the present disclosure, the first and second host materials may be included in one layer or in respective different light-emitting layers. According to one embodiment of the present disclosure, the doping concentration of the dopant compound with respect to the host compound of the light-emitting layer may be less than 20 wt %.

The organic electroluminescent device according to the present disclosure may comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device according to the present disclosure may further comprise an amine-based compound as at least one of a hole injection material, a hole transport material, a hole auxiliary material, a light-emitting material, a light-emitting auxiliary material, and an electron blocking material, in addition to the plurality of host materials according to the present disclosure. In addition, according to one embodiment of the present disclosure, the organic electroluminescent device according to the present disclosure may further comprise an azine-based compound as at least one of an electron transport material, an electron injection material, an electron buffer material, and a hole blocking material, in addition to the plurality of host materials according to the present disclosure.

The plurality of host materials according to the present disclosure may be used as light-emitting materials for a white organic light-emitting device. The white organic light-emitting device has been suggested in various structures such as a side-by-side structure or a stacking structure depending on the arrangement of R (Red), G (Green) or YG (Yellowish Green), and B (Blue) light-emitting parts, or a color conversion material (CCM) method, etc. In addition, the plurality of host materials according to the present disclosure may also be used in the organic electroluminescent device comprising a quantum dot (QD).

A hole injection layer, a hole transport layer, an electron blocking layer, or a combination thereof may be used between an anode and a light-emitting layer. The hole injection layer may be multilayers in order to lower the hole injection barrier (or hole injection voltage) from the anode to the hole transport layer or the electron blocking layer, wherein two compounds may be simultaneously used in each of the multilayers. In addition, the hole injection layer may be doped with a p-dopant. The electron blocking layer may be placed between the hole transport layer (or hole injection layer) and the light-emitting layer, and may block overflow of electrons from the light-emitting layer and confine the excitons in the light-emitting layer to prevent light leakage. The hole transport layer or the electron blocking layer may be multilayers, wherein a plurality of compounds may be used in each of the multilayers.

An electron buffer layer, a hole blocking layer, an electron transport layer, an electron injection layer, or a combination thereof may be used between a light-emitting layer and a cathode. The electron buffer layer may be multilayers in order to control electron injection and improve interfacial properties between the light-emitting layer and the electron injection layer, wherein two compounds may be simultaneously used in each of the multilayers. The hole blocking layer or the electron transport layer may also be multilayers, wherein a plurality of compounds may be used in each of the multilayers. In addition, the electron injection layer may be doped with an n-dopant.

The dopants comprised in the organic electroluminescent device of the present disclosure may be at least one phosphorescent or fluorescent dopant, and is preferably a phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), preferably selected from ortho-metallated complex compounds of iridium (Ir), osmium (Os), copper (Cu), and platinum (Pt), and more preferably an ortho-metallated iridium complex compound.

The dopant comprised in the organic electroluminescent device of the present disclosure may be a compound represented by the following formula 101, but is not limited thereto.

(101)

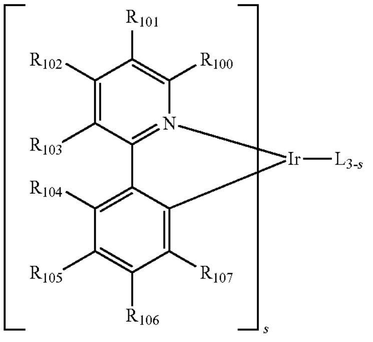

In formula 101,

L is any one selected from the following structures 1 to 3:

[Structure 1]

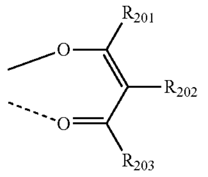

[Structure 2]

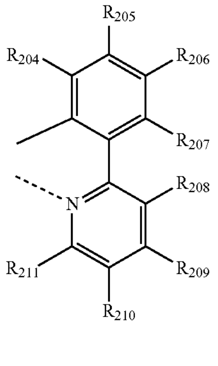

-continued

[Structure 3]

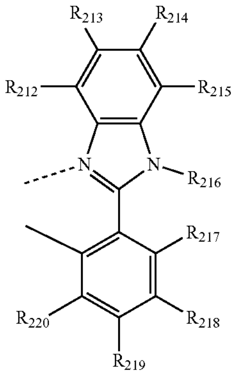

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline, together with pyridine;

$R_{104}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring(s), e.g., a substituted or unsubstituted, naphthalene, fluorene, dibenzothiophene, dibenzofuran, indenopyridine, benzofuropyridine, or benzothienopyridine, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or may be linked to an adjacent substituent to form a ring(s); and s represents an integer of 1 to 3.

The specific examples of the dopant compound are as follows, but are not limited thereto.

D-1

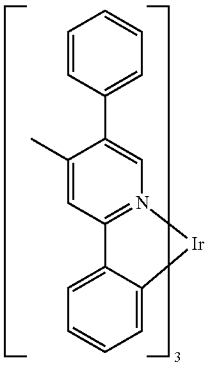

-continued

D-2

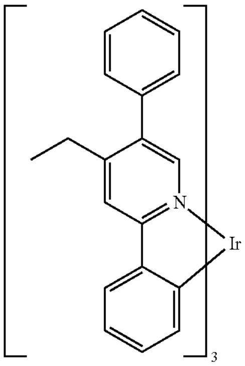

D-3

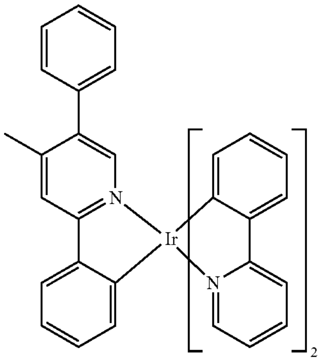

D-4

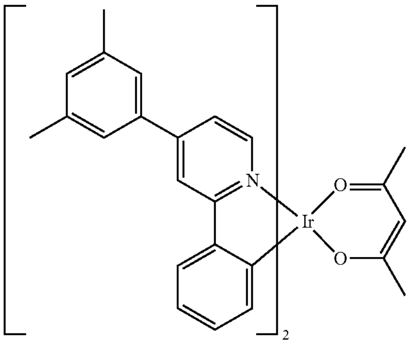

D-5

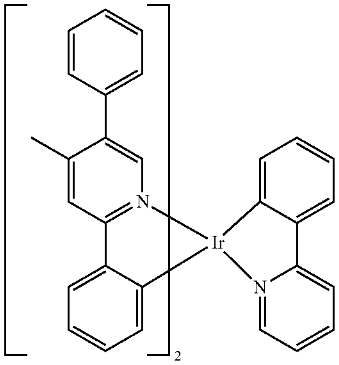

-continued
D-6
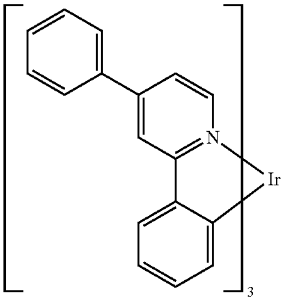
D-7
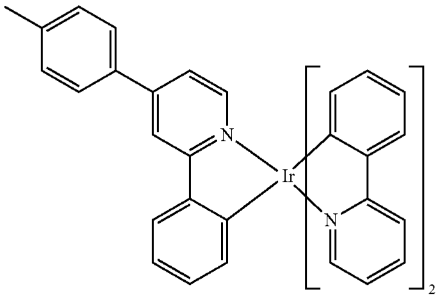
D-8
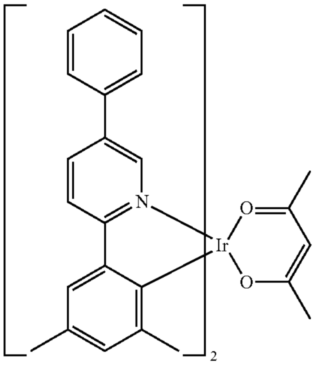
D-9
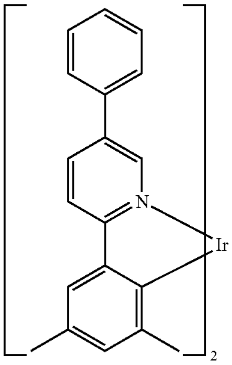
-continued
D-10
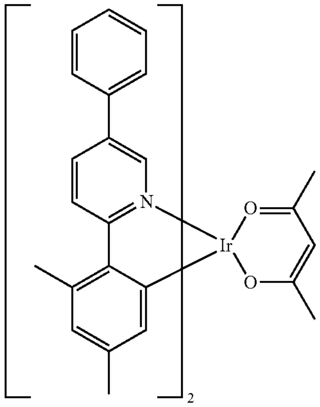
D-11
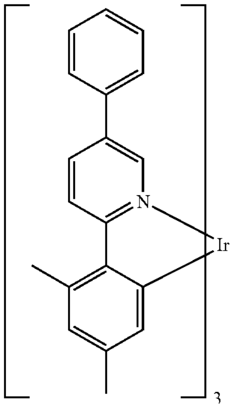
D-12
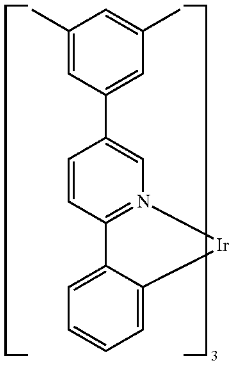
D-13
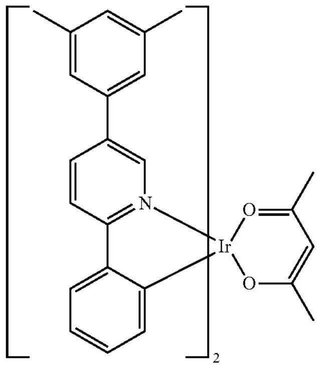

-continued
D-14
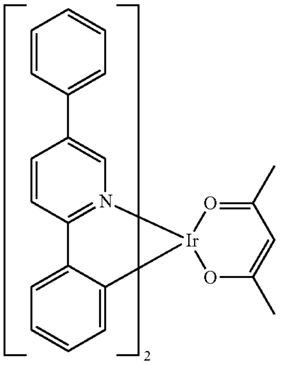
D-15
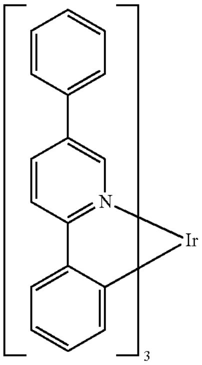
D-16
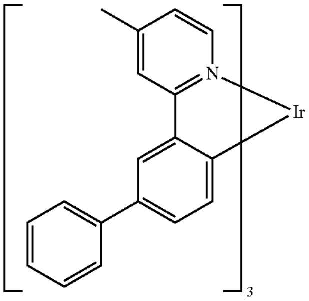
D-17
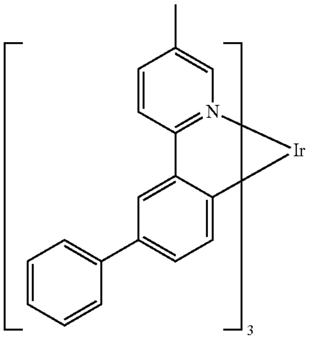
-continued
D-18
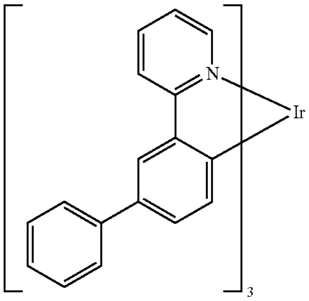
D-19
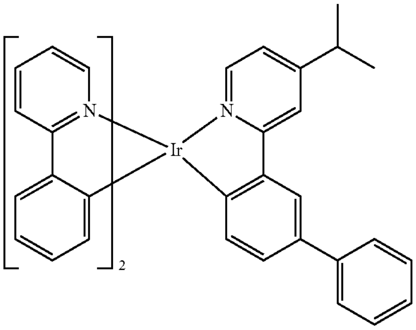
D-20
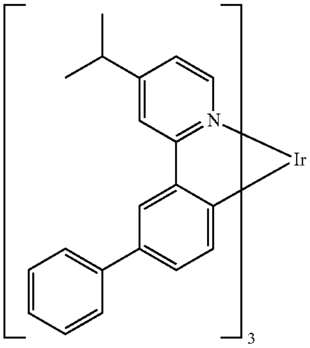
D-21
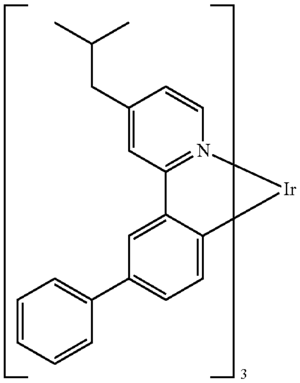

-continued
D-22
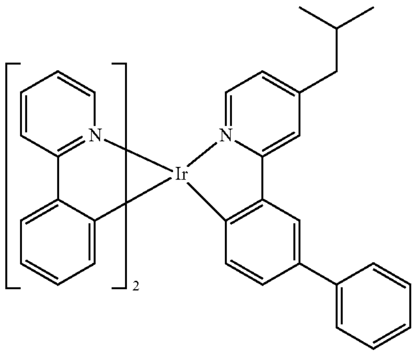
D-23
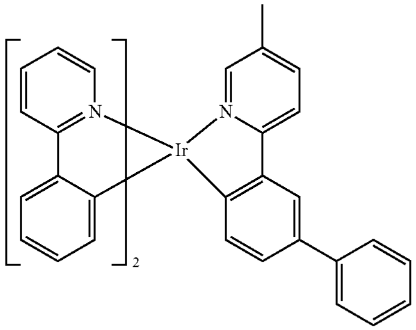
D-24
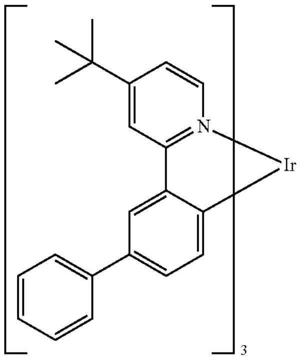
D-25
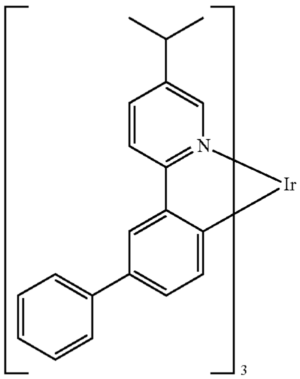
-continued
D-26
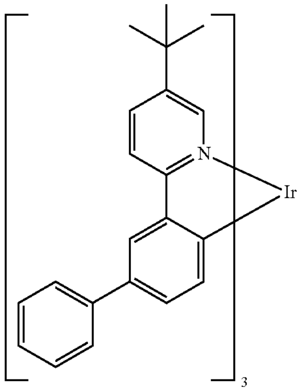
D-27
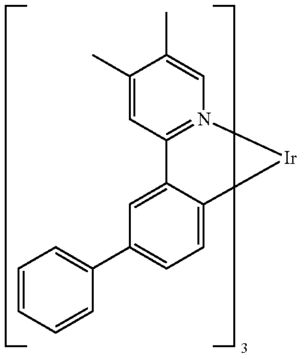
D-28
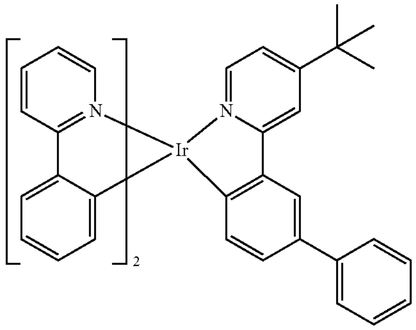
D-29
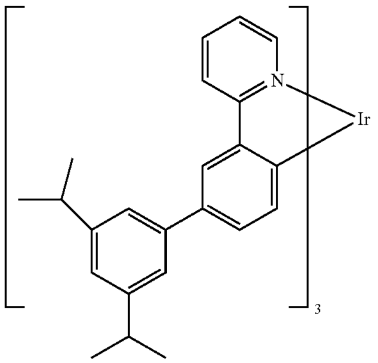

-continued
D-30
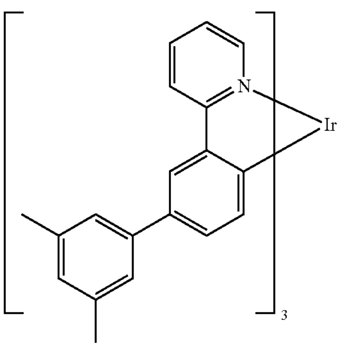
D-31
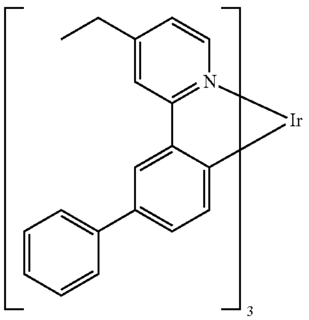
D-32
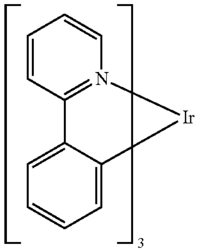
D-33
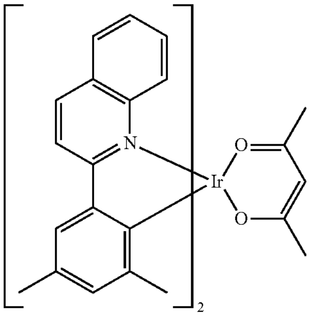
D-34
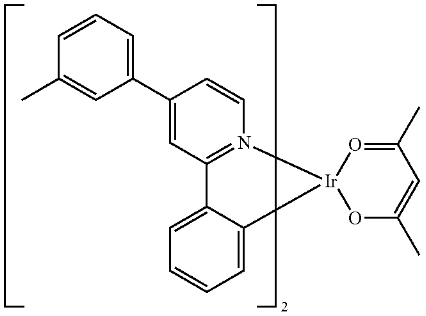
-continued
D-35
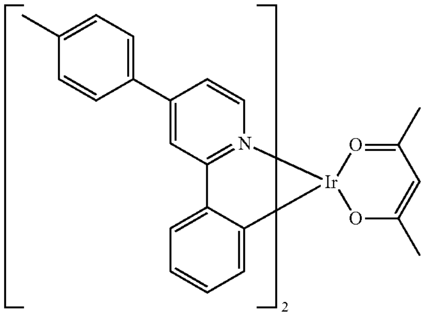
D-36
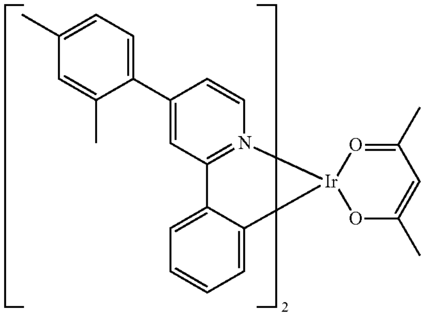
D-37
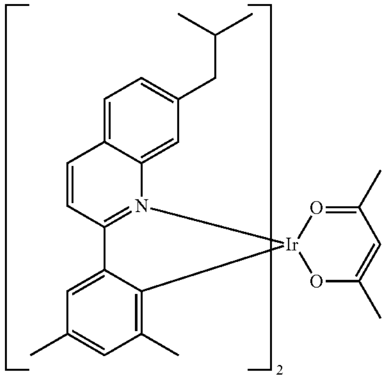
D-38
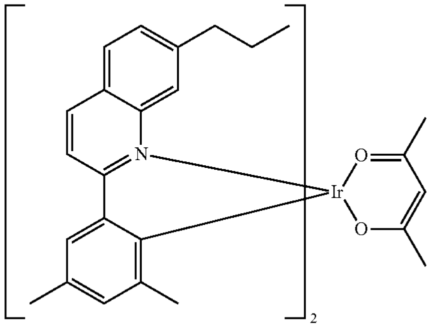

-continued
D-39
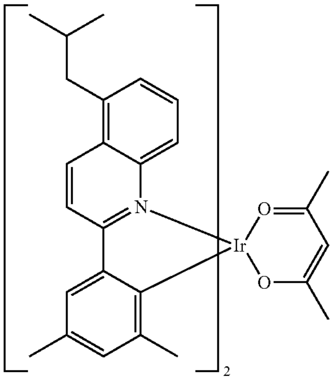
D-40
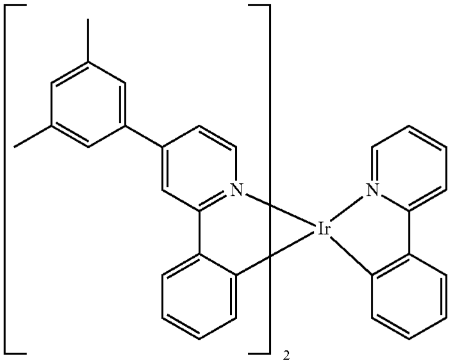
D-41
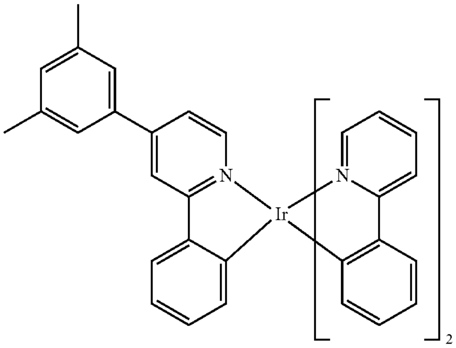
D-42
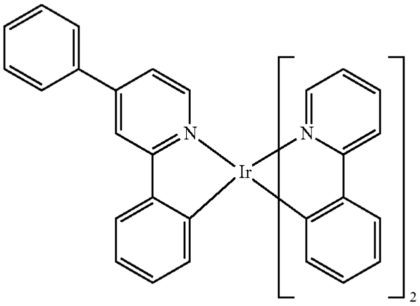
-continued
D-43
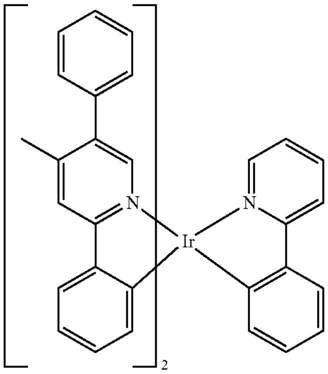
D-44
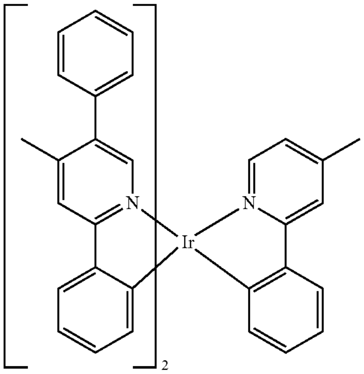
D-45
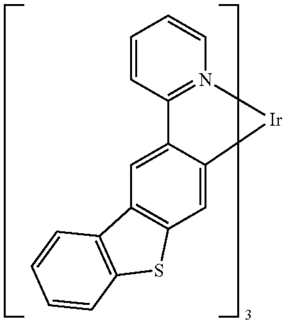
D-46
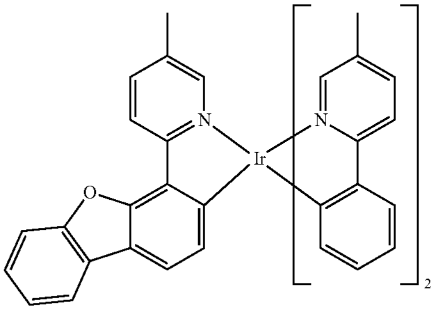

-continued
D-47
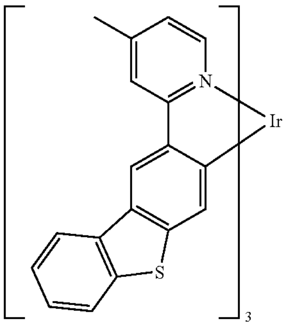
D-48
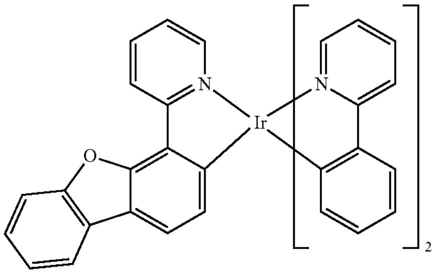
D-49
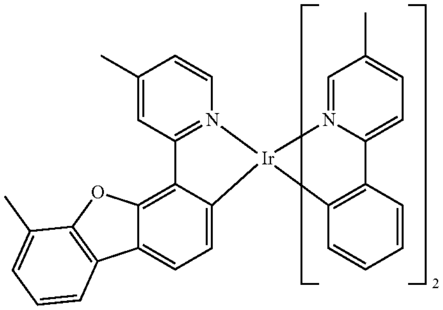
D-50
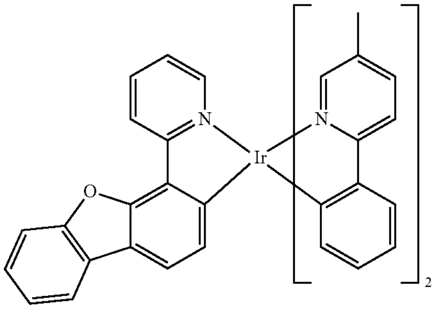
D-51
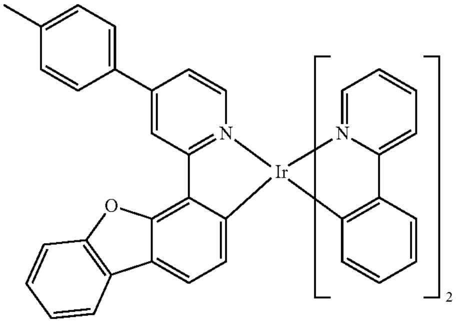
-continued
D-52
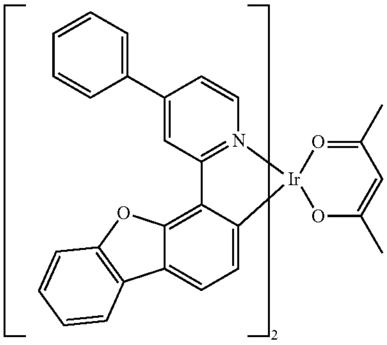
D-53
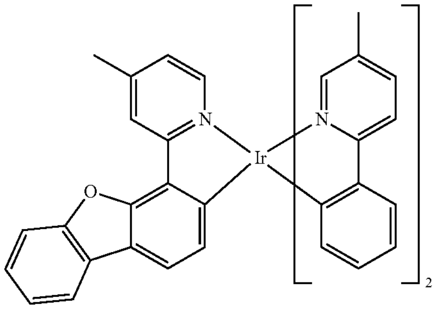
D-54
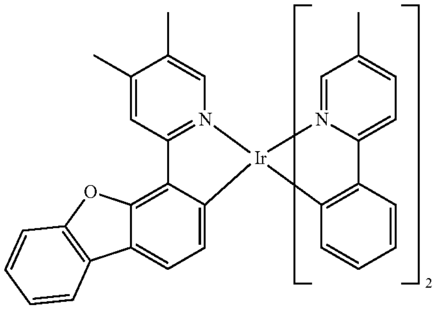
D-55
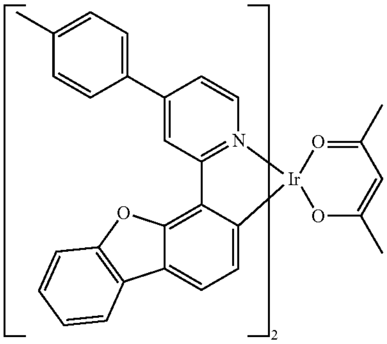
D-56
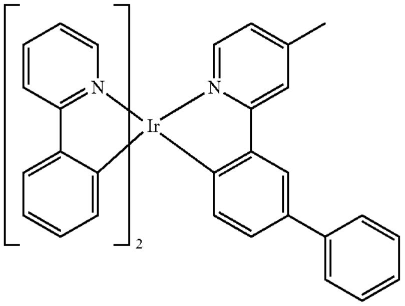

-continued
D-57
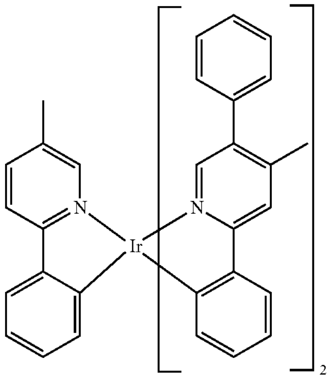
D-58
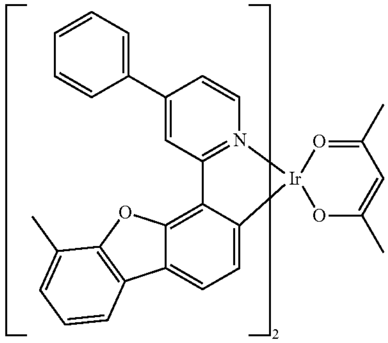
D-59
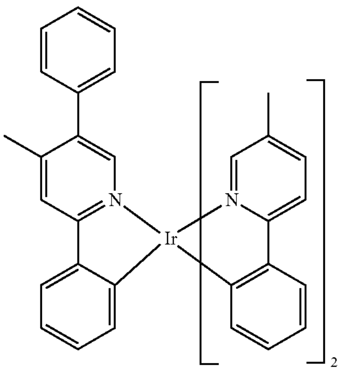
D-60
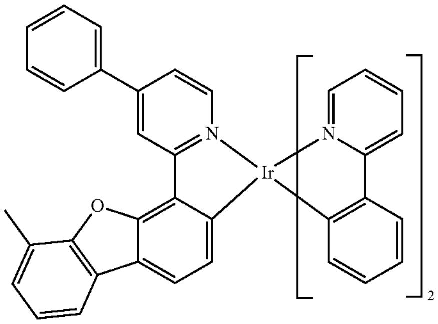
-continued
D-61
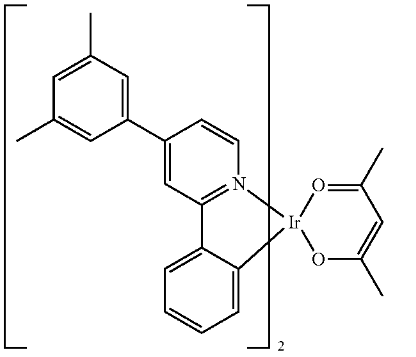
D-62
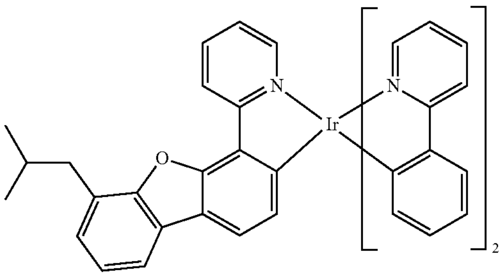
D-63
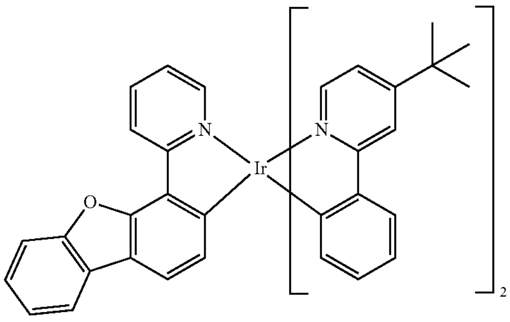
D-64
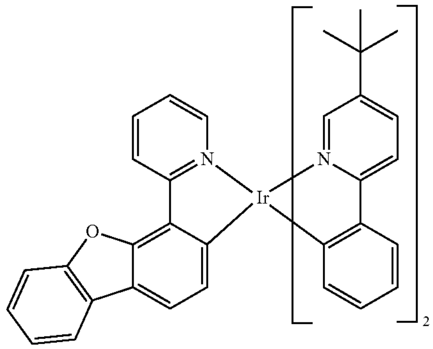

-continued
D-65
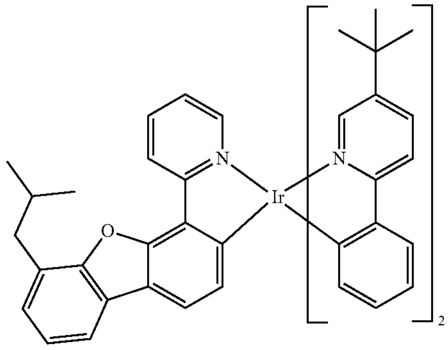
D-66
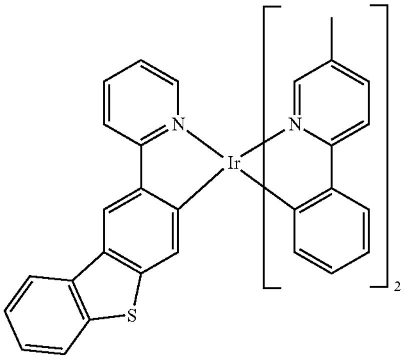
D-67
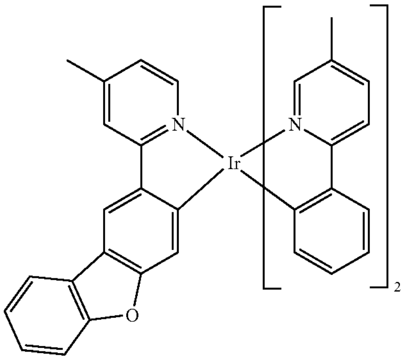
D-68
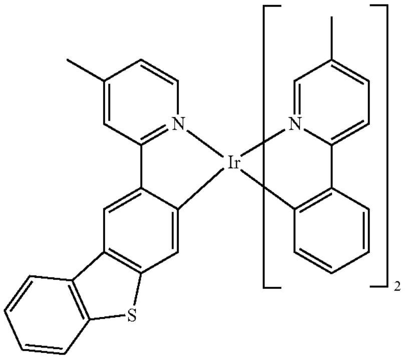
-continued
D-69
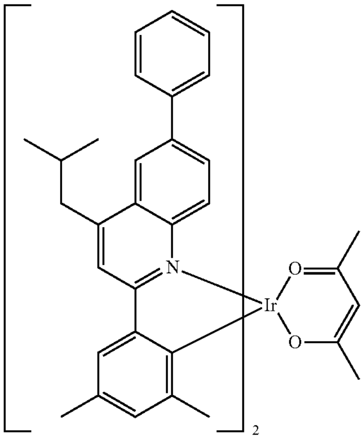
D-70
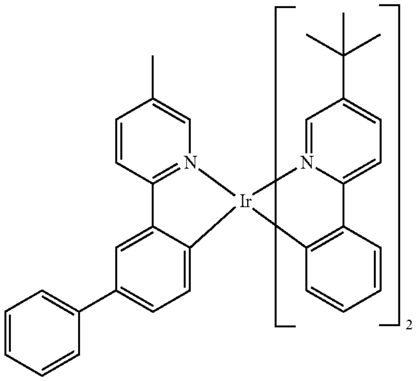
D-71
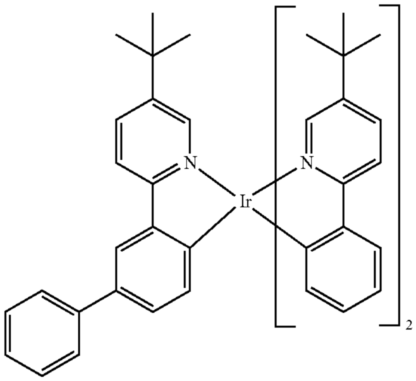
D-72
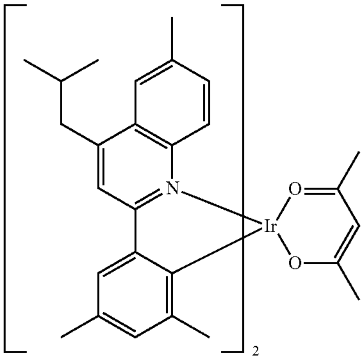

D-73
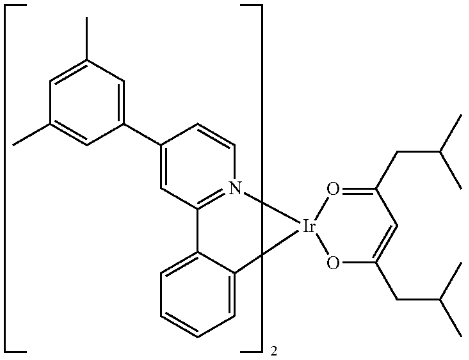
D-74
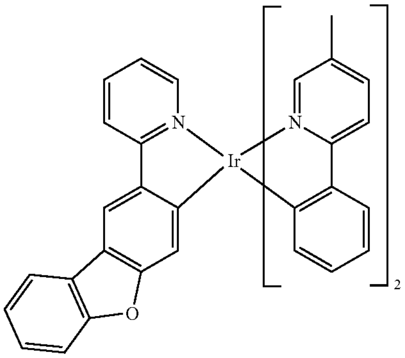
D-75
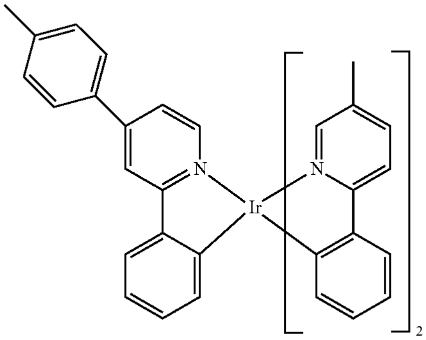
D-76
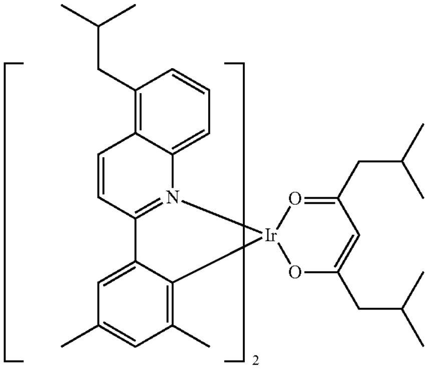
D-77
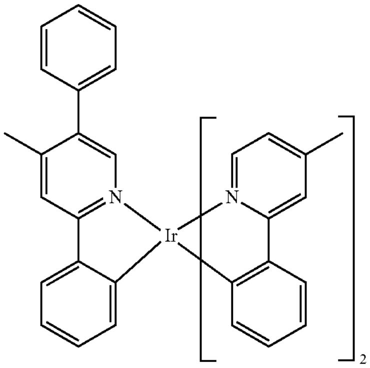
D-78
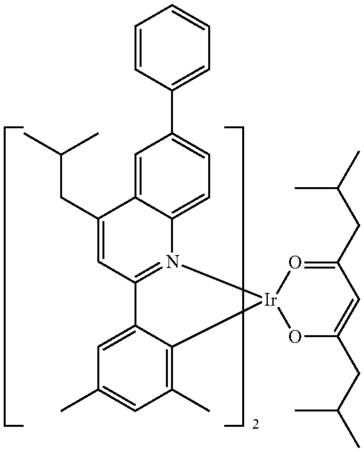
D-79
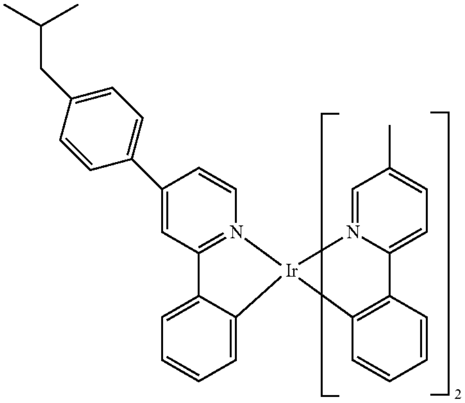
D-80
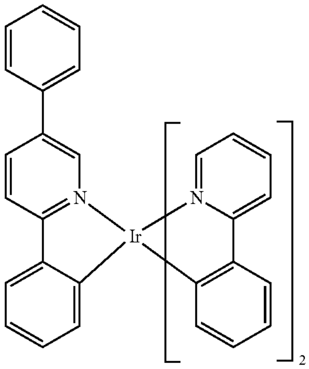

-continued
D-81
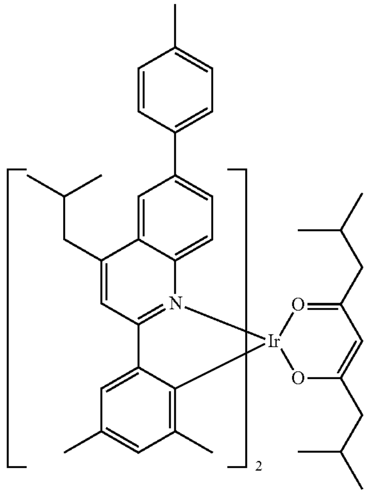
D-82
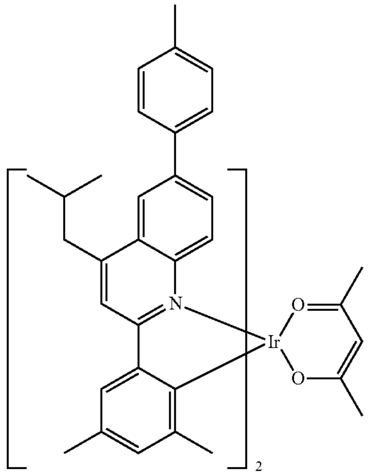
D-83
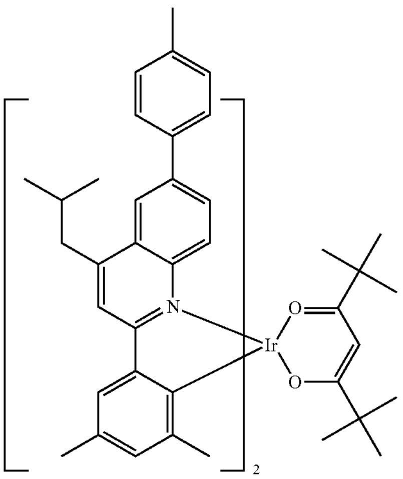
-continued
D-84
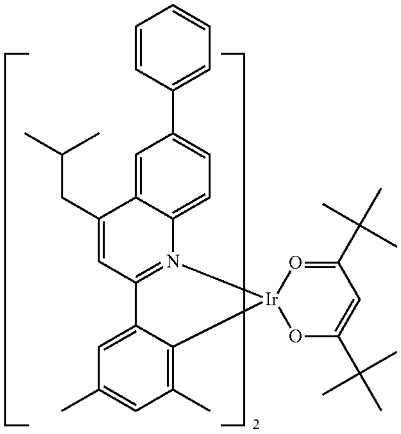
D-85
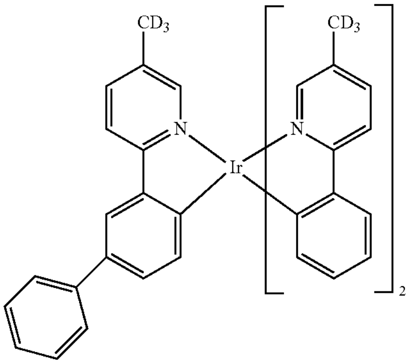
D-86
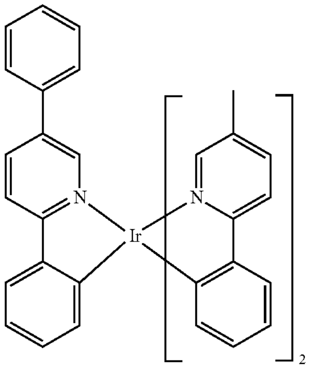
D-87
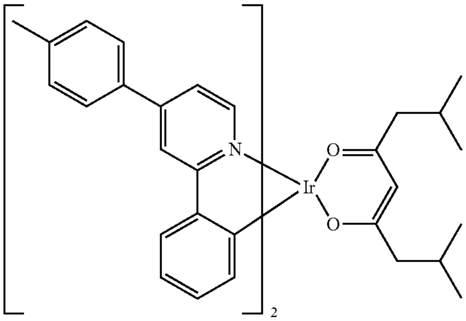

-continued
D-88
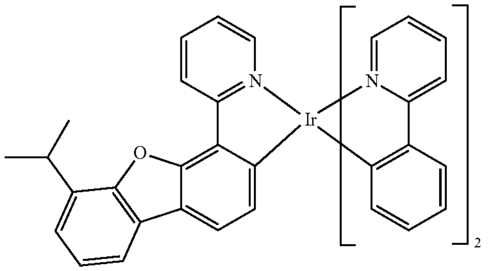
D-89
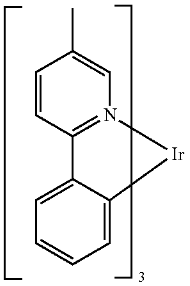
D-90
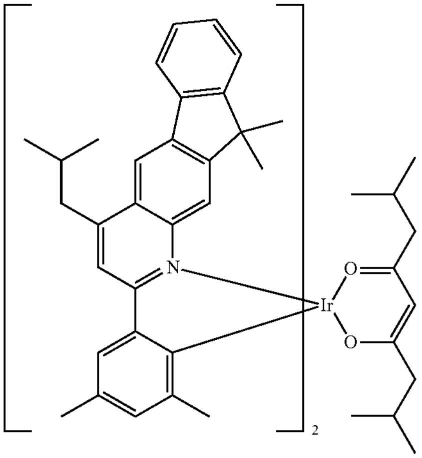
D-91
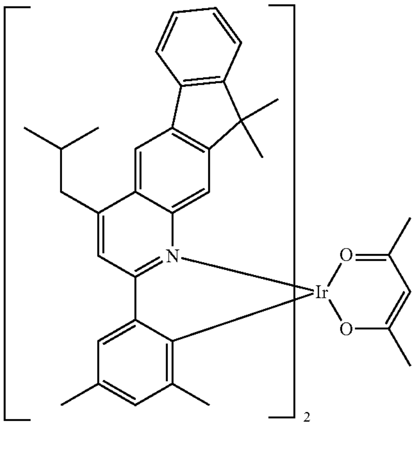
-continued
D-92
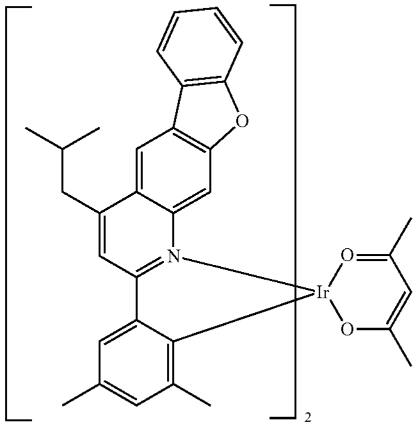
D-93
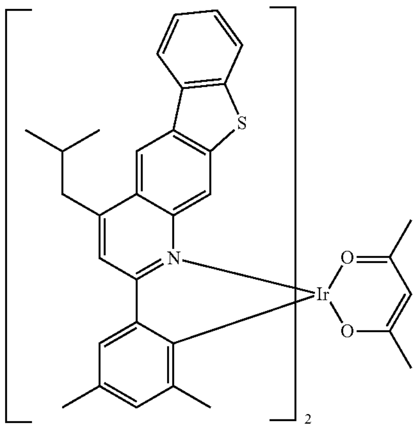
D-94
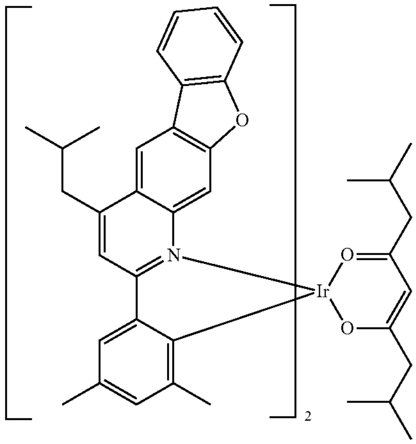

-continued
D-95
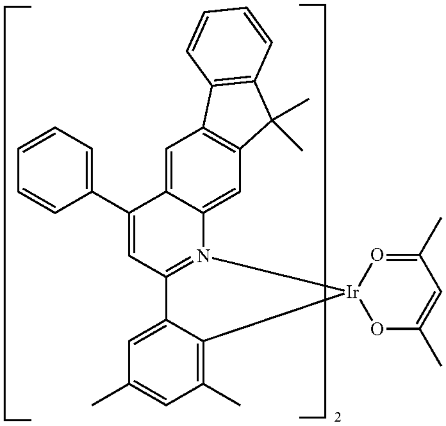
D-96
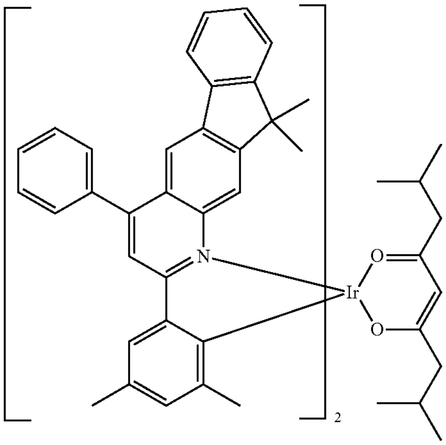
D-97
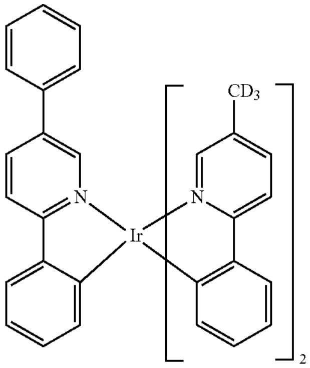
D-98
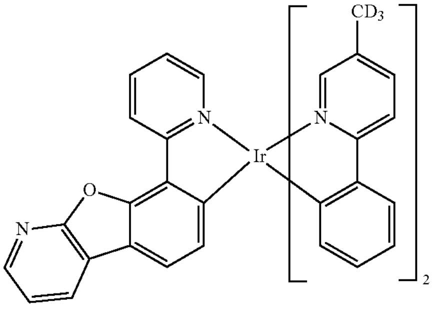
-continued
D-99
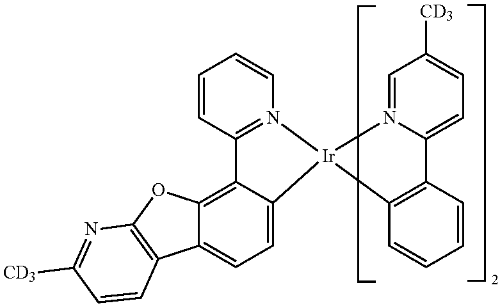
D-100
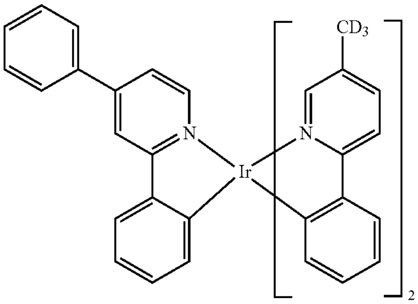
D-101
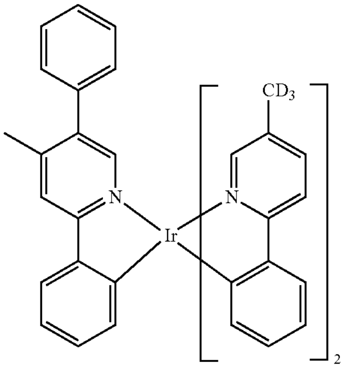
D-102
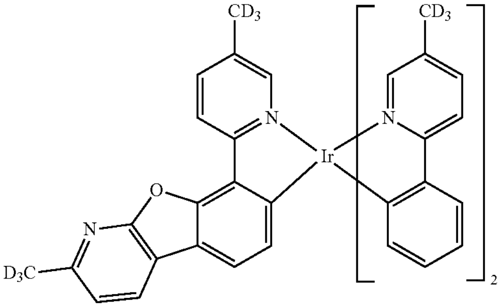

-continued
D-103
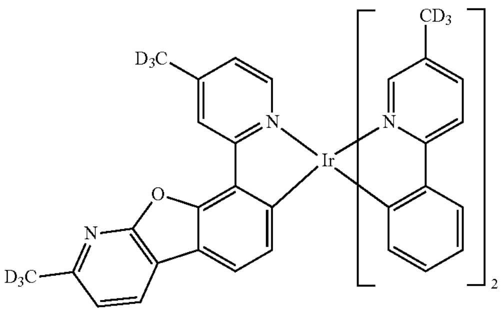
D-104
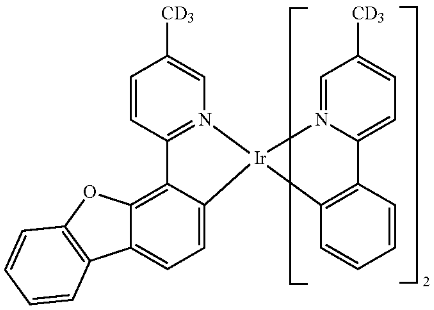
D-105
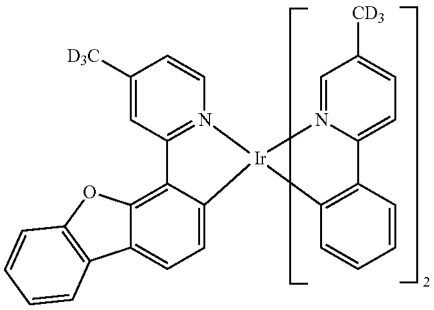
D-106
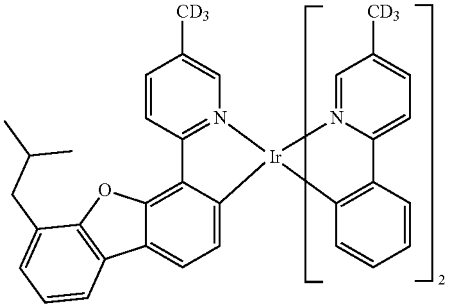
-continued
D-107
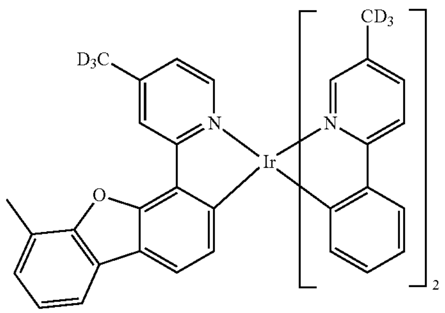
D-108
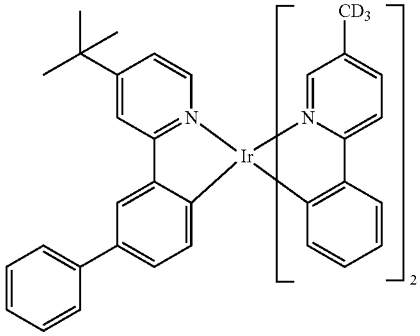
D-109
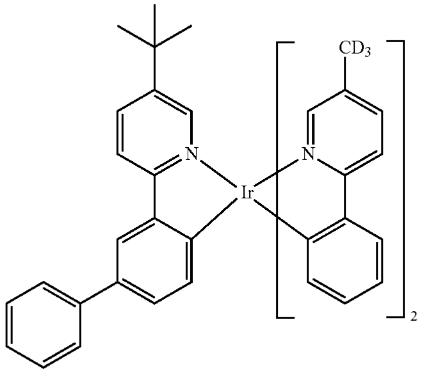
D-110
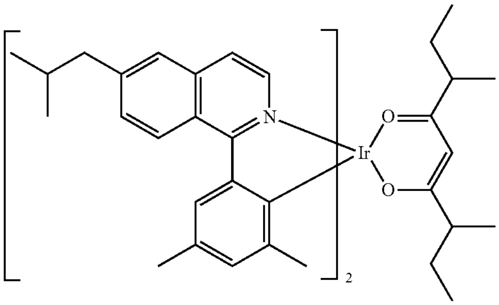

-continued
D-111
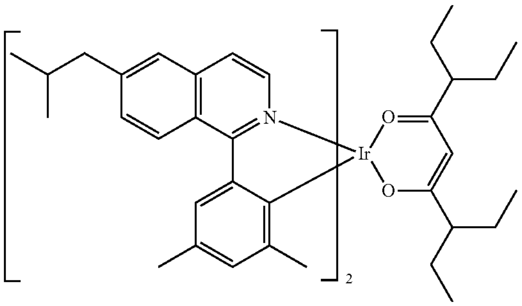
D-112
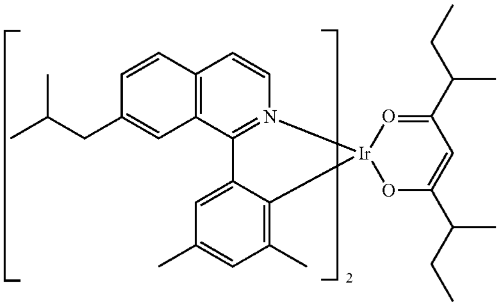
D-113
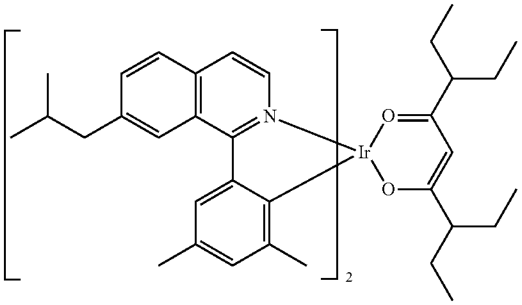
D-114
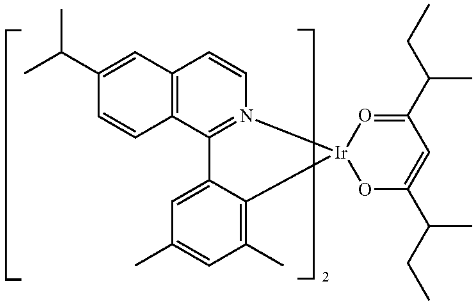
D-115
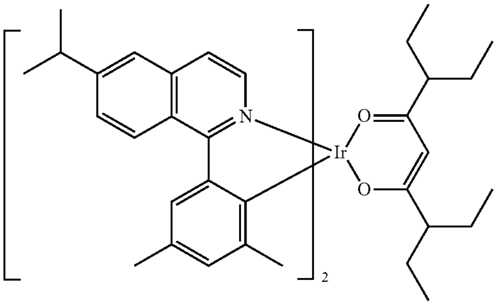
-continued
D-116
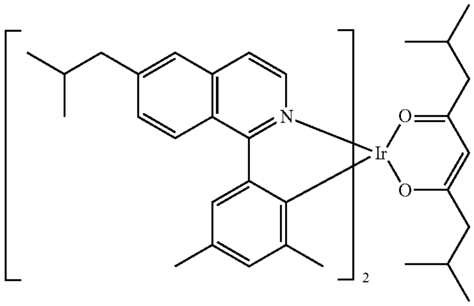
D-117
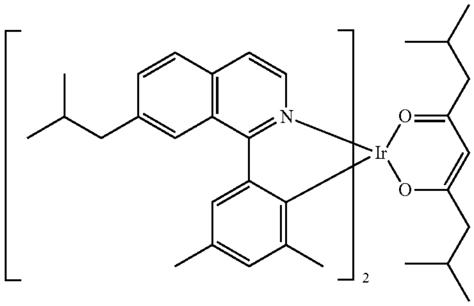
D-118
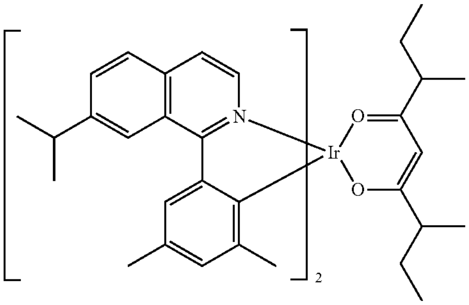
D-119
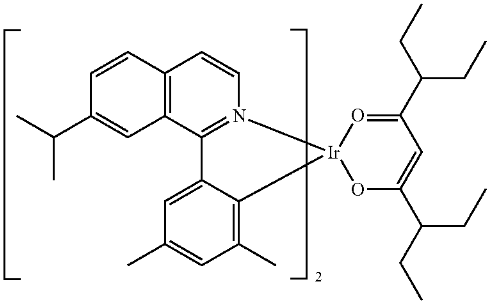

-continued
D-120
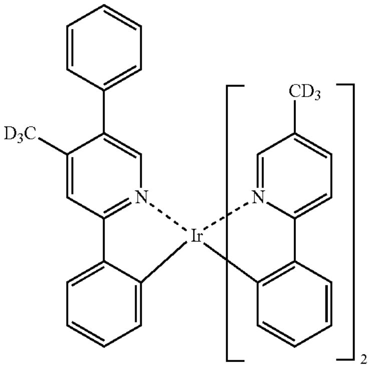
D-121
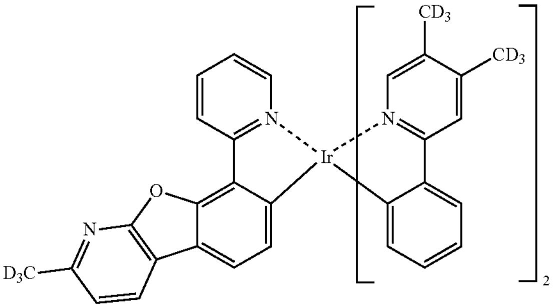
D-122
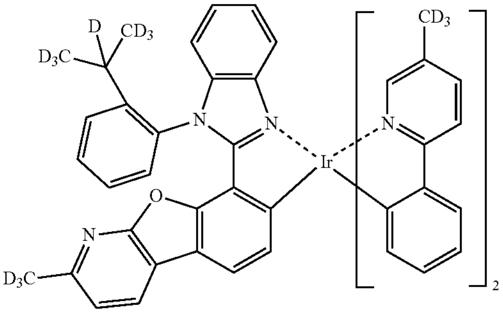
D-123
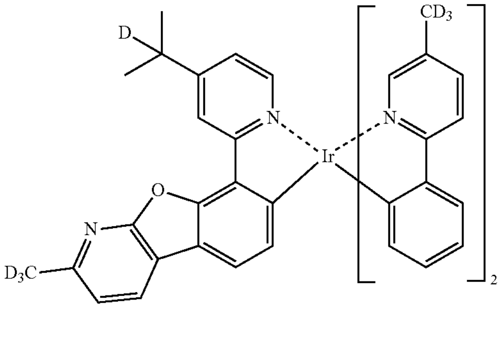
-continued
D-124
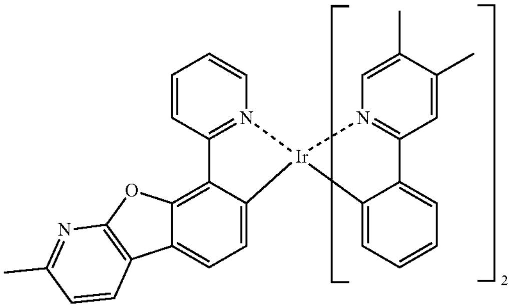
D-125
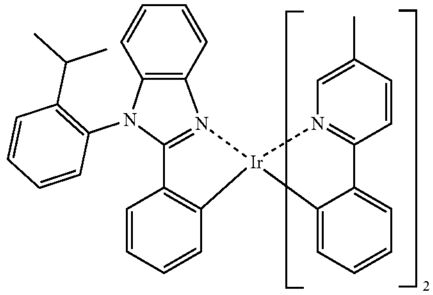
D-126
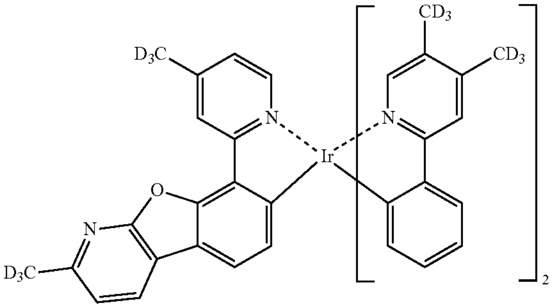
D-127
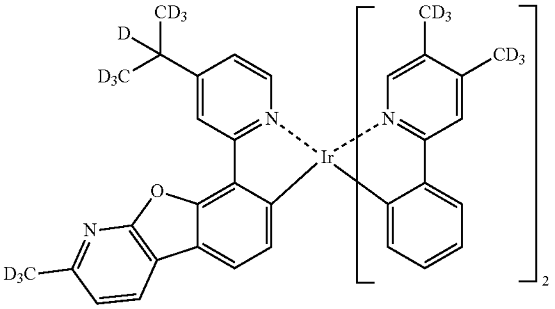
D-128
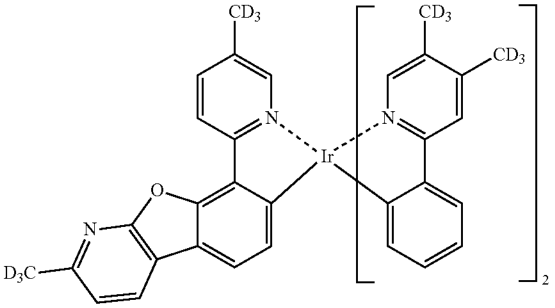

-continued
D-129
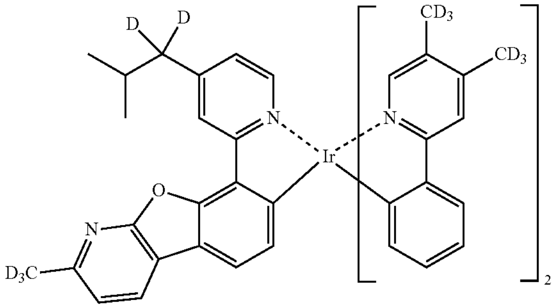
D-130
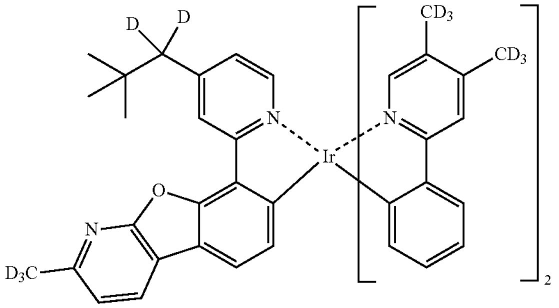
D-131
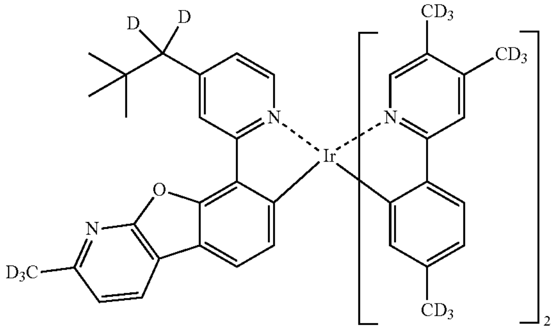
D-132
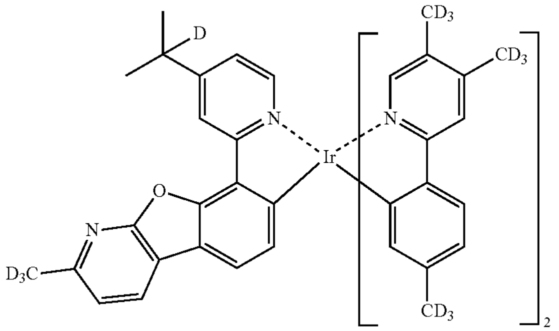
-continued
D-133
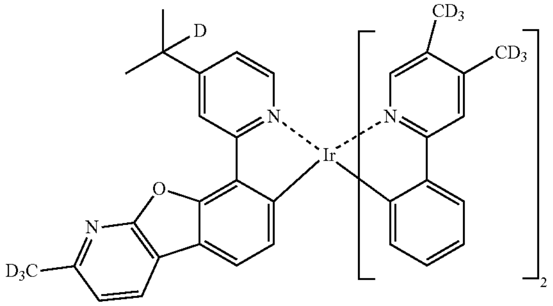
D-134
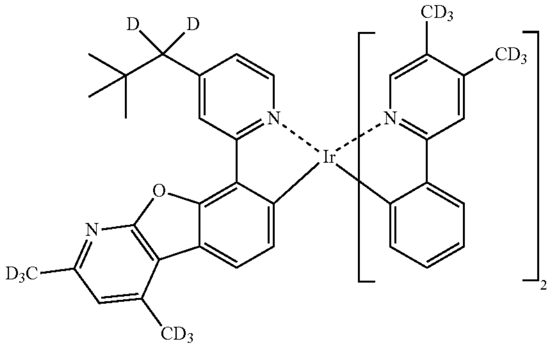
D-135
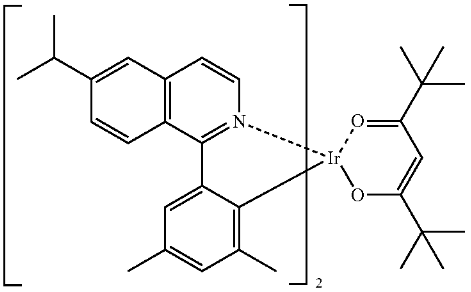
D-136
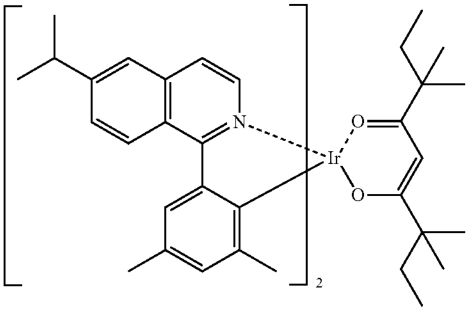

-continued
D-137
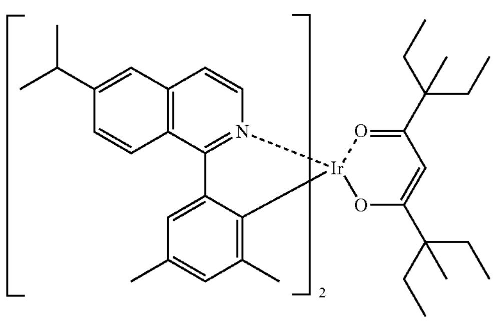
D-138
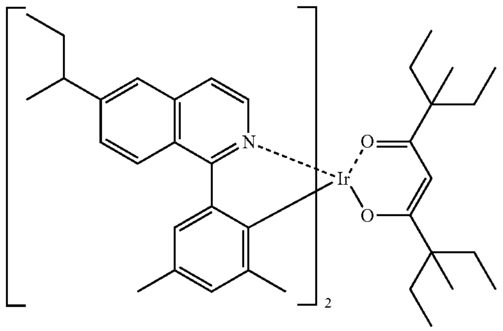
D-139
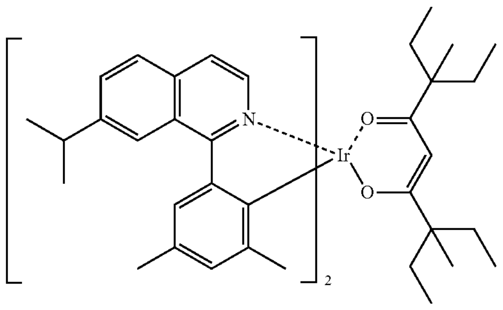
D-140
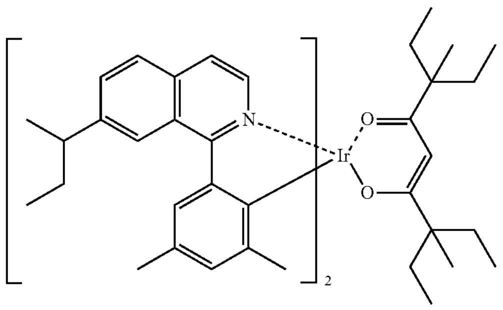
-continued
D-141
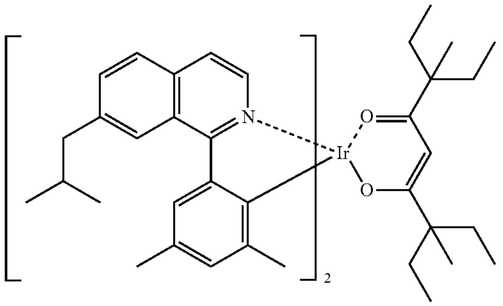
D-142
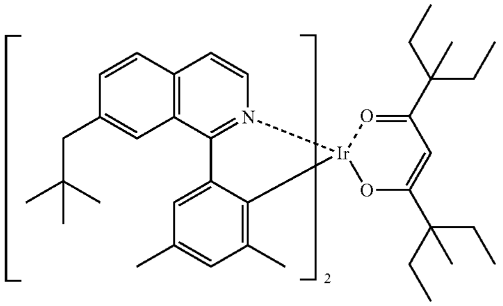
D-143
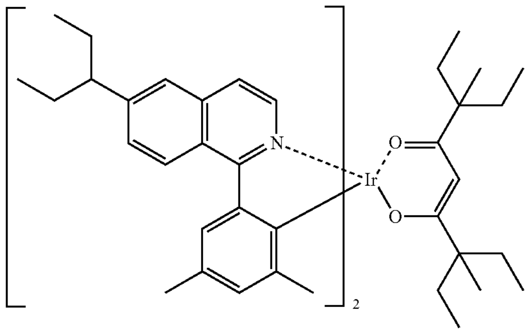
D-144
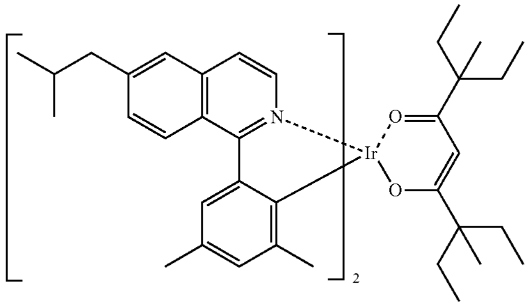

-continued

D-145

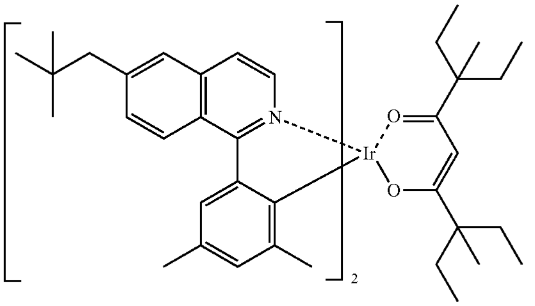

D-146

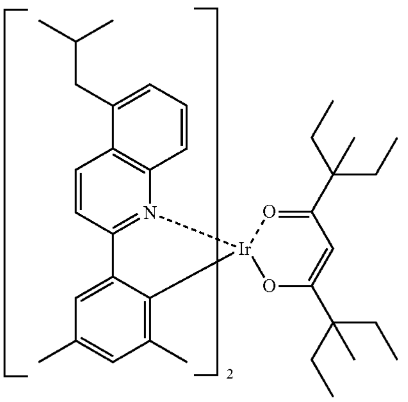

D-147

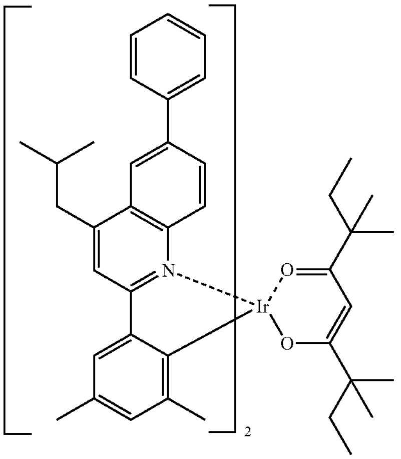

-continued

D-148

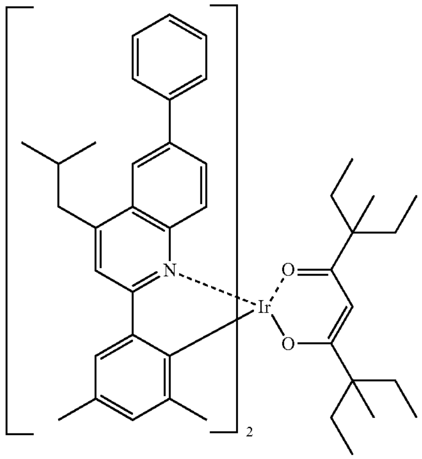

D-149

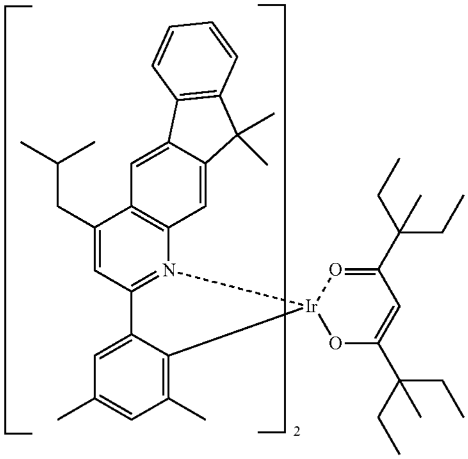

Each layer of the organic electroluminescent device of the present disclosure may be formed by any one method of dry film-forming methods such as vacuum evaporation, sputtering, plasma, ion plating, etc., or wet film-forming methods such as ink jet printing, nozzle printing, slot coating, spin coating, dip coating, flow coating, etc.

When using a wet film-forming method, a thin film can be formed by dissolving or diffusing materials forming each layer into any suitable solvent such as ethanol, chloroform, tetrahydrofuran, dioxane, etc. The solvent can be any one where the material forming each layer is soluble or dispersible in the solvent and where there are no problems in film formation capability.

In addition, the first and the second host compounds according to the present disclosure may be film-formed by the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporation, and a current is applied to the cell to evaporate the materials. In addition, when the first and second host compounds are present in the same layer or in different layers in an organic electroluminescent device, the two host compounds may be film-formed individually, respectively. For example, the second host compound may be evaporated after the first host compound is evaporated.

The present disclosure may provide a display system by using a plurality of host materials comprising the compound represented by formula 1 and the compound represented by formula 2. That is, it is possible to produce a display system or a lighting system by using a plurality of host materials of the present disclosure. Specifically, it is possible to produce a display system, e.g., a display system for a white organic light-emitting device, smartphones, tablets, notebooks, PCs, TVs, or cars, or a lighting system, e.g., an outdoor or indoor lighting system by using a plurality of host materials of the present disclosure.

Hereinafter, the preparation method of the compound of the present disclosure, and the properties thereof, and the properties of the organic electroluminescent device comprising a plurality of host materials according to the present disclosure will be explained in detail with reference to the representative compounds of the present disclosure. However, the following examples only explain the properties of the organic electroluminescent device comprising the compound or the plurality of host materials according to the present disclosure, and the present disclosure is not limited to the following examples.

Example 1: Preparation of Compound H1-176

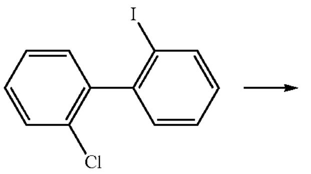

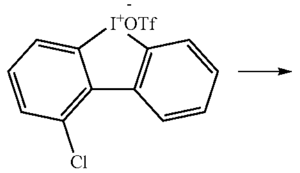

1-1

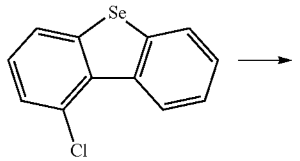

1-2

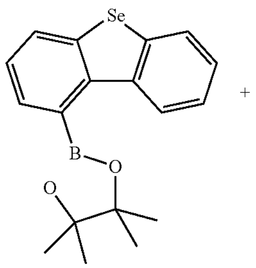

1-3

-continued

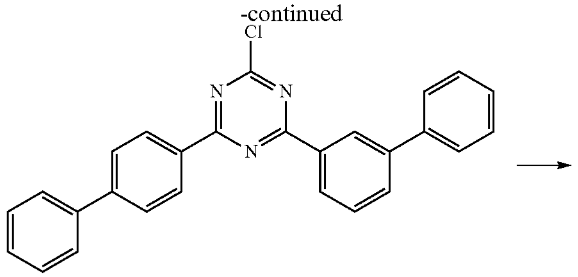

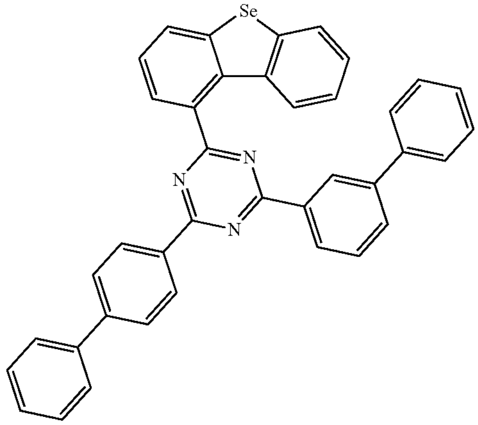

H1-176

Synthesis of Compound 1-1

2-chloro-2'-iodo-1,1'-biphenyl (20 g, 63.5 mmol), 3-chloroperoxybenzoic acid (21.3 g, 95.3 mmol), 16 mL of triflic acid, and 320 mL of methylene chloride were added to a reaction vessel and reacted for 1 hour. After the reaction was completed, the organic solvent was removed by evaporation. The residue was washed with ethyl acetate to obtain compound 1-1 (25 g).

Synthesis of Compound 1-2

Compound 1-1 (19.7 g), potassium tert-butoxide (20.6 g, 184 mmol), selenium (10.9 g, 138 mmol), and 460 mL of dimethyl sulfoxide were added to a reaction vessel and stirred at 80° C. for 2 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound 1-2 (8.6 g, yield: 71%).

Synthesis of Compound 1-3

Compound 1-2 (4.1 g, 15.4 mmol), bis(pinacolato)diboron (4.7 g, 18.5 mmol), tris(dibenzylindenacetone)dipalladium(0) (0.71 g, 0.77 mmol), tricyclohexylphosphine tetrafluoroborate (0.56 g, 1.54 mmol), potassium acetate (4.5 g, 46.2 mmol), and 80 mL of o-xylene were added to a reaction vessel and stirred under reflux for 2 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound 1-3 (5 g, yield: 92%).

Synthesis of Compound H1-176

Compound 1-3 (4.5 g, 12.6 mmol), 2-[1,1'-biphenyl]-3-yl-4-[1,1'-biphenyl]-4-yl-6-chloro-1,3,5-triazine (5.3 g, 12.7 mmol), tetrakis(triphenylphosphine)palladium(0) (0.73 g, 0.63 mmol), potassium carbonate (4.3 g, 31.5 mmol), 65 mL of toluene, 17 mL of ethanol, and 17 mL of distilled water were added to a reaction vessel and stirred under reflux for 3 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound H1-176 (7.3 g, yield: 94%).

| Compound | MW | M.P. |
|---|---|---|
| H1-176 | 614.6 | 222° C. |

Example 2: Preparation of Compound H1-177

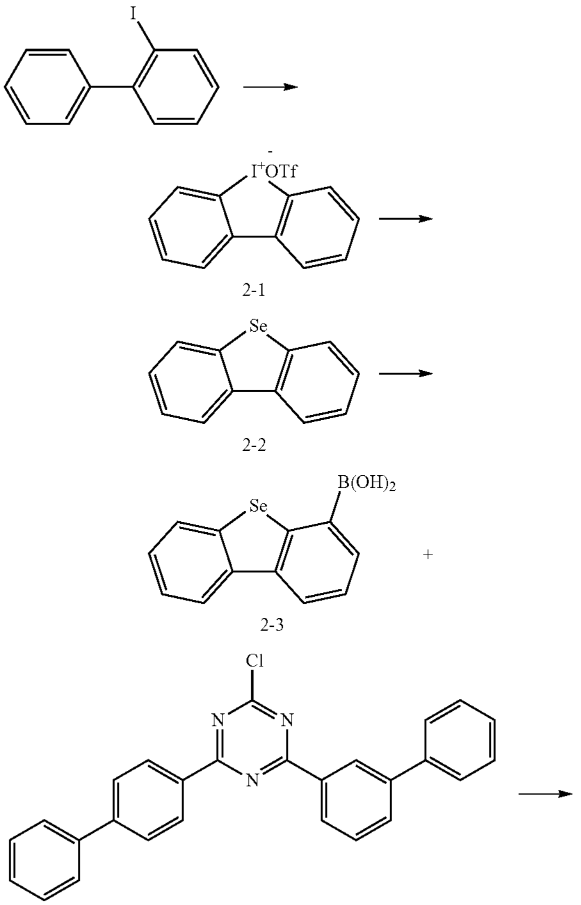

2-1

2-2

2-3

-continued

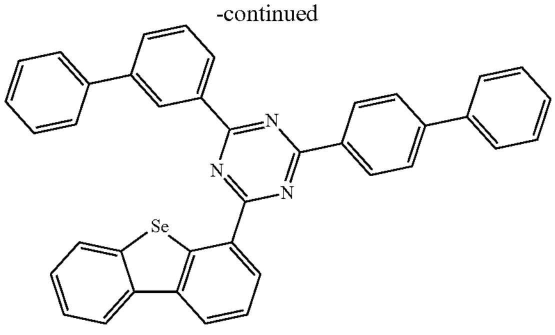

H1-177

Synthesis of Compound 2-1

2-iodo-1,1'-biphenyl (41.6 g, 148 mmol), 3-chloroperoxybenzoic acid (50 g, 223 mmol), 40 mL of triflic acid, and 750 mL of methylene chloride were added to a reaction vessel and reacted for 1 hour. After the reaction was completed, the organic solvent was removed by evaporation. The residue was washed with ethyl acetate to obtain compound 2-1 (64 g).

Synthesis of Compound 2-2

Compound 2-1 (64 g), potassium tert-butoxide (67.3 g, 600 mmol), selenium (35.5 g, 450 mmol), and 1500 mL of dimethyl sulfoxide were added to a reaction vessel and stirred at 80° C. for 2 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound 2-2 (22.8 g, yield: 65%).

Synthesis of Compound 2-3

Compound 2-2 (22.8 g, 98.6 mmol) and 500 mL of tetrahydrofuran were added to a reaction vessel under nitrogen atmosphere and cooled to −78° C. Then, n-butyllithium (41 mL, 103 mmol) was slowly added dropwise. Then, trimethyl borate (12.6 ml, 113 mmol) was added dropwise and reacted at room temperature for 12 hours. After the reaction was completed, the reaction was terminated with water, and the organic layer was extracted with ethyl acetate. After residual moisture was removed using magnesium sulfate, the residue was dried and separated by column chromatography to obtain compound 2-3 (10 g, yield: 40%).

Synthesis of Compound H1-177

Compound 2-3 (4 g, 14.5 mmol), 2-[1,1'-biphenyl]-3-yl-4-[1,1'-biphenyl]-4-yl-6-chloro-1,3,5-triazine (6.1 g, 14.5 mmol), tetrakis(triphenylphosphine)palladium(0) (0.84 g, 0.72 mmol), potassium carbonate (5 g, 36.2 mmol), 80 mL of toluene, 20 mL of ethanol, and 20 mL of distilled water were added to a reaction vessel and stirred under reflux for 5 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound H1-177 (3.5 g, yield: 41%).

| Compound | MW | M.P. |
|---|---|---|
| H1-177 | 614.6 | 361° C. |

Example 3: Preparation of Compound H1-161

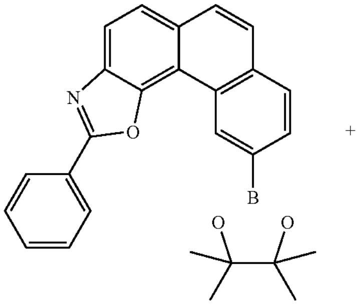

3-2

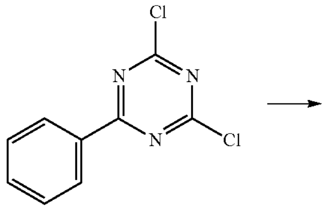

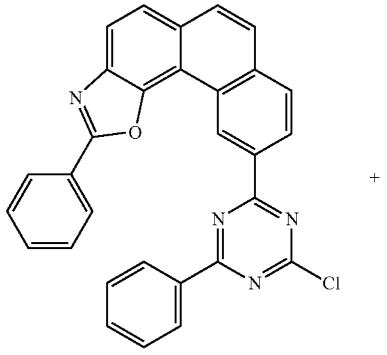

3-3

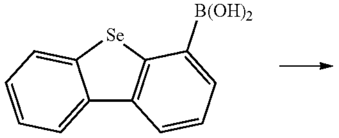

2-3

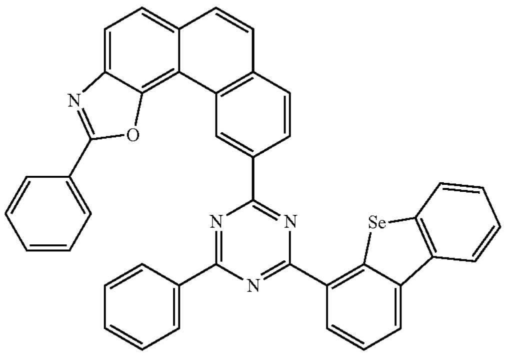

H1-161

Synthesis of Compound 3-3

Compound 3-2 (4.0 g, 9.5 mmol), 2,4-dichloro-6-phenyl-1,3,5-triazine (2.1 g, 9.5 mmol), tetrakis(triphenylphosphine)palladium(0) (0.5 g, 0.5 mmol), $Cs_2CO_3$ (6.2 g, 19 mmol), and 30 mL of toluene were added to a reaction vessel and stirred under reflux for 6 hours. After the reaction was completed, the mixture was cooled to room temperature and stirred at room temperature, followed by adding methanol. The resulting solid was filtered under reduced pressure and separated by column chromatography using methylene chloride to obtain compound 3-3 (3.7 g, yield: 80%).

Synthesis of Compound H1-161

Compound 3-3 (7 g, 14.5 mmol), compound 2-3 (4 g, 14.5 mmol), tetrakis(triphenylphosphine)palladium(0) (0.84 g, 0.72 mmol), potassium carbonate (5 g, 36.2 mmol), 80 mL of toluene, 20 mL of ethanol, and 20 mL of distilled water were added to a reaction vessel and stirred under reflux for 5 hours. After the reaction was completed, the precipitated solid was washed with distilled water and methanol. Compound H1-161 (8.4 g, yield: 85%) was obtained by purification using column chromatography.

| Compound | MW | M.P. |
|---|---|---|
| H1-161 | 679.6 | 291° C. |

Example 4: Preparation of Compound H1-78

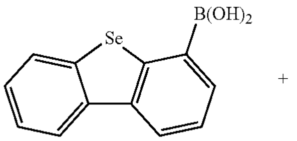

2-3

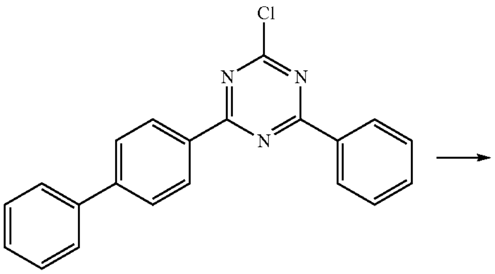

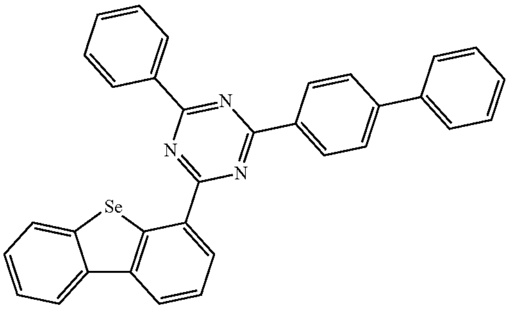

H1-78

Compound 2-3 (5 g, 18.1 mmol), 2-[1,1'-biphenyl]-4-yl-4-chloro-6-phenyl-1,3,5-triazine (6.2 g, 18.1 mmol), tetrakis (triphenylphosphine)palladium(0) (1.05 g, 0.909 mmol), potassium carbonate (6.2 g, 45.4 mmol), 90 mL of toluene, 23 mL of ethanol, and 23 mL of distilled water were added to a reaction vessel and stirred under reflux for 5 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound H1-78 (8 g, yield: 83%).

| Compound | MW | M.P. |
| --- | --- | --- |
| H1-78 | 538.5 | 290° C. |

Example 5: Preparation of Compound H1-190

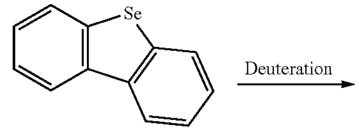

2-2

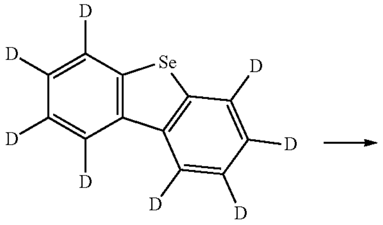

D1-1

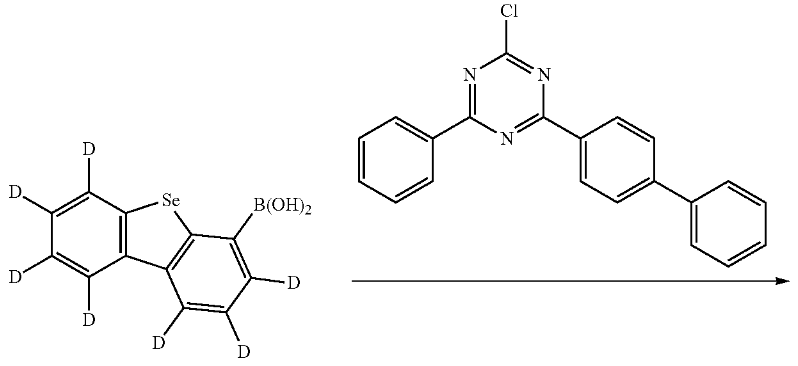

D1-2

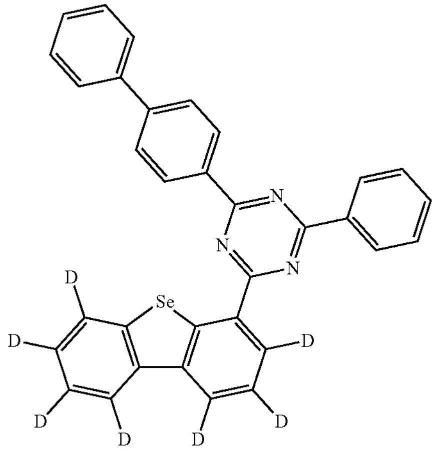

H1-190

Synthesis of Compound D1-1

Compound 2-2 (8.5 g, 36.77 mmol), 85 mL of benzene-D6, and trifluoromethanesulfonic acid (8.5 mL, 96.28 mmol) were added to a reaction vessel and stirred at 45° C. for 3 hours. After cooling to room temperature, 8.5 mL of $D_2O$ was added and stirred for 10 minutes. After neutralization with an aqueous $K_3PO_4$ solution, the organic layer was extracted with ethyl acetate. After residual moisture was removed using magnesium sulfate, the residue was distilled under reduced pressure and separated by column chromatography to obtain compound D1-1 (8.2 g, yield: 93%).

Synthesis of Compound D1-2

Compound D-1 (7.2 g, 30.1 mmol) and 150 mL of tetrahydrofuran were added to a reaction vessel under nitrogen atmosphere and cooled to −78° C. Then, n-butyllithium (14 mL, 36.1 mmol) was slowly added dropwise. Thereafter, trimethyl borate (8.1 ml, 72.2 mmol) was added dropwise and reacted at room temperature for 12 hours. After the reaction was completed, the reaction was terminated with water, and the organic layer was extracted with ethyl acetate. After residual moisture was removed using magnesium sulfate, the residue was dried and separated by column chromatography to obtain compound D1-2 (1.7 g, yield: 20%).

Synthesis of Compound H1-190

Compound D1-2 (1.7 g, 6.03 mmol), 2-[1,1'-biphenyl]-4-yl-4-chloro-6-phenyl-1,3,5-triazine (2.1 g, 6.33 mmol), tetrakis(triphenylphosphine)palladium(0) (0.35 g, 0.30 mmol), potassium carbonate (2.1 g, 15.1 mmol), 30 mL of toluene, 8 mL of ethanol, and 8 mL of distilled water were added to a reaction vessel and stirred under reflux for 4 hours. After the reaction was completed, the mixture was washed with distilled water and the organic layer was extracted with ethyl acetate. After residual moisture in the organic layer was removed with magnesium sulfate, the residue was dried and separated by column chromatography to obtain compound H1-190 (2.1 g, yield: 65%).

| Compound | MW | M.P. |
| --- | --- | --- |
| H1-190 | 545.5 | 290° C. |

Example 6: Preparation of Compound H2-45

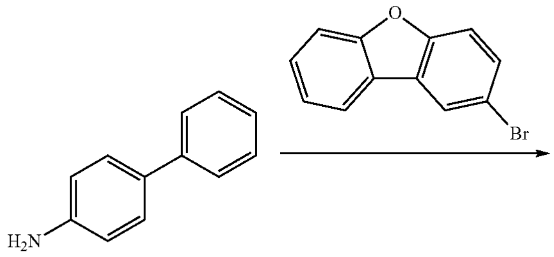

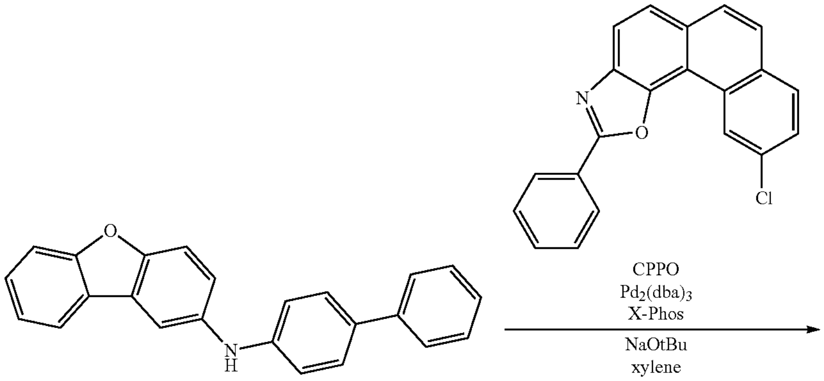

6-1

-continued

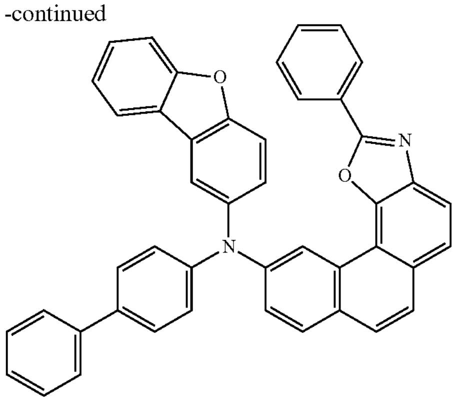

H2-45

Synthesis of Compound 6-1

[1,1'-biphenyl]-4-amine (60 g, 354 mmol), 2-bromodibenzo[b,d]furan (58.5 g, 236 mmol), $Pd(OAc)_2$ (0.54 g, 3.23 mmol), $P(Cy)_3$ (1.35 g, 3 mmol), and NaOtBu (40.9 g, 425.5 mmol) were dissolved in 600 mL of toluene in a reaction vessel and stirred under reflux for 2 hours. After the reaction was completed, the mixture was cooled to room temperature. A solid was produced by using a Celite filter, and separaged by column chromatography to obtain compound 6-1 (65.7 g, yield: 83%).

Synthesis of Compound H2-45

Compound 6-1 (20 g, 59.6 mmol), compound CPPO (19.7 g, 59.7 mmol), $Pd_2(dba)_3$ (0.55 g, 0.6 mmol), X-Phos (0.57 g, 1.2 mmol), and NaOt-Bu (11.5 g, 119.6 mmol) were dissolved in 200 mL of o-xylene in a reaction vessel and stirred under reflux for 3 hours. After the reaction was completed, the mixture was cooled to room temperature. A solid was produced by using a Celite filter, and separated by column chromatography to obtain compound H2-45 (12.7 g, yield: 34%).

| Compound | MW | M.P. |
|---|---|---|
| H2-45 | 628.73 | 252° C. |

Example 7: Preparation of Compound H2-145

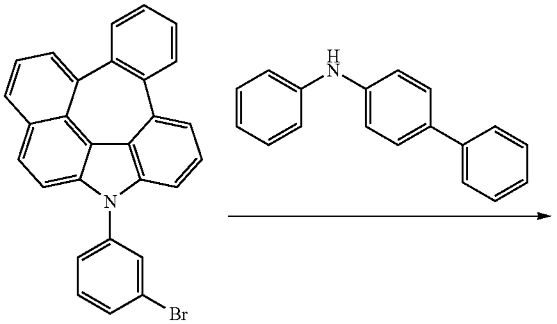

7-1

-continued

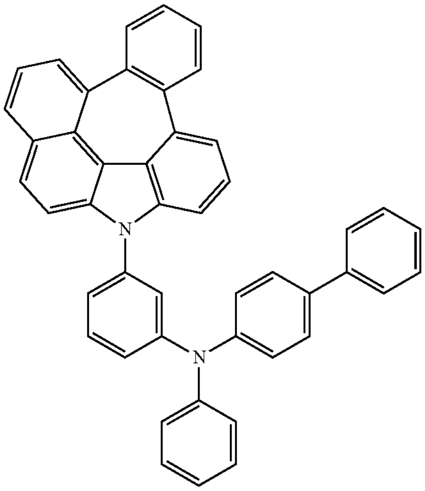

H2-145

60 mL of toluene was added to compound 7-1 (5.0 g, 11.2 mmol), N-phenyl-[1,1'-biphenyl]-4-amine (3.0 g, 12.3 mmol), $Pd_2(dba)_3$ (0.5 g, 0.56 mmol), s-phos (0.46 g, 1.12 mmol), and NaOtBu (2.7 g, 28 mmol) in a reaction vessel and stirred under reflux for 6 hours. After the reaction was completed, the mixture was cooled to room temperature and stirred at room temperature, followed by adding MeOH. The resulting solid was filtered under reduced pressure and separated by column chromatography using methylene chloride/hexane to obtain compound H2-145 (2.3 g, 34%).

| Compound | MW | M.P. |
|---|---|---|
| H2-145 | 610.8 | 132° C. |

Example 8: Preparation of Compound H2-157

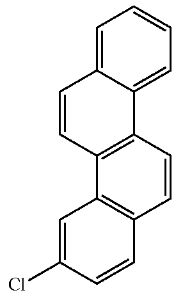

9-3

+

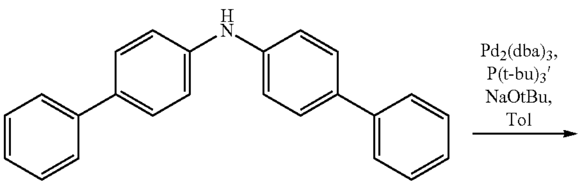

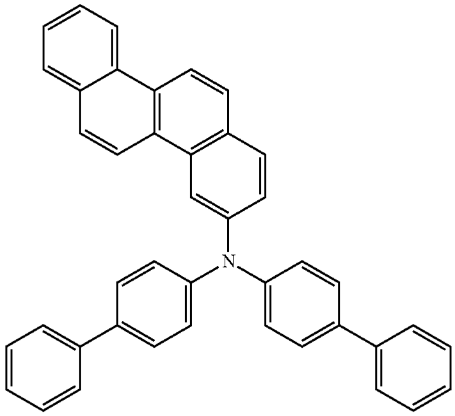

H2-157

Compound 9-3 (5.0 g, 19.0 mmol), di([1,1'-biphenyl]-4-yl)amine (6.1 g, 19.0 mmol), $Pd_2(dba)_3$ (0.9 g, 0.95 mmol), $P(t\text{-}bu)_3$ (1.0 mL, 1.90 mmol), and NaOtBu (2.7 g, 28.5 mmol), were dissolved in 95 mL of toluene in a reaction vessel, and stirred under reflux for 2 hours. After the reaction was completed, the mixture was extracted with ethyl acetate/$H_2O$ and separated by column chromatography to obtain compound H2-157 (8.4 g, yield: 81%).

| Compound | MW | M.P. |
|---|---|---|
| H2-157 | 547.7 | 247° C. |

Hereinafter, the luminous efficiency and lifespan properties of an OLED according to the present disclosure will be explained. However, the following examples only explain the properties of the OLED according to the present disclosure for a detailed understanding of the present disclosure, and the present disclosure is not limited by the following examples.

Device Examples 1 to 5: Producing a Red Light-Emitting OLED Deposited with a Plurality of Host Materials According to the Present Disclosure as Hosts An OLED according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone, and isopropyl alcohol, sequentially, and then was stored in isopropyl alcohol. The ITO substrate was mounted on a substrate holder of a vacuum vapor deposition apparatus. Compound HI-1 of Table 5 was introduced into a cell of the vacuum vapor deposition apparatus, and compound HT-1 of Table 5 was introduced into another cell. The two materials were evaporated at different rates, and compound HI-1 was deposited in a doping amount of 3 wt % based on the total amount of compound HI-1 and compound HT-1 to form a first hole injection layer with a thickness of 10 nm. Subsequently, compound HT-1 was deposited on the first hole injection layer to form a first hole transport layer with a thickness of 80 nm. Next, compound HT-2 was introduced into another cell of the vacuum vapor deposition apparatus and was evaporated by applying an electric current to the cell, thereby depositing a second hole transport layer with a thickness of 60 nm on the first hole transport layer. After forming the hole injection layer and the hole transport layers, a light-emitting layer was deposited thereon as follows: A first host compound and a second host compound shown in Tables 1 to 3 below were introduced into two cells of the vacuum vapor deposition apparatus as hosts and compound D-39 was introduced into another cell as a dopant. The two host materials were evaporated at a rate of 1:1 and the dopant material was simultaneously evaporated at a different rate, and the dopant was deposited in a doping amount of 3 wt % based on the total amount of the hosts and dopant to form a light-emitting layer having a thickness of 40 nm on the second hole transport layer. Compound ETL-1 and compound EIL-1 as electron transport materials were evaporated in a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. Each compound for each material was purified by vacuum sublimation under $10^{-6}$ torr before use.

Device Examples 6 and 7: Producing a Red Light-Emitting OLED Deposited with a Single Host Material According to the Present Disclosure as a Host OLEDs were produced in the same manner as in Device Examples 1 to 5, except that the first host compound shown in Table 4 below was used alone as a host of a light-emitting layer.

Comparative Example 1: Producing a Red Light-Emitting OLED Deposited with a Comparative Compound as a Single Host Material An OLED was produced in the same manner as in Device Examples 1 to 5, except that comparative compound T-1 shown in Table 4 below was used alone as a host of a light-emitting layer.

Comparative Examples 2 to 4: Producing a Red Light-Emitting OLED Deposited with a Comparative Compound as a First Host Compound OLEDs were produced in the same manner as in Device Examples 1 to 5, except that a first host compound (comparative compound) and a second host compound shown in Tables 1 to 3 below were used as a host of a light-emitting layer.

The driving voltage, luminous efficiency, and light-emitting color at a luminance of 1,000 nit, and the time taken for reduction of luminance from 100% to 95% (lifespan: T95) at a luminance of 5,000 nit of the OLEDs produced in Device Examples 1 to 7 and Comparative Examples 1 to 4 are provided in Tables 1 to 4 below.

TABLE 1

| | First Host | Second Host | Driving Voltage (V) | Luminous Efficiency (cd/A) | Light-Emitting Color | Lifespan (T95, hr) |
|---|---|---|---|---|---|---|
| Device Example 1 | H1-177 | H2-45 | 3.1 | 33.2 | Red | 244 |
| Device Example 2 | H1-161 | H2-45 | 3.1 | 32.2 | Red | 425 |
| Device Example 5 | H1-78 | H2-45 | 3.1 | 35.6 | Red | 203 |
| Comparative Example 4 | T-1 | H2-45 | 3.2 | 34.0 | Red | 144 |

TABLE 2

| | First Host | Second Host | Driving Voltage (V) | Luminous Efficiency (cd/A) | Light-Emitting Color | Lifespan (T95, hr) |
|---|---|---|---|---|---|---|
| Device Example 4 | H1-78 | H2-145 | 3.0 | 35.0 | Red | 263 |
| Comparative Example 3 | T-1 | H2-145 | 3.2 | 34.2 | Red | 181 |

TABLE 3

| | First Host | Second Host | Driving Voltage (V) | Light-Emitting Color | Lifespan (T95, hr) |
|---|---|---|---|---|---|
| Device Example 3 | H1-78 | H2-157 | 3.6 | Red | 111 |
| Comparative Example 2 | T-1 | H2-157 | 3.7 | Red | 86 |

TABLE 4

| | First Host | Driving Voltage (V) | Luminous Efficiency (cd/A) | Light-Emitting Color | Lifespan (T95, hr) |
|---|---|---|---|---|---|
| Device Example 6 | H1-161 | 3.9 | 29.0 | Red | 45 |
| Device Example 7 | H1-78 | 3.9 | 31.5 | Red | 10.7 |
| Comparative Example 1 | T-1 | 3.9 | 25.6 | Red | 4.6 |

From Tables 1 to 3 above, it can be confirmed that the organic electroluminescent devices deposited with a plurality of host materials comprising a first host material and a second host material according to the present disclosure exhibit significantly improved lifespan properties while exhibiting an equivalent level of driving voltage and luminous efficiency, compared to the organic electroluminescent device deposited with a plurality of host materials by using the comparative compound as a first host material. In addition, from Table 4 above, it can be confirmed that the organic electroluminescent devices deposited with a first host material according to the present disclosure as a single host material exhibit significantly improved lifespan properties while exhibiting an equivalent level of driving voltage and luminous efficiency, compared to the organic electroluminescent device deposited with the comparative compound as a single host material.

The compounds used in the Device Examples and Comparative Examples are shown in Table 5 below.

TABLE 5
| | |
|---|---|
| Hole Injection Layer/Hole Transport Layer | 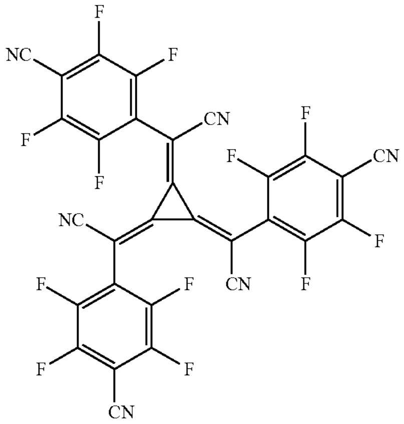 HI-1 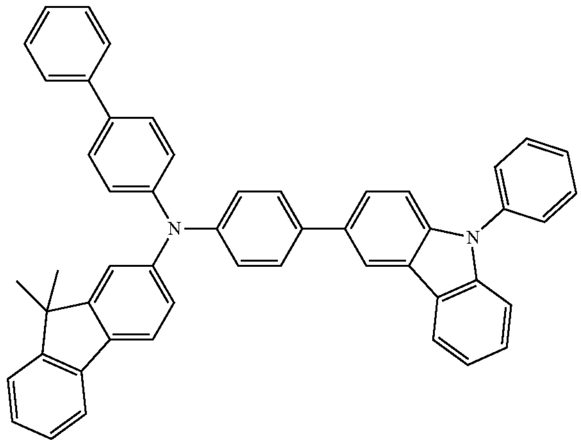 HT-1 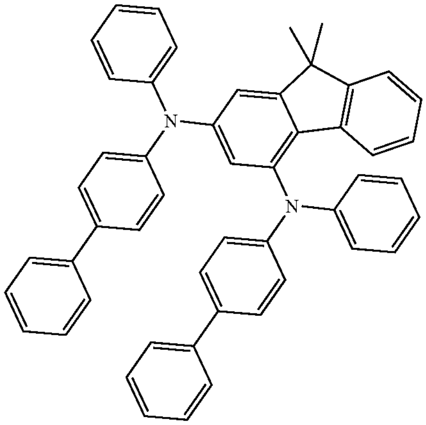 HT-2 |

TABLE 5-continued
Light-Emitting Layer
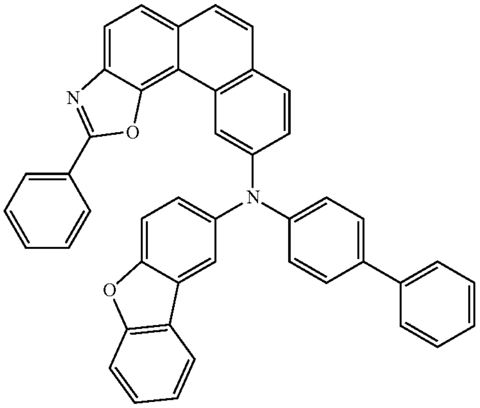
H2-45
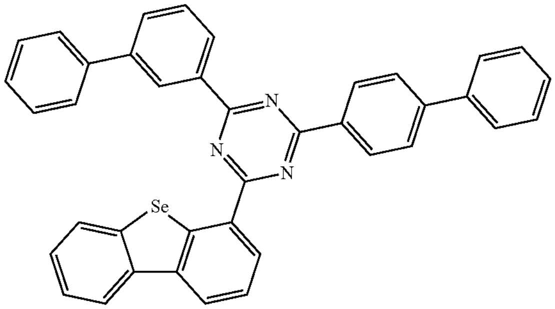
H1-177
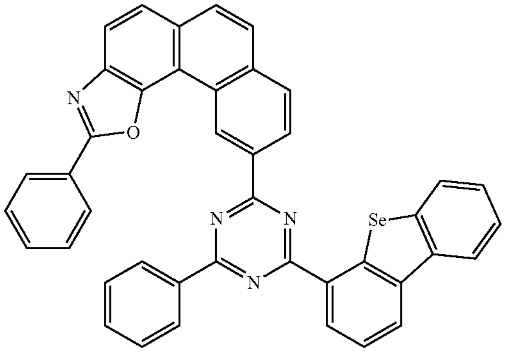
H1-161
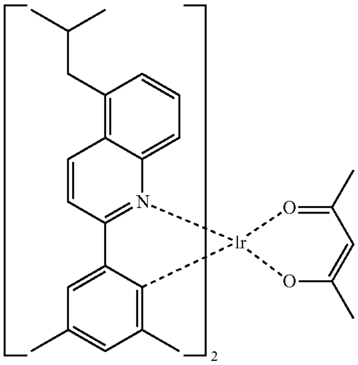
D-39

TABLE 5-continued
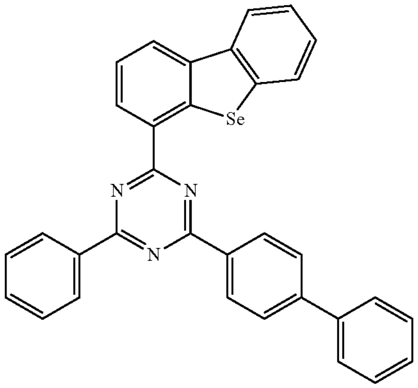
H1-78
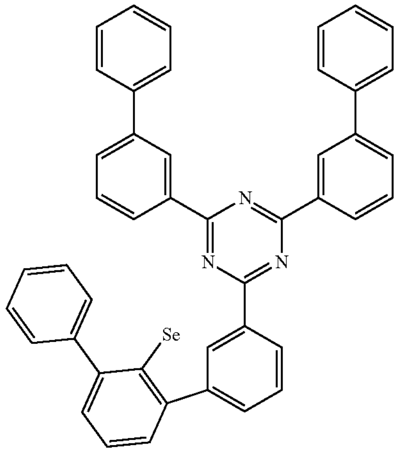
T-1
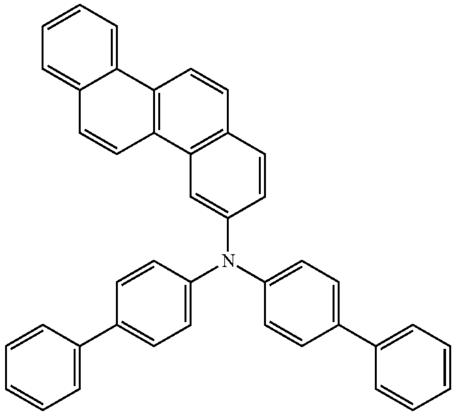
H2-157

TABLE 5-continued

| | |
|---|---|
| | 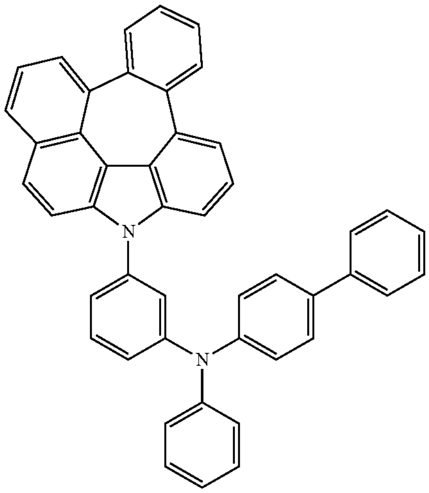 H2-145 |
| Electron Transport Layer/ Electron Injection Layer | 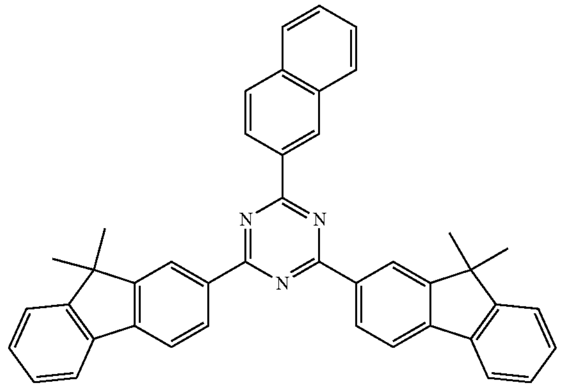 ETL-1 |
| | 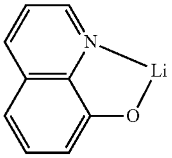 EIL-1 |

The invention claimed is:

1. A plurality of host materials comprising at least one first host compound and at least one second host compound, wherein the first host compound is represented by the following formula 1, and the second host compound is represented by the following formula 2:

(1)

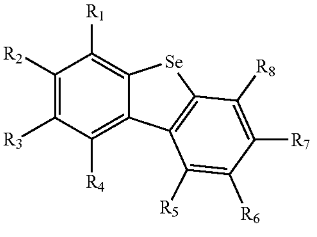

in formula 1, $R_1$ to $R_8$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30)aliphatic ring(s) and a (C6-C30)aromatic ring(s), or $-(L)_a$-HAr;

at least one of $R_1$ to $R_8$ is $-(L)_a$-HAr;

HAr represents a substituted or unsubstituted nitrogen-containing (3- to 20-membered)heteroaryl;

L each independently represents a single bond, a substituted or unsubstituted (C6-C30)arylene, or a substituted or unsubstituted (3- to 30-membered)heteroarylene; and a represents 1 or 2;

(2)

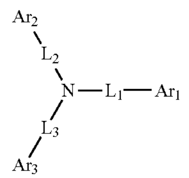

in formula 2, $L_1$ to $L_3$ each independently represent a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ to $Ar_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or an unsubstituted fused ring group of a (C3-C30)aliphatic ring(s) and a (C6-C30)aromatic ring(s), or $-L_b-N(Ar_c)(Ar_d)$;

$L_b$ represents a single bond, a substituted or unsubstituted (C6-C30)arylene, or a substituted or unsubstituted (3- to 30-membered)heteroarylene; and $Ar_c$ and $Ar_d$ each independently represent hydrogen, a substituted or unsubstituted (C1-C30)alkyl, a substituted or unsubstituted (C2-C30)alkenyl, a substituted or unsubstituted fused ring group of a (C3-C30)aliphatic ring(s) and a (C6-C30)aromatic ring(s), a substituted or unsubstituted (C6-C30)aryl, or a substituted or unsubstituted (3- to 30-membered)heteroaryl;

with the proviso that the case where all of $L_1$ to $L_3$ are single bonds and all of Ar1 to Ar3 are hydrogen is excluded.

2. The plurality of host materials according to claim 1, wherein the substituents of the substituted alkyl(ene), the substituted alkenyl, the substituted aryl(ene), the substituted heteroaryl(ene), the substituted cycloalkyl(ene), the substituted alkoxy, the substituted trialkylsilyl, the substituted dialkylarylsilyl, the substituted alkyldiarylsilyl, the substituted triarylsilyl, and the substituted fused ring group of an aliphatic ring(s) and an aromatic ring(s) each independently are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium and a (3- to 30-membered)heteroaryl(s); tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30)aliphatic ring(s) and a (C6-C30)aromatic ring(s); an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The plurality of host materials according to claim 1, wherein the formula 1 is represented by any one of the following formulas 1-1 to 1-4:

(1-1)

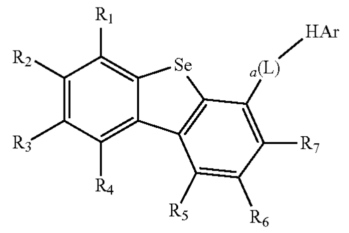

(1-2)

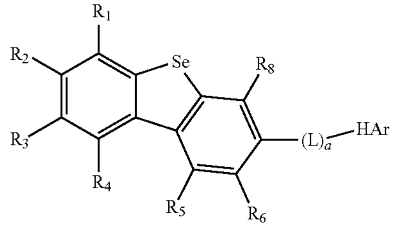

(1-3)

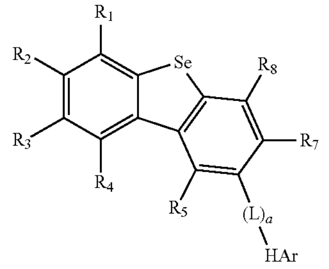

(1-4)

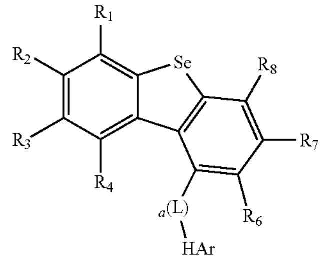

in formulas 1-1 to 1-4,
$R_1$ to $R_8$, L, HAr, and a are as defined in claim 1.
4. The plurality of host materials according to claim 1, wherein the formula 2 is represented by any one of the following formulas 2-1 to 2-14:
(2-1)
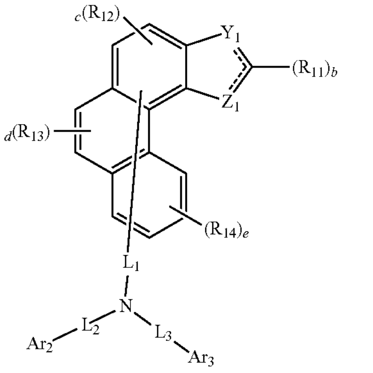
(2-2)
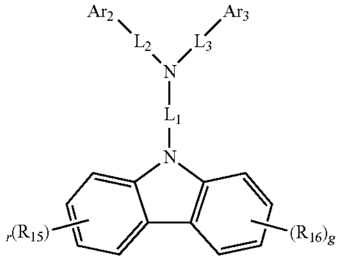
(2-3)
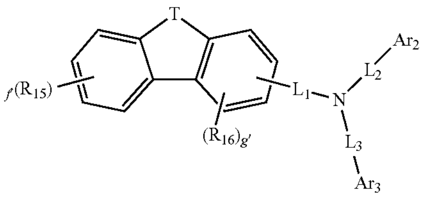
(2-4)
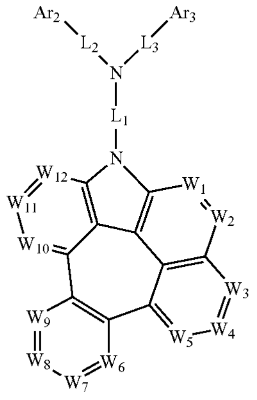
-continued
(2-5)
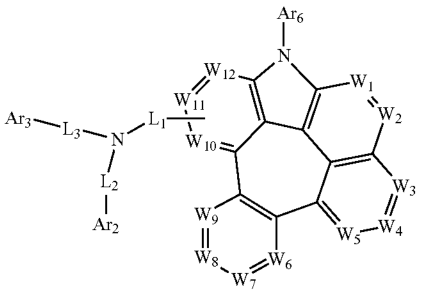
(2-6)
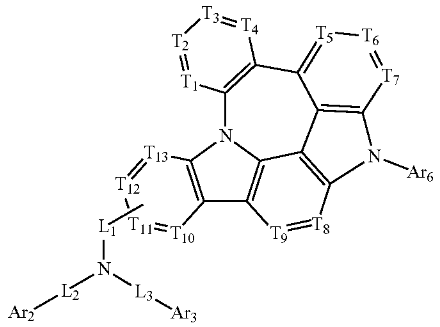
(2-7)
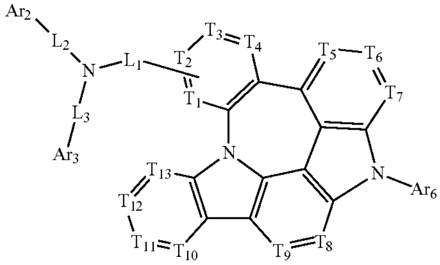
(2-8)
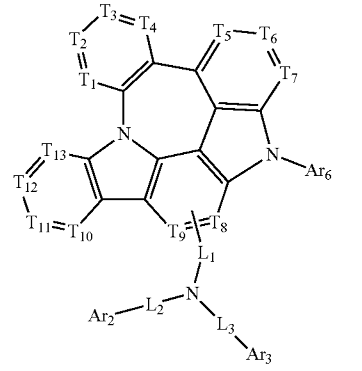
(2-9)
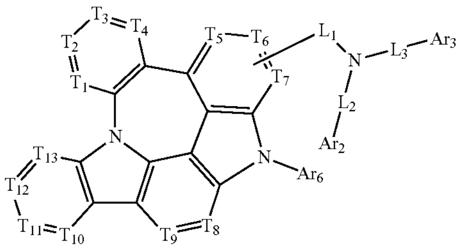

-continued (2-10)

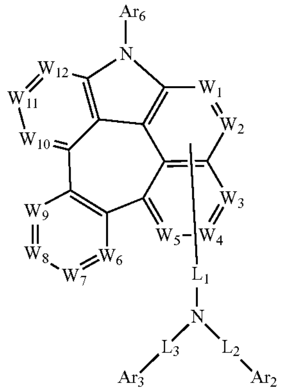

(2-11)

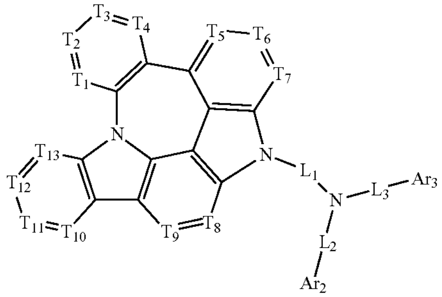

(2-12)

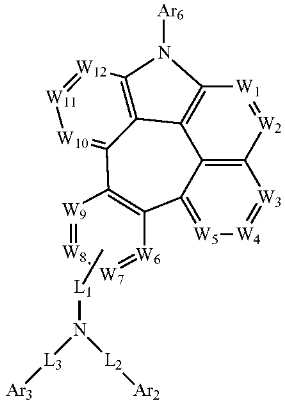

(2-13)

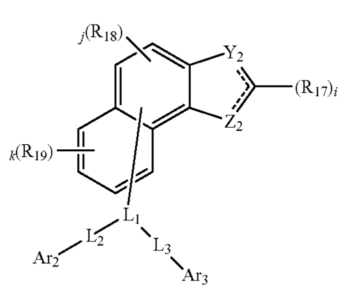

-continued (2-14)

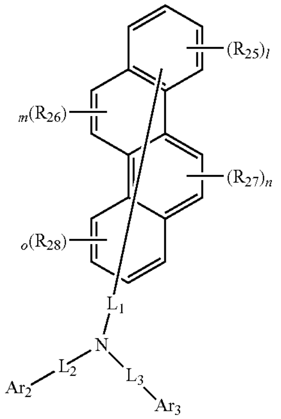

in formulas 2-1 to 2-14, $Y_1$, $Y_2$, $Z_1$, and $Z_2$ each independently represent —N═, —$NR_{21}$—, —O—, or —S—, with the proviso that any one of $Y_1$ and $Z_1$ represents —N═, and the other one of $Y_1$ and $Z_1$ represents —$NR_{21}$—, —O—, or —S—, and with the proviso that any one of $Y_2$ and $Z_2$ represents —N═, and the other one of $Y_2$ and $Z_2$ represents —$NR_{21}$—, —O—, or —S—;

T represents $CR_{22}R_{23}$, $NR_{24}$, O, or S;

$T_1$ to $T_{13}$ and $W_1$ to $W_{12}$ each independently represent N or $CV_1$;

$R_{11}$ and $Ar_6$ each independently represent a substituted or unsubstituted (C6-C30)aryl, or a substituted or unsubstituted (3- to 30-membered)heteroaryl;

$R_{12}$ to $R_{19}$, $R_{21}$ to $R_{28}$, and $V_1$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30)aliphatic ring(s) and a (C6-C30)aromatic ring(s), or $-L_c-N(Ar_e)(Ar_f)$; or may be linked to an adjacent substituent to form a substituted or unsubstituted ring(s);

$L_c$ represents a single bond, a substituted or unsubstituted (C6-C30)arylene, or a substituted or unsubstituted (3- to 30-membered)heteroarylene;

$Ar_e$ and $Ar_f$ each independently represent hydrogen, a substituted or unsubstituted (C1-C30)alkyl, a substituted or unsubstituted (C2-C30)alkenyl, a substituted or unsubstituted fused ring group of a (C3-C30)aliphatic ring(s) and a (C6-C30)aromatic ring(s), a substituted or unsubstituted (C6-C30)aryl, or a substituted or unsubstituted (3- to 30-membered)heteroaryl;

b and i represent 1; c, d, j, m, and n each independently represent 1 or 2; e, f, g, f', k, l, and o each independently represent an integer of 1 to 4; g' represents an integer of 1 to 3; in which if c to g, f', g', l, m, n, and o are an integer of 2 or more, each of $R_{12}$ to each of $R_{19}$ and each of $R_{25}$ to each of $R_{28}$ may be the same as or different from each other; and $Ar_2$, $Ar_3$, and $L_1$ to $L_3$ are as defined in claim 1.

5. The plurality of host materials according to claim 1, wherein HAr of formula 1 is at least one selected from the following structures:

(1-5)

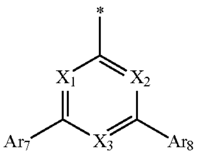

(1-6)

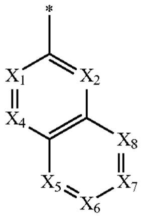

(1-7)

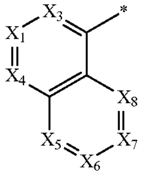

in formulas 1-5 to 1-7, $X_1$ to $X_8$ each independently represent $CR_{25}$ or N;

$R_{25}$, $Ar_7$, and $Ar_8$ each independently represent hydrogen, deuterium, a substituted or unsubstituted (C1-C30) alkyl, a substituted or unsubstituted (C6-C30)aryl, or a substituted or unsubstituted (3- to 30-membered)heteroaryl, wherein $R_{25}$ may be linked to an adjacent substituent to form a ring(s); and

* represents a site linked to dibenzoselenophene.

6. The plurality of host materials according to claim 1, wherein the compound represented by formula 1 is at least one selected from the following compounds:

H1-1

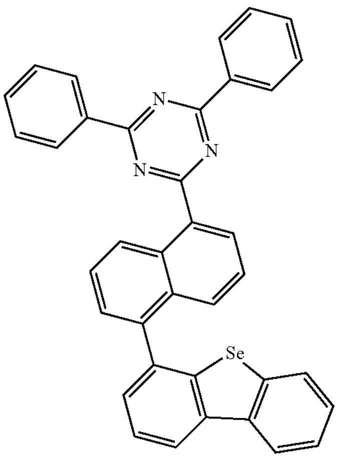

-continued

H1-2

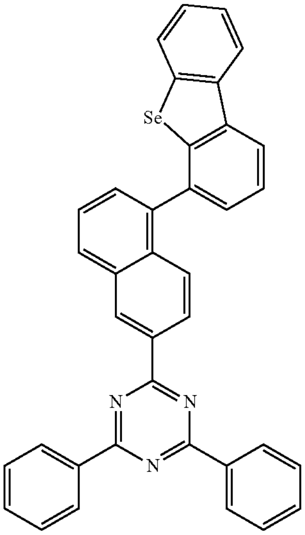

H1-3

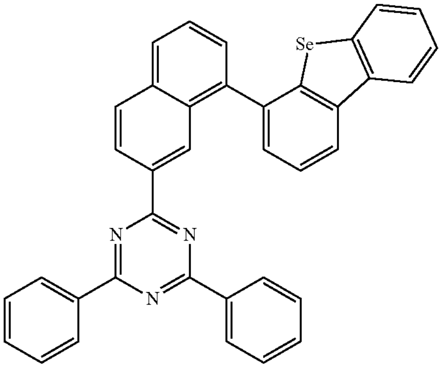

H1-4

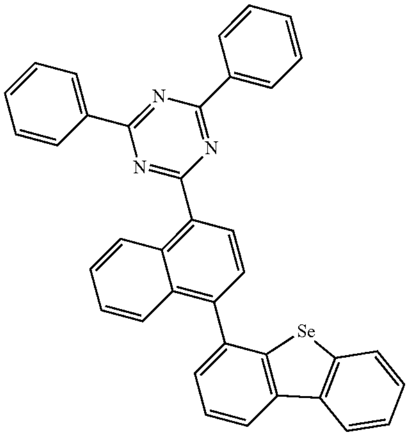

-continued
H1-5
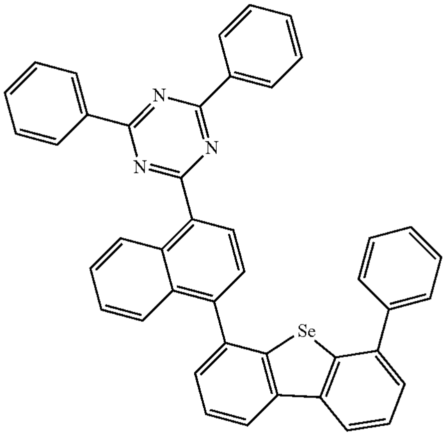
H1-6
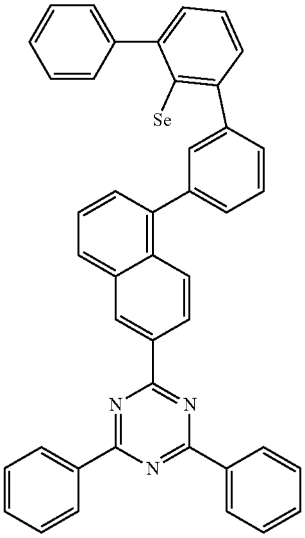
H1-7
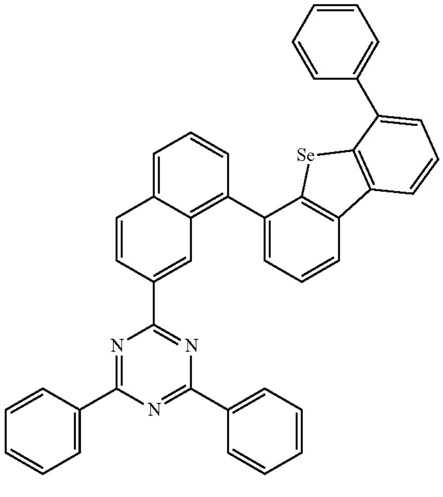
-continued
H1-8
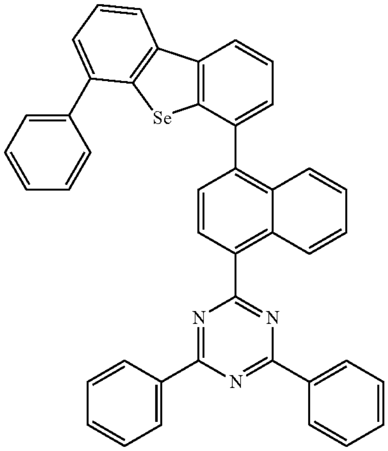
H1-9
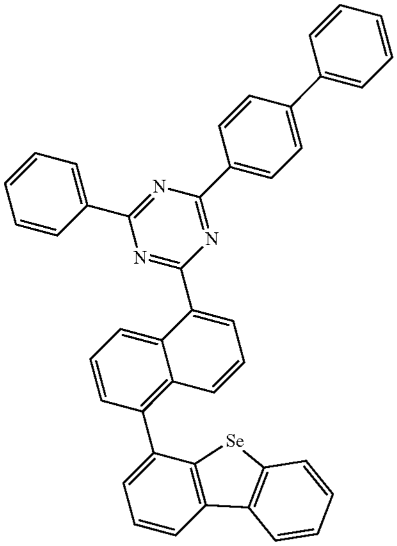
H1-10
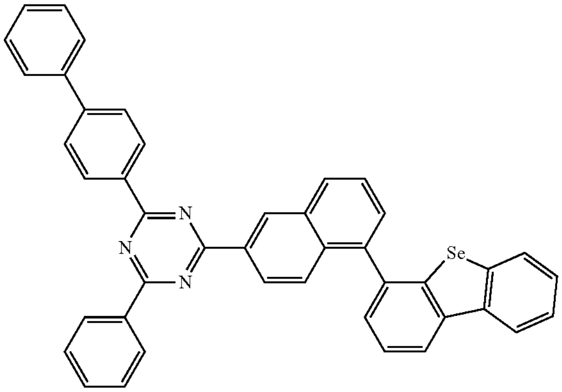

-continued
H1-11
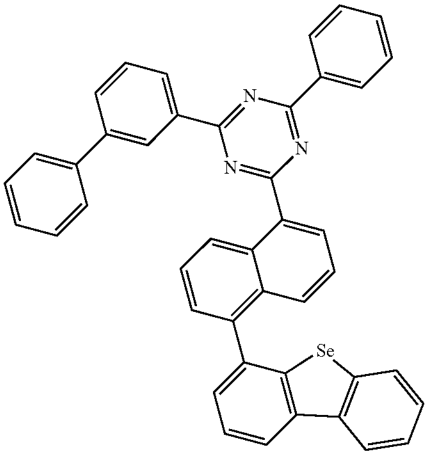
H1-12
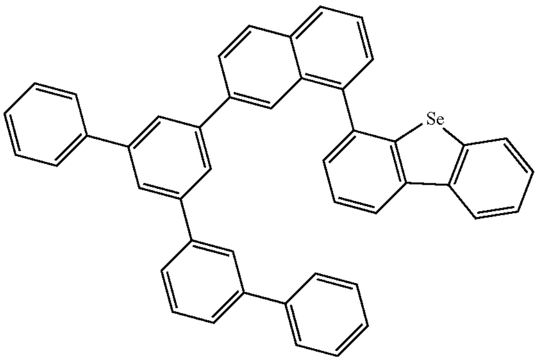
H1-13
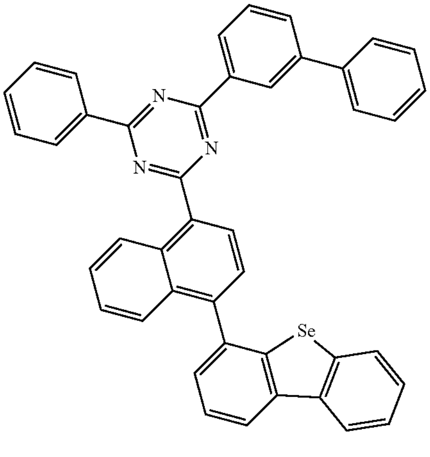
-continued
H1-14
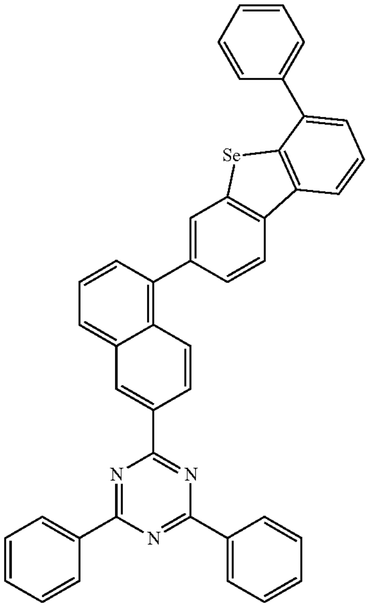
H1-15
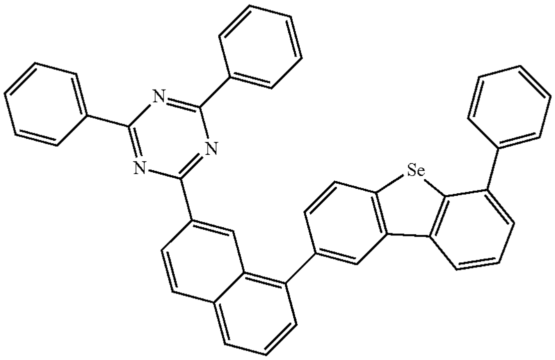
H1-16
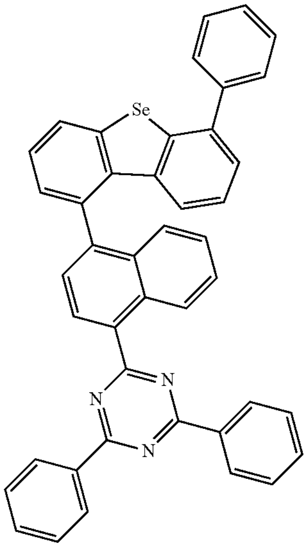

-continued
H1-17
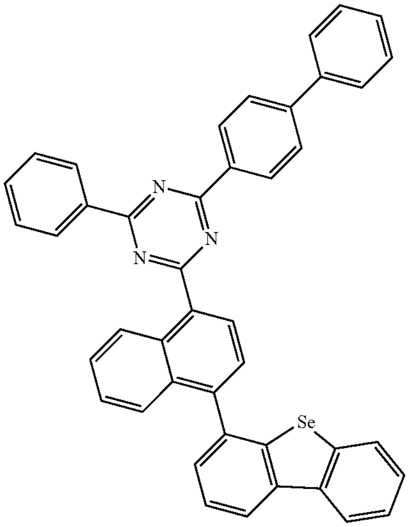
H1-18
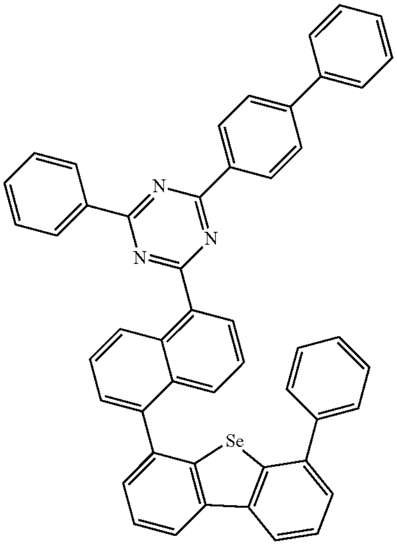
H1-19
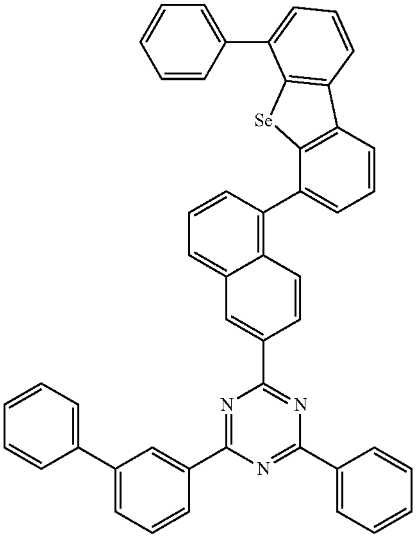
-continued
H1-20
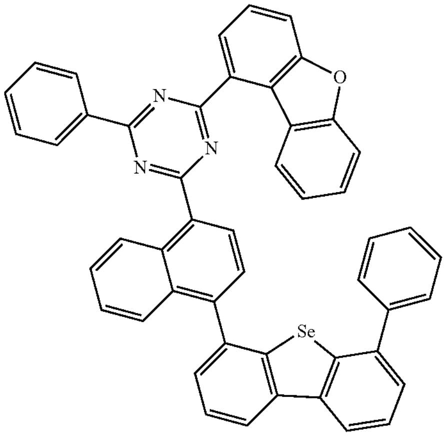
H1-21
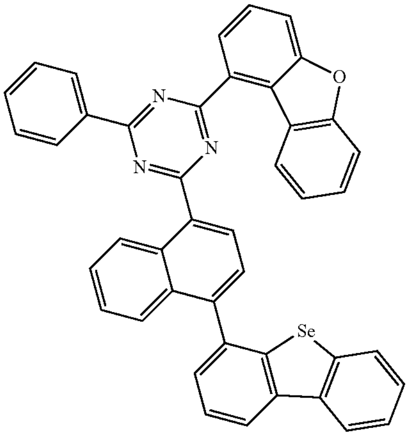
H1-22
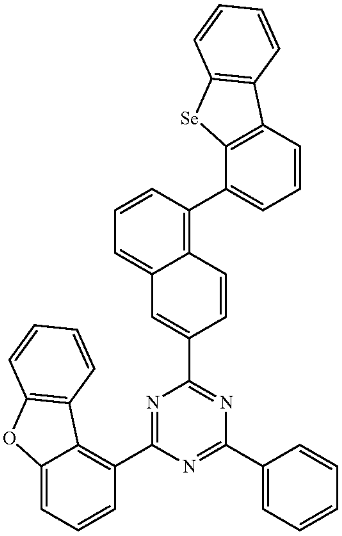

-continued
H1-23
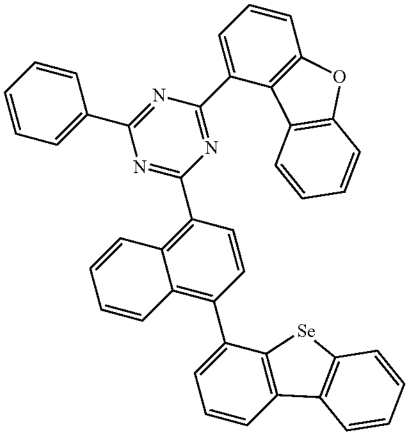
H1-24
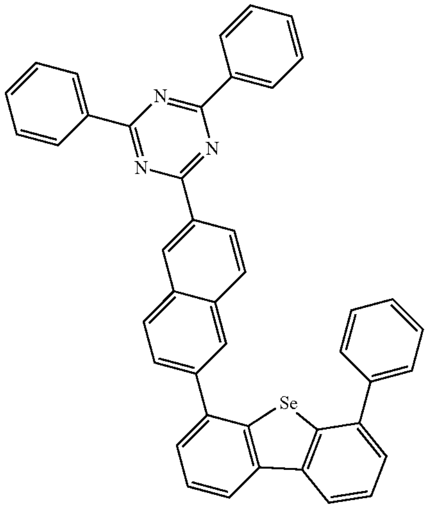
H1-25
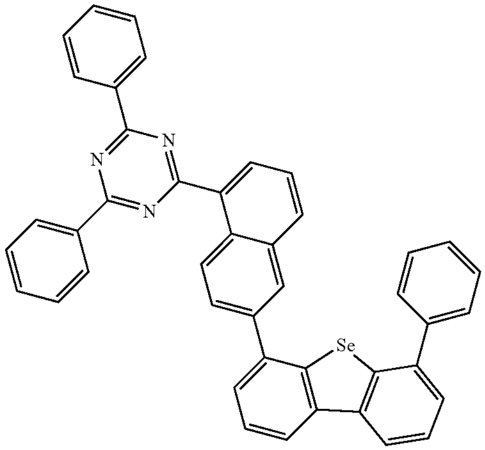
-continued
H1-26
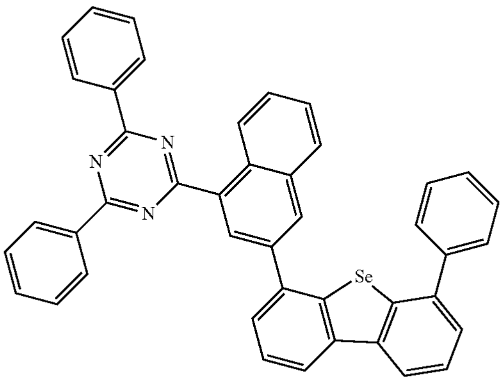
H1-27
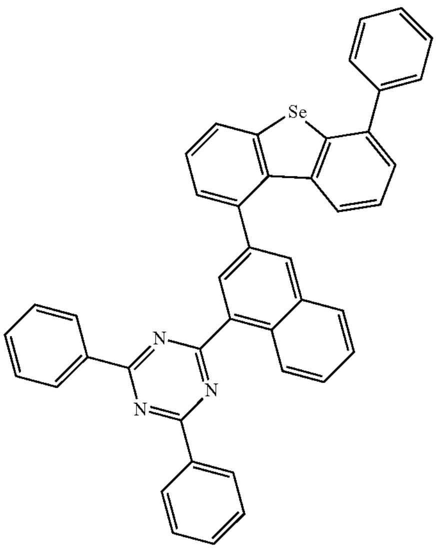
H1-28
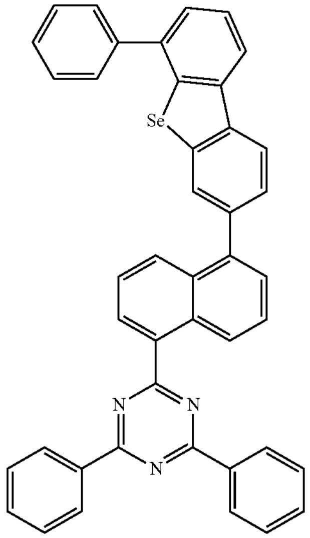

-continued
H1-29
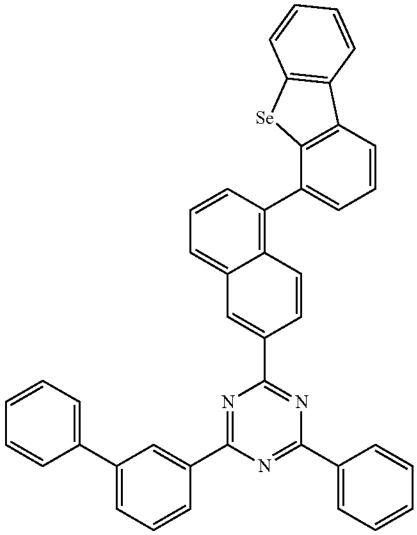
H1-30
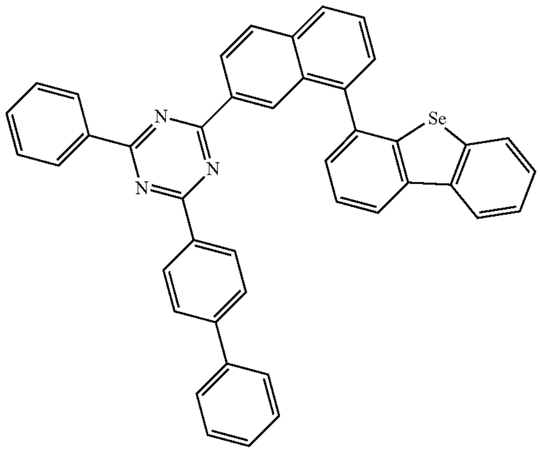
H1-31
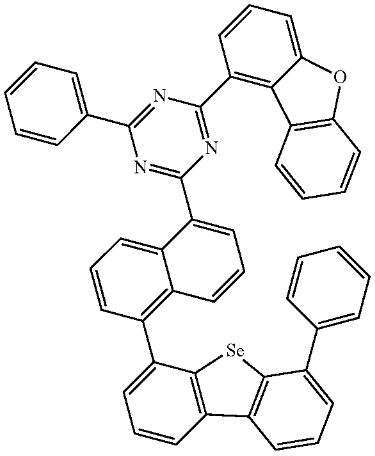
-continued
H1-32
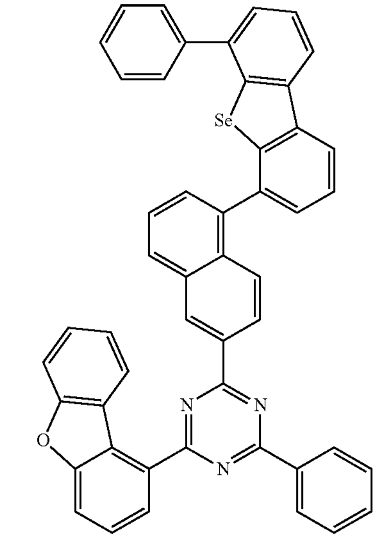
H1-33
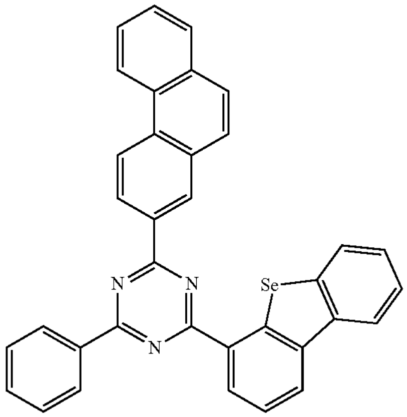
H1-34
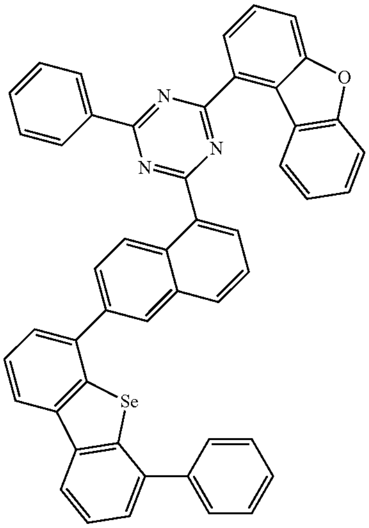

-continued
H1-35
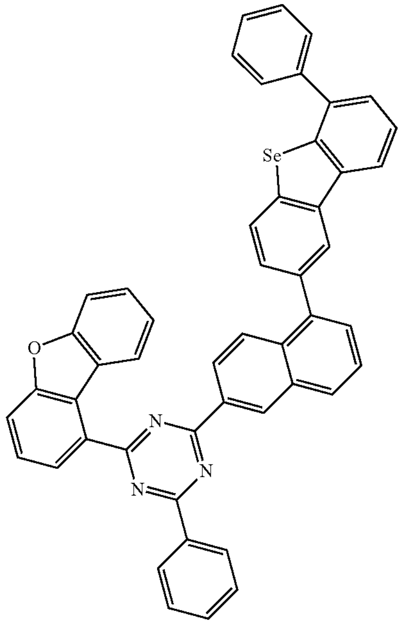
H1-36
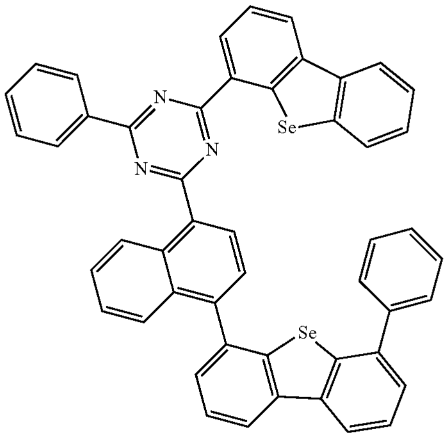
H1-37
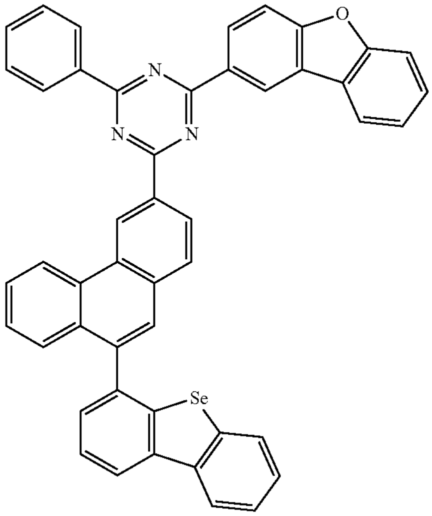
-continued
H1-38
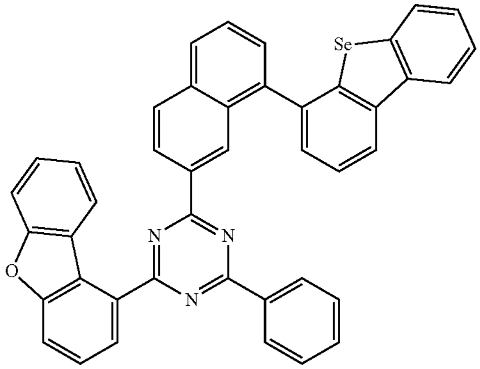
H1-39
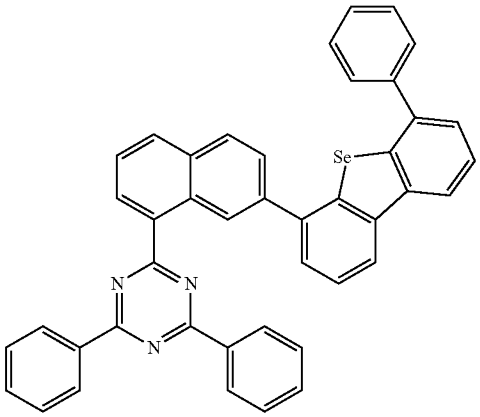
H1-40
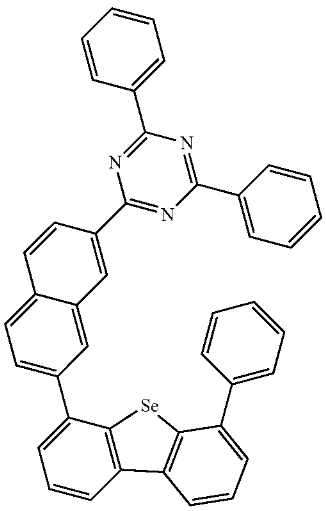

-continued
H1-41
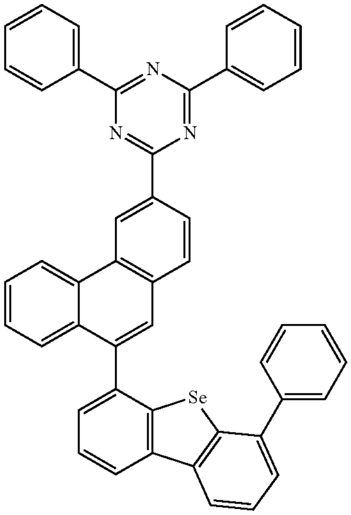
H1-42
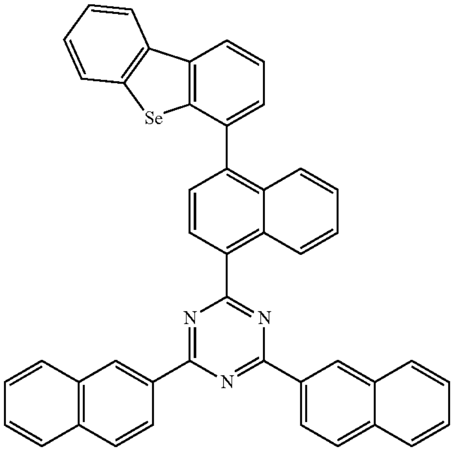
H1-44
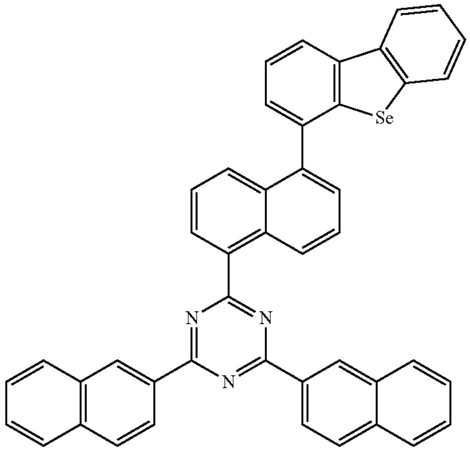
-continued
H1-45
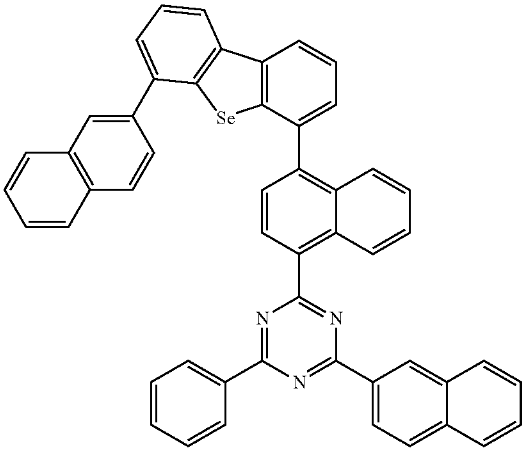
H1-46
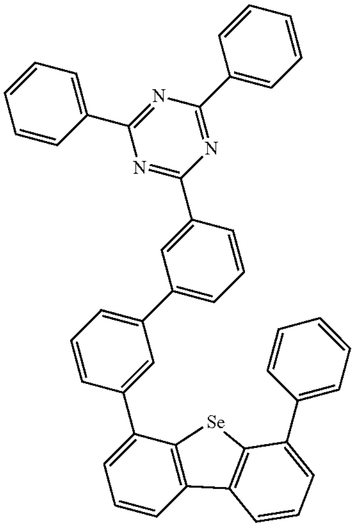
H1-47
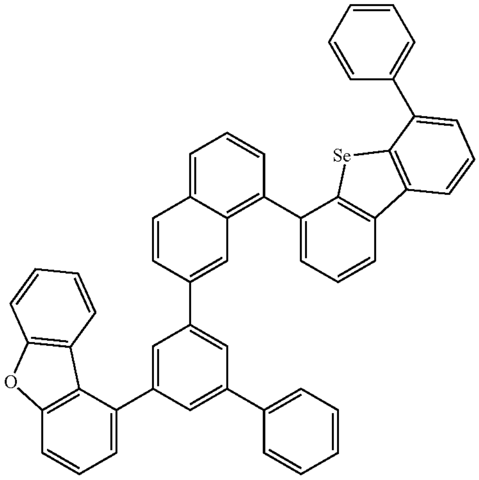

-continued
H1-48
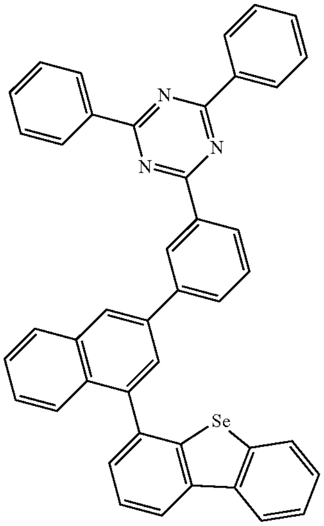
H1-49
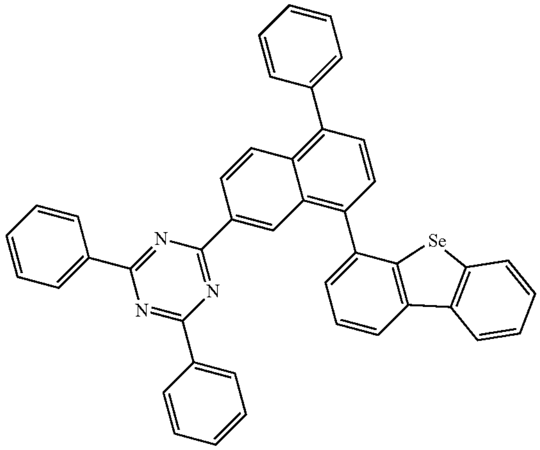
H1-50
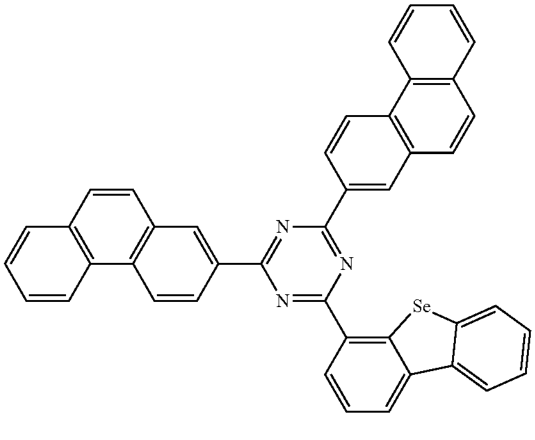
-continued
H1-51
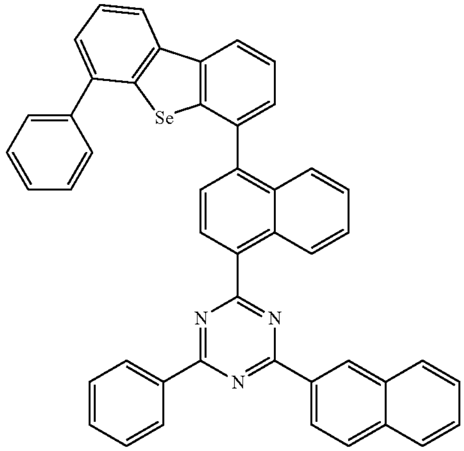
H1-52
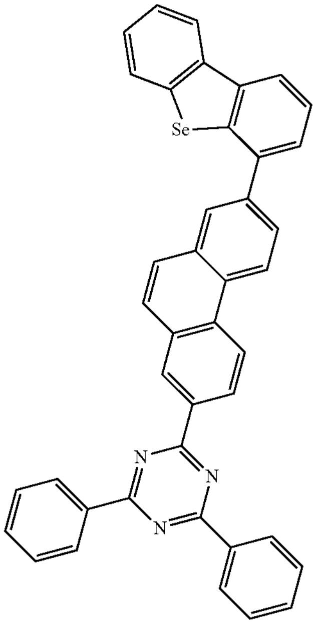
H1-53
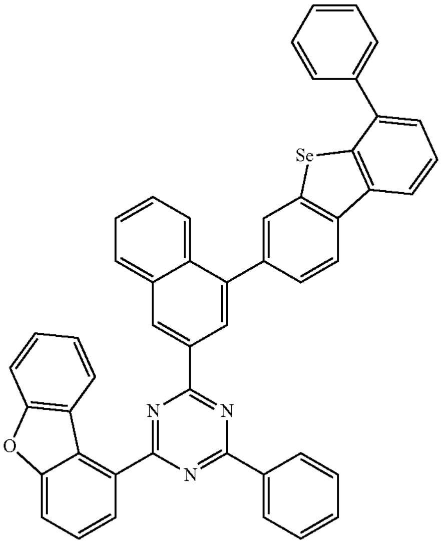

-continued
H1-54
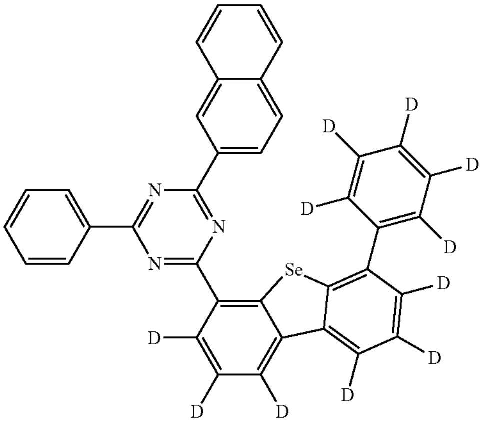
H1-55
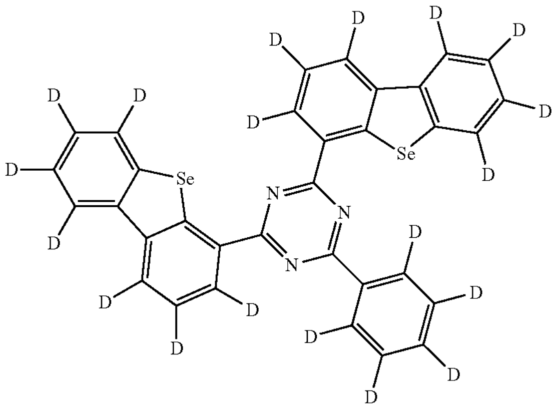
H1-56
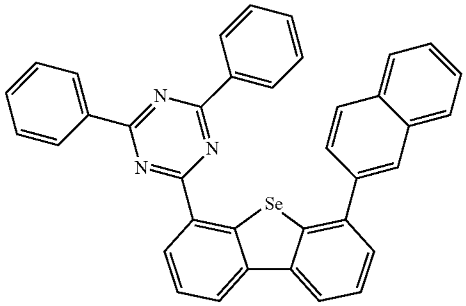
H1-57
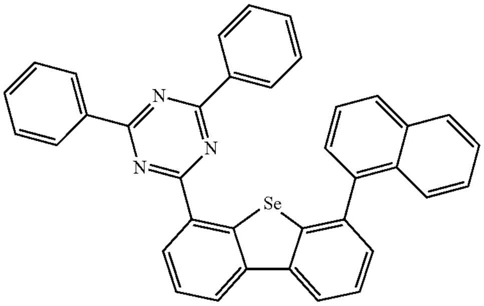
-continued
H1-58
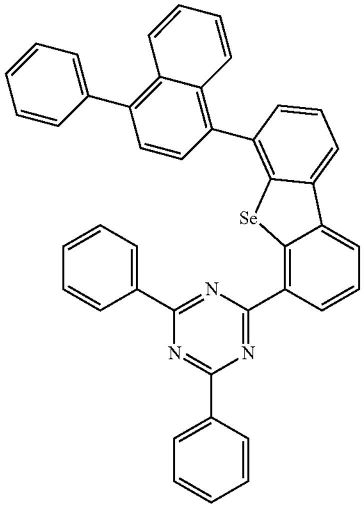
H1-59
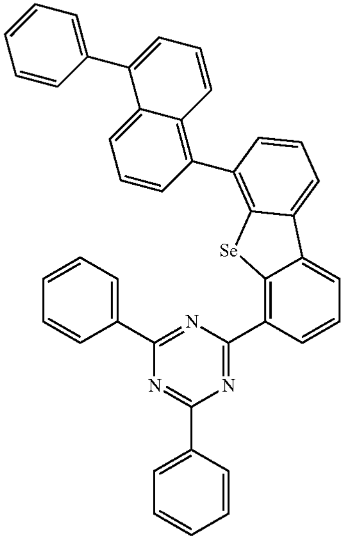
H1-60
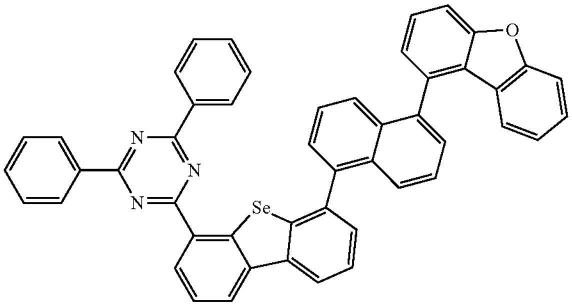

-continued
H1-61
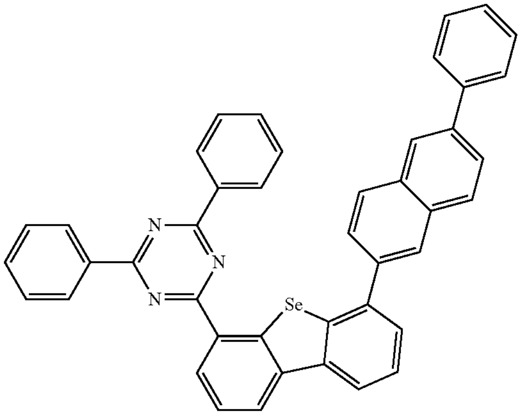
H1-62
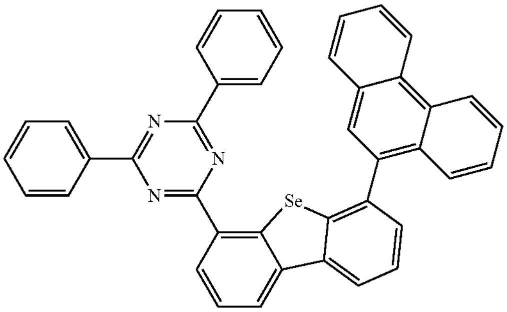
H1-63
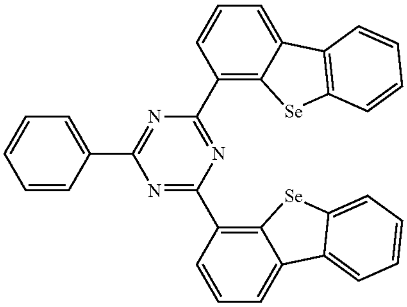
H1-64
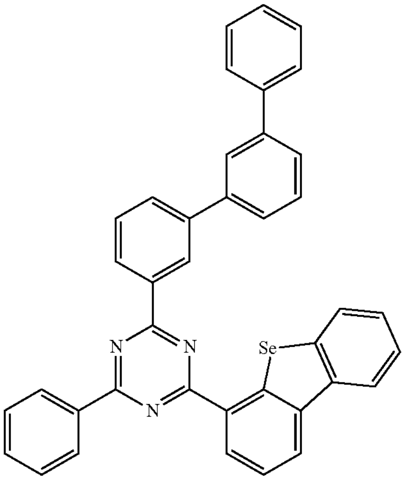
-continued
H1-65
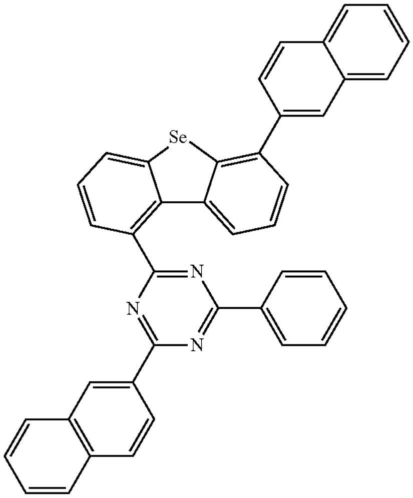
H1-66
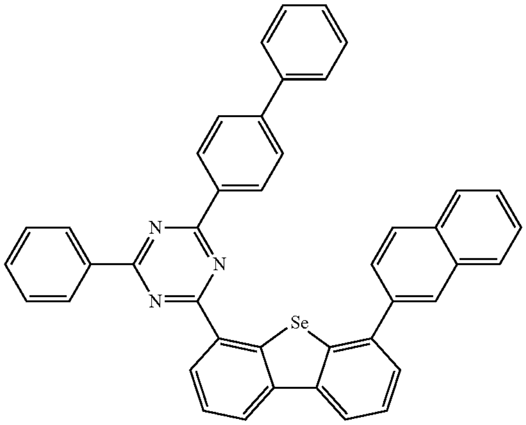
H1-67
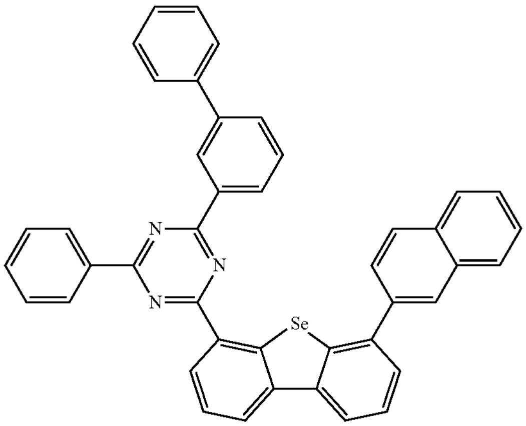

-continued
H1-68
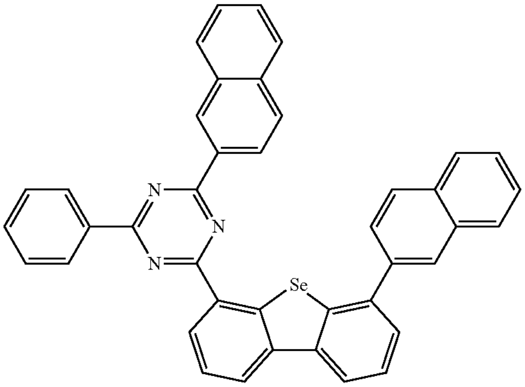
H1-69
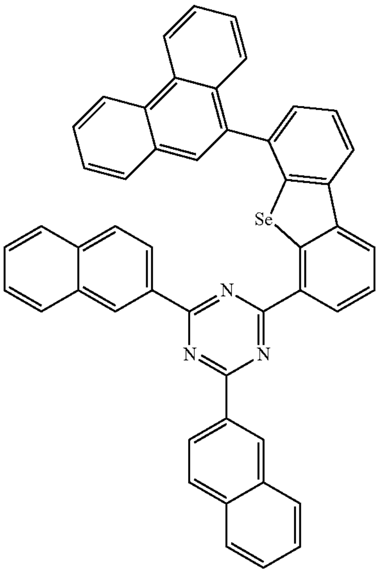
H1-70
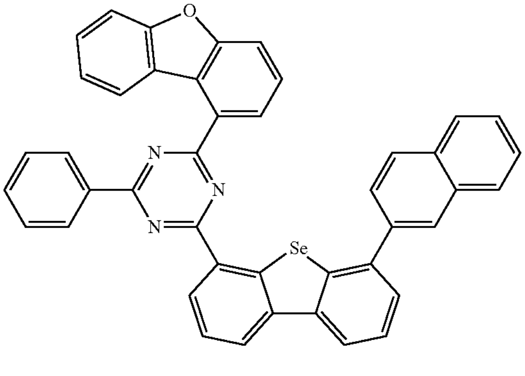
-continued
H1-71
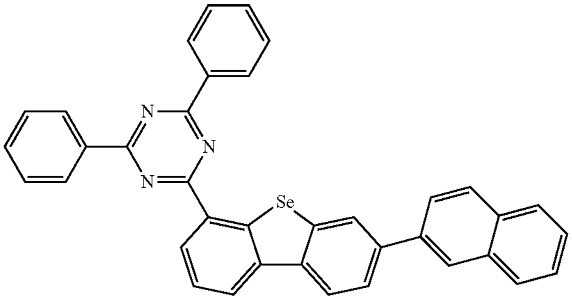
H1-72
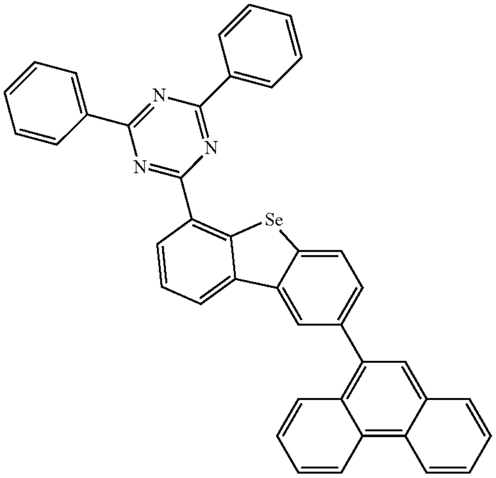
H1-73
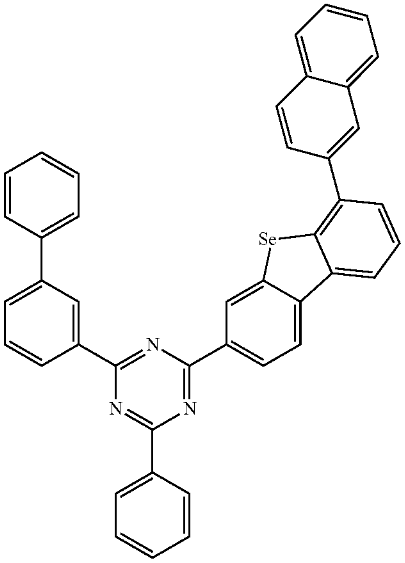

-continued
H1-74
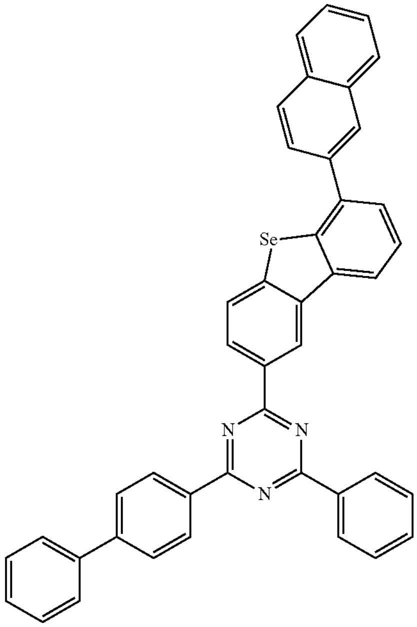
H1-75
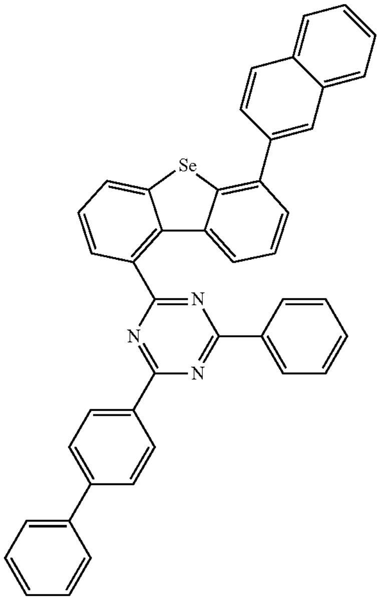
H1-76
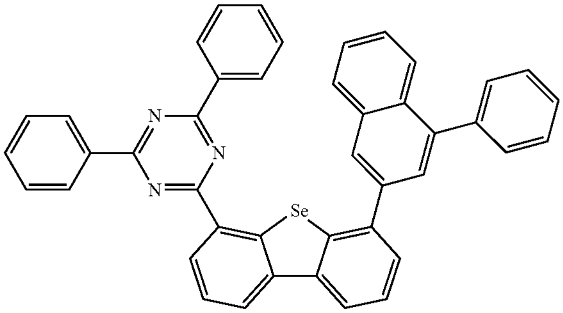
-continued
H1-77
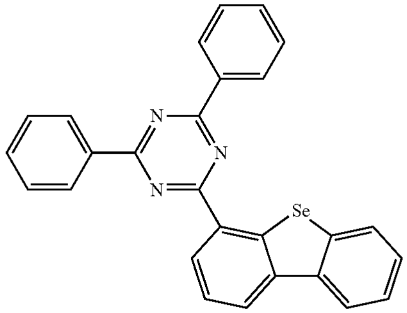
H1-78
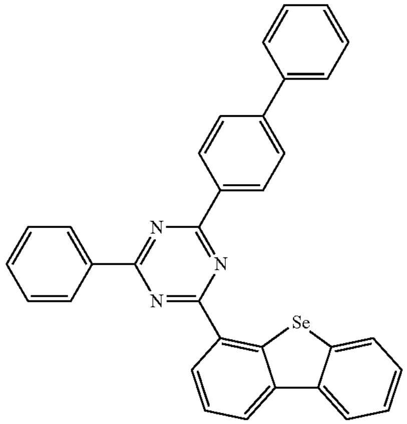
H1-79
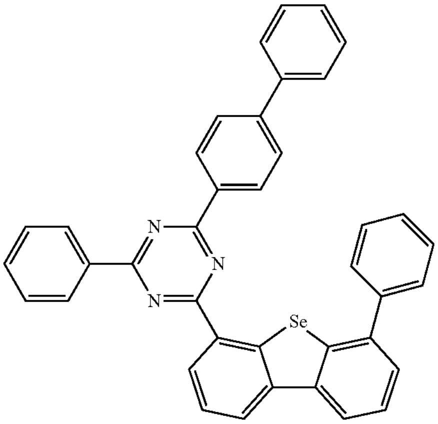
H1-80
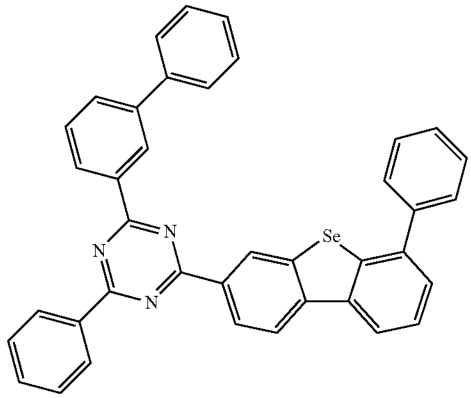

-continued
H1-81
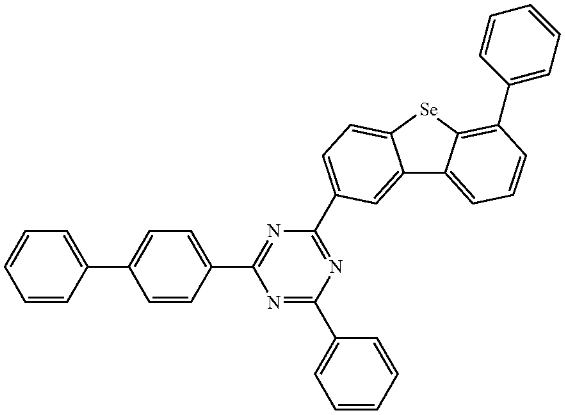
H1-82
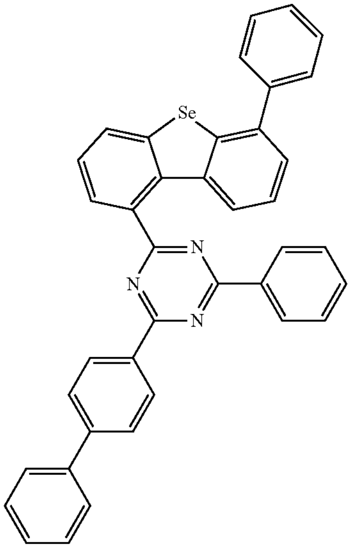
H1-83
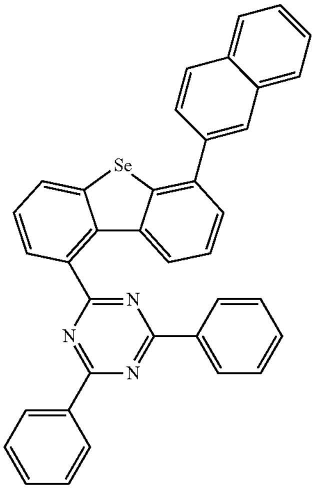
-continued
H1-84
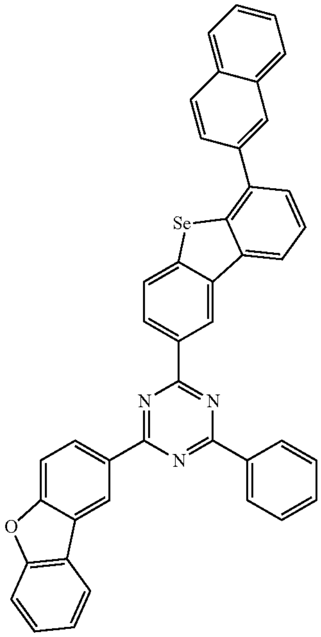
H1-85
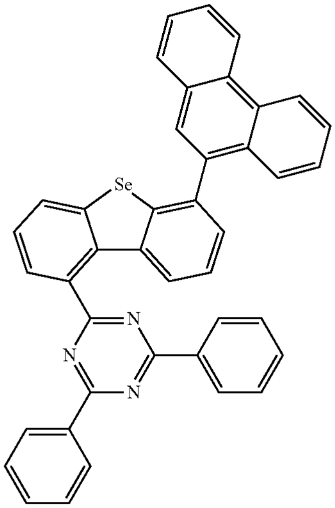
H1-86
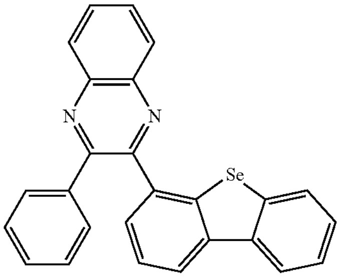

-continued
H1-87
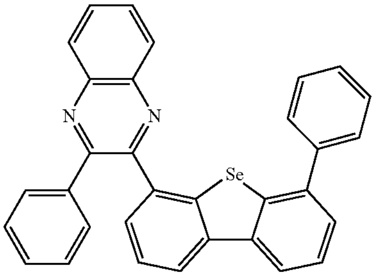
H1-88
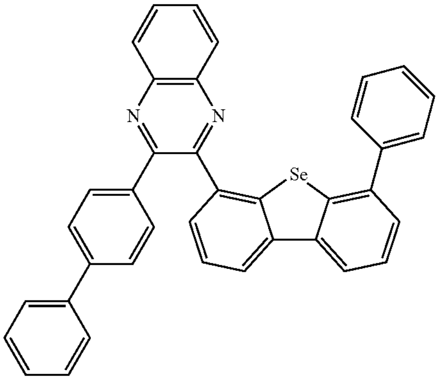
H1-89
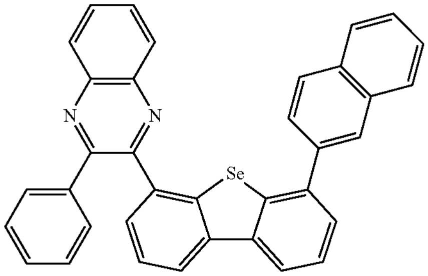
H1-90
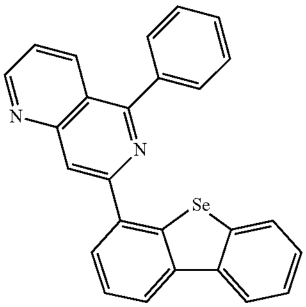
-continued
H1-91
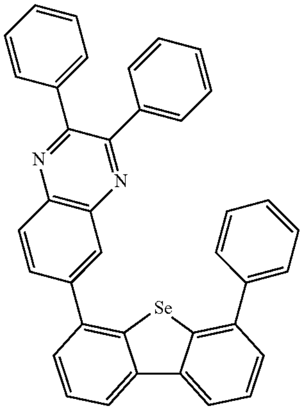
H1-92
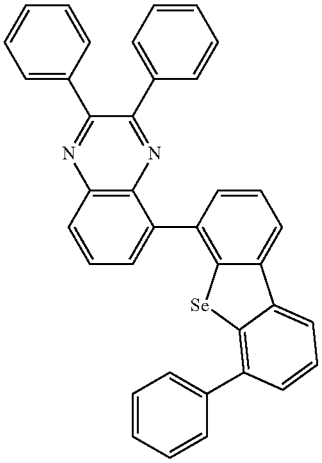
H1-93
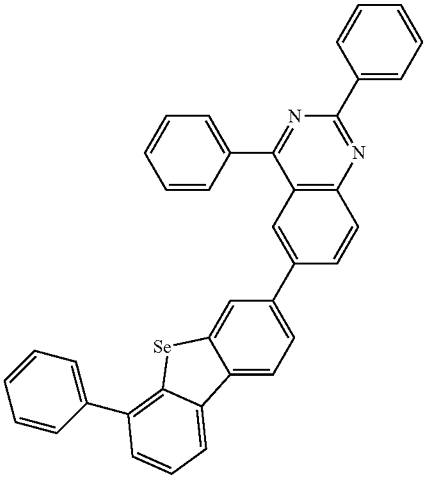

-continued
H1-94
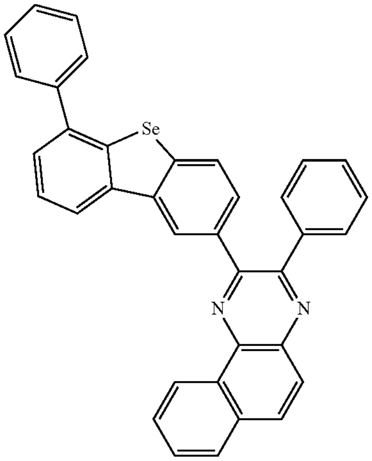
H1-95
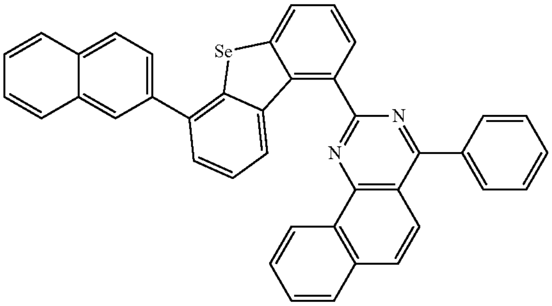
H1-96
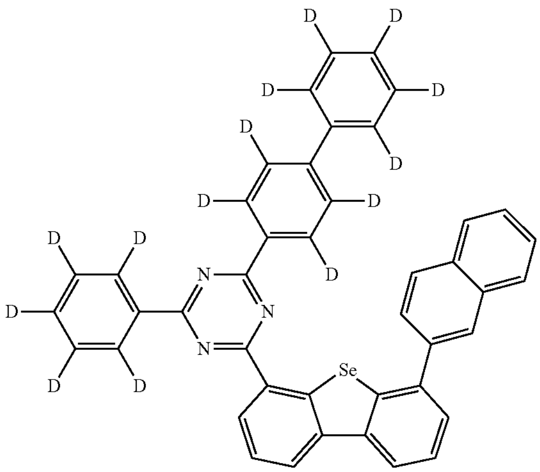
-continued
H1-97
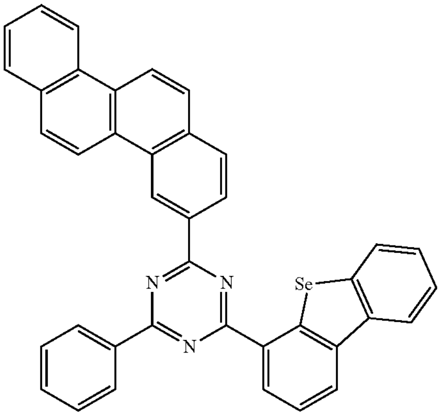
H1-98
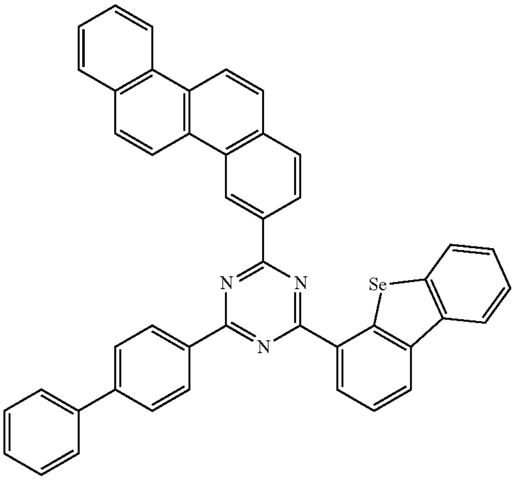
H1-99
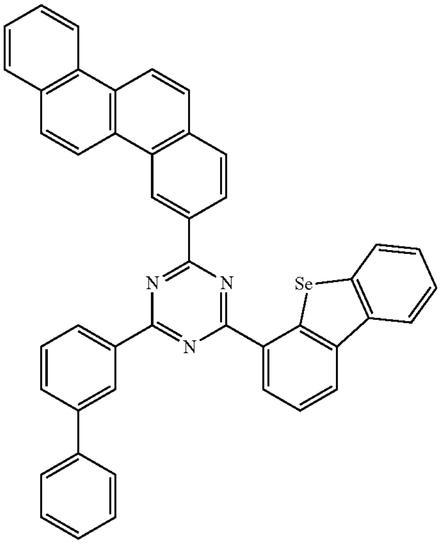

-continued
H1-100
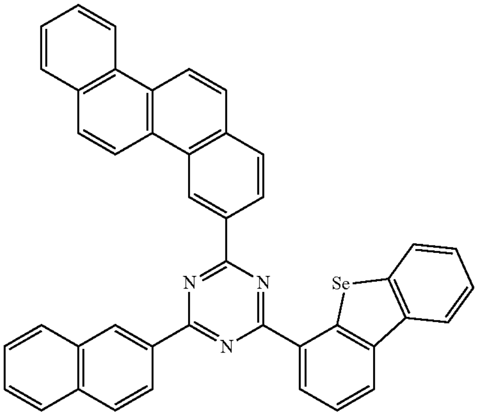
H1-101
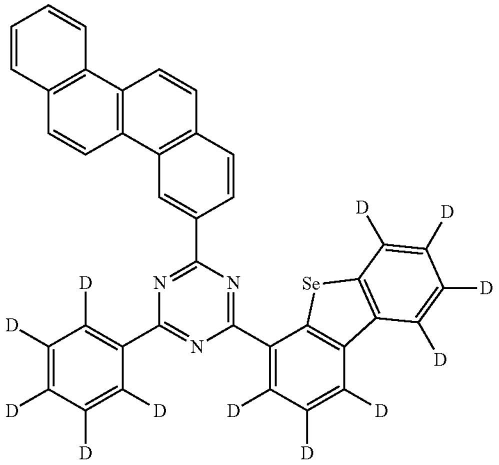
H1-102
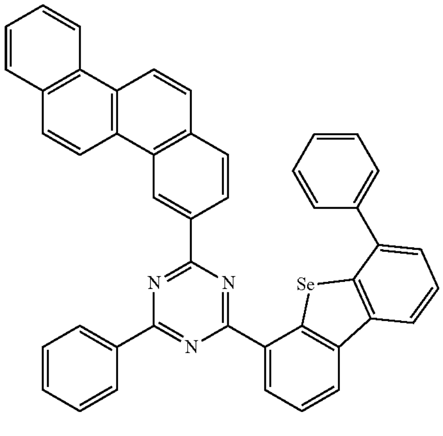
-continued
H1-103
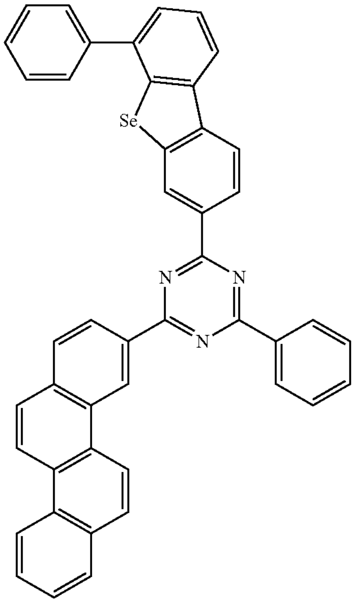
H1-104
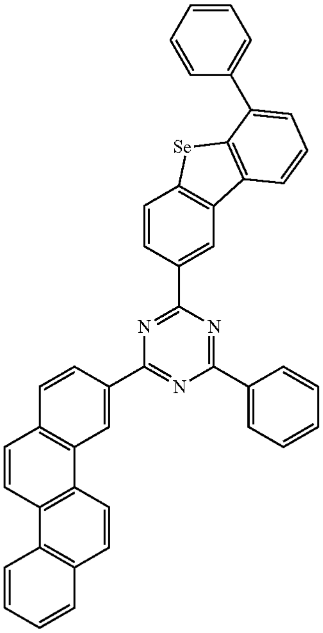

-continued
H1-105
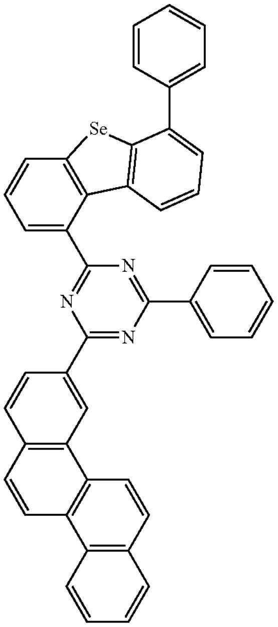
H1-106
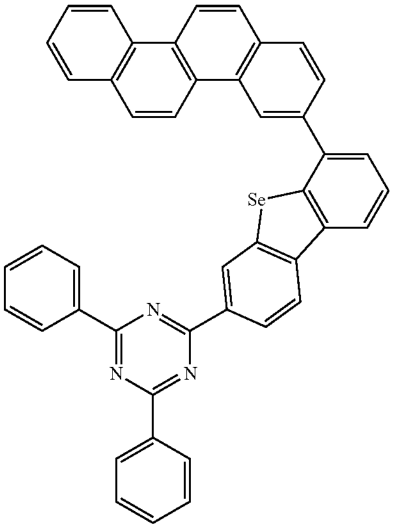
-continued
H1-107
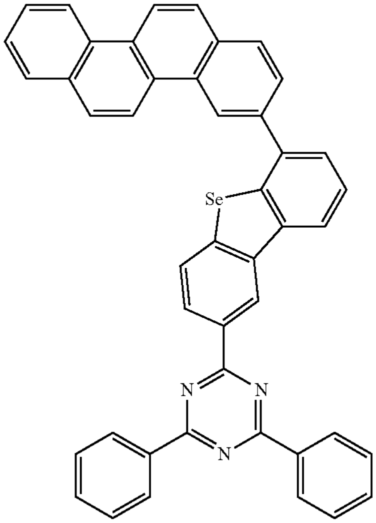
H1-108
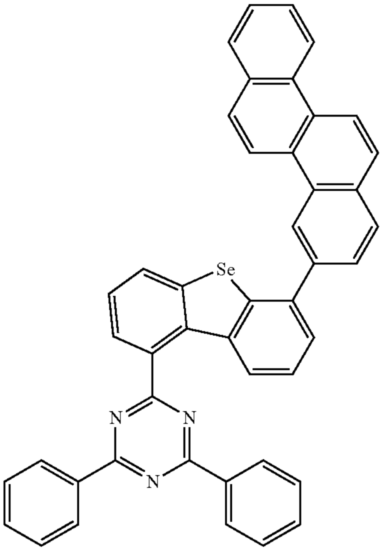
H1-109
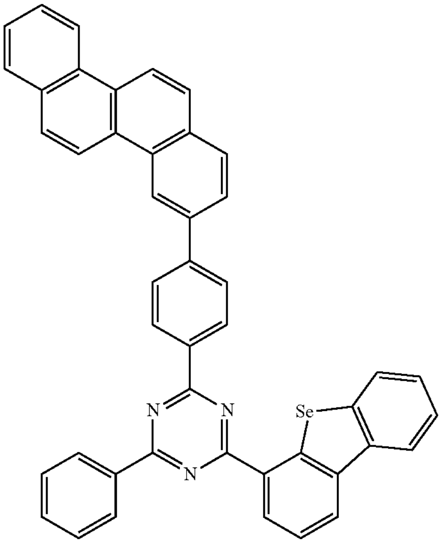

-continued
H1-110
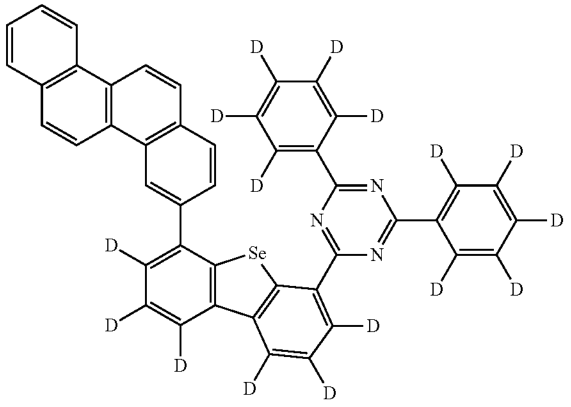
H1-111
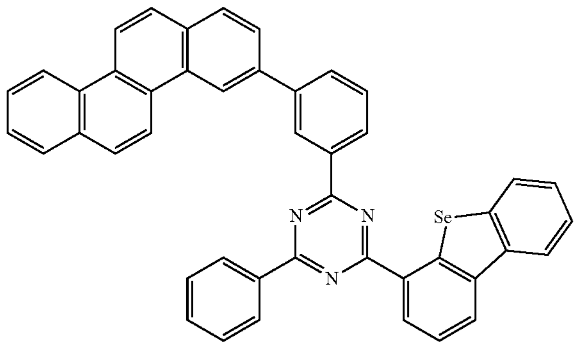
H1-112
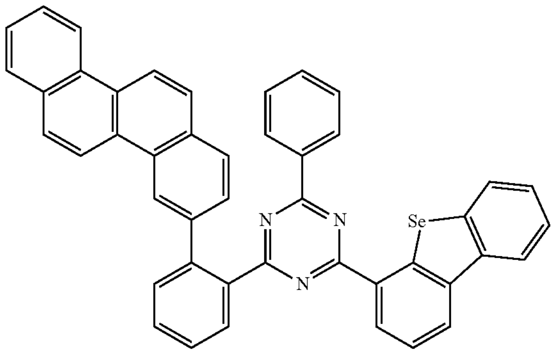
-continued
H1-113
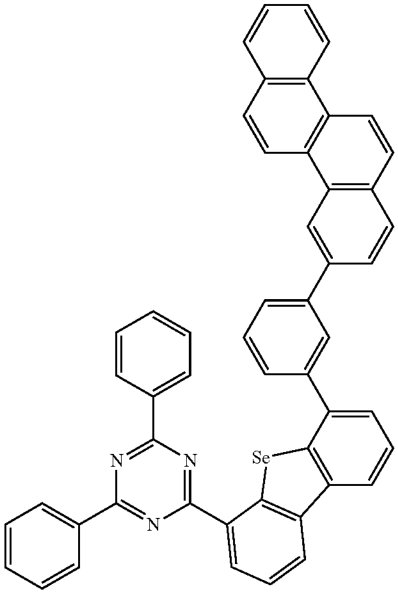
H1-114
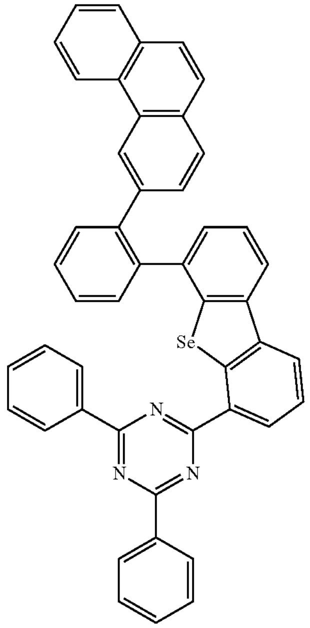
H1-115
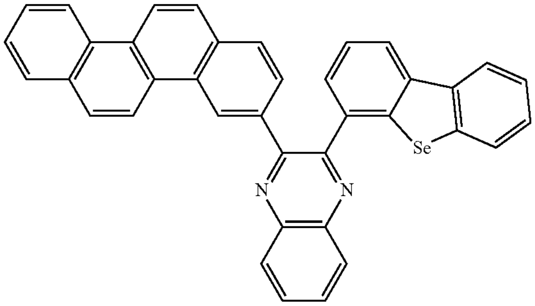

-continued
H1-116
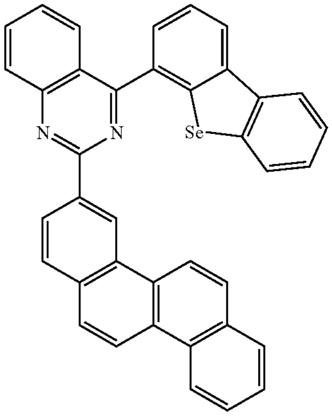
H1-117
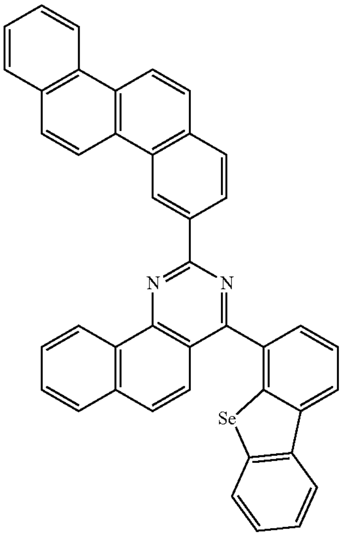
H1-118
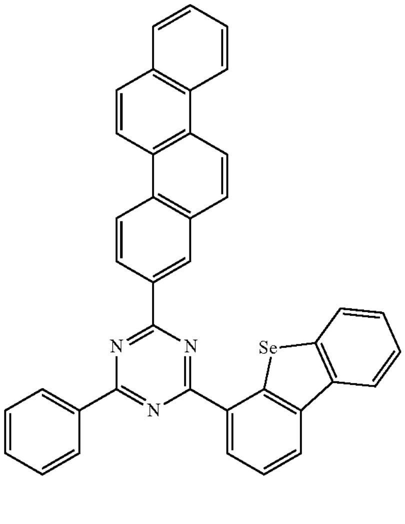
-continued
H1-119
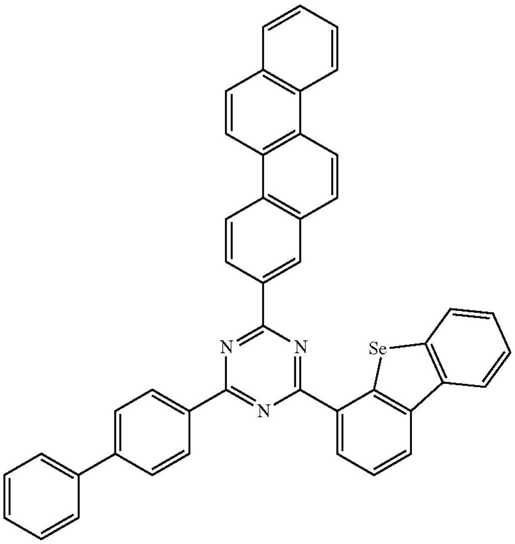
H1-120
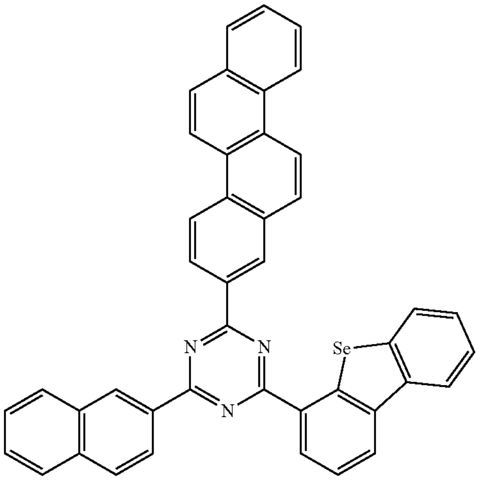
H1-121
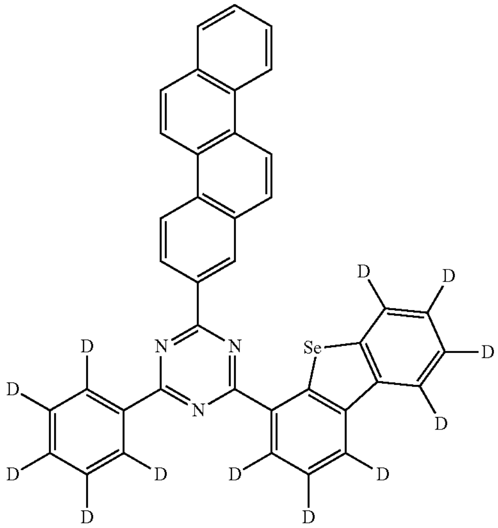

H1-122
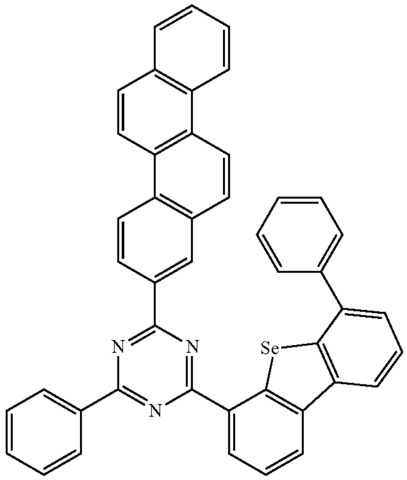
H1-123
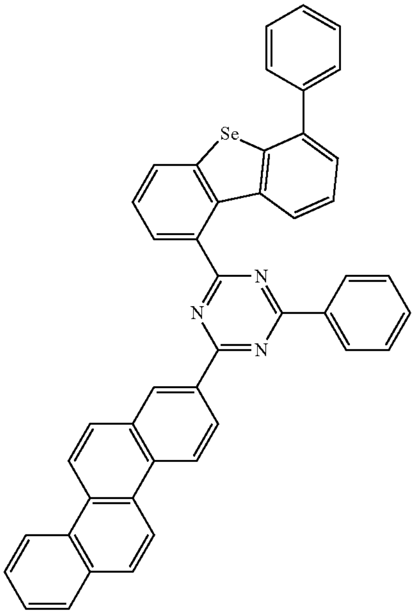
H1-124
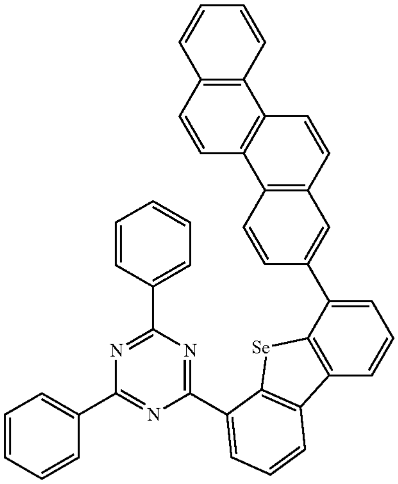
H1-125
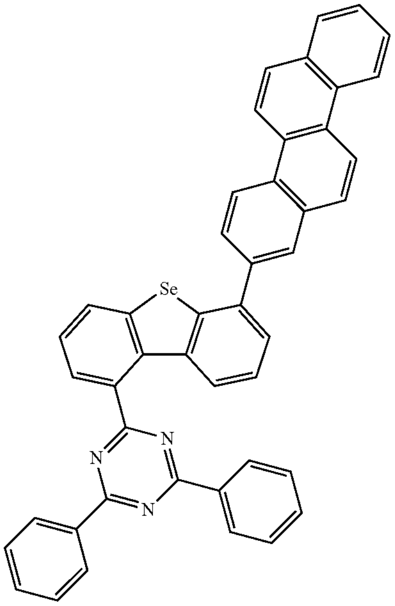
H1-126
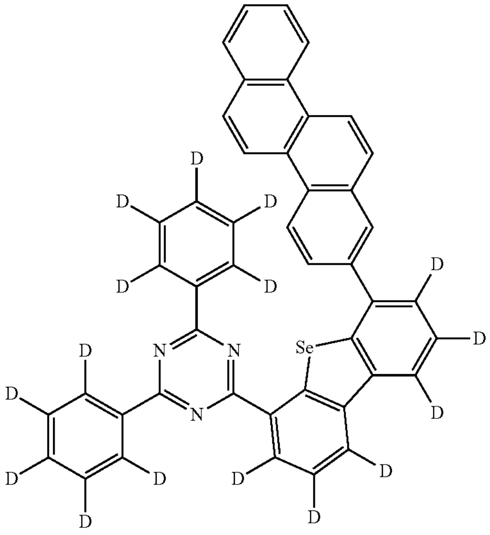

-continued
H1-127
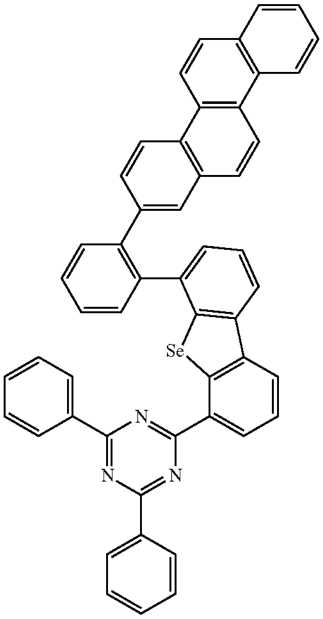
H1-128
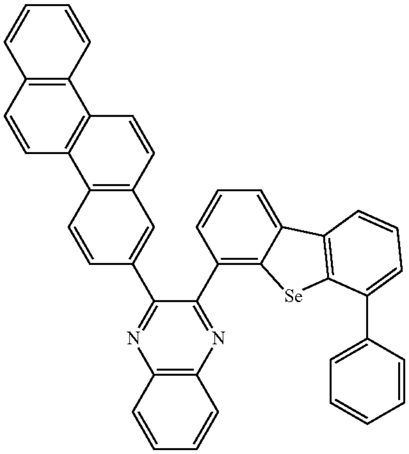
H1-129
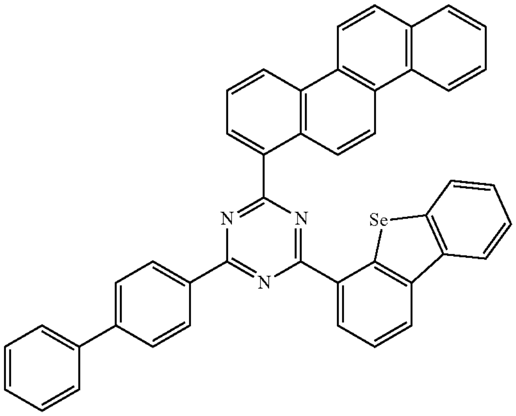
-continued
H1-130
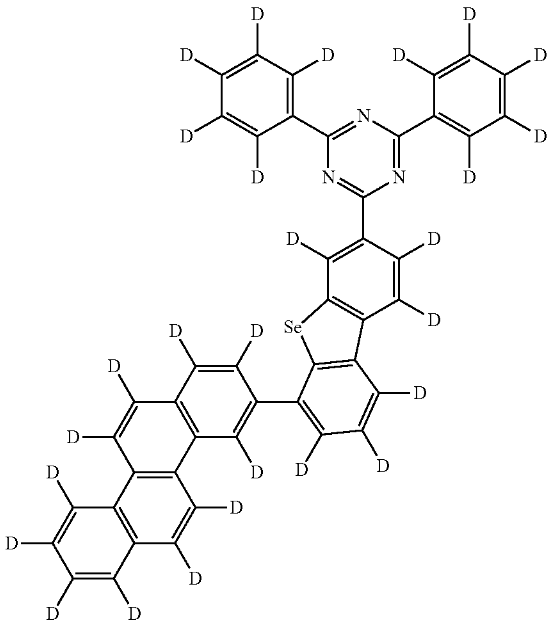
H1-131
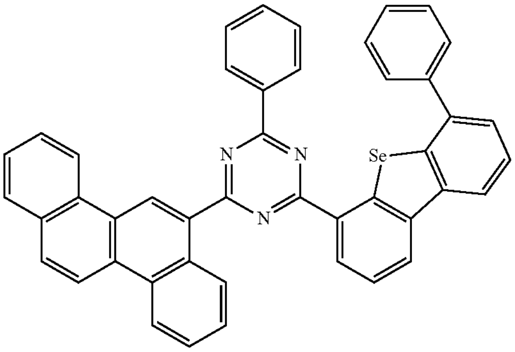
H1-132
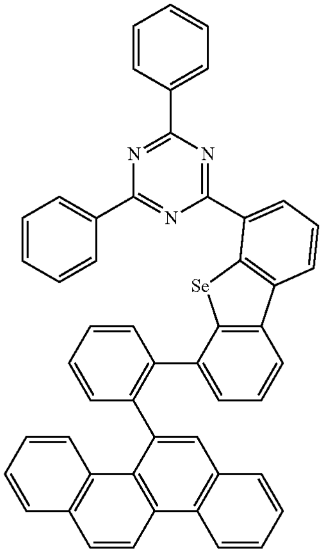

-continued
H1-133
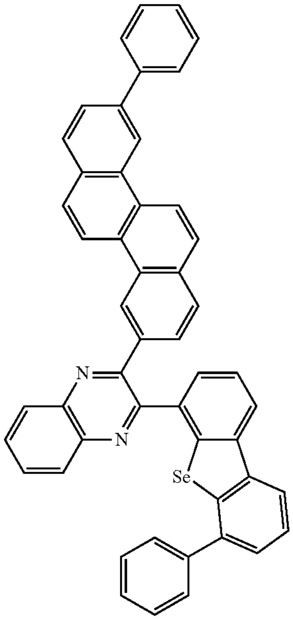
H1-134
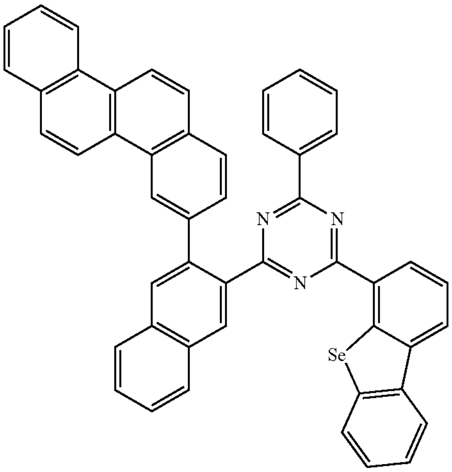
H1-135
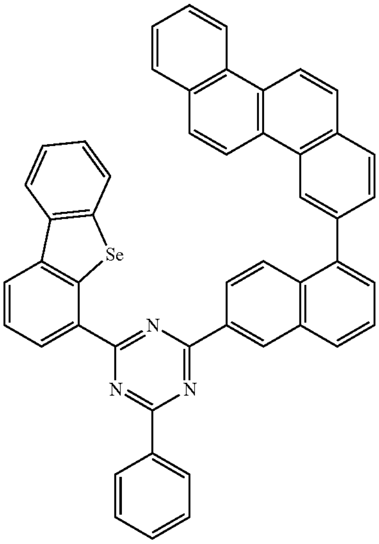
-continued
H1-136
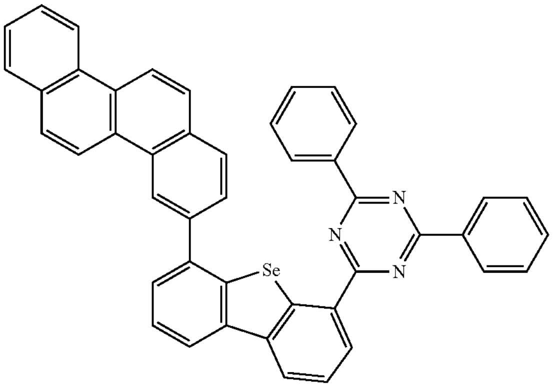
H1-137
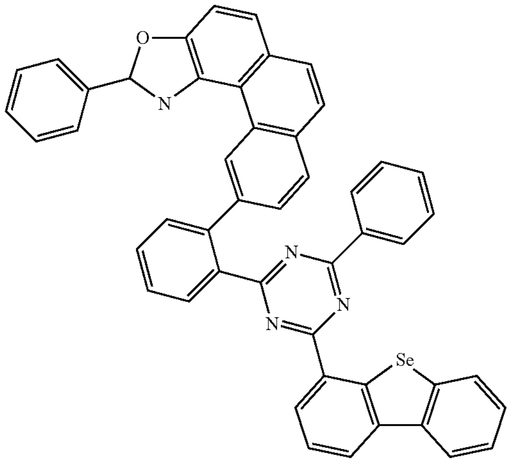
H1-138
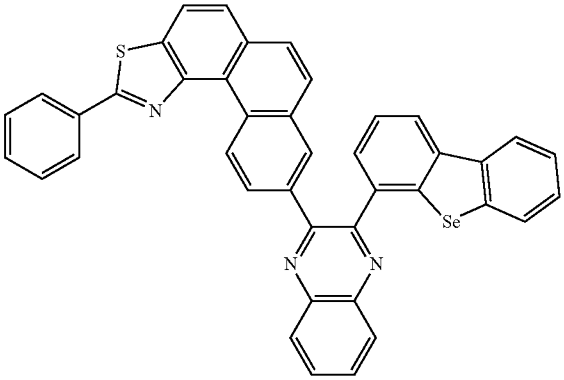

-continued
H1-139
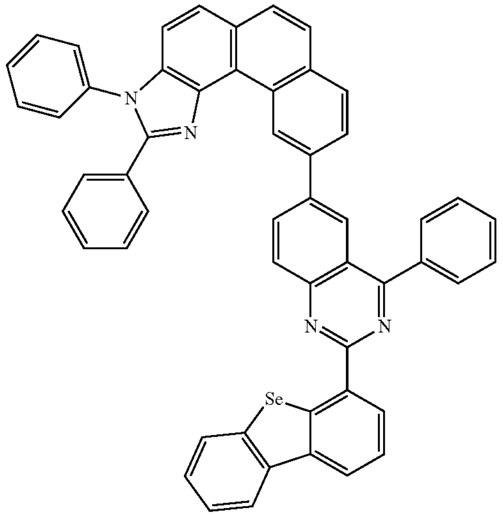
H1-140
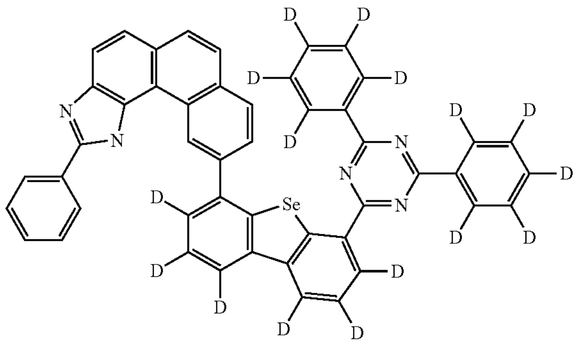
H1-141
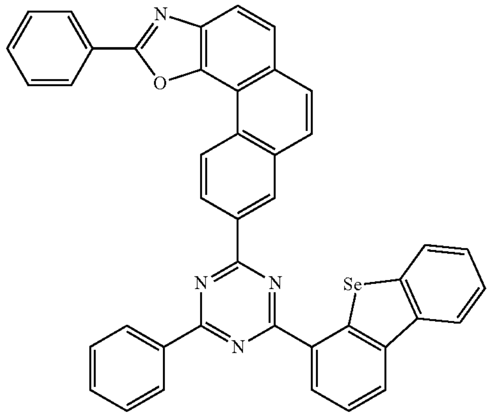
-continued
H1-142
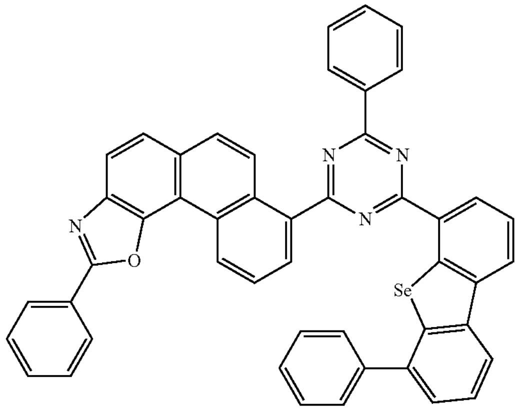
H1-143
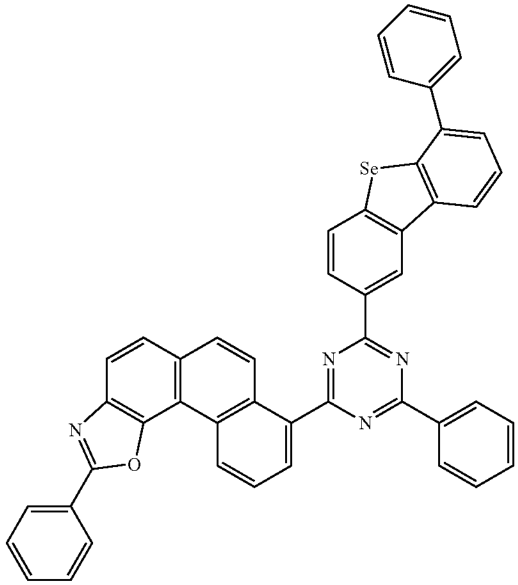
H1-144
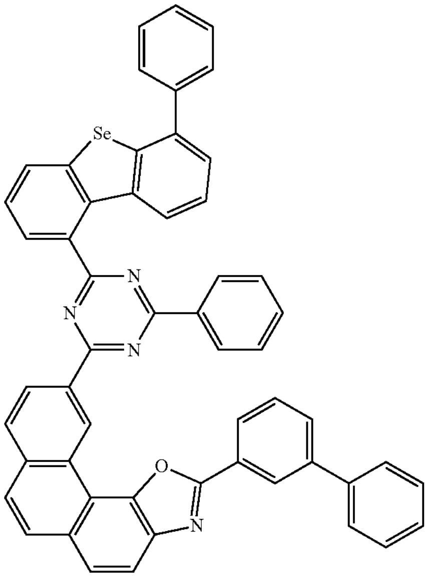

-continued
H1-145
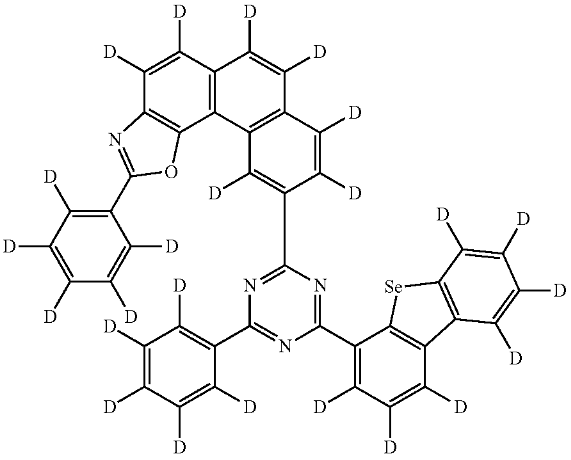
H1-146
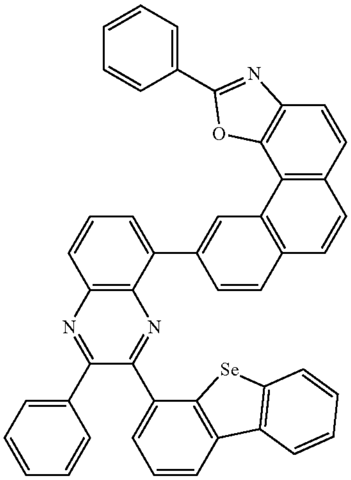
H1-147
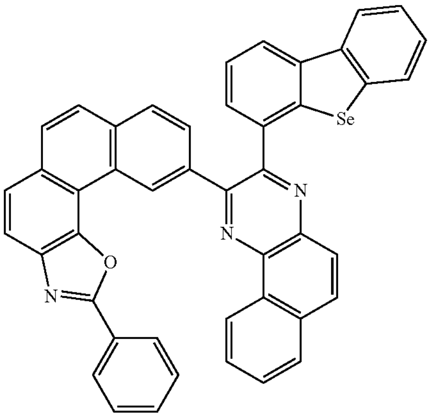
-continued
H1-148
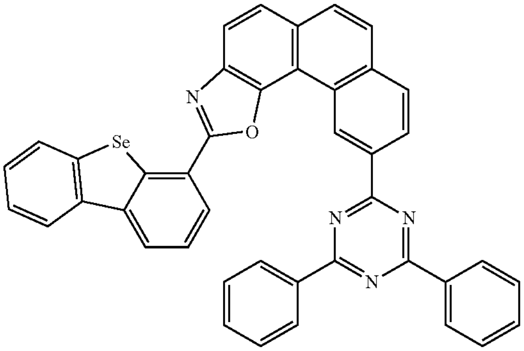
H1-149
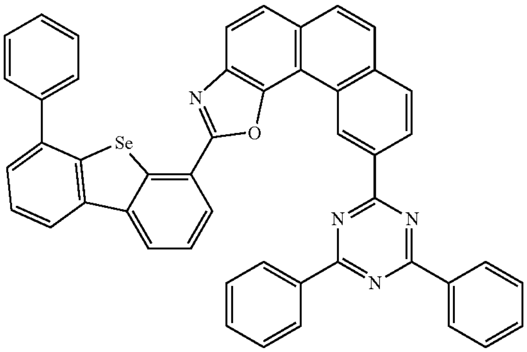
H1-150
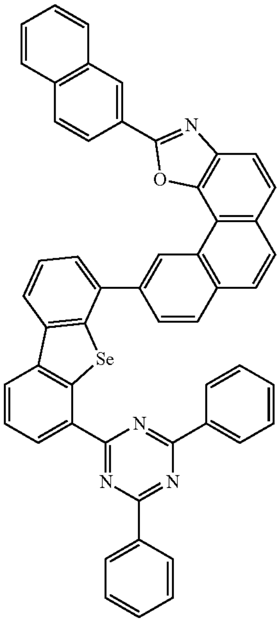

-continued
H1-151
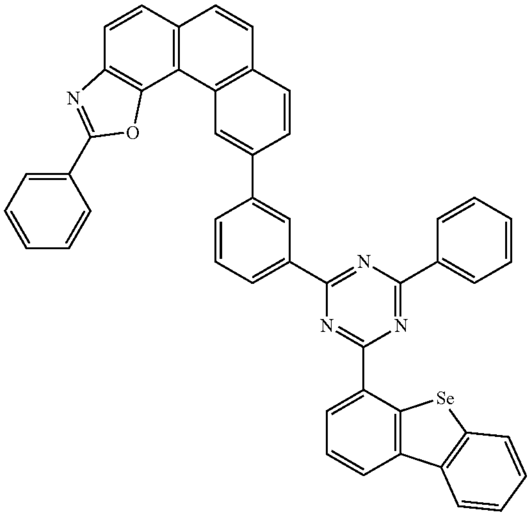
H1-152
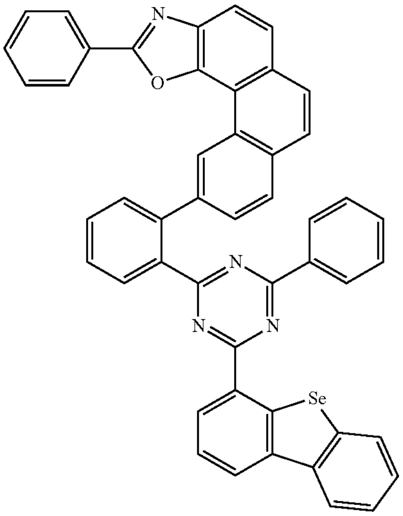
H1-153
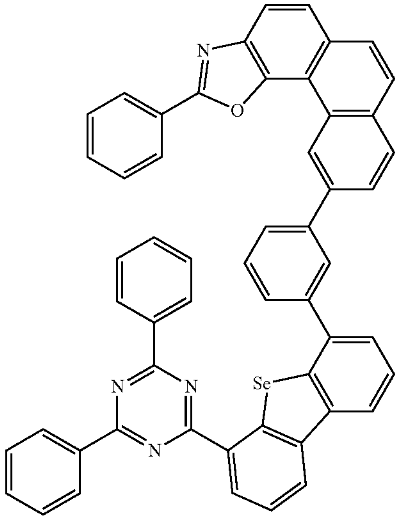
-continued
H1-154
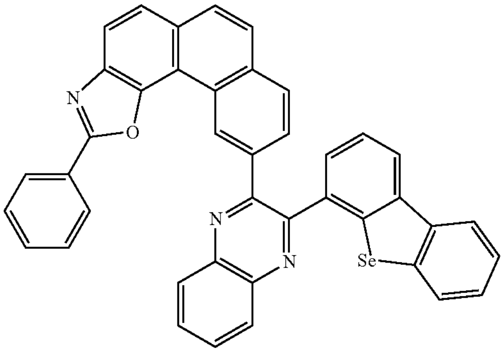
H1-155
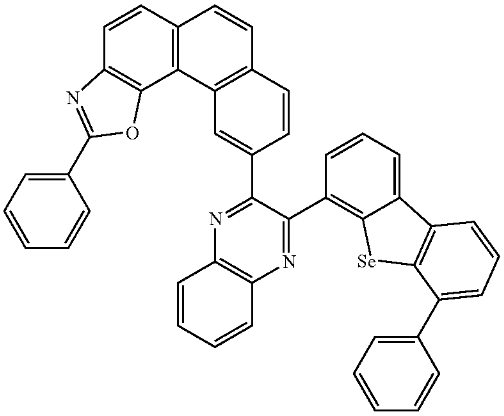
H1-156
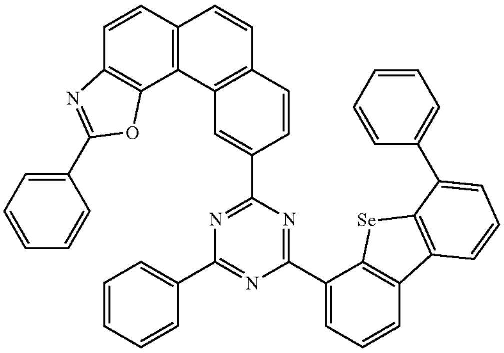

-continued
H1-157
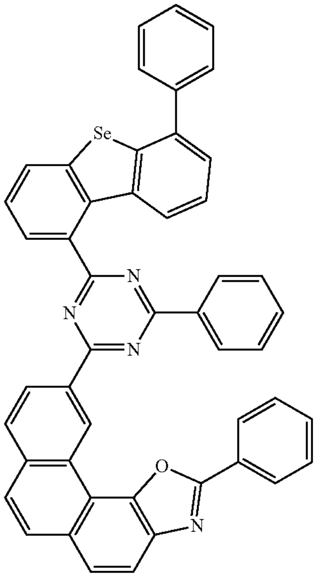
H1-158
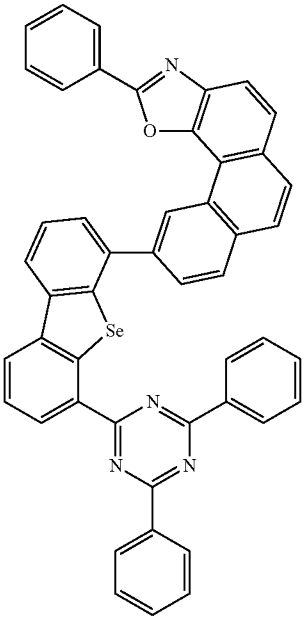
-continued
H1-159
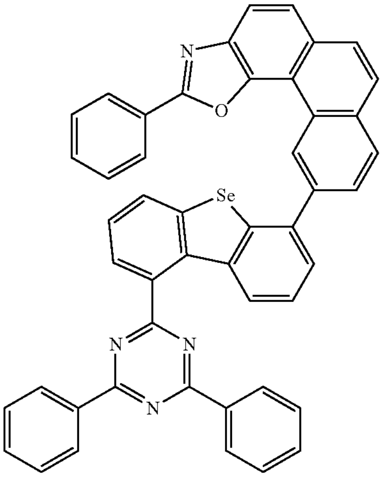
H1-160
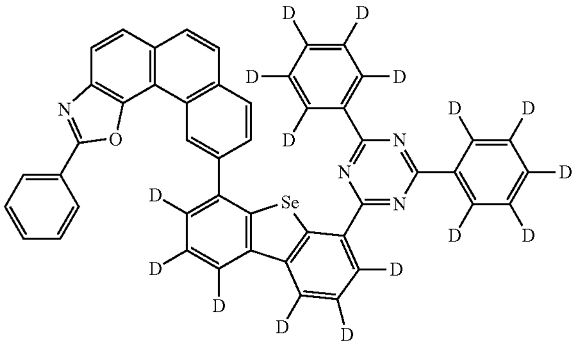
H1-161
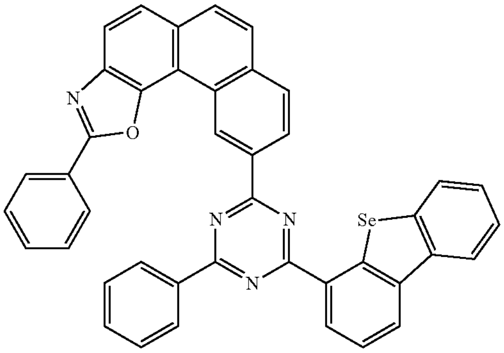
H1-162
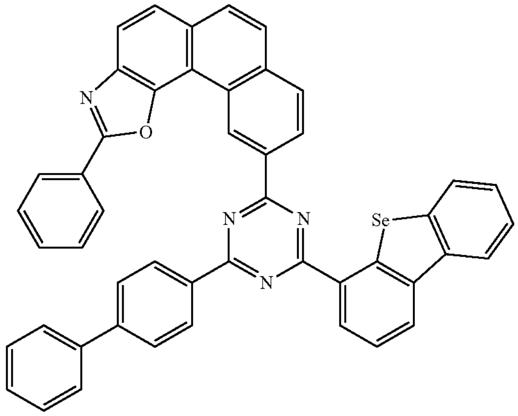

H1-163
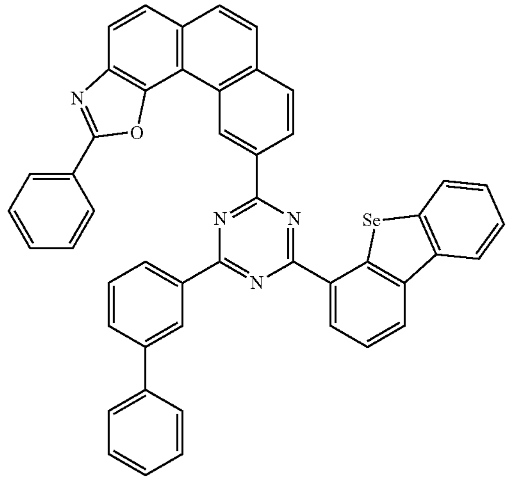
H1-164
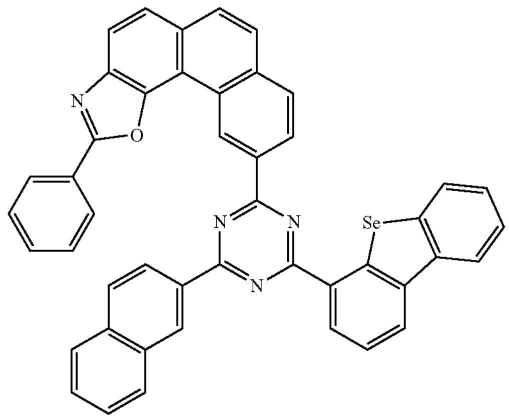
H1-165
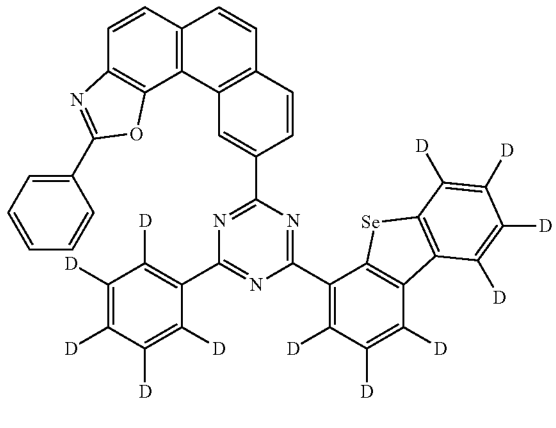
H1-166
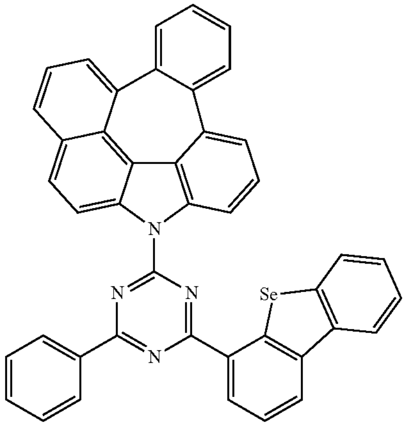
H1-167
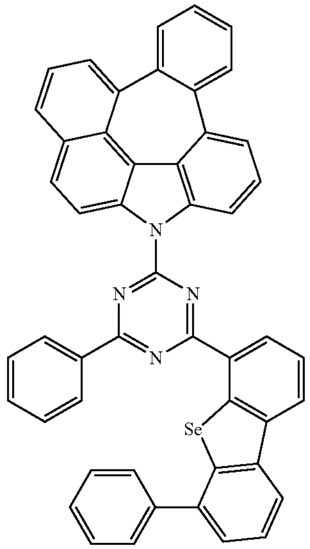
H1-168
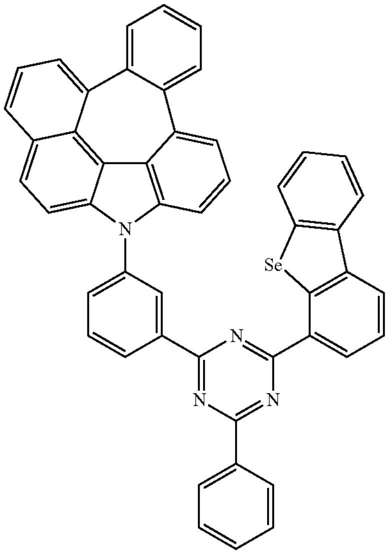

-continued
H1-169
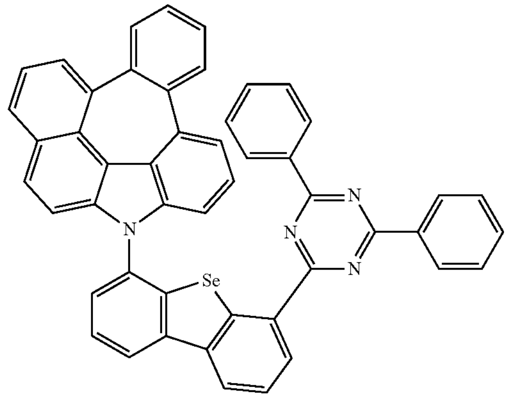
H1-170
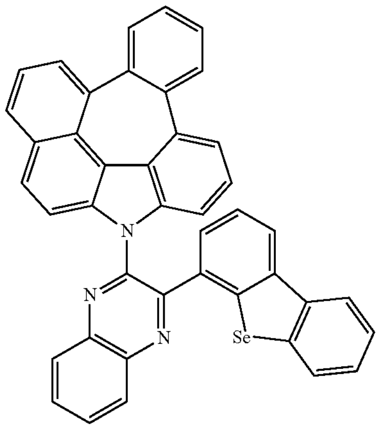
H1-171
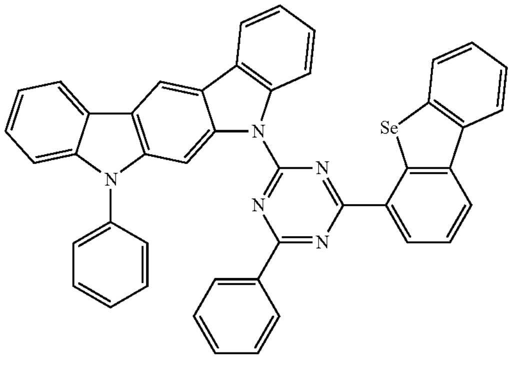
-continued
H1-172
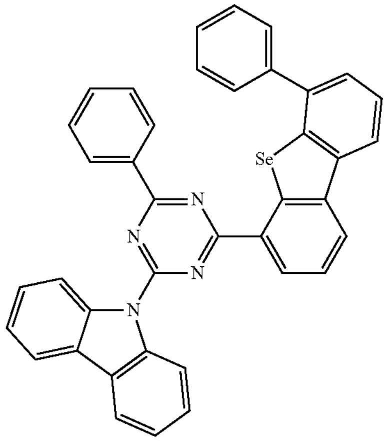
H1-173
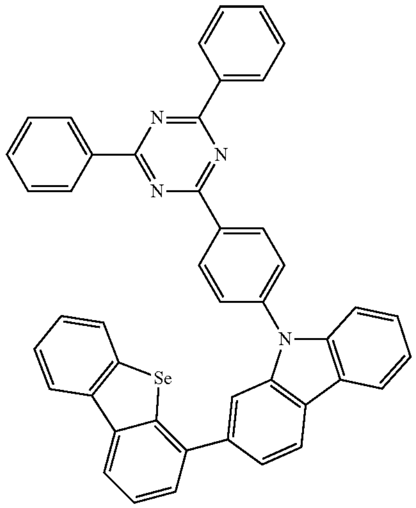
H1-174
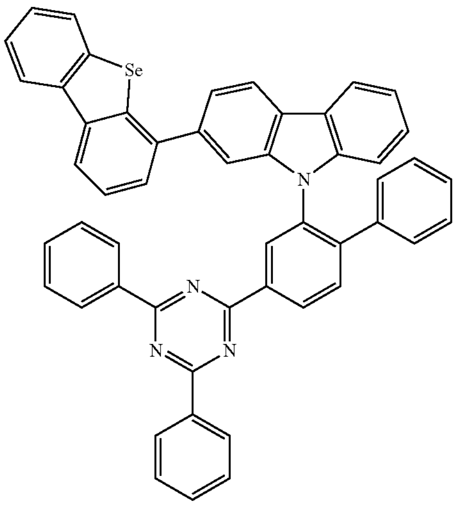

-continued
H1-175
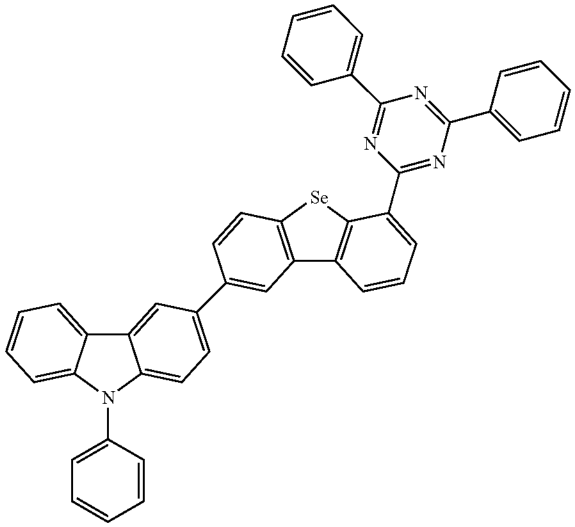
H1-176
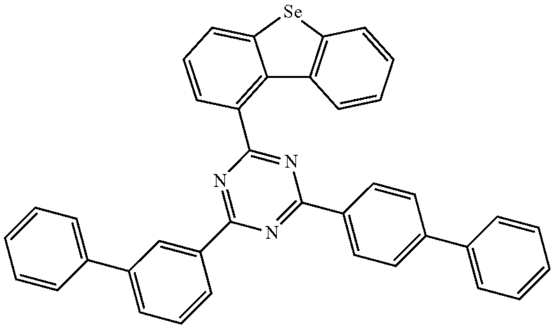
H1-177
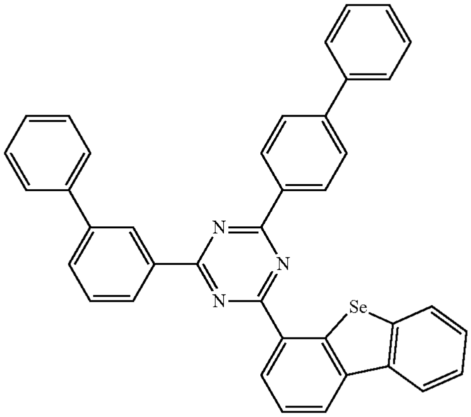
-continued
H1-178
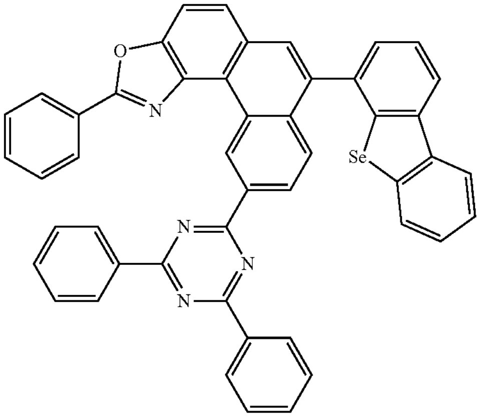
H1-179
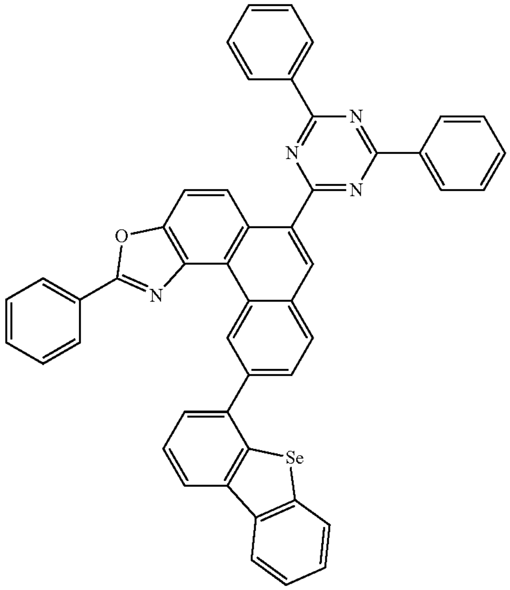
H1-180
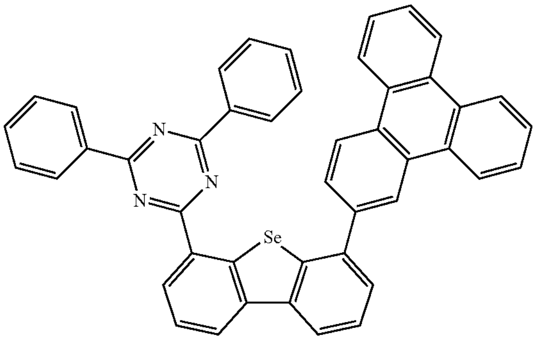

-continued
H1-181
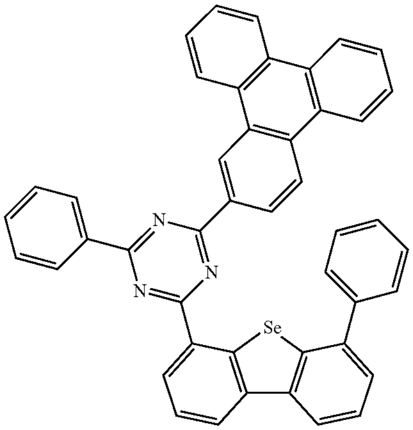
H1-182
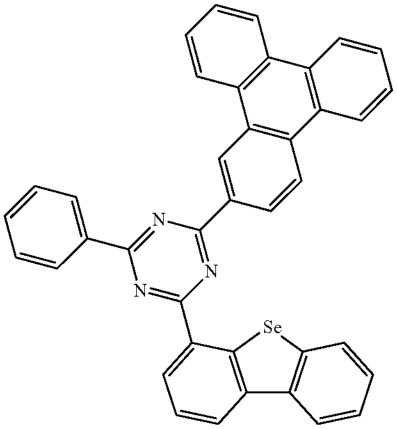
H1-183
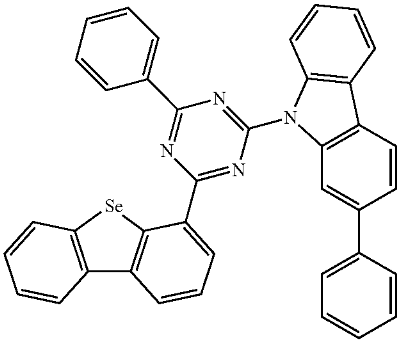
H1-184
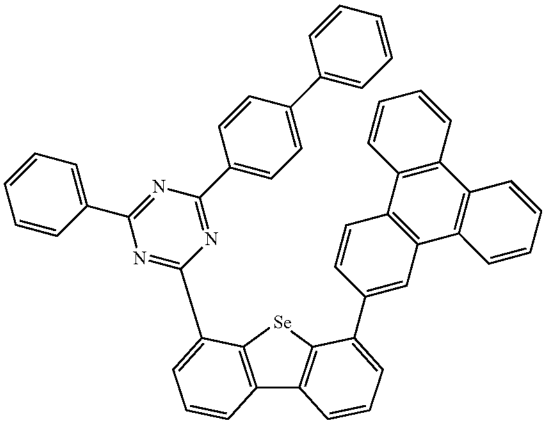
-continued
H1-185
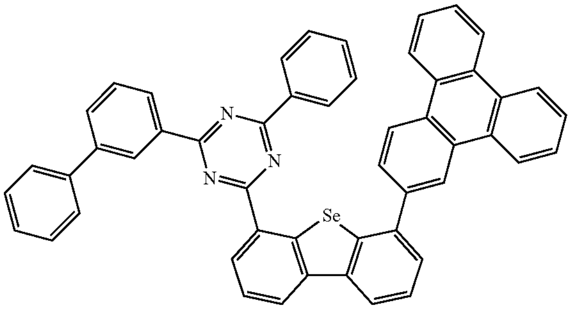
H1-186
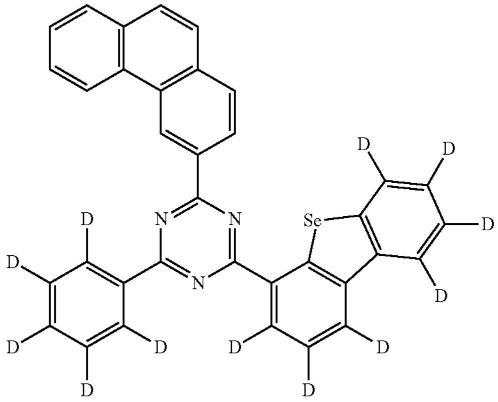
H1-187
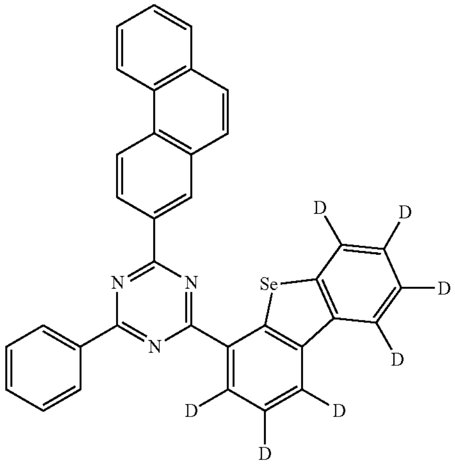
H1-188
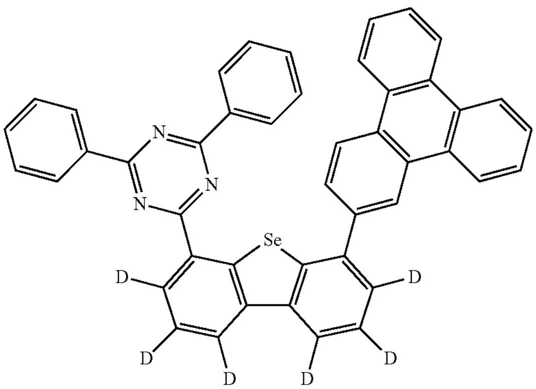

-continued
H1-189
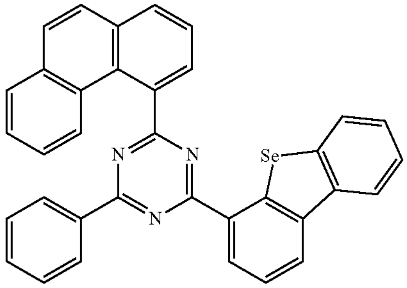
H1-190
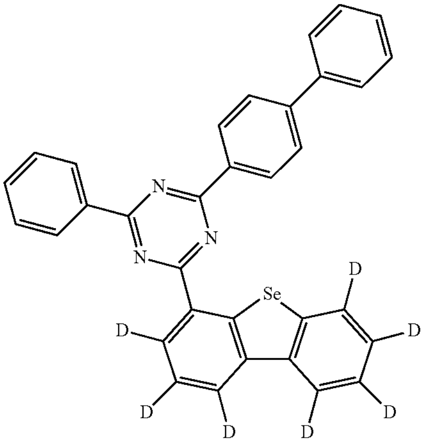
H1-191
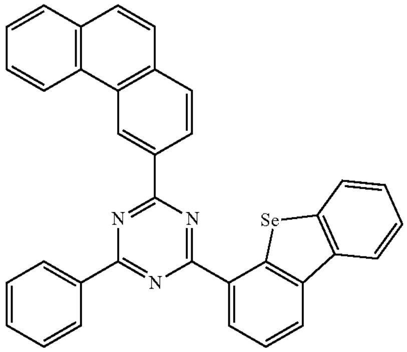
H1-192
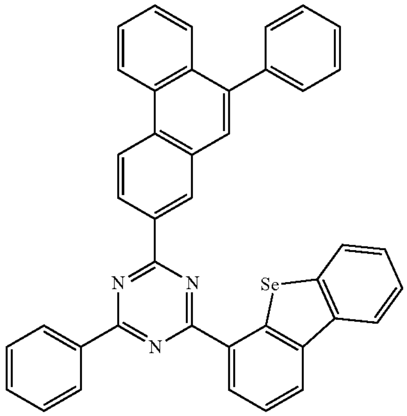
-continued
H1-193
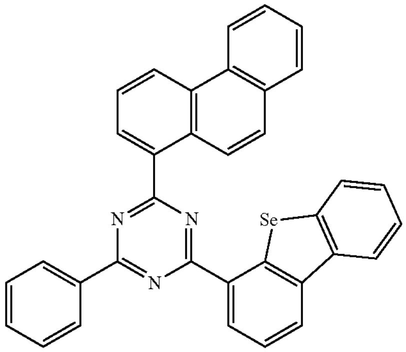
and
H1-194
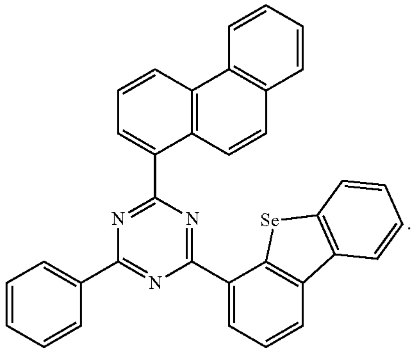
.
7. The plurality of host materials according to claim 1, wherein the compound represented by formula 2 is at least one selected from the following compounds:
H2-1
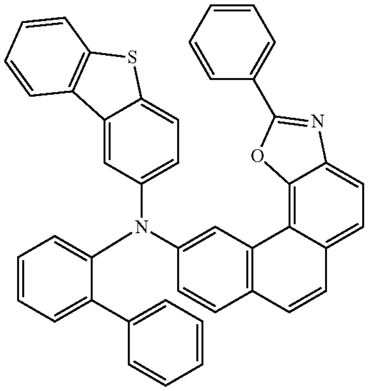
H2-2
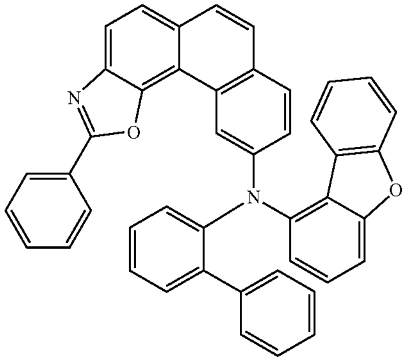

-continued
H2-3
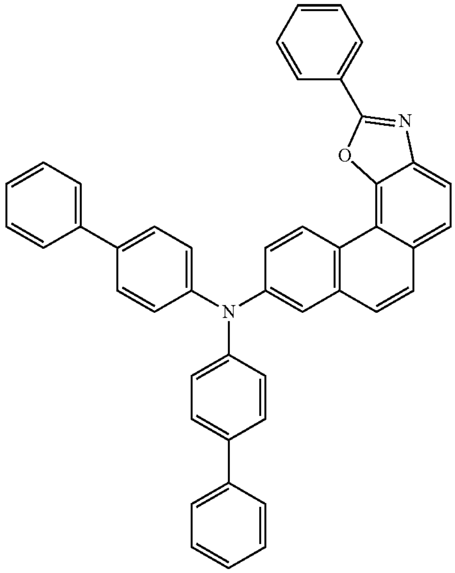
H2-4
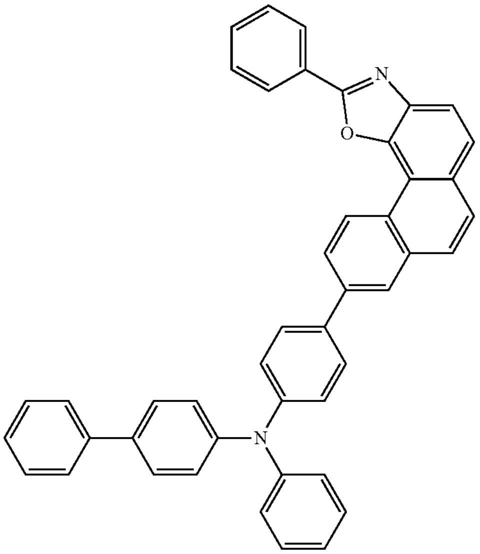
H2-5
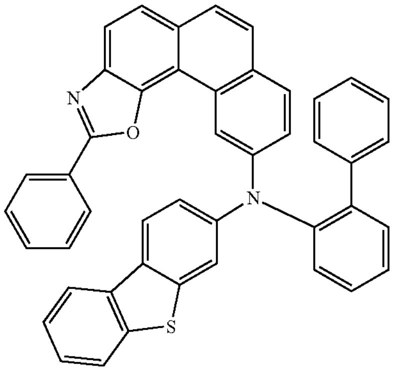
-continued
H2-6
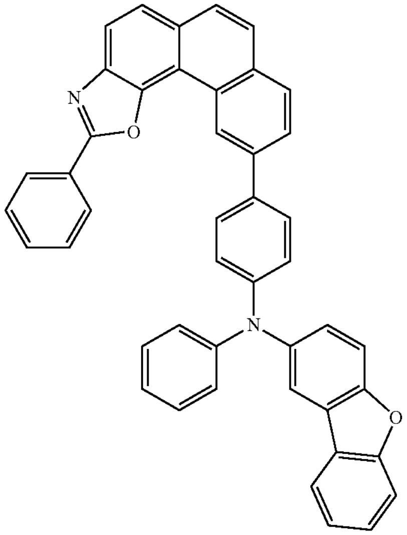
H2-7
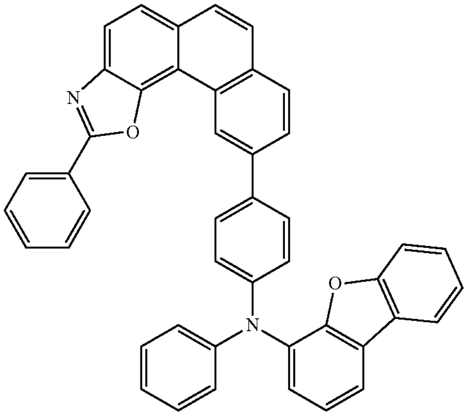
H2-8
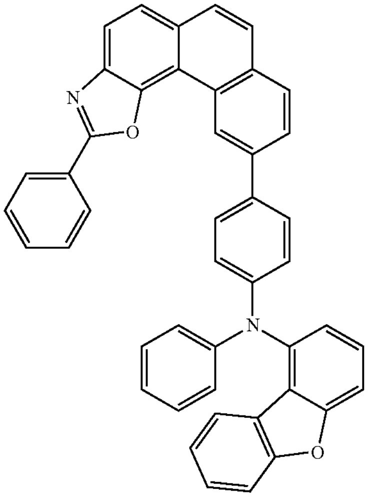

-continued
H2-9
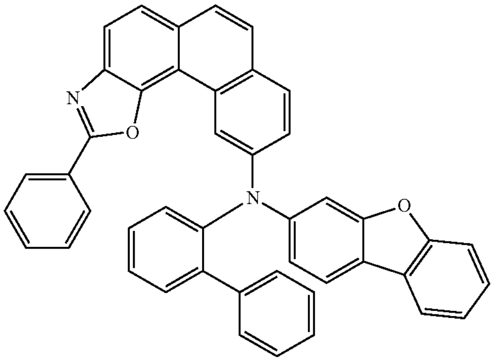
H2-10
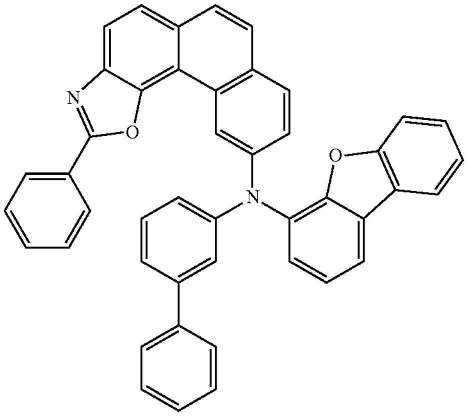
H2-11
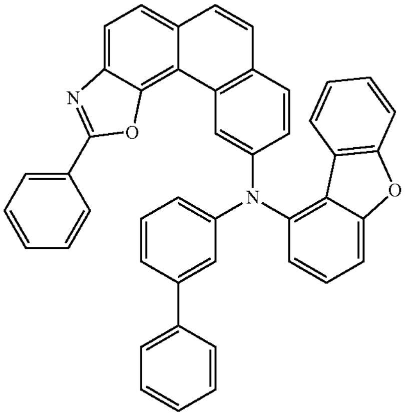
H2-12
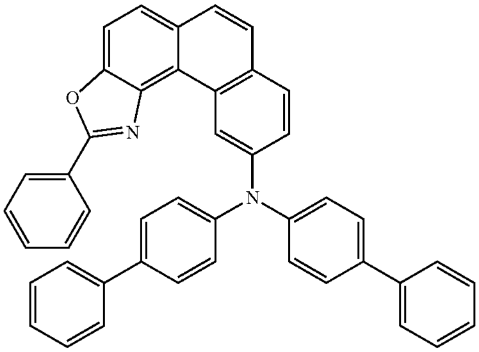
-continued
H2-13
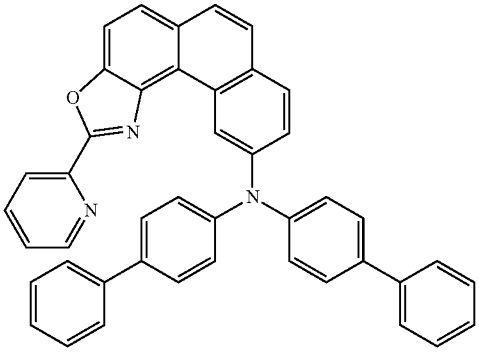
H2-14
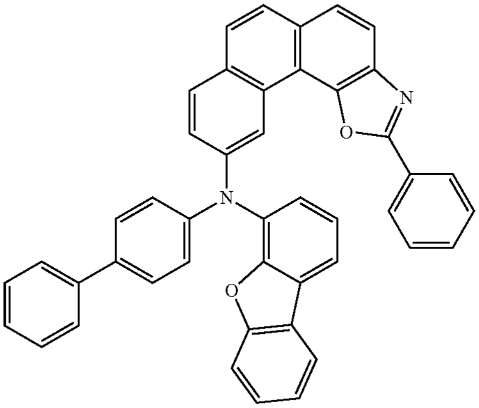
H2-15
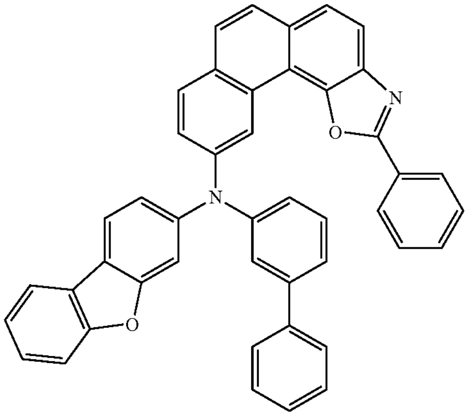
H2-16
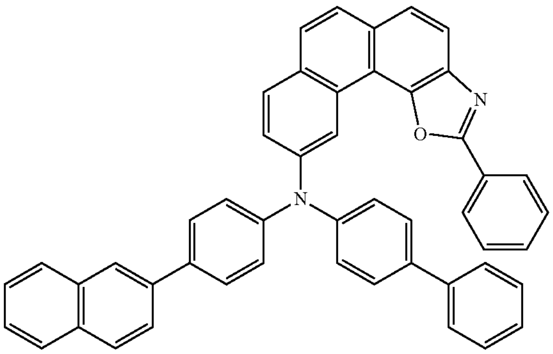

-continued
H2-17
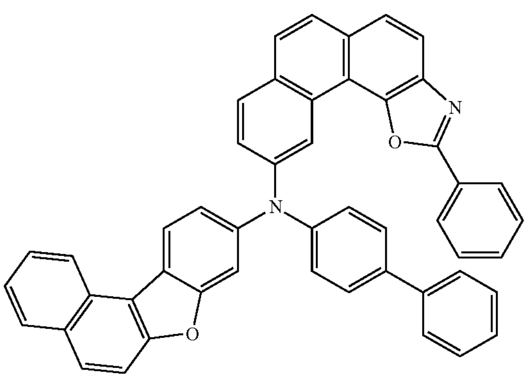
H2-18
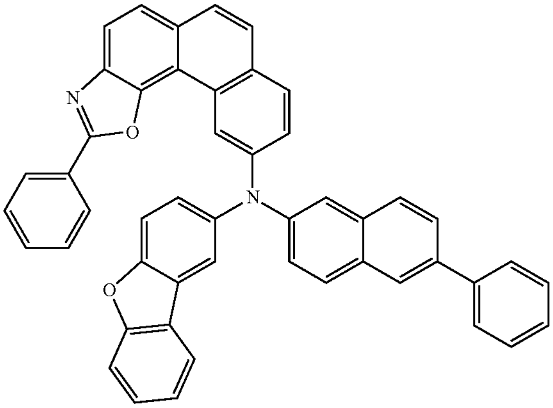
H2-19
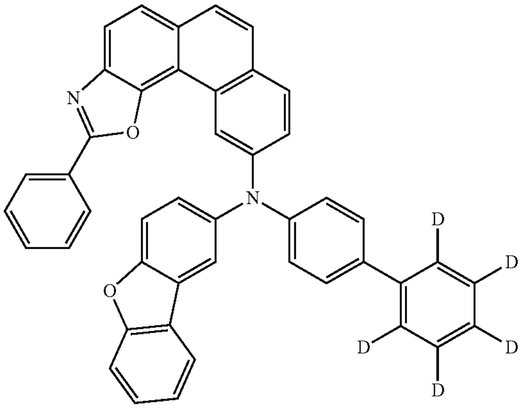
-continued
H2-20
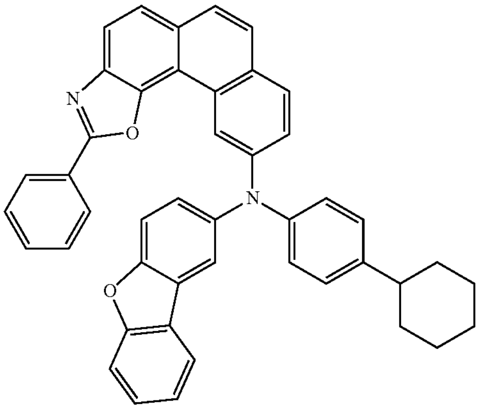
H2-21
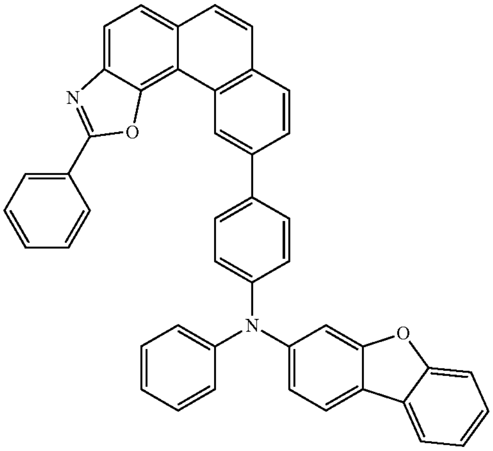
H2-22
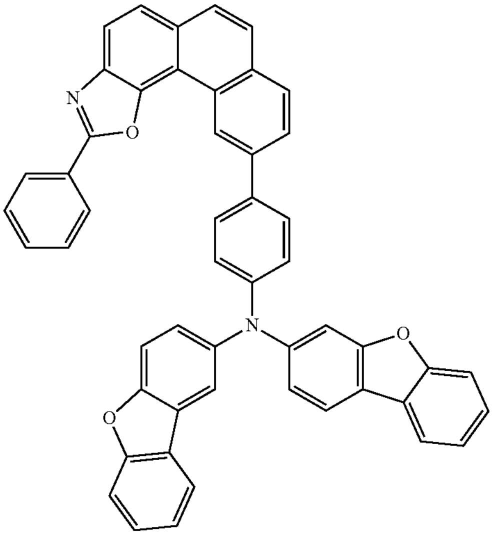

-continued
H2-23
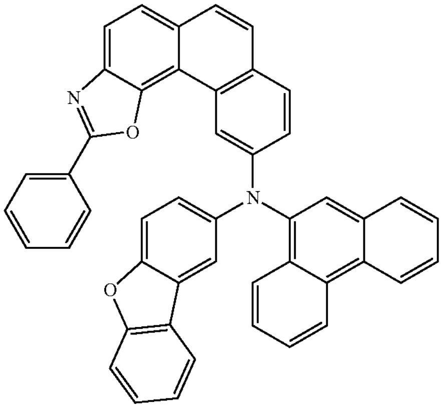
H2-24
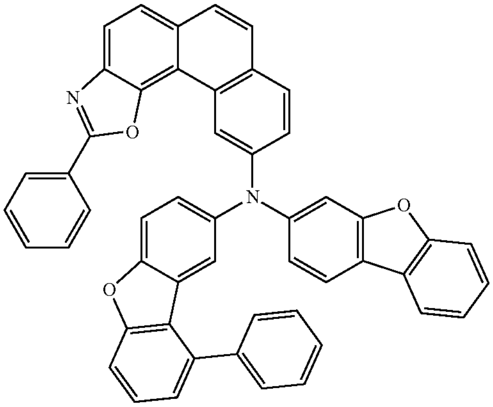
H2-25
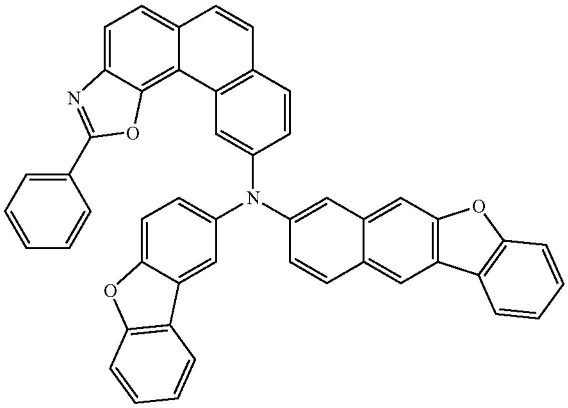
-continued
H2-26
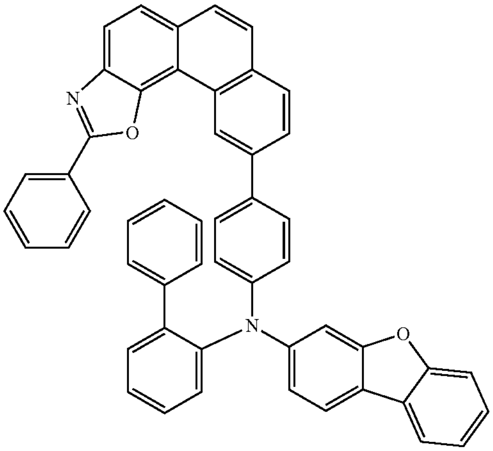
H2-27
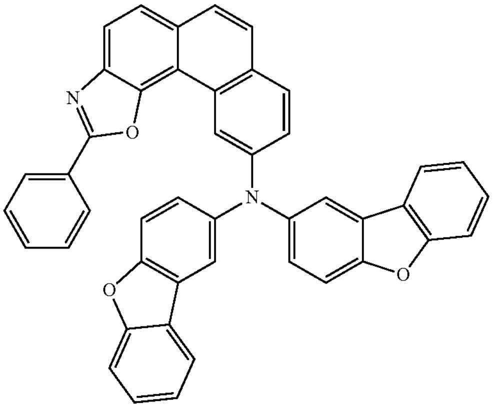
H2-28
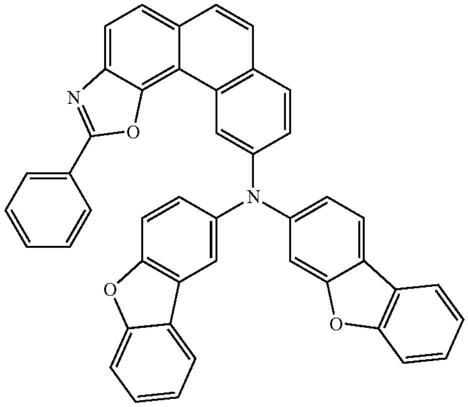

-continued
H2-29
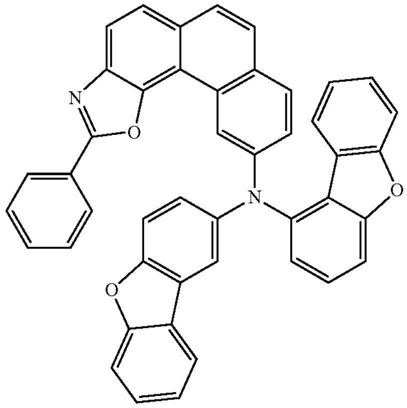
H2-30
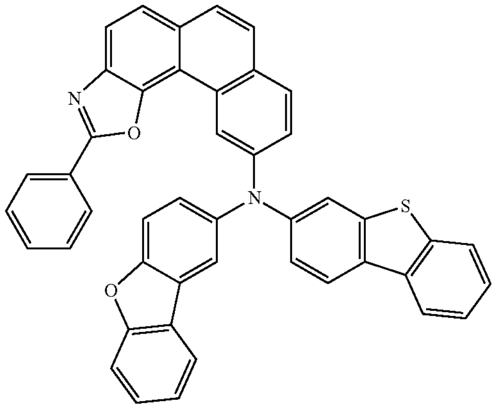
H2-31
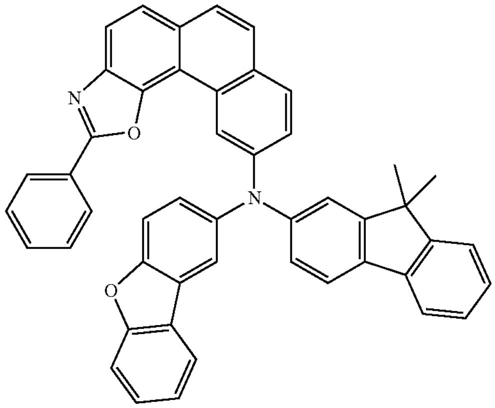
H2-32
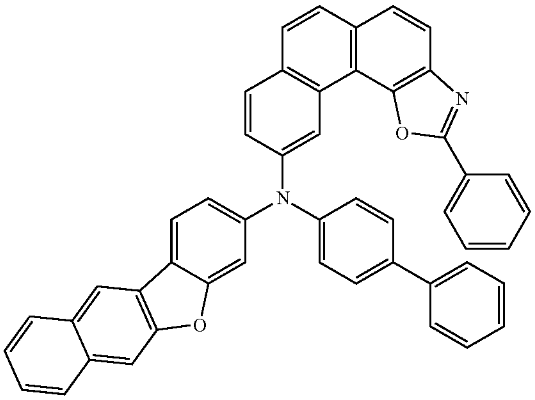
-continued
H2-33
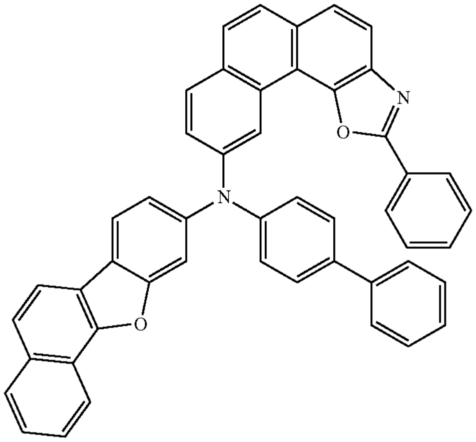
H2-34
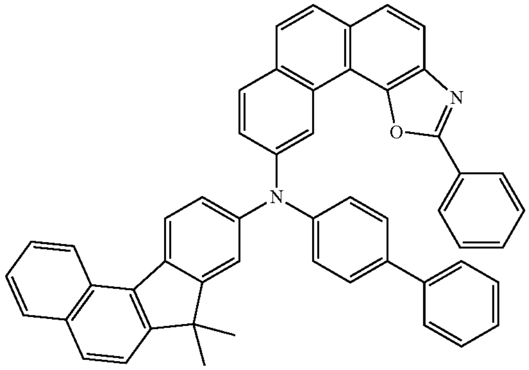
H2-35
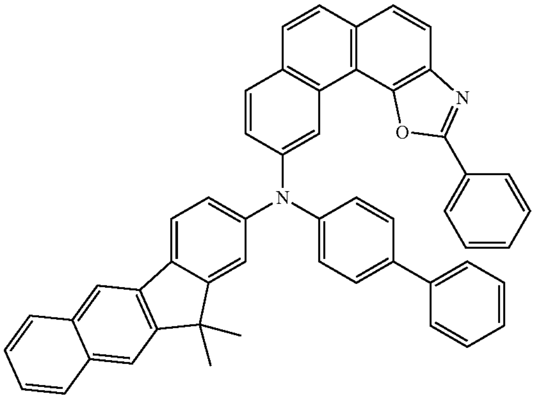
H2-36
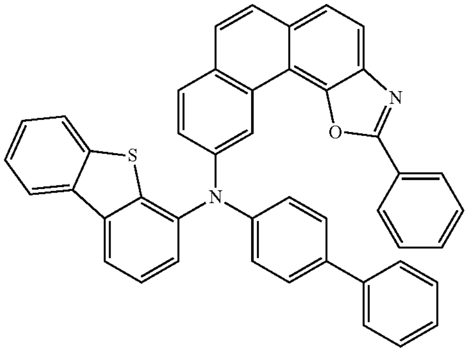

-continued
H2-37
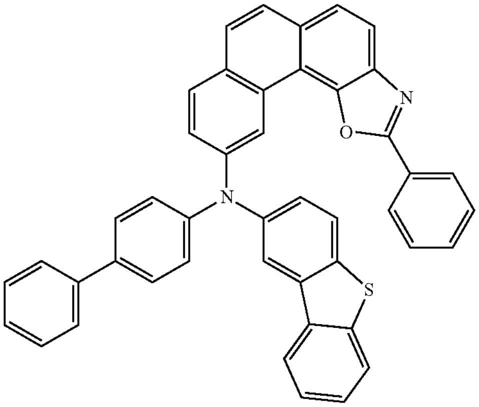
H2-38
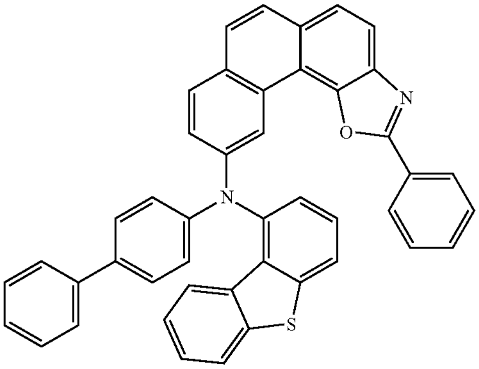
H2-39
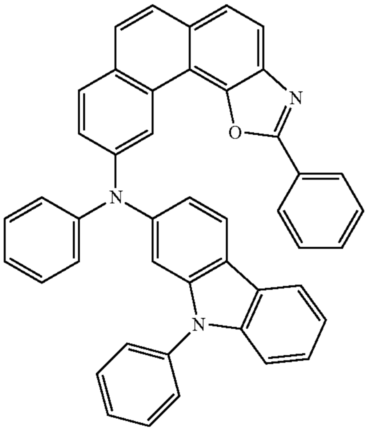
-continued
H2-40
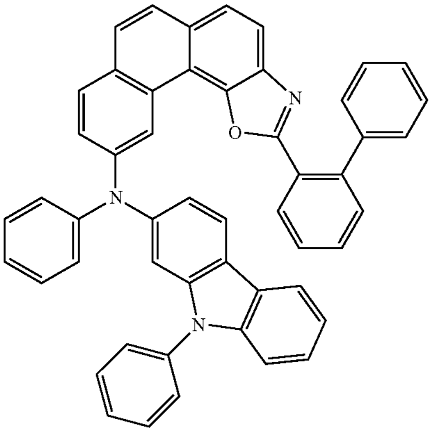
H2-41
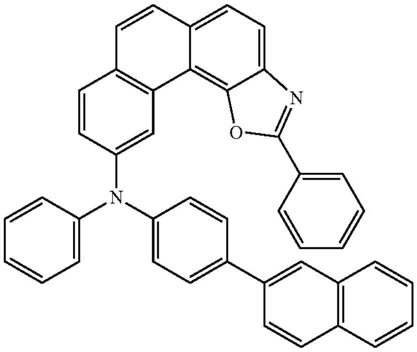
H-42
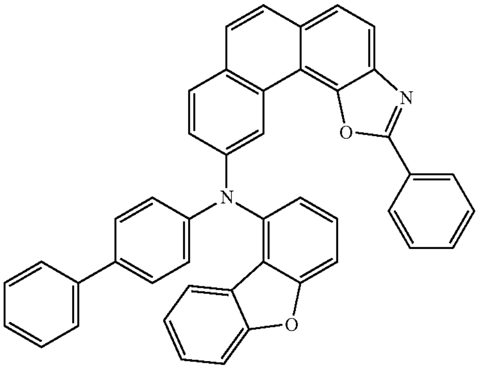
H2-43
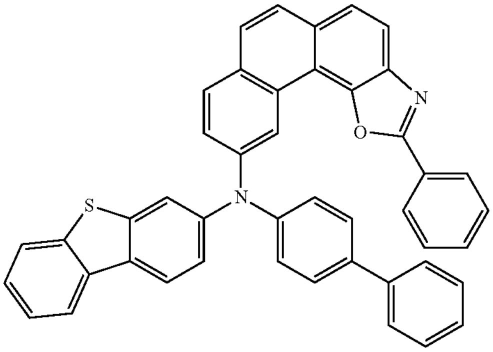

-continued
H2-44
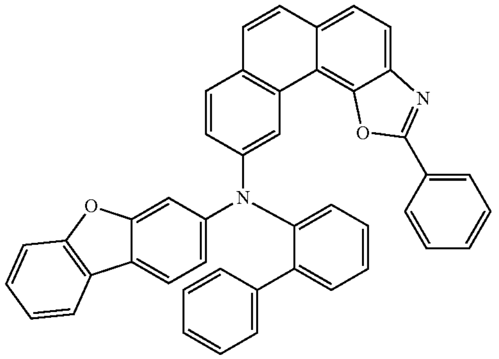
H2-45
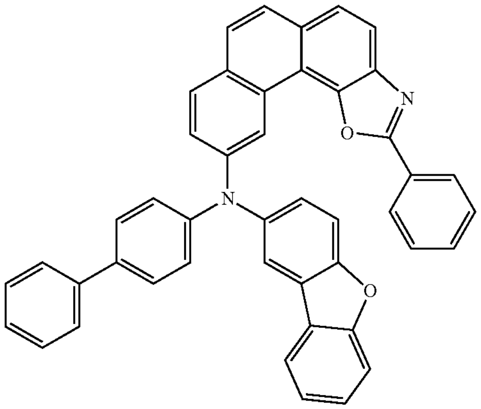
H2-47
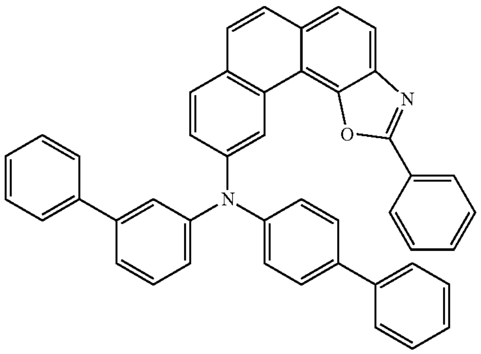
H2-48
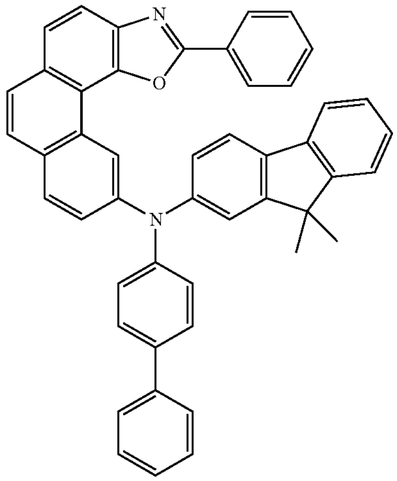
-continued
H2-49
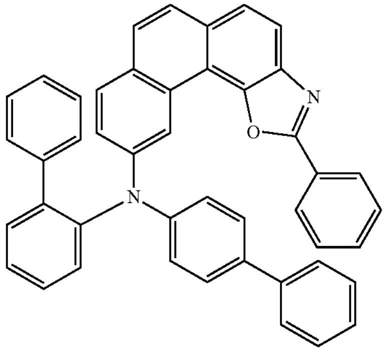
H2-50
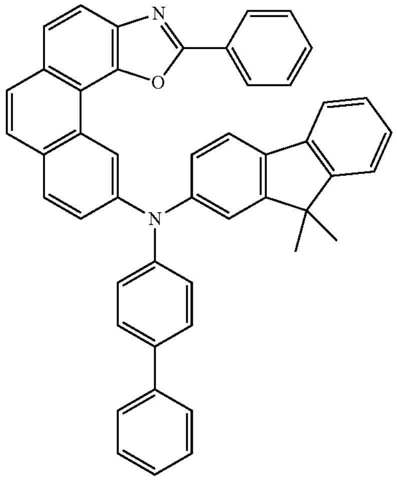
H2-51
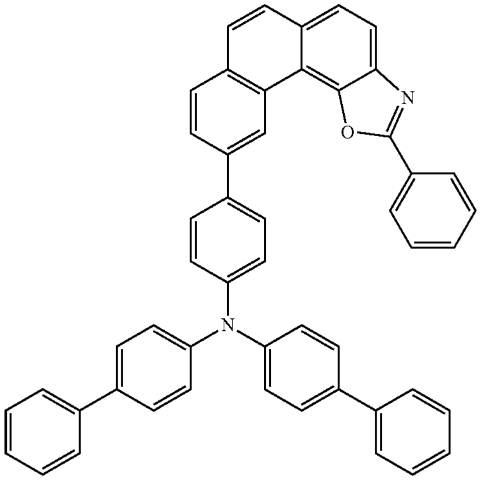

-continued
H2-52
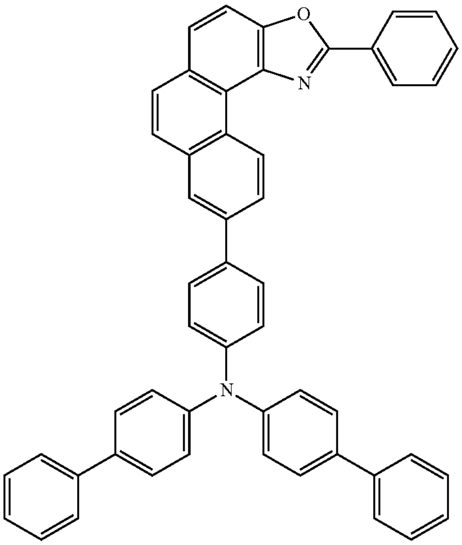
H2-53
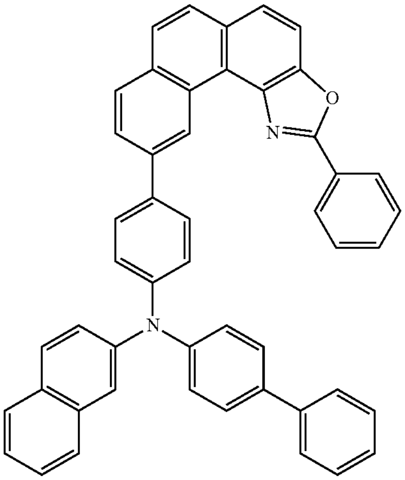
H2-54
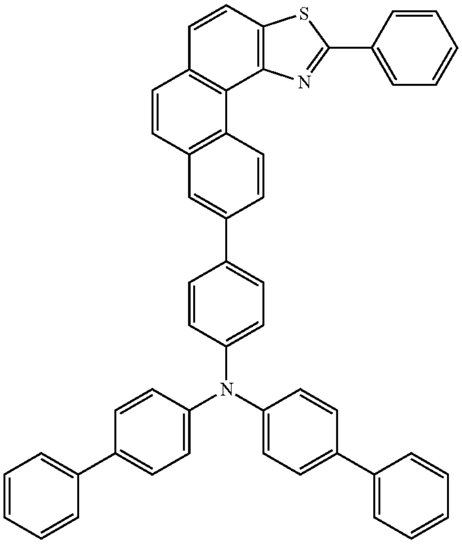
-continued
H2-55
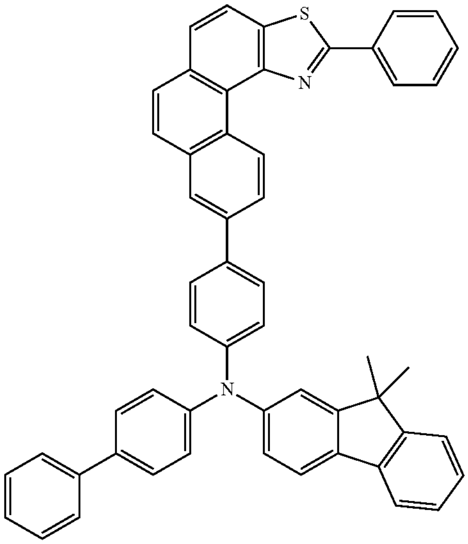
H2-56
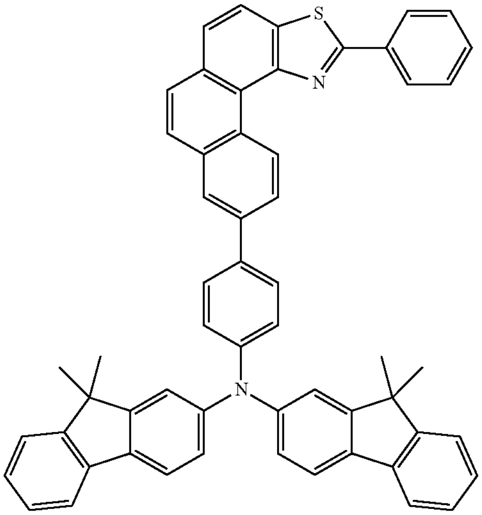
H2-57
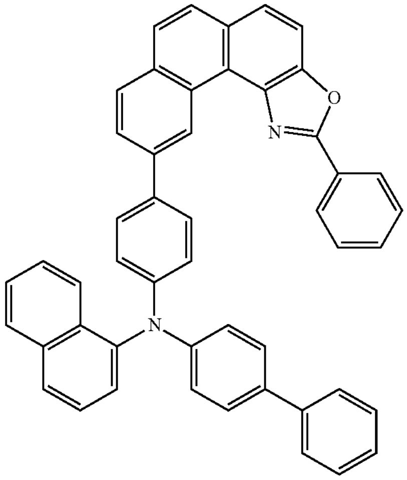

-continued
H2-58
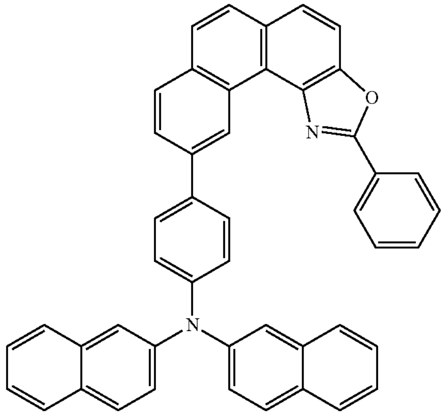
H2-59
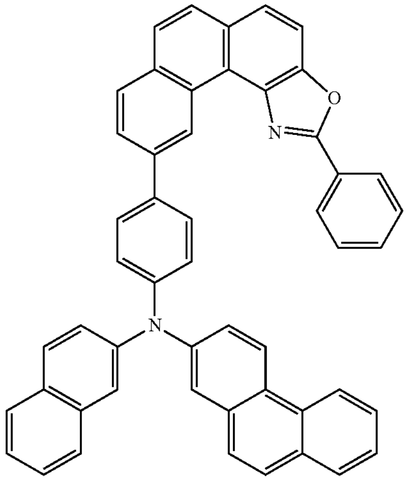
H2-60
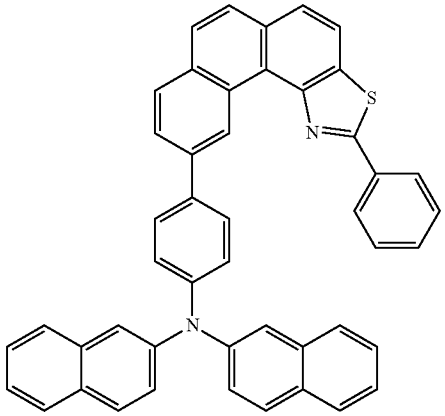
-continued
H2-61
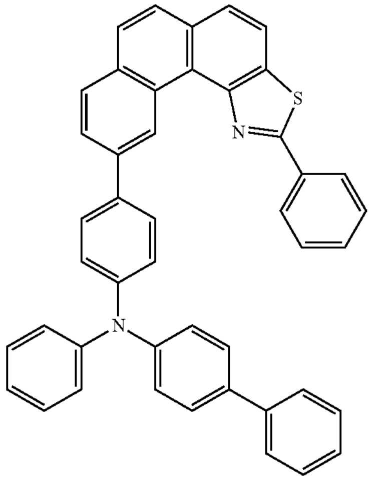
H2-62
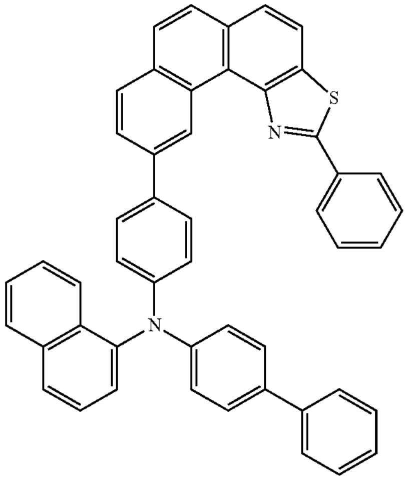
H2-63
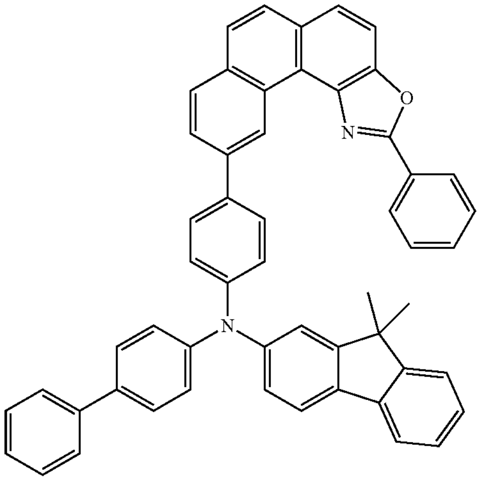

-continued
H2-64
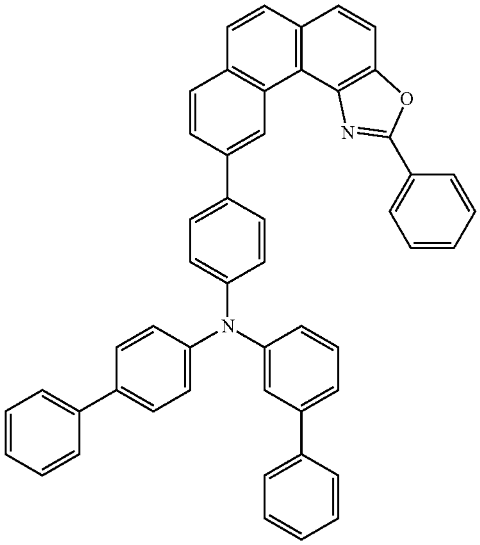
H2-65
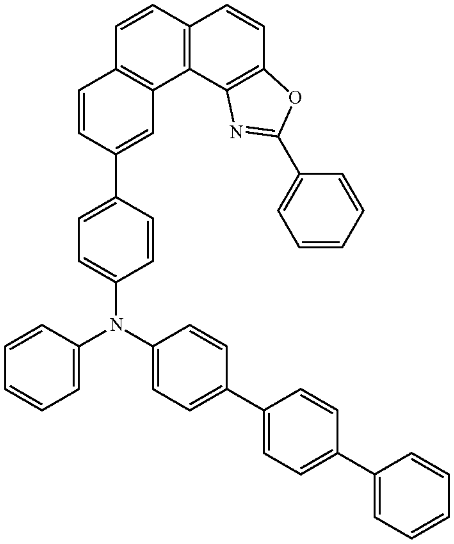
H2-66
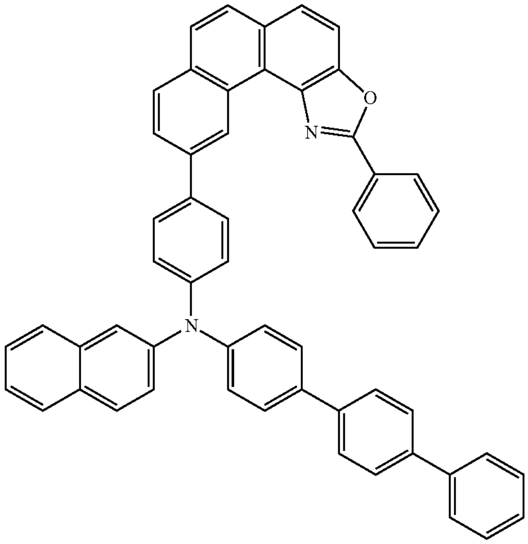
-continued
H2-67
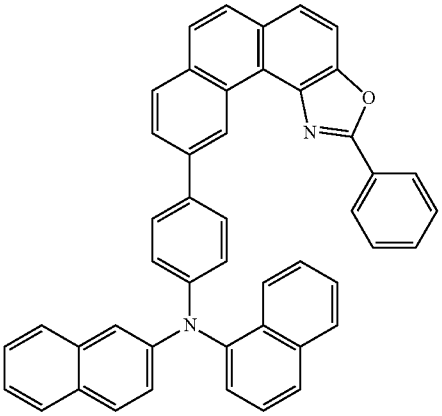
H2-68
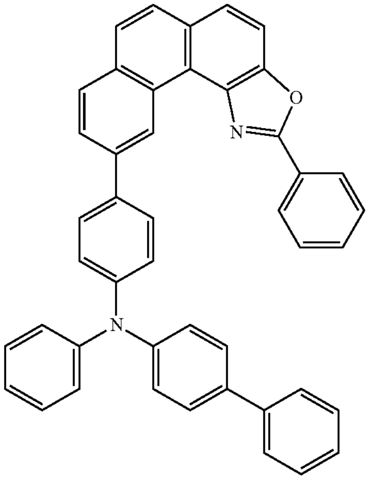
H2-69
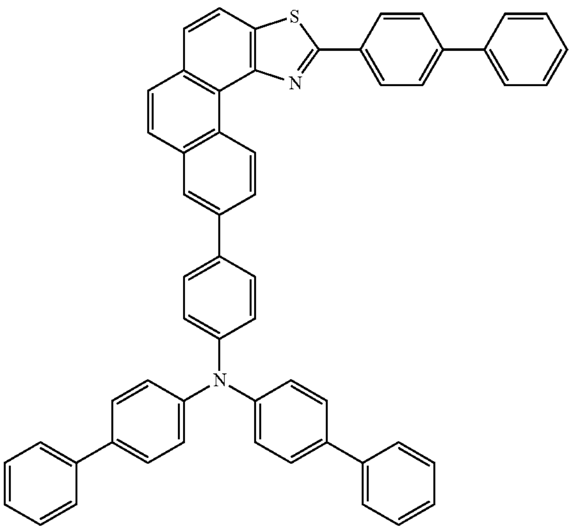

-continued
H2-70
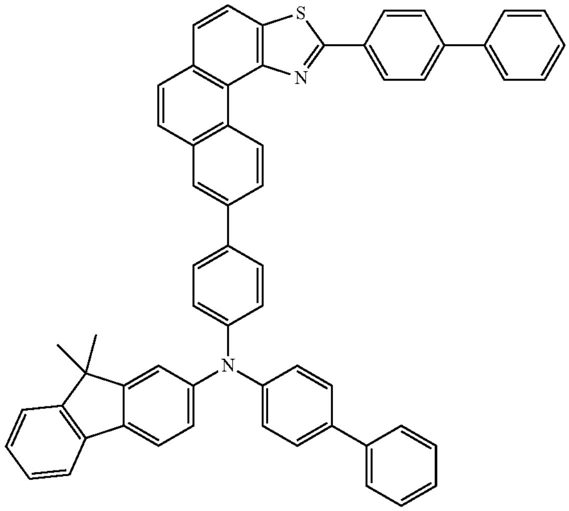
H2-71
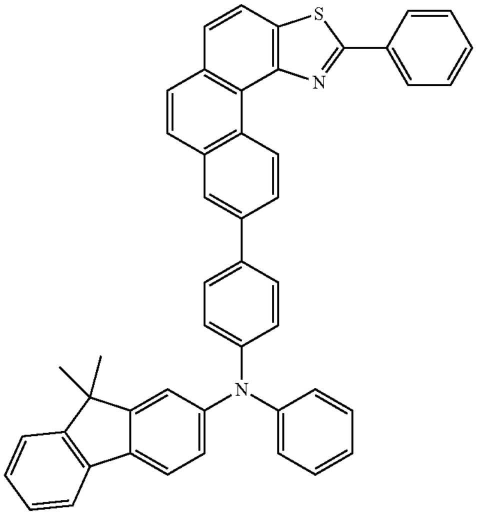
H2-72
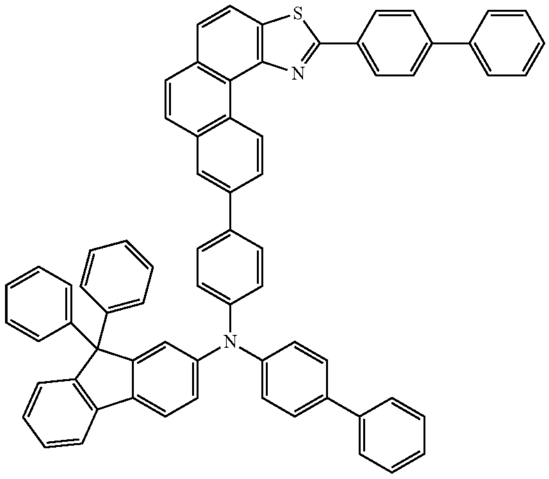
-continued
H2-73
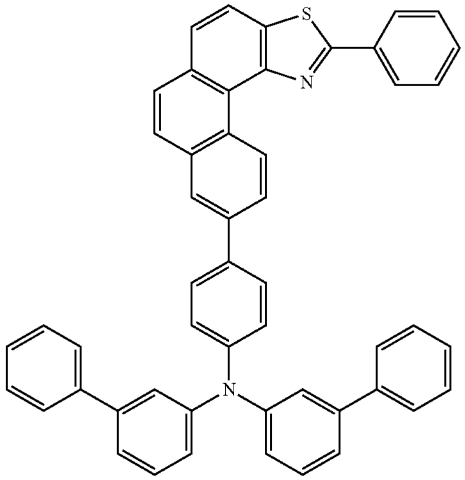
H2-74
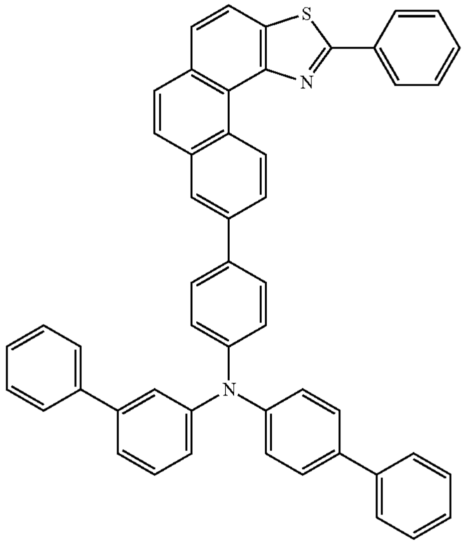
H2-75
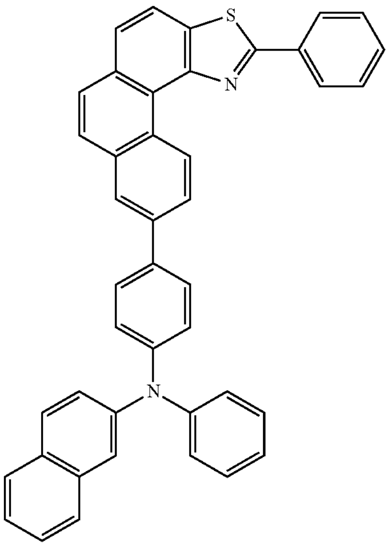

-continued
H2-76
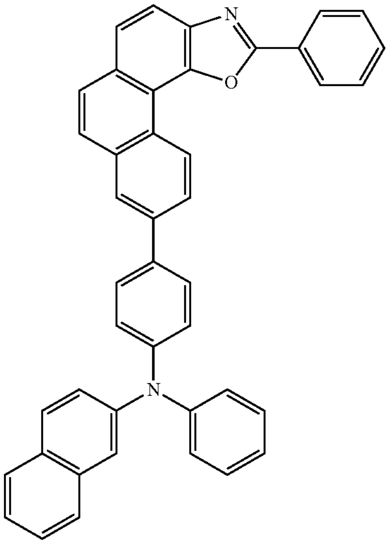
H2-77
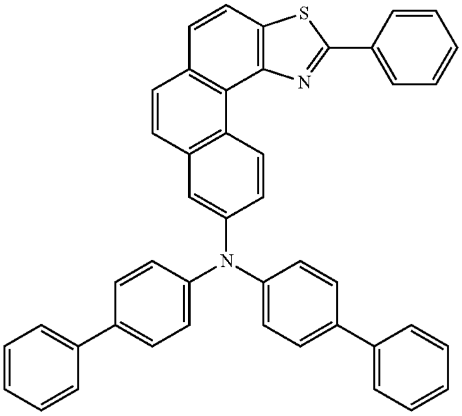
H2-78
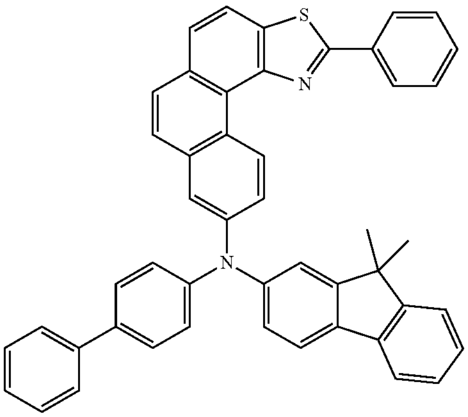
-continued
H2-79
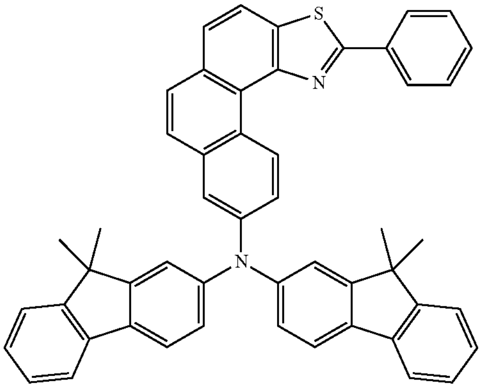
H2-80
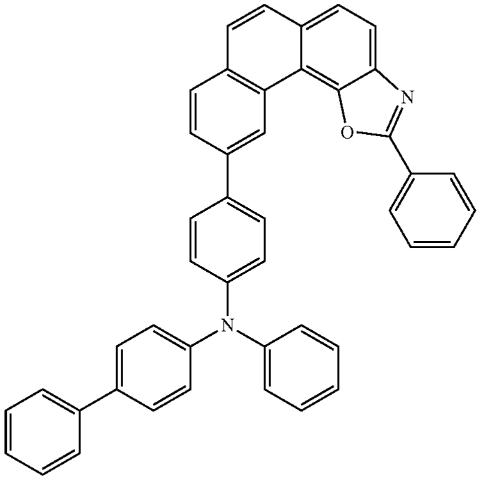
H2-81
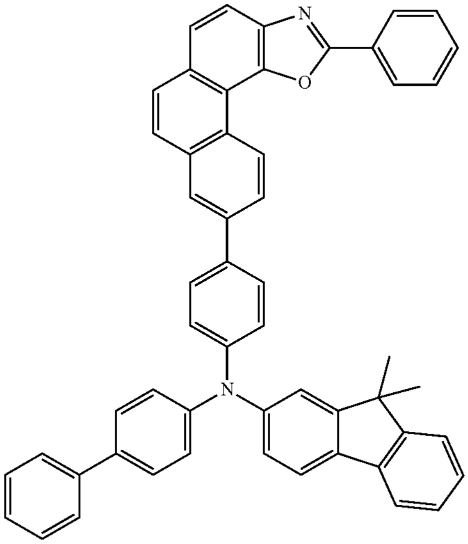

H2-82
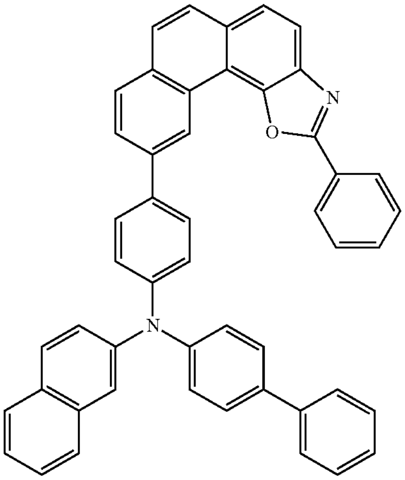
H2-83
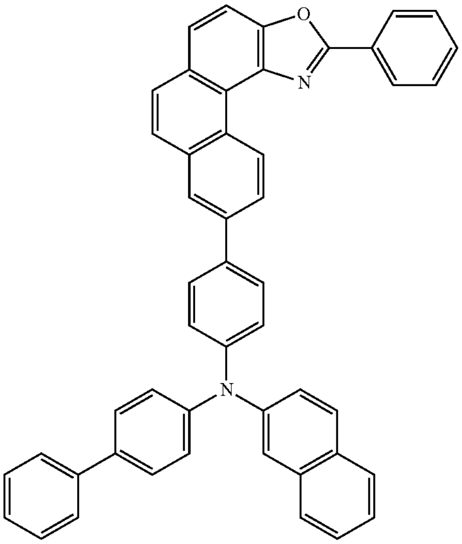
H2-84
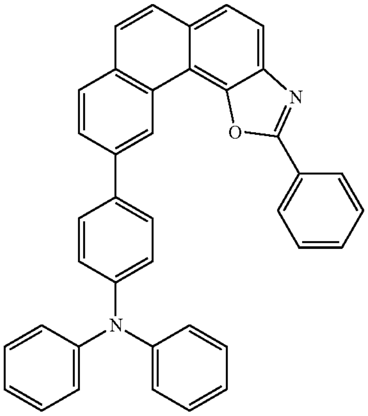
H2-85
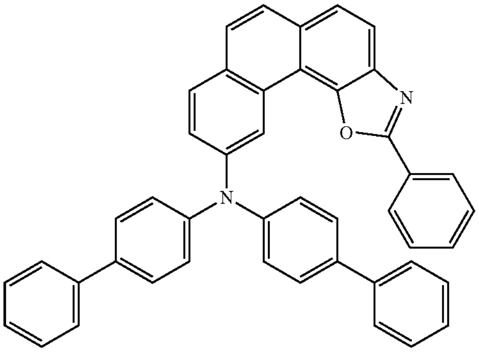
H2-86
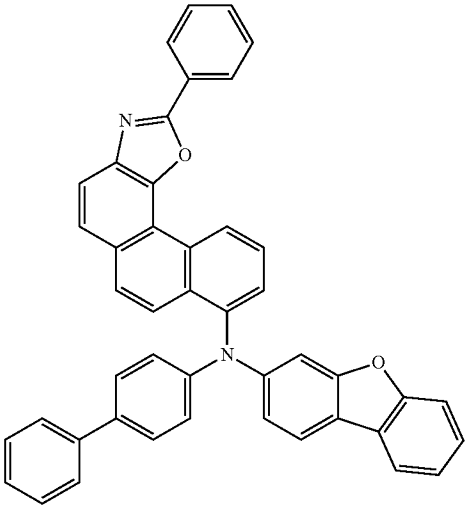
H2-87
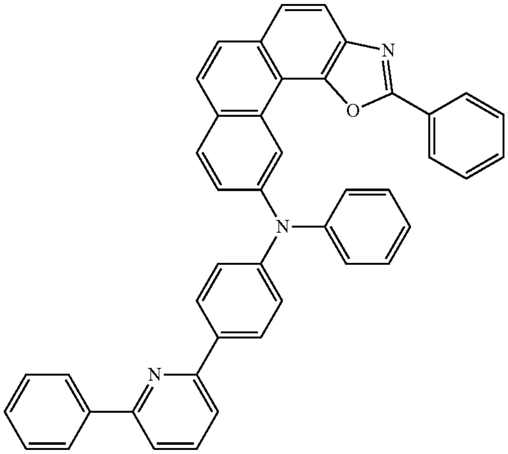

-continued
H2-88
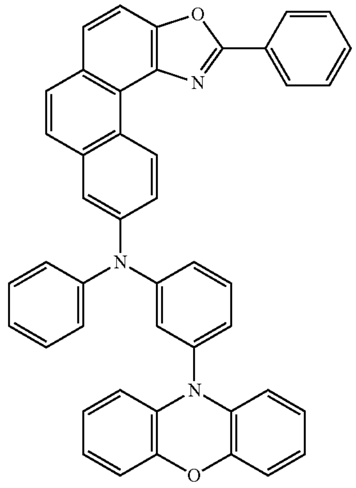
H2-89
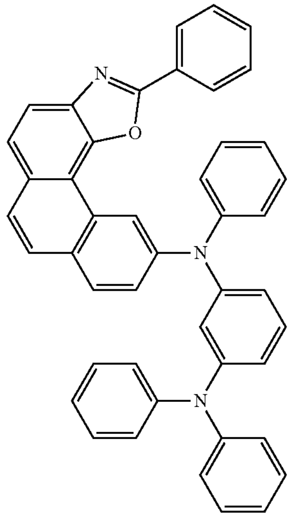
H2-90
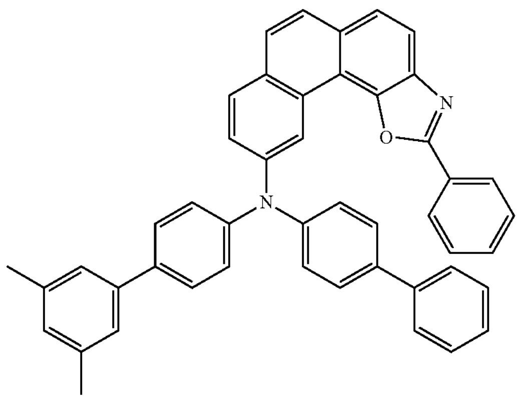
-continued
H2-91
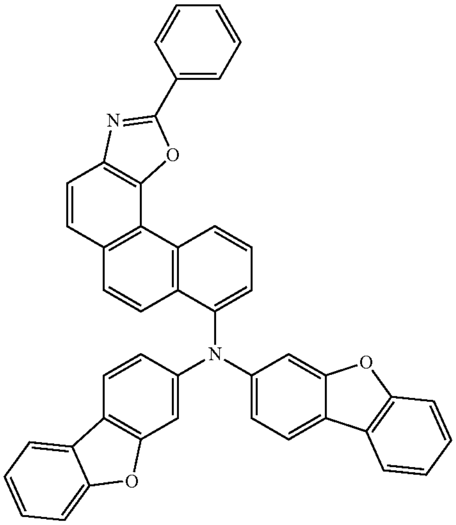
H2-92
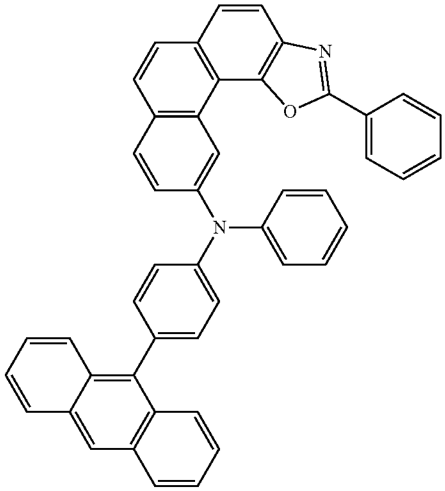
H2-93
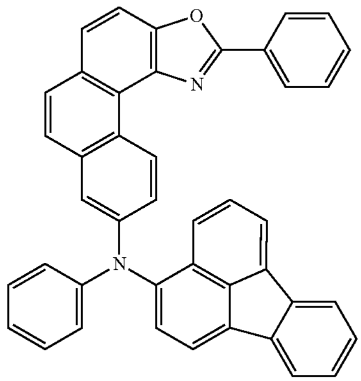

H2-94
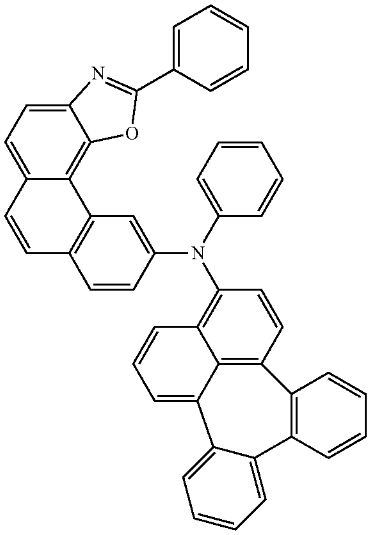
H2-95
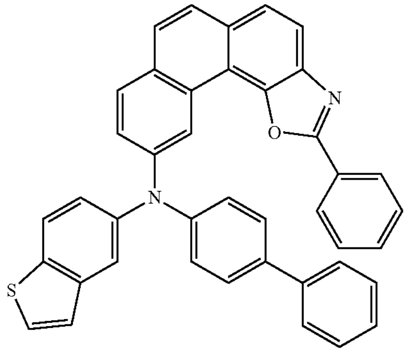
H2-96
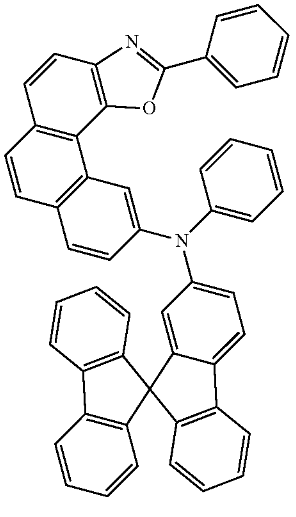
H2-97
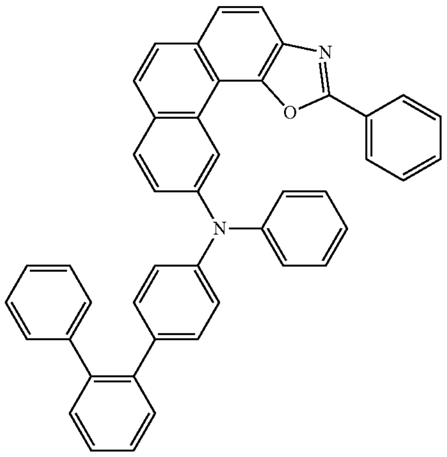
H2-98
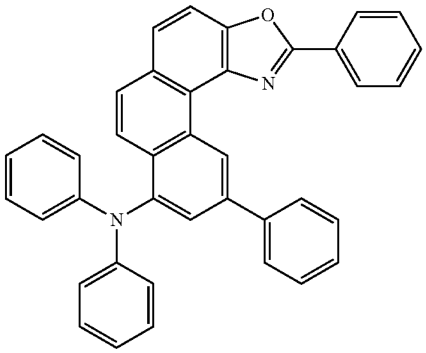
H2-99
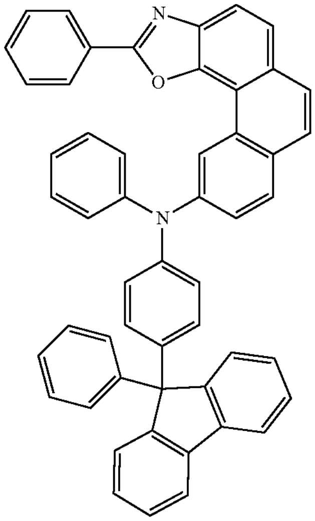

-continued
H2-100
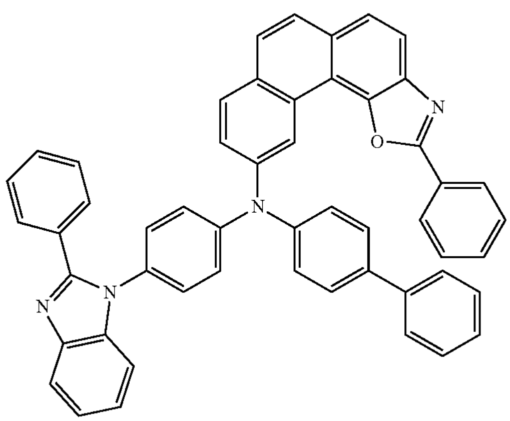
H2-101
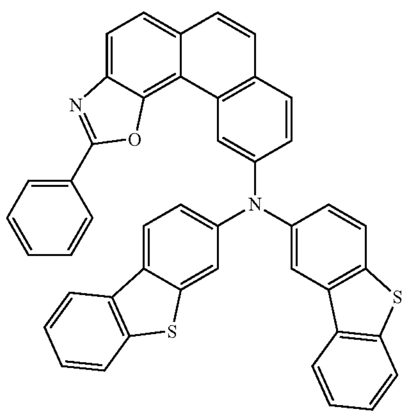
H2-102
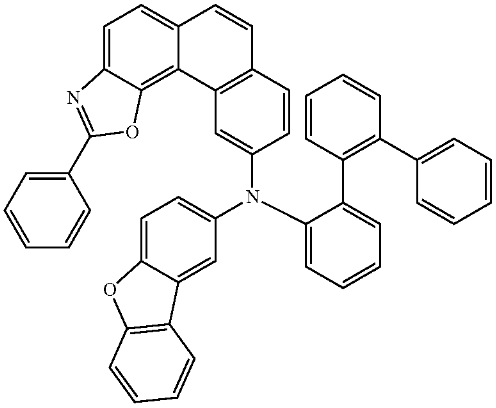
-continued
H2-103
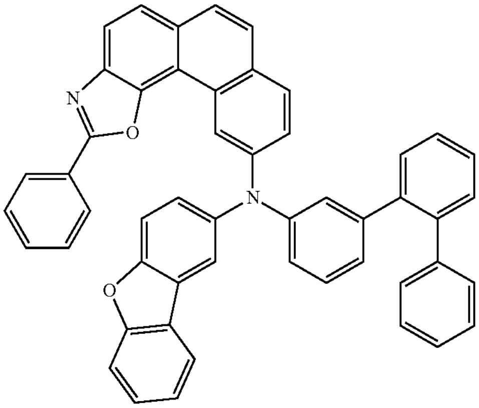
H2-104
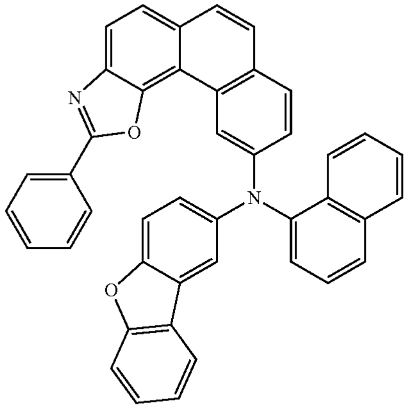
H2-105
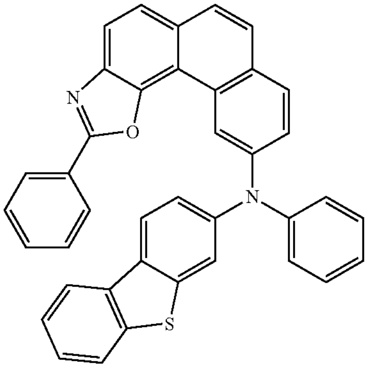
H2-106
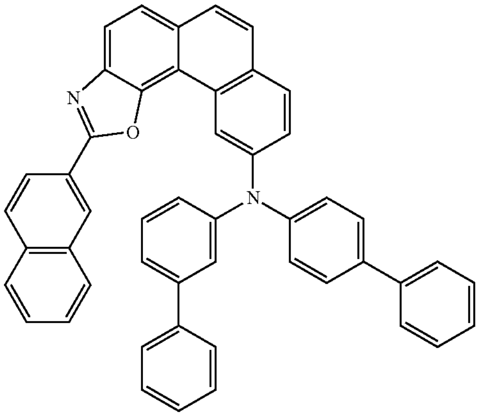

-continued
H2-107
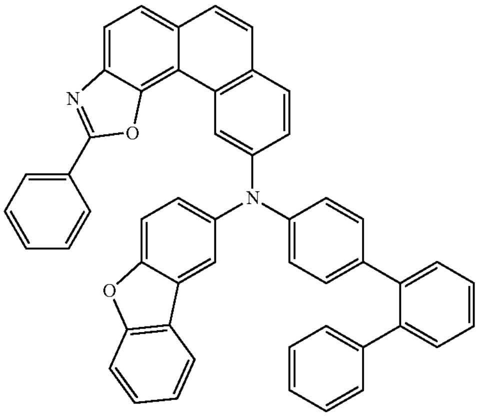
H2-108
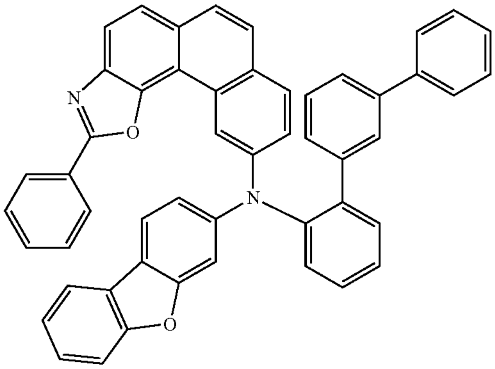
H2-109
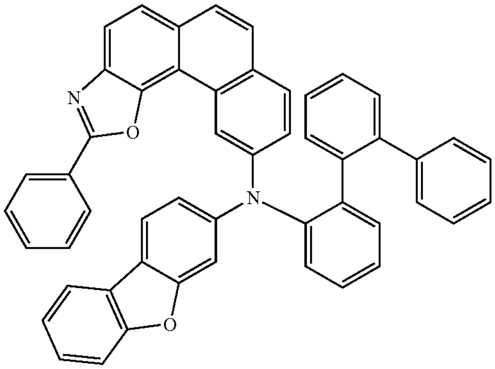
H2-110
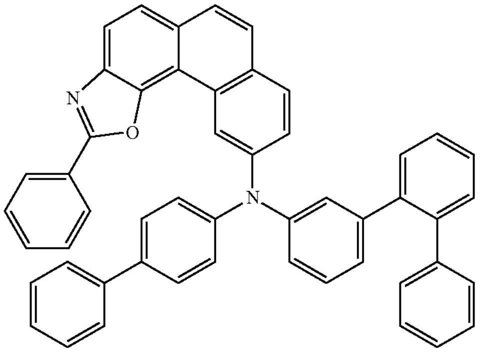
-continued
H2-111
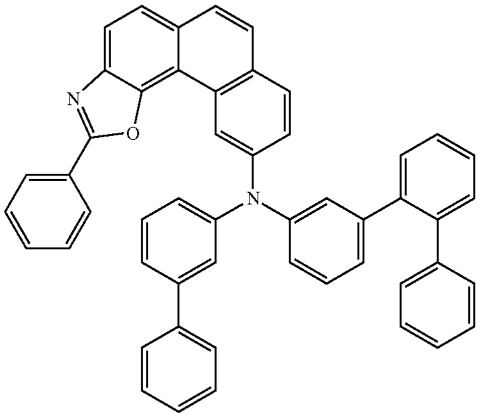
H2-112
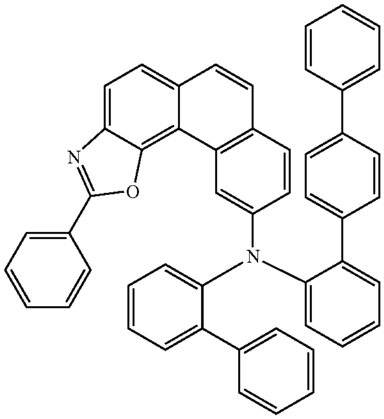
H2-113
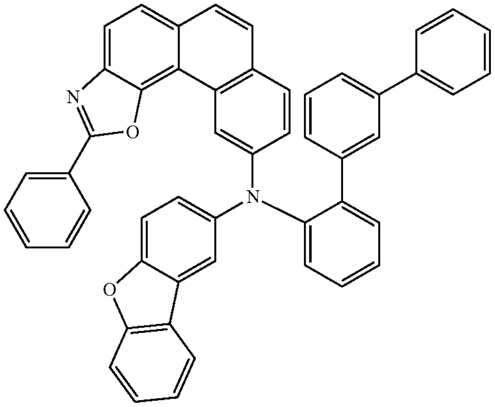

-continued
H-114
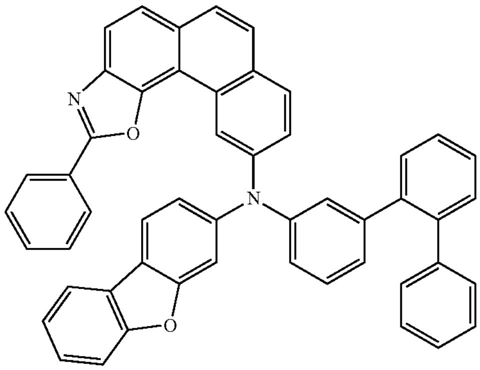
H2-115
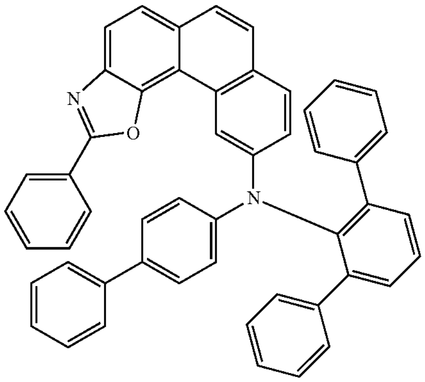
H2-116
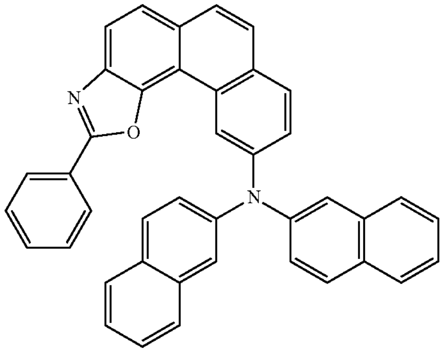
H2-117
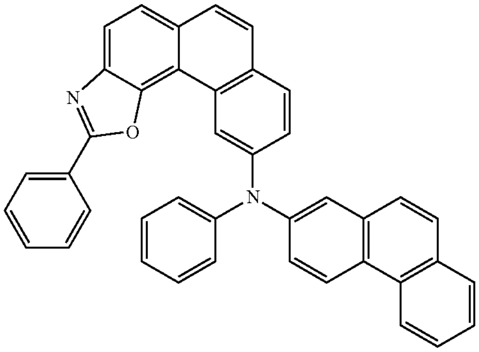
-continued
H2-118
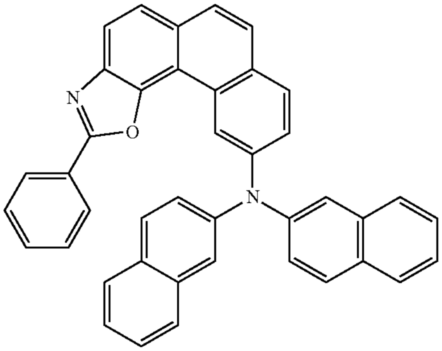
H2-119
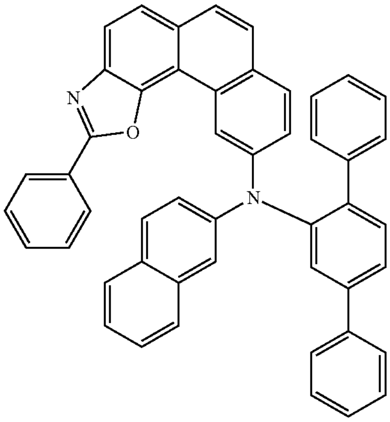
H2-120
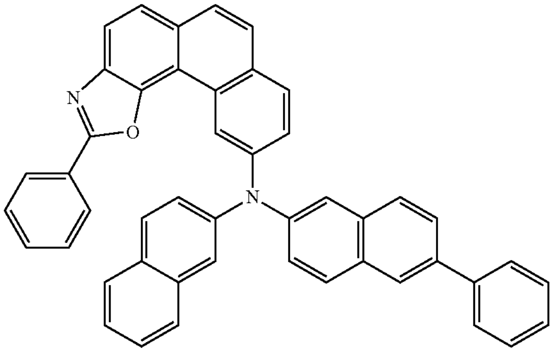
H2-121
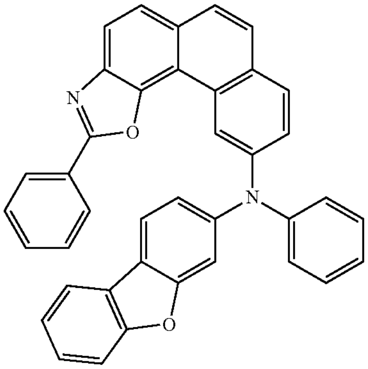

H2-122
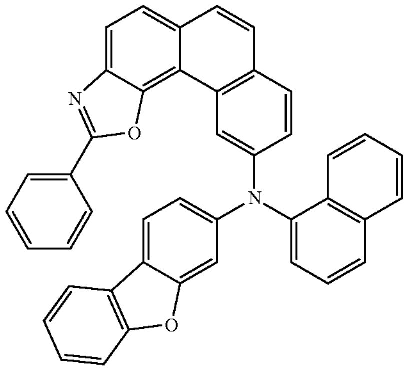
H2-123
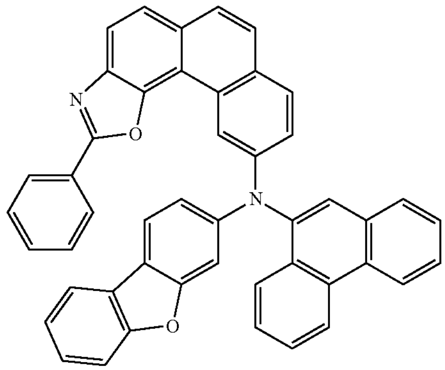
H2-124
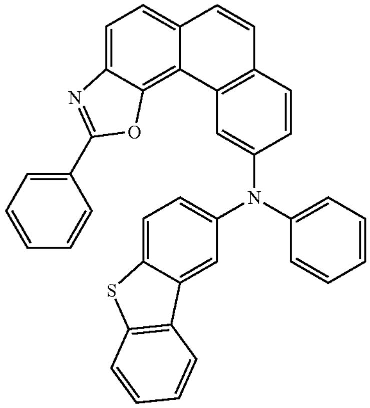
H2-125
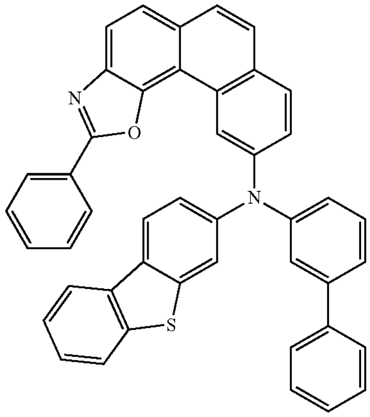
H2-126
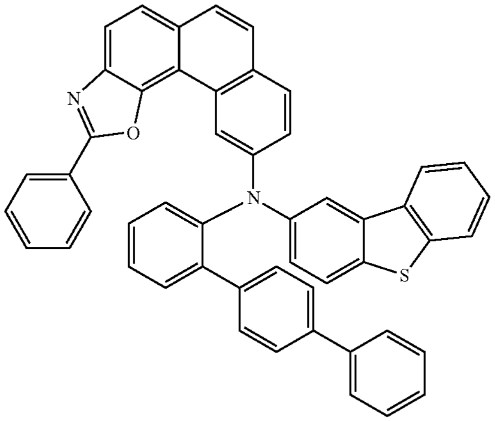
H2-127
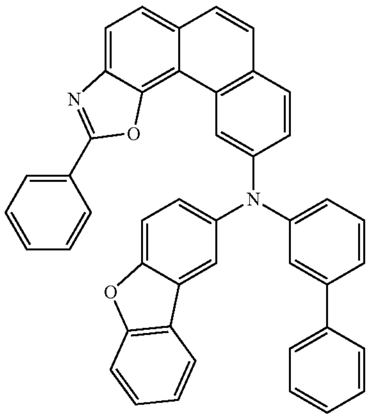
H2-128
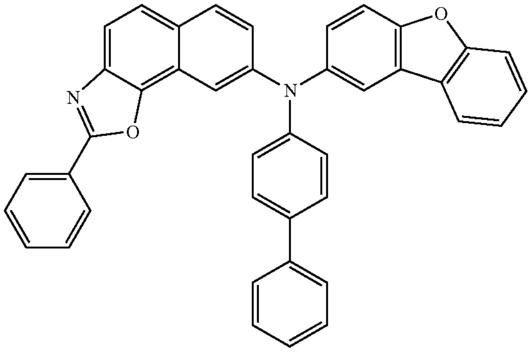
H2-129
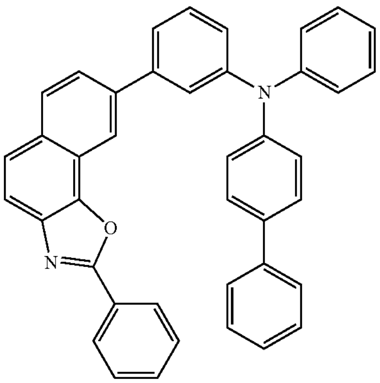

-continued
H2-130
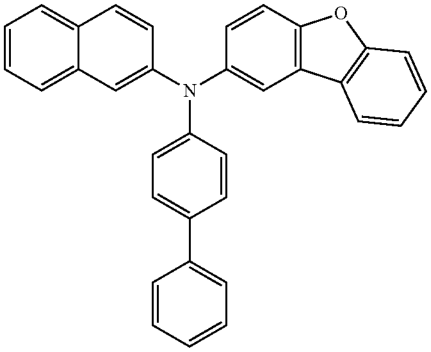
H2-131
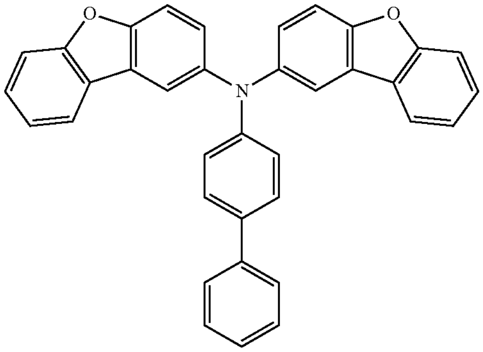
H2-132
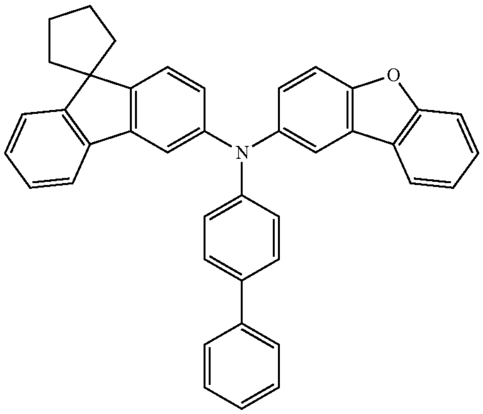
H2-133
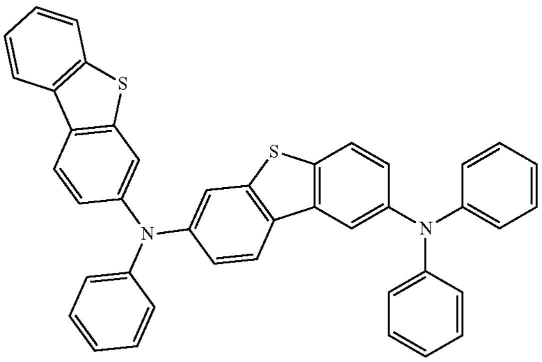
-continued
H2-134
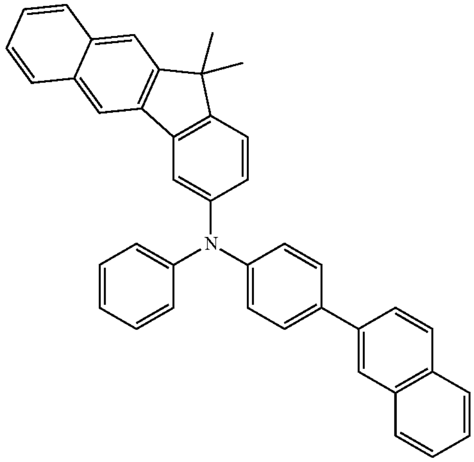
H2-135
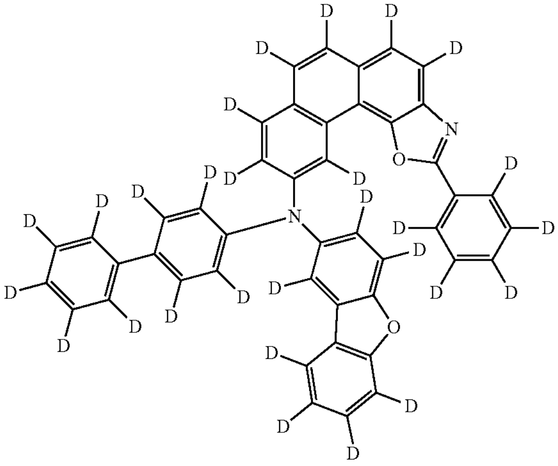
H2-136
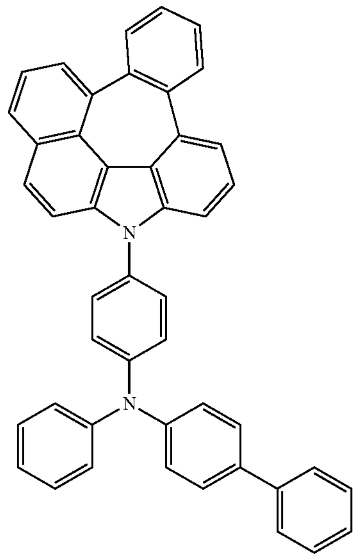

-continued
H2-137
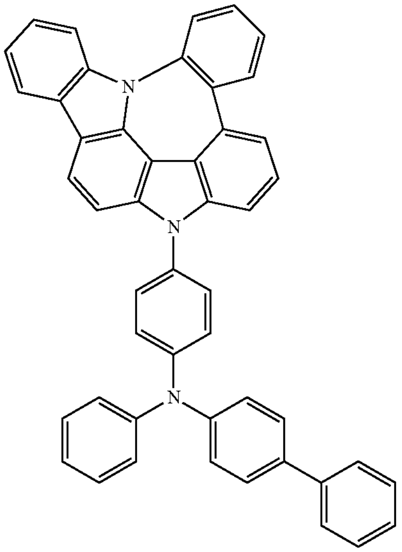
H2-138
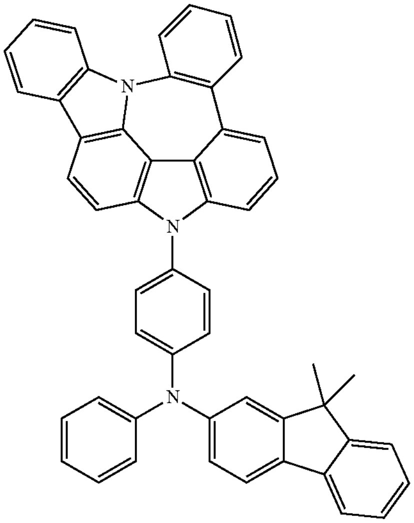
H2-139
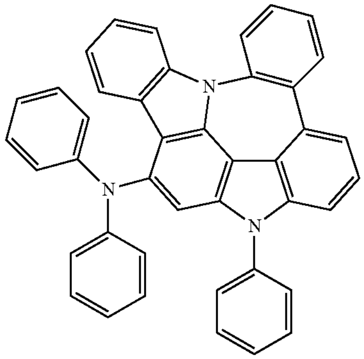
-continued
H2-140
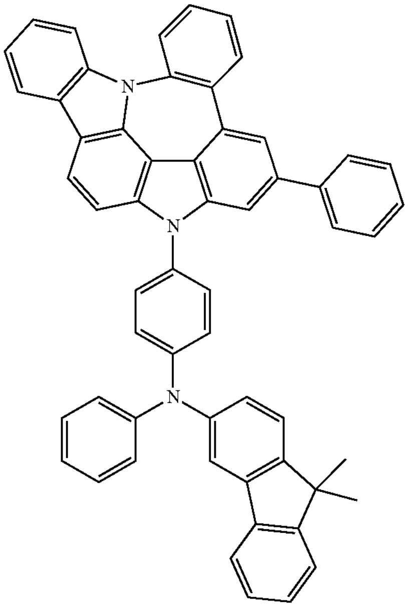
H2-141
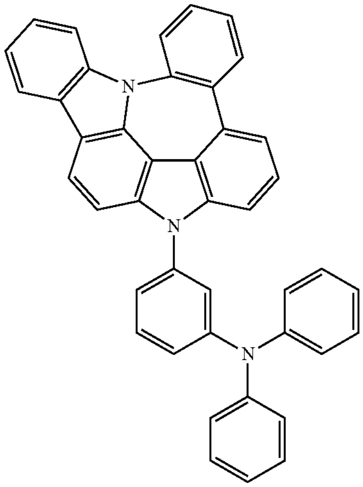
H2-142
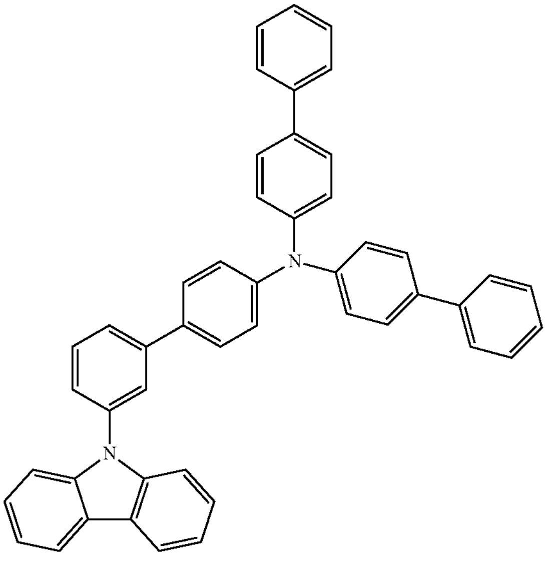

-continued
H2-143
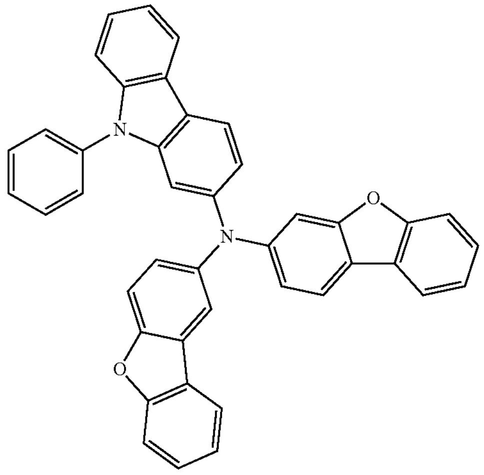
H2-144
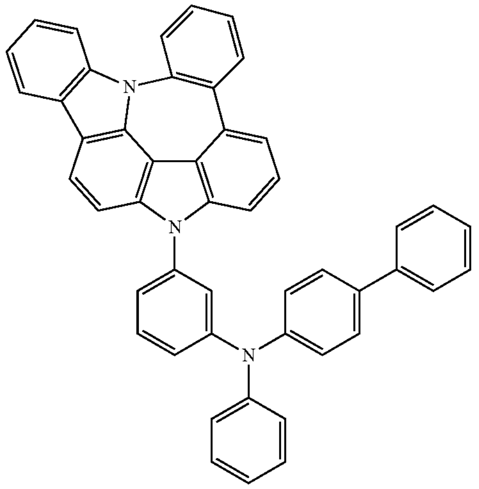
H2-145
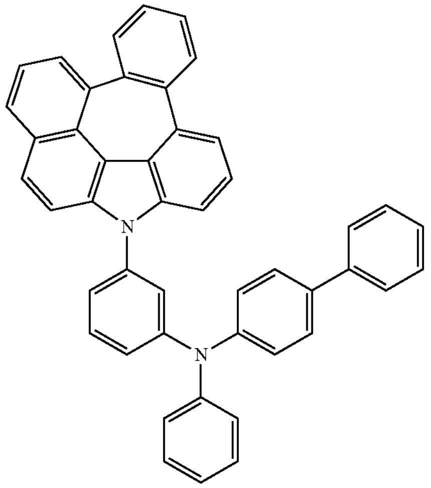
-continued
H2-146
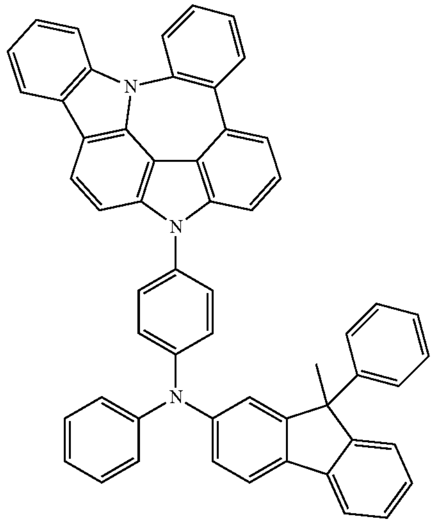
H2-147
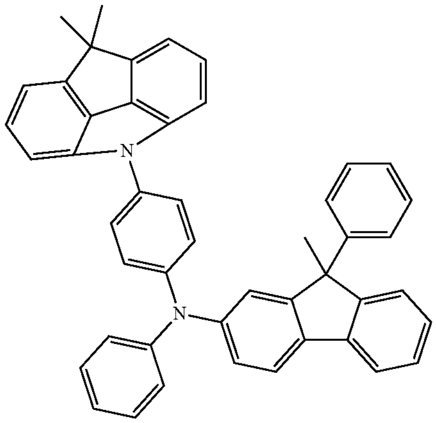
H2-148
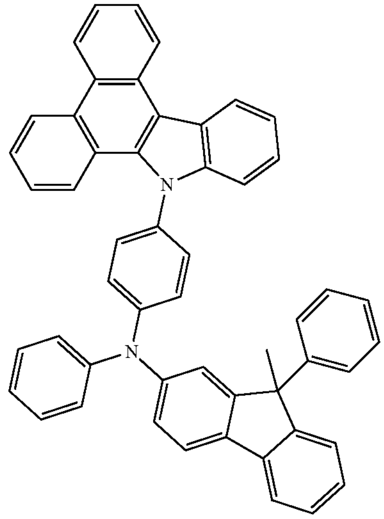

-continued
H2-149
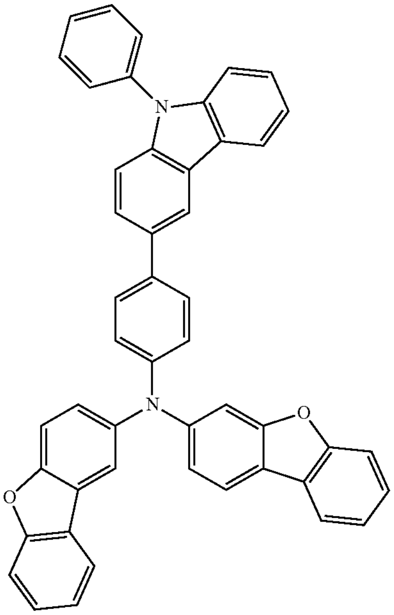
H2-150
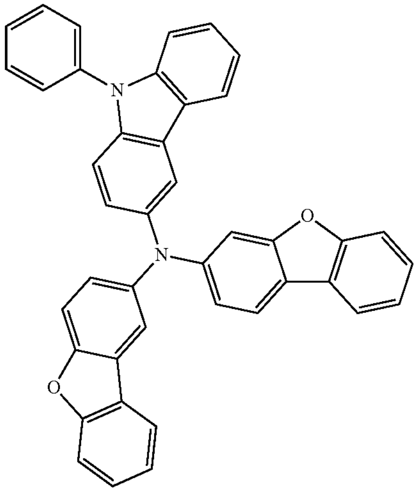
H2-151
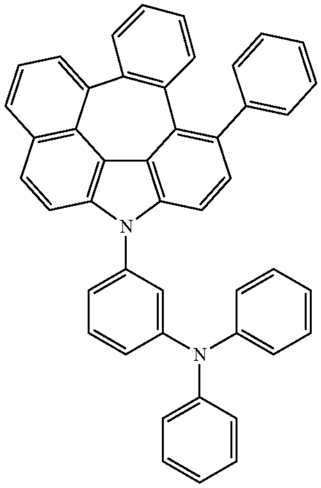
-continued
H2-152
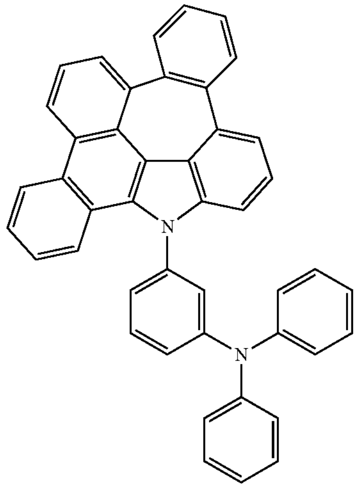
H2-153
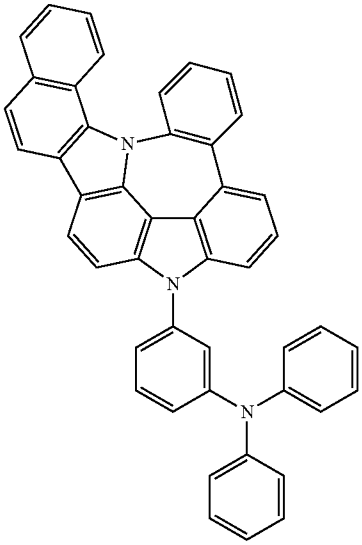
H2-154
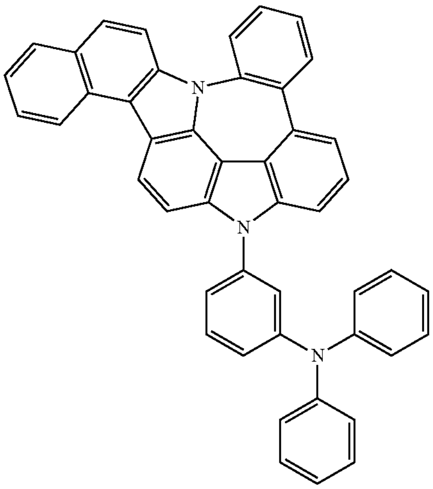

-continued
H2-155
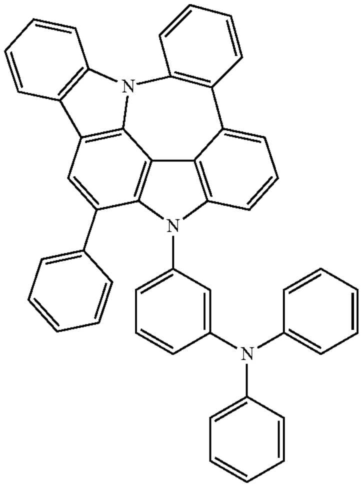
H2-156
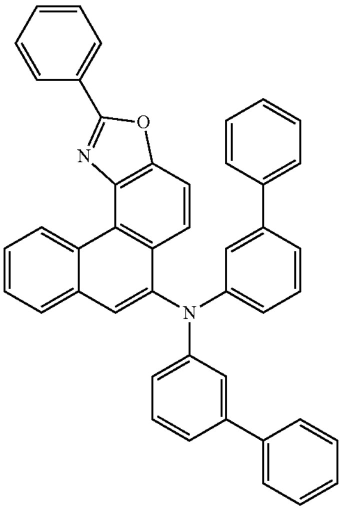
H2-157
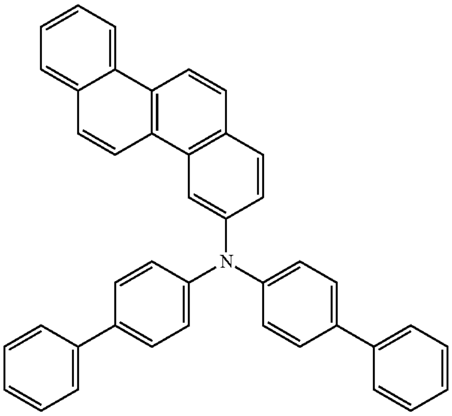
-continued
H2-158
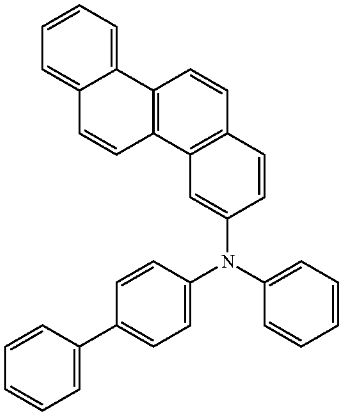
and
H2-159
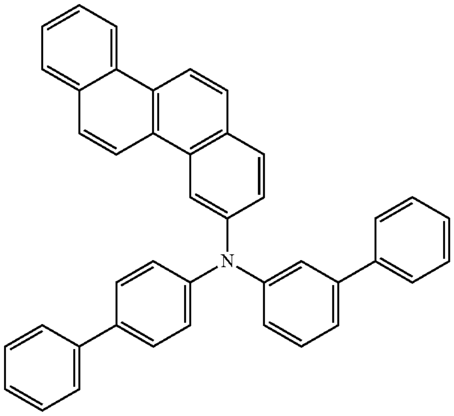
.
8. An organic electroluminescent device comprising an anode; a cathode; and at least one light-emitting layer between the anode and the cathode, wherein at least one of the light-emitting layers comprises the plurality of host materials according to claim 1.
* * * * *